(12) United States Patent
Bastos et al.

(10) Patent No.: US 10,174,014 B2
(45) Date of Patent: Jan. 8, 2019

(54) COMPOUNDS, COMPOSITIONS, AND METHODS FOR INCREASING CFTR ACTIVITY

(71) Applicant: Proteostasis Therapeutics, Inc., Cambridge, MA (US)

(72) Inventors: Cecilia M. Bastos, South Grafton, MA (US); Benito Munoz, Newtonville, MA (US); Bradley Tait, Malden, MA (US)

(73) Assignee: Proteostasis Therapeutics, Inc., Boston, MA (US)

( * ) Notice: Subject to any disclaimer, the term of this patent is extended or adjusted under 35 U.S.C. 154(b) by 0 days.

(21) Appl. No.: 15/320,172

(22) PCT Filed: Jun. 19, 2015

(86) PCT No.: PCT/US2015/036691
§ 371 (c)(1),
(2) Date: Dec. 19, 2016

(87) PCT Pub. No.: WO2015/196071
PCT Pub. Date: Dec. 23, 2015

(65) Prior Publication Data
US 2017/0233379 A1 Aug. 17, 2017

Related U.S. Application Data

(60) Provisional application No. 62/102,230, filed on Jan. 12, 2015, provisional application No. 62/096,389, filed on Dec. 23, 2014, provisional application No. 62/014,400, filed on Jun. 19, 2014, provisional application No. 62/014,409, filed on Jun. 19, 2014.

(51) Int. Cl.

| | |
|---|---|
| *A61K 31/422* | (2006.01) |
| *C07D 413/12* | (2006.01) |
| *C07F 7/18* | (2006.01) |
| *C07D 413/14* | (2006.01) |
| *C07D 231/12* | (2006.01) |
| *C07D 233/61* | (2006.01) |
| *C07D 417/12* | (2006.01) |
| *C07D 261/18* | (2006.01) |
| *C07D 285/12* | (2006.01) |
| *A61K 31/16* | (2006.01) |
| *A61K 31/42* | (2006.01) |
| *A61K 31/4245* | (2006.01) |
| *A61K 31/433* | (2006.01) |
| *A61K 31/695* | (2006.01) |
| *A61K 45/06* | (2006.01) |
| *C07C 243/36* | (2006.01) |

(52) U.S. Cl.
CPC ............ *C07D 413/12* (2013.01); *A61K 31/16* (2013.01); *A61K 31/42* (2013.01); *A61K 31/422* (2013.01); *A61K 31/4245* (2013.01); *A61K 31/433* (2013.01); *A61K 31/695* (2013.01); *A61K 45/06* (2013.01); *C07C 243/36* (2013.01); *C07D 231/12* (2013.01); *C07D 233/61* (2013.01); *C07D 261/18* (2013.01); *C07D 285/12* (2013.01); *C07D 413/14* (2013.01); *C07D 417/12* (2013.01); *C07F 7/1804* (2013.01); *C07F 7/1844* (2013.01)

(58) Field of Classification Search
CPC ..... C07D 261/08; C07D 413/12; C07D 413/14
See application file for complete search history.

(56) References Cited

U.S. PATENT DOCUMENTS

| | | | |
|---|---|---|---|
| 5,780,393 A | 7/1998 | Newton | |
| 5,888,941 A | 3/1999 | Bartroli et al. | |
| 7,705,027 B2* | 4/2010 | Drysdale | C07D 261/08 514/378 |
| 7,846,951 B2 | 12/2010 | Miller et al. | |
| 7,915,297 B2 | 3/2011 | Cho et al. | |
| 7,981,935 B2 | 7/2011 | Olson et al. | |
| 8,193,225 B2 | 6/2012 | Schneider et al. | |
| 8,211,927 B2* | 7/2012 | Roughton | C07D 413/12 514/378 |
| 8,236,838 B2 | 8/2012 | Jones et al. | |
| 8,623,860 B2 | 1/2014 | Fleck et al. | |
| 8,815,924 B2 | 8/2014 | Dorsch et al. | |
| 2006/0041006 A1 | 2/2006 | Ibrahim et al. | |
| 2006/0100226 A1 | 5/2006 | Sikorski et al. | |

(Continued)

FOREIGN PATENT DOCUMENTS

| | | |
|---|---|---|
| CA | 2736441 A1 | 10/2012 |
| EP | 0337263 A2 | 10/1989 |

(Continued)

OTHER PUBLICATIONS

Cas Data Base Compounds (Entered Stn 2014).*
U.S. Appl. No. 14/900,345, published as U.S. 2016-0151335 A1 on Jun. 2, 2016, Methods of Modulating CFTR Activity, filed Dec. 21, 2015.
U.S. Appl. No. 15/125,827; published as U.S. 2017-0001993 A1 on Jan. 5, 2017, Compounds, Compositions and Methods for Increasing CFTR Activity, filed Sep. 13, 2016.
U.S. Appl. No. 15/125,830; published as U.S. 2017-0001991 A1 on Jan. 5, 2017, Compounds, Compositions and Methods for Increasing CFTR Activity, filed Sep. 13, 2016.
U.S. Appl. No. 15/539,392, Compounds, Compositions and Methods for Increasing CFTR Activity, filed Jun. 23, 2017.
U.S. Appl. No. 15/539,397, Derivatives of 5-Phenyl- or 5-Heteroarylathiazol-2-Carboxylic Amide Useful for the Treatment of Inter Alia Cystic Fibrosis, filed Jun. 23, 2017.

(Continued)

*Primary Examiner* — Alexander R Pagano
(74) *Attorney, Agent, or Firm* — Goodwin Procter LLP

(57) ABSTRACT

The present disclosure features disclosed compounds which can increase cystic fibrosis transmembrane conductance regulator (CFTR) activity as measured in human bronchial epithelial (hBE) cells. The present disclosure also features methods of treating a condition associated with decreased CFTR activity or a condition associated with a dysfunction of proteostasis comprising administering to a subject an effective amount of a disclosed compound.

25 Claims, No Drawings

(56) References Cited

U.S. PATENT DOCUMENTS

| | | | |
|---|---|---|---|
| 2006/0241106 A1* | 10/2006 | Drysdale | C07D 261/08 514/227.8 |
| 2008/0090882 A1 | 4/2008 | Dorsch et al. | |
| 2009/0069288 A1 | 3/2009 | Breinlinger et al. | |
| 2009/0163545 A1 | 6/2009 | Goldfarb | |
| 2009/0264486 A1 | 10/2009 | Jones et al. | |
| 2009/0318429 A1 | 12/2009 | Doyle et al. | |
| 2010/0234367 A1 | 9/2010 | Nomura et al. | |
| 2011/0003784 A1 | 1/2011 | Garvey et al. | |
| 2011/0082181 A1 | 4/2011 | Seiders et al. | |
| 2011/0212975 A1 | 9/2011 | Kao et al. | |
| 2012/0095002 A1 | 4/2012 | Ratcliffe et al. | |
| 2012/0264738 A1 | 10/2012 | Sugimoto et al. | |
| 2013/0217883 A1 | 8/2013 | Adaway | |
| 2013/0237502 A1 | 9/2013 | Curtis et al. | |
| 2014/0364467 A1 | 12/2014 | Schneider et al. | |
| 2015/0284371 A1* | 10/2015 | Dockendorff | C07D 405/04 514/326 |
| 2016/0151335 A1* | 6/2016 | Tait | A61K 31/422 514/236.8 |
| 2017/0001991 A1 | 1/2017 | Bastos et al. | |
| 2017/0001993 A1 | 1/2017 | Bastos et al. | |
| 2018/0147187 A1* | 5/2018 | Bastos | A61K 31/33 |
| 2018/0214419 A1* | 8/2018 | Munoz | C07D 413/14 |

FOREIGN PATENT DOCUMENTS

| | | |
|---|---|---|
| EP | 0957099 A2 | 11/1999 |
| JP | 2006176443 A | 7/2006 |
| WO | WO-2002000651 A2 | 1/2002 |
| WO | WO-2003093297 A2 | 11/2003 |
| WO | WO-2005035514 A2 | 4/2005 |
| WO | WO-2005077345 A1 | 8/2005 |
| WO | WO-2005077373 A2 | 8/2005 |
| WO | WO-2006014134 A1 | 2/2006 |
| WO | WO-2006136924 A1 | 12/2006 |
| WO | WO-2007075896 A2 | 7/2007 |
| WO | WO-2007078113 A1 | 7/2007 |
| WO | WO-2007086584 A1 | 8/2007 |
| WO | WO-2007126362 A1 | 11/2007 |
| WO | WO-2008046072 A2 | 4/2008 |
| WO | WO-2008051757 A1 | 5/2008 |
| WO | WO-2008070739 A1 | 6/2008 |
| WO | WO-2009005269 A2 | 1/2009 |
| WO | WO-2009011850 A2 | 1/2009 |
| WO | WO-2009016241 A1 | 2/2009 |
| WO | WO-2010089297 A1 | 8/2010 |
| WO | WO-2010142801 A1 | 12/2010 |
| WO | WO-2011008931 A2 | 1/2011 |
| WO | WO-2012007500 A2 | 1/2012 |
| WO | WO-2013019561 A1 | 2/2013 |
| WO | WO-2013146970 A1 | 10/2013 |
| WO | WO-2014144860 A1 | 9/2014 |
| WO | WO-2014181287 A1 | 11/2014 |
| WO | WO-2014210159 A1 | 12/2014 |
| WO | WO-2015051230 A1 | 4/2015 |
| WO | WO-2015138909 A1 | 9/2015 |
| WO | WO-2015138934 A1 | 9/2015 |
| WO | WO-2015196071 A1 | 12/2015 |
| WO | WO-2016054560 A1 | 4/2016 |
| WO | WO-2016105468 A1 | 6/2016 |
| WO | WO-2016105477 A1 | 6/2016 |
| WO | WO-2016105484 A1 | 6/2016 |
| WO | WO-2016105485 A2 | 6/2016 |
| WO | WO-2016115090 A1 * | 7/2016 |
| WO | WO-2017019589 A1 | 2/2017 |

OTHER PUBLICATIONS

U.S. Appl. No. 15/539,401, Derivatives of 5-(Hetero)Arylpyrazol-3-Carboxylic Amide or 1-(Hetero)Aryltriazol-4-Carboxylic Amide Useful for the Treatment of Inter Alia Cystic Fibrosis, filed Jun. 23, 2017.

U.S. Appl. No. 15/539,405, Derivatives of 3-Heteroarylisoxazol-5-Carboxylic Amide Useful for the Treatment of Inter Alia Cystic Fibrosis, filed Jun. 23, 2017.

"AID 775-Screen for Chemicals that Extend Yeast Lifespan," PubChem, 1-11 (Jul. 12, 2007), XP055331102.

Bai et al., "Synthesis and Structure-Activity Relationship Studies of Conformationally Flexible Tetrahydroisoquinolinyl Triazole Carboxamide and Triazole Substituted Benzamide Analogues as sigma 2 Receptor Ligands," Journal of Medicinal Chemistry, 57:10 4239-4251(2014), XP002754990.

CAS Registry No. 797781-85-2 (available Dec. 15, 2004).

Chang, X., "3-(2-chlorophenyl)-N-methylisoxazole-5-Carboxamide," Acta Crystallographica, Section E: Structure Reports Online, vol. E63(7), pp. 03074-sup-7 (2007).

Compound Summary for CID 70741394, PUBCHEM: Create Date: Mar. 4, 2013 [retrieved on May 12, 2015].

Compound Summary for CID 70756362, PUBCHEM: Create Date: Mar. 4, 2013 [retrieved on May 12, 2015].

Compound Summary for: CID 36257620, PUBCHEM: Create Date: May 29, 2009 [retrieved on May 12, 2015].

Compound Summary for: CID 55795703, PUBCHEM: Create Date: Jan. 25, 2012 [retrieved on May. 12, 2015].

Demina et al., "5-substituted Pyridylisoxazoles as Effective Inhibitors of Platelet Aggregation," Russian Chemical Bulletin, International Edition, vol. 63(2) 2095-2113 (2014).

International Search Report and Written Opinion for International Application No. PCT/US2014/044100, dated Oct. 10, 2014, 8 pages.

International Search Report and Written Opinion for International Application No. PCT/US2015/000189, dated Mar. 18, 2016, 10 pages.

International Search Report and Written Opinion for International Application No. PCT/US2015/000202, dated Mar. 22, 2016, 8 pages.

International Search Report and Written Opinion for International Application No. PCT/US2015/000211, dated Mar. 29, 2016, 10 pages.

International Search Report and Written Opinion for International Application No. PCT/US2015/000212, dated Jul. 1, 2016, 22 pages.

International Search Report and Written Opinion for International Application No. PCT/US2015/020460, dated Jun. 9, 2015, 7 pages.

International Search Report and Written Opinion for International Application No. PCT/US2015/020499, dated Jun. 9, 2015, 8 pages.

International Search Report and Written Opinion for International Application No. PCT/US2015/036691, dated Aug. 20, 2015, 12 pages.

International Search Report and Written Opinion for International Application No. PCT/US2016/012982, dated Mar. 7, 2016, 12 pages.

International Search Report and Written Opinion for International Application No. PCT/US2016/043835, dated Oct. 10, 2016, 8 pages.

Kalid et al., "Small Molecule Correctors of F508del-CFTR Discovered by Structure-based Virtual Screening," Journal of Computer-Aided Molecular Design, vol. 24:971-991 (2010).

Lack et al., "Targeting the Binding Function 3 (BF3) Site of the Human Androgen Receptor through Virtual Screening," Journal of Medicinal Chemistry, vol. 54(24) 8563-8573 (2011).

Liedtke, W., "Role of TRPV ion Channels in Sensory Transduction of Osmotic Stimuli in Mammals," Experimental Physiology, 92:3 507-512 (2007) XP055252392.

Lukevics et al.,"Synthesis and Cytotoxicity of Silyl- and Carbonyl-substituted Isoxazoles,"Chemistry of Heterocyclic Compounds, Springer New York LLC, vol. 36(10); 1226-1231 (1995).

Munchhof et al., "Discovery of PF-04449913, a Potent and Orally Bioavailable Inhibitor of Smoothened," ACS Medicinal Chemistry Letters, vol . 3(2) 106-111 (2012).

Phuan Puay-Wah et al., "Potentiators of Defective Delta F508-CFTR Gating that Do Not Interfere with Corrector Action," XP002754658, Database Accession No. PREV201500722877, Database Biosis [Online] Biosciences Information Service, Philadelphia, PA, US; Oct. 1, 2015 (Oct. 1, 2015). 1 page.

(56) References Cited

OTHER PUBLICATIONS

Qian et al., "Potent MCH-1 Receptor Antagonists from Cis-1,4-Diaminocyclohexane-derived Indane Analogs," Bioorganic & Medicinal Chemistry Letters, 23:14 4216-4220 (2013).
Stoops et al., "Identification and Optimization of Small Molecules that Restore E-cadherin Expression and Reduce Invasion in Colorectal Carcinoma Cells," ACS Chemical Biology, American Chemical Society, Washington, DC, US, vol. 6., No. 5, pp. 452-465 (2011).
Supplemental European Search Report dated Jan. 9, 2017 in European Patent No. 14816975.8 (19 pages).
Pubchem: "ST062658 I C15H12N2O3—PubChem", Jul. 9, 2005 (Jul. 9, 2005), XP055331105, Retrieved from the Internet: URL:https://pubchem.ncbi.nlm.nih.gov/compound/973870#section=Biological-Test-Results [retrieved on Dec. 22, 2016].

* cited by examiner

COMPOUNDS, COMPOSITIONS, AND METHODS FOR INCREASING CFTR ACTIVITY

CROSS-REFERENCE TO RELATED APPLICATIONS

This application is a national stage filing under 35 U.S.C. § 371 of PCT/US2015/036691, filed Jun. 19, 2015, which claims priority to provisional applications U.S. Ser. No. 62/014,400, filed Jun. 19, 2014; U.S. Ser. No. 62/014,409, filed Jun. 19, 2014; U.S. Ser. No. 62/096,389, filed Dec. 23, 2014 and U.S. Ser. No. 62/102,230, filed Jan. 12, 2015, each of which is hereby incorporated by reference in their entirety.

BACKGROUND

Cells normally maintain a balance between protein synthesis, folding, trafficking, aggregation, and degradation, referred to as protein homeostasis, utilizing sensors and networks of pathways (Sitia et al., *Nature* 426: 891-894, 2003; Ron et al., *Nat Rev Mol Cell Biol* 8: 519-529, 2007). The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation (Wiseman et al., *Cell* 131: 809-821, 2007). Whether a given protein folds in a certain cell type depends on the distribution, concentration, and subcellular localization of chaperones, folding enzymes, metabolites and the like (Wiseman et al.). Cystic fibrosis and other maladies of protein misfolding arise as a result of an imbalance in the capacity of the protein homeostasis (proteostasis) environment to handle the reduced energetic stability of misfolded, mutated proteins that are critical for normal physiology (Balch et al., *Science* 319, 916-9 (2008); Powers, et al., *Annu Rev Biochem* 78, 959-91 (2009); Hutt et al., *FEBS Lett* 583, 2639-46 (2009)).

Cystic Fibrosis (CF) is caused by mutations in the cystic fibrosis transmembrane conductance regulator (CFTR) gene which encodes a multi-membrane spanning epithelial chloride channel (Riordan et al., *Annu Rev Biochem* 77, 701-26 (2008)). Approximately ninety percent of patients have a deletion of phenylalanine (Phe) 508 (ΔF508) on at least one allele. This mutation results in disruption of the energetics of the protein fold leading to degradation of CFTR in the endoplasmic reticulum (ER). The ΔF508 mutation is thus associated with defective folding and trafficking, as well as enhanced degradation of the mutant CFTR protein (Qu et al., *J Biol Chem* 272, 15739-44 (1997)). The loss of a functional CFTR channel at the plasma membrane disrupts ionic homeostasis (Cl$^-$, Na$^+$, HCO$_3^-$) and airway surface hydration leading to reduced lung function (Riordan et al.). Reduced periciliary liquid volume and increased mucus viscosity impede mucociliary clearance resulting in chronic infection and inflammation, phenotypic hallmarks of CF disease (Boucher, *J Intern Med* 261, 5-16 (2007)).

In addition to respiratory dysfunction, ΔF508 CFTR also impacts the normal function of additional organs (pancreas, intestine, gall bladder), suggesting that the loss-of-function impacts multiple downstream pathways that will require correction.

In addition to cystic fibrosis, mutations in the CFTR gene and/or the activity of the CFTR channel has also been implicated in other conditions, including for example, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), dry eye disease, Sjogren's syndrome and chronic sinusitis, (Sloane et al. (2012), PLoS ONE 7 (6): e39809.doi:10.1371/journal. pone.0039809; Bombieri et al. (2011), J Cyst Fibros. 2011 June; 10 Suppl 2:S86-102; (Albert et al. (2008). Clinical Respiratory Medicine, Third Ed., Mosby Inc.; Levin et al. (2005), Invest Ophthalmol Vis Sci., 46 (4):1428-34; Froussard (2007), Pancreas 35 (1): 94-5).

There remains a need in the art for compounds, compositions and methods of increasing CFTR activity as well as for methods of treating CF, other CFTR-related diseases, and other maladies of protein misfolding.

SUMMARY

The present disclosure is based, in part, on the discovery that disclosed compounds such as those having the formulas as disclosed herein increase cystic fibrosis transmembrane conductance regulator (CFTR) activity as measured in human bronchial epithelial (hBE) cells.

Disclosed herein, in an embodiment, are compounds having the formula:

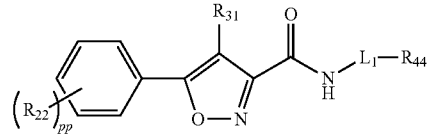

and pharmaceutically acceptable salts, stereoisomers, and prodrugs thereof, wherein:

$R_{22}$ is selected, independently, for each occurrence, from the group consisting of hydrogen, halogen, and $C_{1-4}$alkyl (optionally substituted by one, two or three halogens);

pp is 0, 1, 2, 3, 4 or 5;

$R_{31}$ is selected from the group consisting of hydrogen, halogen, and $C_{1-4}$alkyl;

$L_1$ is selected from the group consisting of $C_{3-9}$ cycloalkylene, $C_1$alkylene —$C_{3-9}$ cycloalkylene- and —$C_{3-9}$ cycloalkylene-$C_1$alkylene, wherein $L_1$ may be optionally substituted by one, two or three substituents selected from the group consisting of halogen, hydroxyl, and $C_{1-3}$alkyl (optionally substituted by one, two or three substituents each selected independently from $R_{ff}$);

$R_{44}$ is selected from the group consisting of $C_{1-3}$alkyl, —C(O)—OR', 4 to 6 membered heterocycloalkyl, a 5-6 membered monocyclic heteroaryl, and a 9-10 membered bicyclic heteroaryl, wherein the heteroaryl has one, two or three heteroatoms each selected from O, N, and S; and wherein the heteroaryl or heterocycloalkyl may be optionally substituted by one or two substituents each selected independently from $R_{gg}$;

$R_{ff}$ is selected for each occurrence from group consisting of halogen, hydroxyl, $C_{1-4}$alkyl, $C_{1-4}$alkyoxy, $C_{2-4}$alkenyl, oxo, —NR'R", NR'—S(O)$_w$—NR'R", and —S(O)$_w$—$C_{1-3}$alkyl, where w is 0, 1, or 2, wherein $C_{1-4}$alkyl, $C_{1-4}$alkyoxy, and $C_{2-4}$alkenyl may be optionally substituted by one, two or three substituents each independently selected from the group consisting of halogen, hydroxyl, —NR'R", —NR'—S(O)$_w$—C$_{1-3}$alkyl, S(O)$_w$—NR'R", and —S(O)$_w$—C$_{1-3}$alkyl;

$R_{gg}$ is selected for each occurrence from group consisting of halogen, hydroxyl, $C_{1-6}$alkyl, $C_{1-6}$alkoxy, $C_{2-6}$alkenyl, $C_{3-6}$cycloalkyl, —O—C(O)—C$_{1-6}$alkyl, —C(O)—O—C$_{1-6}$alkyl, —C(O)—O— phenyl, —O—C(O)-phenyl, phenyl, 4 to 6 membered heterocycloalkyl, —NR'R", oxo, —NR'—S(O)$_w$—C$_{1-3}$alkyl, S(O)$_w$—NR'R", and —S(O)$_w$—C$_{1-3}$alkyl, where w is 0, 1, or 2, wherein $C_{1-6}$alkyl, $C_{1-6}$alkyoxy, $C_{2-6}$alkenyl $C_{3-6}$cycloalkyl, phenyl and heterocycloalkyl may each be optionally substituted by one, two or three substituents each independently selected from the group consisting of halogen, $C_{1-6}$alkyl, $C_{1-6}$alkoxy, hydroxyl, C(O)OH, —C(O)OC$_{1-6}$alkyl, —O—C(O)C$_{1-6}$alkyl, O—C(O)-phenyl, —C(O)O—NR'—C$_{1-6}$alkyl, —O—C$_{3-6}$cycloalkyl, —O-heterocycle, phenyl, —O-heteroaryl, —O-phenyl, —NR'R", —NR'—S(O)$_w$—C$_{1-3}$alkyl, S(O)$_w$—NR'R", and —S(O)$_w$—C$_{1-3}$alkyl, where w is 0, 1, or 2; and R' and R" are each independently selected for each occurrence from H and $C_{1-4}$alkyl or taken together with a nitrogen to which they are attached form a heterocyclic ring.

Also contemplated herein are pharmaceutical compositions that include a disclosed compound and a pharmaceutically acceptable carrier or excipient. In certain embodiments, the compositions can include at least one additional CFTR modulator as described anywhere herein or at least two additional CFTR modulators, each independently as described anywhere herein.

In additional embodiments, a method of enhancing (e.g., increasing) cystic fibrosis transmembrane conductance regulator (CFTR) activity in a subject in need thereof is provided comprising administering to said subject an effective amount of a compound disclosed herein.

In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). In certain embodiments, ΔF508 CFTR activity is enhanced (e.g., increased). In other embodiments, the activities of two mutant CFTRs (e.g., ΔF508 and G551D; ΔF508 and A455E; or G542X; Δ508F) are enhanced (e.g., increased).

In certain of these embodiments, the subject (e.g., a human patient) is suffering from a disease associated with decreased CFTR activity (e.g., cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), chronic sinusitis, dry eye disease, protein C deficiency, A-β-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, Sjogren's syndrome, familial hypercholesterolemia, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, nephrogenic DI, Charcot-Marie Tooth syndrome, Perlizaeus-Merzbacher disease, Alzheimer's disease, Parkinson's disease, amyotrophic lateral sclerosis, progressive supranuclear palsy, Pick's disease, Huntington's disease, spinocerebellar ataxia type I, spinal and bulbar muscular atrophy, dentatorubral pallidoluysian, myotonic dystrophy, hereditary Creutzfeldt-Jakob disease (due to prion protein processing defect), Fabry disease, and Straussler-Scheinker syndrome). In certain embodiments, a method is provided for treating cystic fibrosis in a patient in need thereof comprising administering a disclosed compound. In another embodiment, a method is provided for treating chronic obstructive pulmonary disease (COPD), in a patient in need thereof comprising administering a disclosed compound.

In yet additional aspects, the disclosure is directed to treating a patient suffering from cystic fibrosis comprising administering to said patient an effective amount of a disclosed compound.

In some embodiments, the methods described herein can further include administering an additional therapeutic agent or administering at least two additional CFTR therapeutic agents. In some embodiments, the methods described herein can further include administering an additional CFTR modulator or administering at least two additional CFTR modulators. In certain embodiments, at least one CFTR modulator is a CFTR corrector (e.g., VX-809, VX-661, VX-983, GLPG2222 and) or potentiator (e.g., ivacaftor, genistein and GLPG1837). In certain of these embodiments, one of the at least two additional therapeutic agents is a CFTR corrector (e.g., VX-809, VX-661 and VX-983) and the other is a CFTR potentiator (e.g., ivacaftor and genistein). In certain of these embodiments, one of the at least two additional therapeutic agents is a CFTR corrector (e.g., GLPG2222) and the other is a CFTR potentiator (e.g., GLPG1837).

In a further aspect, a method of identifying a candidate agent that increases CFTR activity is provided, which includes: (i) contacting a cell that expresses a CFTR protein with the candidate agent and a disclosed compound; (ii) measuring the CFTR activity in the cell in the presence of the candidate agent and the disclosed compound; and (iii) comparing the CFTR activity to that in the absence of the test agent, wherein an increase in CFTR activity in the presence of the test agent indicates that the agent increases CFTR activity. In certain embodiments, the cell expresses a mutant CFTR protein. In certain embodiments, CFTR activity is measured by measuring chloride channel activity of the CFTR, and/or other ion transport activity. In certain of these embodiments, the method is high-throughput. In certain of these embodiments, the candidate agent is a CFTR corrector or a CFTR potentiator.

DETAILED DESCRIPTION

As used herein, the words "a" and "an" are meant to include one or more unless otherwise specified. For example, the term "an agent" encompasses both a single agent and a combination of two or more agents.

As discussed above, the present disclosure is directed in part to compounds as described herein having e.g., the above formula or e.g., Formula I(a), (IIa), (IIb), (IIc), (IId), (IIIa), and (IIIb), or a pharmaceutically acceptable salt, prodrug or solvate thereof, pharmaceutical compositions, methods of increasing CFTR activity and methods of treating cystic fibrosis.

For example, provided herein are compounds having the Formula (Ia):

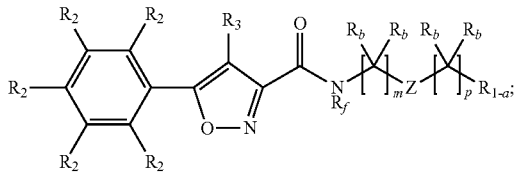

(Ia)

or a pharmaceutically acceptable salt, solvate, clathrate or prodrug thereof, wherein:

$R_{1-a}$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, optionally substituted heterocyclic and optionally substituted heteroaryl;

Z is an optionally substituted $C_3$-$C_7$ cycloalkyl;

Each $R_2$ is independently selected from the group consisting of hydrogen, halo, CN, and optionally substituted $C_1$-$C_{10}$ alkyl;

$R_3$ is hydrogen or fluoro;

each $R_b$ is independently selected from the group consisting of hydrogen, halo, optionally substituted $C_1$-$C_{10}$ alkyl, and optionally substituted $C_3$-$C_6$ cycloalkyl, or two geminal $R_b$ groups are independently taken together with the carbon atom to which they are attached to form an optionally substituted heterocyclic or an optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl;

$R_f$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

m is 0, 1 or 2;

each n is independently 0, 1 or 2; and p is 0, 1 or 2.

Disclosed herein, in an embodiment, are compounds such as those having the Formula (IIa) or (IIb):

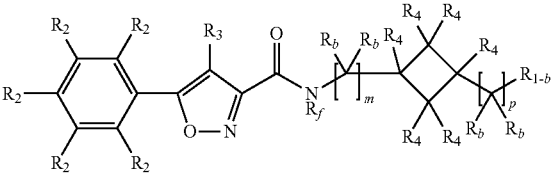

(IIa)

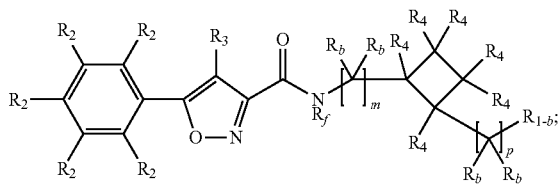

(IIb)

or a pharmaceutically acceptable salt, solvate, clathrate or prodrug of any of thereof, wherein:

$R_{1-b}$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_e$, $S(O)_nNR_dR_d$, $OC(O)OR_c$, $(C=NR_d)R_c$, optionally substituted heterocyclic and optionally substituted heteroaryl (e.g., wherein $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, heterocyclic, phenyl and heteroaryl may each be optionally substituted by one, two or three substituents each independently selected from $R''$);

each $R_2$ is independently selected from the group consisting of hydrogen, halo, CN, and optionally substituted $C_1$-$C_{10}$ alkyl;

$R_3$ is hydrogen or fluoro;

each $R_4$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, optionally substituted heterocyclic and optionally substituted heteroaryl; alternatively, two geminal $R_4$ groups are taken together with the carbon atom to which they are attached to form a spiro $C_3$-$C_{12}$ cycloalkyl, a spiro $C_3$-$C_{12}$ cycloalkenyl, a spiro heterocyclic, a spiro aryl or spiro heteroaryl, each optionally substituted; or yet alternatively, two vicinal $R_4$ groups are taken together with the carbon atoms to which they are attached to form a fused, optionally substituted cyclic group selected from the group consisting of $C_4$-$C_8$ cycloalkyl, $C_4$-$C_8$ cycloalkenyl, 4- to 8-membered heterocyclic, substituted aryl and heteroaryl, each optionally substituted; or further alternatively, two $R_4$ groups attached to non-adjacent carbon atoms are taken together with the carbon atoms to which they are attached to form a bridged cyclic group selected from the group consisting of $C_4$-$C_8$ cycloalkyl, $C_4$-$C_8$ cycloalkenyl, and 4- to 8-membered heterocyclic, each optionally substituted;

each $R_b$ is independently selected from the group consisting of hydrogen, halo, optionally substituted $C_1$-$C_{10}$ alkyl, and optionally substituted $C_3$-$C_6$ cycloalkyl, or two geminal $R_b$ groups are independently taken together with the carbon atom to which they are attached to form an optionally substituted heterocyclic or an optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl;

$R_e$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

$R_f$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

$R_g$ is independently selected for each occurrence from the group consisting of: $C_1$-$C_6$ alkyl (optionally substituted by one, two or three substituents selected from the group consisting of: heterocyclic, —F, —Cl, —Br, —I, —OH, —NO$_2$, —N$_3$, —CN, —NH$_2$, NHR$_d$, —NR$_d$R$_d$, NR$_d$C(O)R$_d$, —NR$_d$SO$_n$R$_d$ and —OR$_c$), —C$_2$-C$_6$ alkenyl (optionally substituted by one, two or three substituents selected from the group consisting of: heterocyclic, —F, —Cl, —Br, —I, —OH, —NO$_2$, —N$_3$, —CN, —NH$_2$, NHR$_d$, —NR$_d$R$_d$, NR$_d$C(O)R$_d$, —NR$_d$SO$_n$R$_d$ and —OR$_c$), —C$_2$-C$_6$ alkynyl (optionally substituted by one, two or three substituents selected from the group consisting of: heterocyclic, —F, —Cl, —Br, —I, —OH, —NO$_2$, —N$_3$, —CN, —NH$_2$, NHR$_d$, —NR$_d$R$_d$, NR$_1$C(O)R$_d$, —NR$_d$SO$_n$R$_d$ and —OR$_c$), —C$_3$-C$_6$ cycloalkyl (optionally substituted by one, two or three substituents selected from the group consisting of: heterocyclic, $C_1$-$C_6$ alkyl, —F, —Cl, —Br, —I, —OH, —NO$_2$, —N$_3$, —CN, —NH$_2$, NHR$_d$, —NR$_d$R$_d$, NR$_d$C(O)R$_d$, —NR$_d$SO$_n$R$_d$ and —OR$_c$), -heterocyclic (optionally substituted by one, two or three substituents selected from the group consisting of: $C_1$-$C_6$ alkyl, heterocyclic, —F, —Cl, —Br, —I, —OH, —NO$_2$, —N$_3$, —CN, —NH$_2$, NHR$_d$, —NR$_d$R$_d$, NR$_d$C(O)R$_d$, —NR$_d$SO$_n$R$_d$ and —OR$_c$), —F, —Cl, —Br, —I, —OH, —NO$_2$, —N$_3$, —CN, —NH$_2$, oxo, thioxo, —NHR$_d$, —NR$_d$R$_d$, —OR$_c$, —C(O)R$_c$, —C(O)C(O)R$_c$, —OCO$_2$R$_c$, —OC(O)R$_c$, OC(O)C(O)R$_c$, —NHC(O)R$_c$, —NHCO$_2$R$_c$, —NHC(O)C(O)R$_c$, NHC(S)NH$_2$, —NHC(S)NHR$_d$, —NHC(NH)NH$_2$, —NHC(NH)NHR$_c$, —NHC(NH)R$_c$, —C(NH)NHR$_c$, and (C═NR$_c$)R$_c$; —NR$_c$C(O)R$_c$, —NR$_x$C(O)N(R$_x$)$_2$, —NR$_c$CO$_2$R$_y$, —NR$_c$C(O)C(O)R$_y$, —NR$_c$C(S)NH$_2$, —NR$_c$C(S)NHR$_c$, —NR$_x$C(NH)NH$_2$, —NR$_x$C(NH)NHR$_x$, —NR$_x$C(NH)R$_x$, —C(NR$_x$)NHR$_x$—S(O)R$_y$, —NHSO$_2$R$_c$, —CH$_2$NH$_2$, —CH$_2$SO$_2$CH$_3$, -phenyl, and heteroaryl;

m is 0, 1 or 2;

each n is independently 0, 1 or 2; and p is 0, 1 or 2.

In some embodiments, contemplated compounds have the Formula (IIa). In other embodiments, contemplated compounds has the Formula (IIb).

For example, in some embodiments, $R_f$ is hydrogen and/or $R_3$ is hydrogen.

In some embodiments, a disclosed compound has the Formula (IIc):

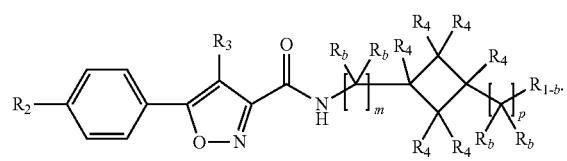

(IIc)

In other embodiments, a contemplated compound has the Formula (IId):

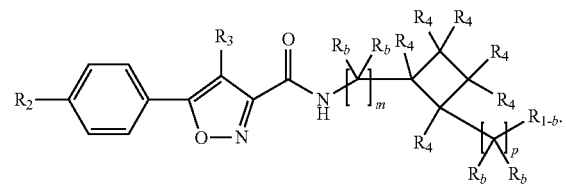

(IId)

In some embodiments, $R_{1-b}$ is selected from the group consisting of optionally substituted heteroaryl, optionally substituted heterocyclic, $C_1$-$C_{10}$ alkyl substituted with OR$_c$, NR$_d$C(O)R$_c$, or NR$_d$S(O)$_n$R$_c$, and $C_1$-$C_{10}$ alkenyl substituted with OR$_c$, NR$_d$C(O)R$_c$, or NR$_d$S(O)$_n$R$_c$. In certain embodiments, $R_{1-b}$ is an optionally substituted heteroaryl or an optionally substituted heterocyclic, e.g., an optionally substituted heteroaryl.

In certain embodiments, $R_{1-b}$ can be selected from the group consisting of:

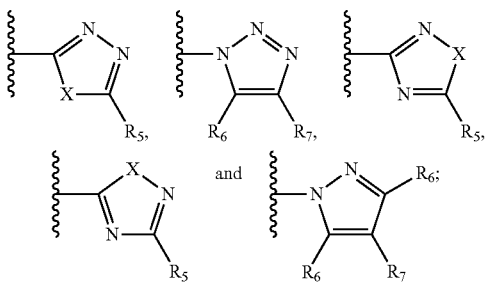

wherein:

each X is independently O, S or $NR_g$;

each $R_g$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; and each of $R_5$, $R_6$ and $R_7$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $NR_d(CO-OR_c)$, $NR_dC(O)C(O)R_c$, $NR_dC(O)NR_dR_d$, $NR_dS(O)_n$-$NR_dR_d$, $NR_dS(O)_nR_c$, $S(O)_nR_c$, $S(O)_nNR_dR_d$, $OC(O)OR_c$, $(C=NR_d)R_c$, optionally substituted heterocyclic and optionally substituted heteroaryl.

For example, $R_{1-b}$ can be:

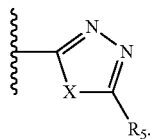

In certain embodiments, X is O or S or $NR_g$.

In certain embodiments, $R_5$ is optionally substituted $C_1$-$C_{10}$ alkyl. For example, $R_5$ can be $C_1$-$C_{10}$ alkyl substituted with $OR_c$, and is optionally further substituted; e.g., $C_1$-$C_4$ alkyl substituted with $OR_c$, and is optionally further substituted; e.g., $C_1$-$C_4$ alkyl substituted with OH, and is optionally further substituted.

In certain embodiments, $R_5$ is:

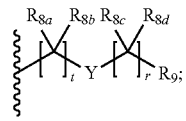

wherein $R_{8a}$, $R_{8b}$, $R_{8c}$, and $R_{8d}$ are each independently selected from the group consisting of hydrogen, fluoro, optionally substituted $C_1$-$C_{10}$ alkyl, and optionally substituted $C_3$-$C_{12}$ cycloalkyl; or alternatively, a geminal $R_{8a}$ and $R_{8b}$, or a geminal $R_{8c}$ and $R_{8d}$, can each independently be taken together with the carbon atom to which they are attached to form an optionally substituted $C_3$-$C_{12}$ cycloalkyl or an optionally substituted heterocyclic;

Y is O, S or $NR_i$;

t and r are each independently 0, 1, 2 or 3;

$R_9$ is selected from the group consisting of hydrogen, optionally substituted $C_1$-$C_{10}$ alkyl, optionally substituted $C_3$-$C_{12}$ cycloalkyl, halo, optionally substituted heterocyclic, optionally substituted aryl, and optionally substituted heteroaryl; and $R_i$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl.

In certain of these embodiments, $R_{8a}$, $R_{8b}$, $R_{8c}$, and $R_{8d}$ are each independently selected from the group consisting of hydrogen and $C_1$-$C_{10}$ alkyl substituted with $OR_c$, and optionally further substituted. In certain of these embodiments, at least one of $R_{8a}$, $R_{8b}$, $R_{8c}$, and $R_{8d}$ is $C_1$-$C_{10}$ alkyl substituted with $OR_c$, optionally further substituted; e.g., at least one of $R_{8a}$, $R_{8b}$, $R_{8c}$, and $R_{8d}$ is $C_1$-$C_{10}$ alkyl substituted with OH, optionally further substituted. In certain of these embodiments, t is 1, 2 or 3. In certain of these embodiments, r is 1, 2 or 3.

As another example, $R_{1-b}$ can be:

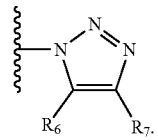

In certain embodiments, at least one of $R_6$ and $R_7$ is optionally substituted $C_1$-$C_4$ alkyl. In certain embodiments, at least one of $R_6$ and $R_7$ is optionally substituted $C_1$-$C_4$ alkyl and the other is hydrogen. For example, at least one of $R_6$ and $R_7$ is $C_1$-$C_{10}$ alkyl substituted with $OR_c$, and is optionally further substituted; at least one of $R_6$ and $R_7$ is $C_1$-$C_4$ alkyl substituted with $OR_c$, and is optionally further substituted; at least one of $R_6$ and $R_7$ is $C_1$-$C_4$ alkyl substituted with OH, and is optionally further substituted. In certain of these embodiments, one of $R_6$ and $R_7$ is hydrogen.

In certain embodiments, at least one of $R_6$ and $R_7$ is independently:

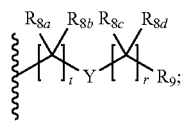

wherein $R_{8a}$, $R_{8b}$, $R_{8c}$, and $R_{8d}$ are each independently selected from the group consisting of hydrogen, fluoro, optionally substituted $C_1$-$C_{10}$ alkyl, and optionally substituted $C_3$-$C_{12}$ cycloalkyl; or alternatively, a geminal $R_{8a}$ and $R_{8b}$, or a geminal $R_{8c}$ and $R_{8d}$, can each independently be taken together with the carbon atom to which they are attached to form an optionally substituted $C_3$-$C_{12}$ cycloalkyl or an optionally substituted heterocyclic;

Y is O, S or $NR_i$;

t and r are each independently 0, 1, 2 or 3;

R$_9$ is selected from the group consisting of hydrogen, optionally substituted C$_1$-C$_{10}$ alkyl, optionally substituted C$_3$-C$_{12}$ cycloalkyl, halo, optionally substituted heterocyclic, optionally substituted aryl, and optionally substituted heteroaryl; and R$_t$ is selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{12}$ cycloalkyl, optionally substituted C$_3$-C$_{12}$ cycloalkenyl, optionally substituted heterocyclic, optionally substituted aryl and optionally substituted heteroaryl.

In certain of these embodiments, R$_{8a}$, R$_{8b}$, R$_{8c}$, and R$_{8d}$ are each independently selected from the group consisting of hydrogen and C$_1$-C$_{10}$ alkyl substituted with OR$_c$, and optionally further substituted. In certain of these embodiments, at least one of R$_{8a}$, R$_{8b}$, R$_{8c}$, and R$_{8d}$ is C$_1$-C$_{10}$ alkyl substituted with OR$_c$, optionally further substituted; e.g., at least one of R$_{8a}$, R$_{8b}$, R$_{8c}$, and R$_{8d}$ is C$_1$-C$_{10}$ alkyl substituted with OH, optionally further substituted. In certain of these embodiments, t is 1, 2 or 3. In certain of these embodiments, r is 1, 2 or 3.

In some embodiments, R$_2$ is hydrogen. In other embodiments, R$_2$ is fluoro.

In some embodiments, m is 0. In other embodiments, m is 1. In some embodiments, p is 0. In other embodiments, p is 1.

In some embodiments, a disclosed compound has the Formula (IIc), wherein R$_2$ is hydrogen, and in another embodiment, R$_{1-b}$ is

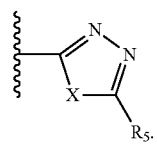

The disclosure thus encompasses compound of Formula (IIc), wherein R$_2$ is hydrogen and R$_{1-b}$ is

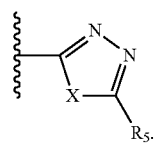

Similarly, in some embodiments, a disclosed compound has the Formula (IIc), wherein R$_2$ is hydrogen, and in some embodiments described above, the compound has the Formula (IIc), wherein R$_1$ is

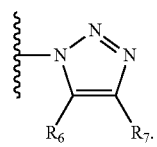

The disclosure thus also encompasses compounds of Formula (IIc), wherein R$_2$ is hydrogen and R$_1$ is

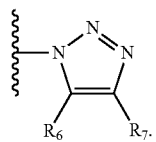

In some embodiments, a disclosed compound has the following formula:

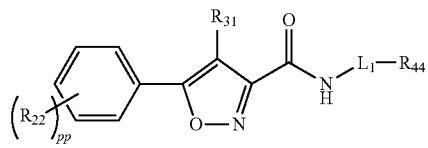

and pharmaceutically acceptable salts, stereoisomers, and prodrugs thereof, wherein:

R$_{22}$ is optional, and is selected, independently, for each occurrence if present from the group consisting of halogen, and C$_{1-4}$alkyl (optionally substituted by one, two or three halogens);

pp is 0, 1, 2 or 3;

R$_{31}$ is selected from the group consisting of hydrogen, halogen, and C$_{1-4}$alkyl;

L$_1$ is selected from the group consisting of C$_{3-9}$ cycloalkylene, C$_1$alkylene —C$_{3-9}$ cycloalkylene- and —C$_{3-9}$ cycloalkylene-C$_1$alkylene (e.g., C$_{3-8}$ cycloalkylene, C$_1$alkylene —C$_{3-9}$ cycloalkylene- and —C$_{3-9}$ cycloalkylene-C$_1$alkylene), wherein L$_1$ may be optionally substituted by one, two or three substituents selected from the group consisting of halogen, hydroxyl, and C$_{1-3}$alkyl (optionally substituted by one, two or three substituents each selected independently from R$_{ff}$);

R$_{44}$ is selected from the group consisting of halogen, hydroxyl, C$_{1-3}$alkyl, —C(O)—OR', 4 to 6 membered heterocycloalkyl, a 5-6 membered monocyclic heteroaryl, and a 9-10 membered bicyclic heteroaryl, wherein the heteroaryl has one, two or three heteroatoms each selected from O, N, and S; and wherein the heteroaryl or heterocycloalkyl may be optionally substituted by one or two substituents each selected independently from R$_{gg}$ (for example, R$_{44}$ may be 5-6 membered monocyclic heteroaryl, optionally substituted by one or two substituents each selected independently from R$_{gg}$, or R$_{44}$ may be a 9-10 membered bicyclic heteroaryl, optionally substituted by one or two substituents each selected independently from R$_{gg}$);

R$_{ff}$ is selected for each occurrence from group consisting of halogen, hydroxyl, C$_{1-4}$alkyl, C$_{1-4}$alkyoxy, C$_{2-4}$alkenyl, oxo, —NR'R", —NR'—S(O)$_w$—C$_{1-3}$alkyl, S(O)$_w$—NR'R", and —S(O)$_w$—C$_{1-3}$alkyl, where w is 0, 1, or 2, wherein C$_{1-4}$alkyl, C$_{1-4}$alkyoxy, and C$_{2-4}$alkenyl may be optionally substituted by one, two or three substituents each independently selected from the group consisting of halogen, hydroxyl, —NR'R", —NR'—S(O)$_w$—C$_{1-3}$alkyl, S(O)$_w$—NR'R", and —S(O)$_w$—C$_{1-3}$alkyl;

R$_{gg}$ is selected for each occurrence from group consisting of halogen, hydroxyl, C$_{1-6}$alkyl, C$_{1-6}$alkoxy, C$_{2-6}$alkenyl, C$_{3-6}$cycloalkyl, —O—C(O)— C$_{1-6}$alkyl, —C(O)—O—C$_{1-6}$alkyl, —C(O)—O— phenyl, —O—

C(O)-phenyl, phenyl, 4 to 6 membered heterocycloalkyl, —NR'R", oxo, —NR'—S(O)$_w$—C$_{1-3}$alkyl, S(O)$_w$—NR'R", and —S(O)$_w$—C$_{1-3}$alkyl, where w is 0, 1, or 2, wherein C$_{1-6}$alkyl, C$_{1-6}$alkyoxy, C$_{2-6}$alkenyl C$_{3-6}$cycloalkyl, phenyl and heterocycloalkyl may each be optionally substituted by one, two or three substituents each independently selected from the group consisting of halogen, C$_{1-6}$alkyl, C$_{1-6}$alkoxy, hydroxyl, C(O)OH, —C(O)OC$_{1-6}$alkyl, —O—C(O)C$_{1-6}$alkyl, O—C(O)-phenyl, —C(O)O—NR'—C$_{1-6}$alkyl, —O—C$_{3-6}$cycloalkyl, —O-heterocycle, phenyl, —O-heteroaryl, —O-phenyl, —NR'R", —NR'—S(O)$_w$—C$_{1-3}$alkyl, S(O)$_w$—NR'R", and —S(O)$_w$—C$_{1-3}$alkyl, where w is 0, 1, or 2; and R' and R" are each independently selected for each occurrence from H and C$_{1-4}$alkyl or taken together with the nitrogen to which they are attached form a heterocyclic ring.

In certain embodiments, R$_{22}$ is selected independently for each occurrence from H (e.g., when pp is 0 and R$_{22}$ is absent); and F.

In certain embodiments, pp is 0 or pp is 1.

L$_1$ may be, for example, C$_{3-6}$ cycloalkylene, e.g., L$_1$ may be selected from the group consisting of C$_3$cycloalkylene, -C$_4$cycloalkylene-, C$_5$cycloalkylene, C$_6$cycloalkylene, -bicyclo[1.1.1]pentane-, -bicyclo[2.2.1]heptane-, and bicyclo [3.2.1]octane-. In certain embodiments, L$_1$ is selected from the group consisting of —C$_1$alkylene-C$_4$cycloalkylene, C$_4$cycloalkylene, and C$_4$cycloalkylene-C$_1$alkylene-. For example, L$_1$ may be C$_4$cycloalkylene. L$_1$ may be substituted by one or two substituents each selected from the group consisting of halogen, hydroxyl, and C$_{1-3}$alkyl.

R$_{44}$, in certain embodiments, may be selected from the group consisting of:

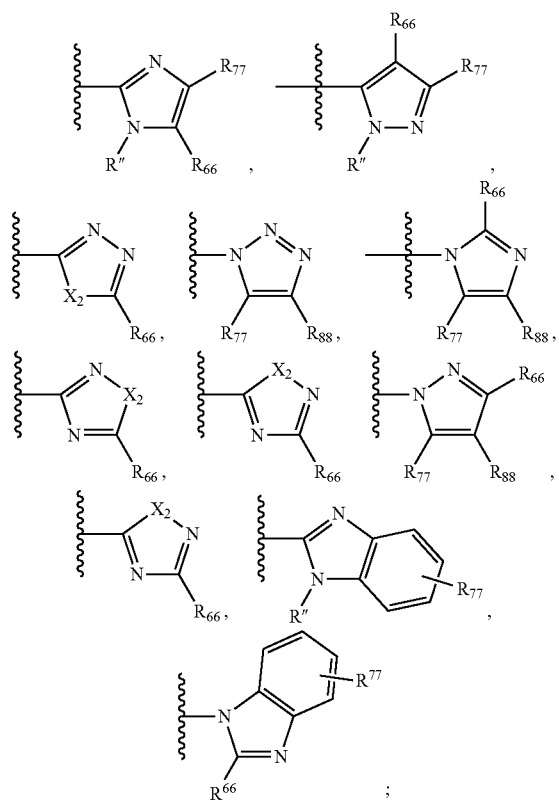

wherein X$_2$ independently for each occurrence is selected from the group consisting of O or S; each R$_{66}$, R$_{77}$ and R$_{88}$ is independently selected for each occurrence from H and R$_{gg}$ (e.g., R$_{66}$, R$_{77}$ and R$_{88}$ are each independently selected for each occurrence from the group consisting of hydrogen, halogen, hydroxyl, C$_{1-6}$alkyl, C$_{3-6}$cycloalkyl, and heterocycloalkyl, wherein C$_{1-6}$alkyl, C$_{3-6}$cycloalkyl, and heterocycloalkyl are optionally substituted by one, two or three substituents each independently selected from the group consisting of hydroxyl, C$_{1-6}$alkyl, C$_{1-6}$alkoxy, —S(O)$_w$—C$_{1-3}$alkyl (w is 0, 1, or 2) and —NR'S(O)$_2$C$_{1-6}$alkyl; and R' and R" are each independently selected for each occurrence from H and C$_{1-4}$alkyl, for example, R$_{66}$, R$_{77}$ and R$_{88}$ may each independently selected from the group selected from C$_{1-4}$alkyl, optionally substituted by one or two hydroxyls). For example, R$_{44}$ may be represented by:

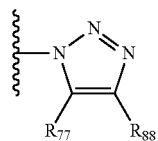

In certain other embodiments, R$_{44}$ is heterocycloalkyl, e.g., R$_{44}$ may be represented by:

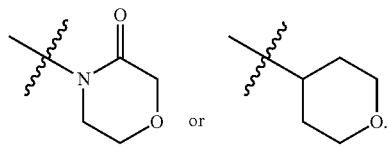 [SMILES: *N1CCOCC1=O ; "or" ; *C1CCOCC1]

In certain embodiments, a disclosed compound is represented by:

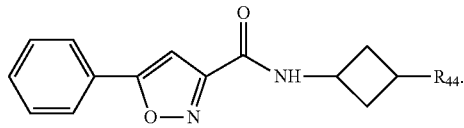

R$_{44}$ may be for example, a 5-membered heteroaryl having two or three nitrogens, e.g., R$_{44}$ may be a 5 membered heteroaryl having three nitrogens. In other embodiments, R$_{44}$ is a 5 membered heteroaryl having two nitrogens and additional heteroatom selected from O or S. In certain of these embodiments, R$_{44}$ is substituted on a free carbon by a substituent selected from the group consisting of: a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy), isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy and isobutyl substituted by one, two or three substituents each selected from halogen, hydroxyl, methoxy and ethoxy.

In other embodiments, $R_{44}$ is substituted on a free carbon by a substituent selected from the group consisting of: (e.g., where a group $R_{66}$, $R_{77}$ or $R_{88}$ may be selected from the group consisting of:)

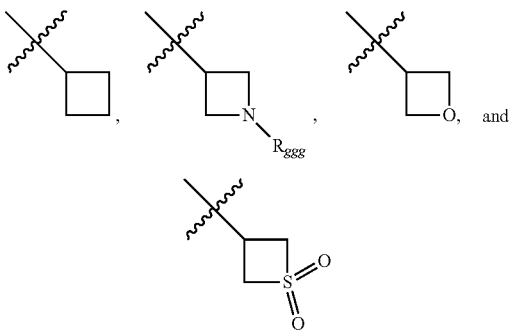

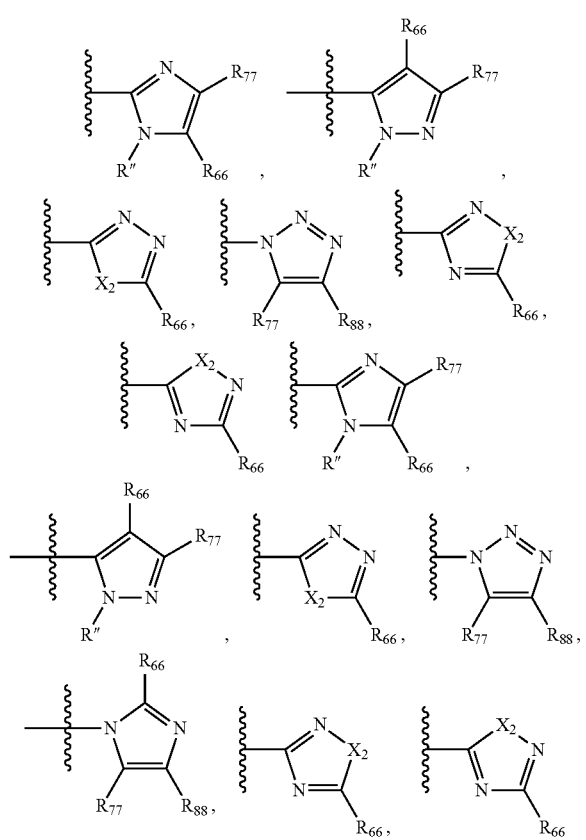

wherein $R_{ggg}$ is selected from the group consisting of H, $C_{1-6}$alkyl, C(O)OH, —C(O)O$C_{1-6}$alkyl, C(O)O-phenyl, and phenyl.

As above, $R_{44}$ may be selected from the group consisting of:

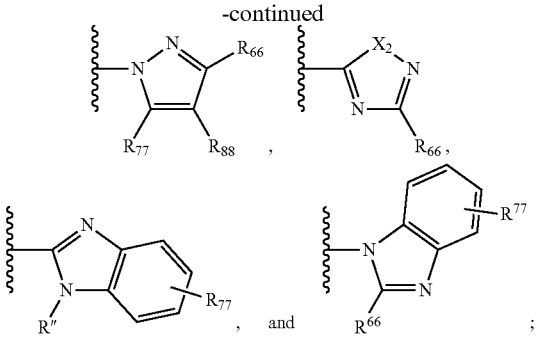

wherein $X_2$ independently for each occurrence is selected from the group consisting of O or S; each $R_{66}$, $R_{77}$ and $R_{88}$ is independently selected for each occurrence from H and $R_{gg}$ as defined above (e.g., in certain embodiments, each $R_{66}$, $R_{77}$ and $R_{88}$ may be independently selected for each occurrence from H, halogen, hydroxyl, and $C_{1-6}$alkyl, wherein $C_{1-6}$alkyl is optionally substituted by one, two or three substituents each independently selected from the group consisting of hydroxyl, $C_{1-6}$alkoxy and —NR'S(O)$_2C_{1-6}$alkyl).

For example, $R_{44}$ may be represented by:

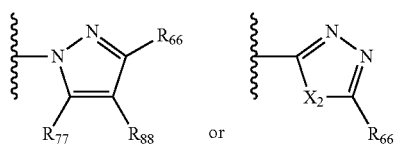

wherein $R_{66}$ is selected from the group consisting of: a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy), isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy, and isobutyl substituted by one, two or three substituents each selected from halogen, hydroxyl, methoxy and ethoxy In another embodiment, $R_{44}$ may be represented by:

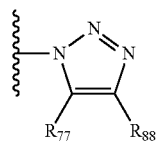

wherein $R_{77}$ and $R_{88}$ are each independently selected from the group consisting of: hydrogen, a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy, isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy, and isobutyl substituted by one, two or three substituents each selected from halogen, hydroxyl, methoxy and ethoxy.

Exemplary compounds provided by this disclosure include compounds and pharmaceutically acceptable salts thereof named below and throughout this disclosure, including the examples and the claims.

For example, contemplated herein is a compound selected from the group consisting of: N-trans-3-(5-(hydroxymethyl)-1H-1,2,3-triazol-1-yl)cyclobutyl)-5-phenylisoxazole-3-carboxamide; N-trans-3-(4-(hydroxymethyl)-1H-1,2,3-triazol-1-yl)cyclobutyl)-5-phenylisoxazole-3-carboxamide; N-cis-3-(5-(hydroxymethyl)-1H-1,2,3-triazol-1-yl) cyclobutyl)-5-phenylisoxazole-3-carboxamide; N-cis-3-(4-(hydroxymethyl)-1H-1,2,3-triazol-1-yl) cyclobutyl)-5-phenylisoxazole-3-carboxamide; N-cis-3-(4-((S)-1-hydroxyethyl)-1H-1,2,3-triazol-1-yl)cyclobutyl)-5-phenylisoxazole-3-carboxamide; N-cis-3-(5-((S)-1-hydroxyethyl)-1H-1,2,3-triazol-1-yl)cyclobutyl)-5-phenylisoxazole-3-carboxamide; N-((trans-3-(5-(hydroxymethyl)-1,3,4-thiadiazol-2-yl)cyclobutyl)methyl)-5-phenylisoxazole-3-carboxamide; N-((cis-3-(5-(hydroxymethyl)-1,3,4-thiadiazol-2-yl)cyclobutyl)methyl)-5-phenylisoxazole-3-carboxamide; N-((trans-3-((5-(hydroxymethyl)-1,3,4-thiadiazol-2-yl)methyl)cyclobutyl)-5-phenylisoxazole-3-carboxamide; N-((cis-3-((5-(hydroxymethyl)-1,3,4-thiadiazol-2-yl)methyl)cyclobutyl)-5-phenylisoxazole-3-carboxamide; N-(trans-3-(5-((S)-1-hydroxyethyl)-1H-1,2,3-triazol-1-yl)cyclobutyl)-5-phenylisoxazole-3-carboxamide; N-(trans-3-(4-((S)-1-hydroxyethyl)-1H-1,2,3-triazol-1-yl)cyclobutyl)-5-phenylisoxazole-3-carboxamide; N-(trans-3-(5-((R)-1-hydroxyethyl)-1H-1,2,3-triazol-1-yl)cyclobutyl)-5-phenylisoxazole-3-carboxamide; N-(trans-3-(4-((R)-1-hydroxyethyl)-1H-1,2,3-triazol-1-yl)cyclobutyl)-5-phenylisoxazole-3-carboxamide; N-(cis-3-(5-((R)-1-hydroxyethyl)-1H-1,2,3-triazol-1-yl)cyclobutyl)-5-phenylisoxazole-3-carboxamide; N-(cis-3-(4-((R)-1-hydroxyethyl)-1H-1,2,3-triazol-1-yl)cyclobutyl)-5-phenylisoxazole-3-carboxamide; N-(trans-3-(5-((R)-1-hydroxyethyl)-1,3,4-oxadiazol-2-yl)cyclobutyl)-5-phenylisoxazole-3-carboxamide; N-(trans-3-(5-((S)-1-hydroxyethyl)-1,3,4-oxadiazol-2-yl)cyclobutyl)-5-phenylisoxazole-3-carboxamide; N-(trans-3-(5-(hydroxymethyl)-1,3,4-oxadiazol-2-yl)cyclobutyl)-5-phenylisoxazole-3-carboxamide; N-trans-3-(5-((R)-1-hydroxyethyl)-1,3,4-thiadiazol-2-yl)cyclobutyl)-5-phenylisoxazole-3-carboxamide; N-trans-3-(5-((S)-1-hydroxyethyl)-1,3,4-thiadiazol-2-yl)cyclobutyl)-5-phenylisoxazole-3-carboxamide; N-trans-3-(5-(hydroxymethyl)-1,3,4-thiadiazol-2-yl)cyclobutyl)-5-phenylisoxazole-3-carboxamide; N-cis-3-(5-(hydroxymethyl)-1,3,4-thiadiazol-2-yl)cyclobutyl)-5-phenylisoxazole-3-carboxamide; N-cis-3-(5-((S)-1-hydroxyethyl)-1,3,4-thiadiazol-2-yl)cyclobutyl)-5-phenylisoxazole-3-carboxamide; N-cis-3-(5-((R)-1-hydroxyethyl)-1,3,4-thiadiazol-2-yl)cyclobutyl)-5-phenylisoxazole-3-carboxamide; N-cis-3-(5-(hydroxymethyl)-1,3,4-oxadiazol-2-yl)cyclobutyl)-5-phenylisoxazole-3-carboxamide; N-cis-3-(5-((R)-1-hydroxyethyl)-1,3,4-oxadiazol-2-yl)cyclobutyl)-5-phenylisoxazole-3-carboxamide; N-cis-3-(5-((S)-1-hydroxyethyl)-1,3,4-oxadiazol-2-yl)cyclobutyl)-5-phenylisoxazole-3-carboxamide; N-cis-3-(5-((R)-1,2-dihydroxyethyl)-1,3,4-thiadiazol-2-yl)cyclobutyl)-5-phenylisoxazole-3-carboxamide; (1-cis-3-(5-phenylisoxazole-3-carboxamido)cyclobutyl)-1H-1,2,3-triazol-4-yl)methyl butylcarbamate; N-trans-3-(4-(R)-1-hydroxyethyl)-1H-pyrazol-1-yl)cyclobutyl)-5-phenylisoxazole-3-carboxamide; N-trans-3-(4-(S)-1-hydroxyethyl)-1H-pyrazol-1-yl)cyclobutyl)-5-phenylisoxazole-3-carboxamide; N-trans-3-(5-((R)-1-hydroxyethyl)-1H-pyrazol-1-yl)cyclobutyl)-5-phenylisoxazole-3-carboxamide; N-trans-3-(5-((S)-1-hydroxyethyl)-1H-pyrazol-1-yl)cyclobutyl)-5-phenylisoxazole-3-carboxamide; N-(cis-3-(4-(hydroxymethyl)-1H-pyrazol-1-yl)cyclobutyl)-5-phenylisoxazole-3-carboxamide; N-(trans-3-(4-(hydroxymethyl)-1H-pyrazol-1-yl)cyclobutyl)-5-phenylisoxazole-3-carboxamide; N-cis-3-(3-(hydroxymethyl)-1H-pyrazol-1-yl)cyclobutyl)-5-phenylisoxazole-3-carboxamide; N-trans-3-(3-(hydroxymethyl)-1H-pyrazol-1-yl)cyclobutyl)-5-phenylisoxazole-3-carboxamide; N-trans-3-(3-(hydroxymethyl)-1,2,4-oxadiazol-5-yl)cyclobutyl)-5-phenylisoxazole-3-carboxamide; N-cis-3-(3-(hydroxymethyl)-1,2,4-oxadiazol-5-yl)cyclobutyl)-5-phenylisoxazole-3-carboxamide; N-cis-3-(5-(hydroxymethyl)-1,2,4-oxadiazol-3-yl)cyclobutyl)-5-phenylisoxazole-3-carboxamide; N-(trans-3-(5-(hydroxymethyl)-1,2,4-oxadiazol-3-yl)cyclobutyl)-5-phenylisoxazole-3-carboxamide; N-(trans-3-((5-((S)-1-hydroxyethyl)-1,3,4-thiadiazol-2-yl)methyl)cyclobutyl)-5-phenylisoxazole-3-carboxamide; N-(cis-3-((5-((S)-1-hydroxyethyl)-1,3,4-thiadiazol-2-yl)methyl)cyclobutyl)-5-phenylisoxazole-3-carboxamide; 5-phenyl-N-[trans-3-([5-[(1R)-1-hydroxyethyl]-1,3,4-thiadiazol-2-yl]methyl)cyclobutyl]isoxazole-3-carboxamide; 5-phenyl-N-[(cis-3-([5-[(1R)-1-hydroxyethyl]-1,3,4-thiadiazol-2-yl]methyl)cyclobutyl]isoxazole-3-carboxamide; N-trans-3-(2-hydroxyethyl)cyclobutyl)-5-phenylisoxazole-3-carboxamide; N-cis-3-(2-hydroxyethyl)cyclobutyl)-5-phenylisoxazole-3-carboxamide; N-(cis-3-(methylsulfonamidomethyl)cyclobutyl)-5-phenylisoxazole-3-carboxamide; N-(trans-3-(3-((S)-1-hydroxyethyl)-1,2,4-oxadiazol-5-yl)cyclobutyl)-5-phenylisoxazole-3-carboxamide; N-(trans-3-(3-((R)-1-hydroxyethyl)-1,2,4-oxadiazol-5-yl)cyclobutyl)-5-phenylisoxazole-3-carboxamide; N-(cis-3-((5-((R)-1-hydroxyethyl)-1,3,4-oxadiazol-2-yl)methyl)cyclobutyl)-5-phenylisoxazole-3-carboxamide; N-(trans-3-((5-((R)-1-hydroxyethyl)-1,3,4-oxadiazol-2-yl)methyl)cyclobutyl)-5-phenylisoxazole-3-carboxamide; N-((trans-3-((5-((S)-1-hydroxyethyl)-1,3,4-oxadiazol-2-yl)methyl)cyclobutyl)-5-phenylisoxazole-3-carboxamide; N-((cis-3-((5-((S)-1-hydroxyethyl)-1,3,4-oxadiazol-2-yl)methyl)cyclobutyl)-5-phenylisoxazole-3-carboxamide; N-(trans-3-(5-((R)-1-hydroxyethyl)-1,2,4-oxadiazol-3-yl)cyclobutyl)-5-phenylisoxazole-3-carboxamide; N-(trans-3-(5-((S)-1-hydroxyethyl)-1,2,4-oxadiazol-3-yl)cyclobutyl)-5-phenylisoxazole-3-carboxamide; 5-phenyl-N-[trans-3-[5-(1-methylazetidin-3-yl)-1,3,4-oxadiazol-2-yl]cyclobutyl]isoxazole-3-carboxamide; 5-(4-fluorophenyl)-N-[trans-3-[5-[(1R)-1- hydroxyethyl]-1,3,4-oxadiazol-2-yl]cyclobutyl]isoxazole-3-carboxamide; 5-phenyl-N-[trans-3-[5-[(1R)-1-methoxyethyl]-1,3,4-oxadiazol-2-yl]cyclobutyl]isoxazole-3-carboxamide; (1R)-1-[5-[trans-3-(5-phenylisoxazole-3-amido)cyclobutyl]-1,3,4-oxadiazol-2-yl]ethyl acetate; (R)-1-(5-(trans-3-(5-phenylisoxazole-3-carboxamido)cyclobutyl)-1,3,4-oxadiazol-2-yl)ethyl benzoate; N-(trans-3-(5-((R)-1-isopropoxyethyl)-1,3,4-oxadiazol-2-yl)cyclobutyl)-5-phenylisoxazole-3-carboxamide; N-(trans-3-(5-((R)-1-isobutoxyethyl)-1,3,4-oxadiazol-2-yl)cyclobutyl)-5-phenylisoxazole-3-carboxamide; tert-butyl 3-(5-(trans-3-(5-phenylisoxazole-3-carboxamido)cyclobutyl)-1,3,4-oxadiazol-2-yl)azetidine-1-carboxylate; (5-phenyl-N-[trans-3-[5-(azetidin-3-yl)-1,3,4-oxadiazol-2-yl]cyclobutyl] isoxazole-3-carboxamide; N-(trans-3-(5-(oxetan-3-yl)-1,3,4-oxadiazol-2-yl)cyclobutyl)-5-phenylisoxazole-3-carboxamide; N-(trans-3-(1-methyl-1H-benzo[d]imidazol-2-yl)cyclobutyl)-5-phenylisoxazole-3-carboxamide; 5-(2,4-difluorophenyl)-N-(trans-3-(5-((R)-1-hydroxyethyl)-1,3,4-oxadiazol-2-yl)cyclobutyl)isoxazole-3-carboxamide; 5-(3-fluorophenyl)-N-(trans-3-(5-((R)-1-hydroxyethyl)-1,3,4-oxadiazol-2-yl)cyclobutyl)isoxazole-3-carboxamide; 5-(2-fluorophenyl)-N-(trans-3-(5-((R)-1-hydroxyethyl)-1,3,4-oxadiazol-2-yl)cyclobutyl)isoxazole-3-carboxamide; 5-(4-hydroxyphenyl)-N-(trans-3-(5-((R)-1-hydroxyethyl)-1,3,4-oxadiazol-2-yl)cyclobutyl)isoxazole-3-carboxamide; 5-(3-hydroxyphenyl)-N-(trans-3-(5-((R)-1-hydroxyethyl)-1,3,4-oxadiazol-2-yl)cyclobutyl)isoxazole-3-carboxamide; 5-(3,4-difluorophenyl)-N-(trans-3-(5-((R)-1-hydroxyethyl)-1,3,4-oxadiazol-2-yl)cyclobutyl)isoxazole-3-carboxamide; N-(trans-3-(5-((R)-1-(methylsulfonyl)ethyl)-1,3,4-oxadiazol-2-yl)cyclobutyl)-5-phenylisoxazole-3-carboxamide; N-(trans-3-(5-cyclobutyl-1,3,4-oxadiazol-2-yl)cyclobutyl)-5-phenylisoxazole-3-carboxamide; N-(trans-3-(1H-imidazol-1-yl)cyclobutyl)-5-phenylisoxazole-3-carboxamide; N-(3-(5-((R)-1-hydroxyethyl)-1,3,4-oxadiazol-2-yl)cyclohexyl)-5-phenylisoxazole-3-carboxamide; N-(3-(4-(hydroxymethyl)-1H-1,2,3-triazol-1-yl)cyclohexyl)-5-phenylisoxazole-3-carboxamide; N-(3-(5-(hydroxymethyl)-1H-1,2,3-triazol-1-yl)cyclohexyl)-5-phenylisoxazole-3-carboxamide; N-[3-[5-(hydroxymethyl)-1,3,4-oxadiazol-2-yl]cyclopentyl]-5-phenylisoxazole-3-carboxamide; N-(cis/trans-4-(5-(hydroxymethyl)-1,3,4-oxadiazol-2-yl)cyclohexyl)-5-phenylisoxazole-3-carboxamide; 5-(3,4-dihydroxyphenyl)-N-(trans-3-(5-((R)-1-hydroxyethyl)-1,3,4-oxadiazol-2-yl)cyclobutyl)isoxazole-3-carboxamide; N-(trans-3-(1H-benzo[d]imidazol-1-yl)cyclobutyl)-5-phenylisoxazole-3-carboxamide; N-(trans-3-(5-(1,1-dioxidothietan-3-yl)-1,3,4-oxadiazol-2-yl)cyclobutyl)-5-phenylisoxazole-3-carboxamide; N-(3-(4-(hydroxymethyl)-1H-1,2,3-triazol-1-yl)cyclopentyl)-5-phenylisoxazole-3-carboxamide; and N-(3-(5-(hydroxymethyl)-1H-1,2,3-triazol-1-yl)cyclopentyl)-5-phenylisoxazole-3-carboxamide, and pharmaceutically acceptable salts thereof.

Also contemplated herein are pharmaceutical compositions that include a disclosed compound such as those compounds having e.g., the above formulas, e.g., Formula Ia, (IIa), (IIb), (IIc) (IId), (IIIa), or (IIIb) and a pharmaceutically acceptable carrier or excipient. In certain embodiments, the compositions can include at least one additional CFTR modulator as described anywhere herein or at least two additional CFTR modulators, each independently as described anywhere herein.

Also contemplated herein are compounds represented by:

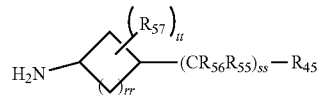

or salt thereof, wherein
tt is 0, 1, or 2;
rr is 1, 2 or 3;
ss is 0 or 1;
$R_{55}$, $R_{56}$, and $R_{57}$ are each independently selected from the group consisting of: halogen, hydroxyl, and $C_{1-3}$alkyl (optionally substituted by one, two or three substituents each selected independently from $R_{ff}$),
$R_{ff}$ is selected for each occurrence from group consisting of halogen, hydroxyl, $C_{1-4}$alkyl, $C_{1-4}$alkyoxy, $C_{2-4}$alkenyl, —NR'R", —NR'—S(O)$_w$—C$_{1-3}$alkyl, S(O)$_w$—NR'R", and —S(O)$_w$—C$_{1-3}$alkyl, where w is 0, 1, or 2, wherein $C_{1-4}$alkyl, $C_{1-4}$alkyoxy, and $C_{2-4}$alkenyl may be optionally substituted by one, two or three substituents each independently selected from the group consisting of halogen, hydroxyl, —NR'R", —NR'—S(O)$_w$—C$_{1-3}$alkyl, S(O)$_w$—NR'R", and —S(O)$_w$—C$_{1-3}$alkyl;
R' and R" are each independently selected for each occurrence from H and $C_{1-4}$alkyl or taken together with the nitrogen to which they are attached form a heterocyclic ring; and
$R_{45}$ is selected from the group consisting of:

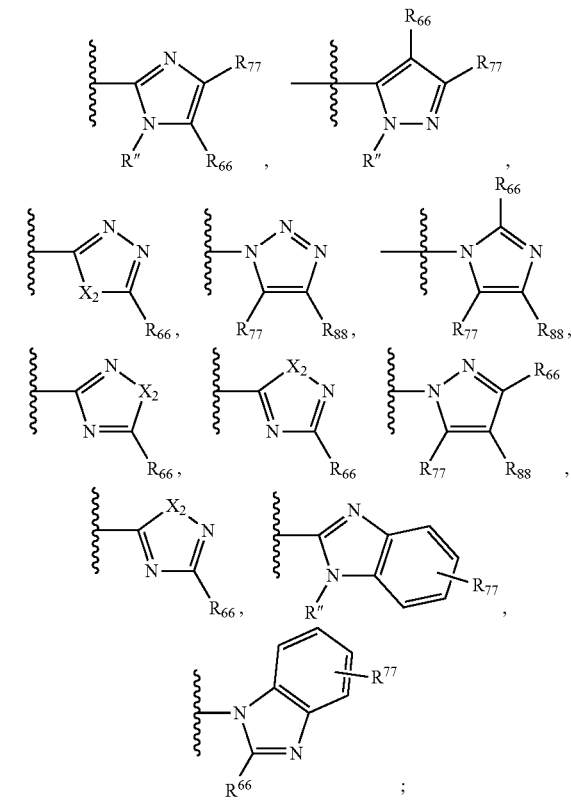

wherein
$X_2$ independently for each occurrence is selected from the group consisting of O or S; and each $R_{66}$, $R_{77}$ and $R_{88}$ is independently selected for each occurrence from H and $R_{gg}$ as defined above, (for example selected from the group consisting of, halogen, hydroxyl, and $C_{1-6}$alkyl, wherein $C_{1-6}$alkyl is optionally substituted by one, two or three substituents each independently selected from the group consisting of hydroxyl, $C_{1-6}$alkoxy and —NR'S(O)$_2$C$_{1-6}$alkyl).

It is to be understood that the specific embodiments described herein can be taken in combination with other specific embodiments delineated herein.

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

It will be appreciated that the description of the disclosure should be construed in congruity with the laws and principals of chemical bonding.

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms, and straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term, "alkynyl", as used herein, refers to both straight and branched-chain moieties having the specified number or carbon atoms and having at least one carbon-carbon triple bond.

The term "cycloalkyl," as used herein, refers to saturated cyclic alkyl moieties having 3 or more carbon atoms, for example, 3-10, 3-8, 3-6, or 4-6 carbons, referred to herein as $C_{3-10}$cycloalkyl, $C_{3-6}$cycloalkyl or $C_{4-6}$cycloalkyl, respectively. The term cycloalkyl also includes bridged or fused cycloalkyls. Examples of cycloalkyl include, but are not limited to, cyclopropyl, cyclobutyl, cyclopentyl, cyclohexyl, cycloheptyl, adamantyl, bicyclo[1.1.1]pentane-, bicyclo[2.2.1]heptane, and bicyclo[3.2.1]octane. The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

Alkylene" means a straight or branched, saturated aliphatic divalent radical having the number of carbons indicated. "Cycloalkylene" refers to a divalent radical of carbocyclic saturated hydrocarbon group having the number of carbons indicated.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "heterocyclic" or "heterocycle" encompasses heterocycloalkyl, heterocycloalkenyl, heterobicycloalkyl, heterobicycloalkenyl, heteropolycycloalkyl, heteropolycycloalkenyl, and the like unless indicated otherwise. Heterocycloalkyl refers to cycloalkyl groups containing one two, or three heteroatoms within the ring (O, S(O)$_w$, or NR where w is 0, 1, or 2 and R is e.g., H, $C_{1-3}$alkyl, phenyl) and for example 3, 4, or 5 carbons within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S(O)$_w$, or NR) within a ring. Heterobicycloalkenyl as used herein refers to bicycloalkenyl groups containing one or more heteroatoms (O, S or N) within a ring. a heterocycle can refer to, for example, a saturated or partially unsaturated 4- to 12 or 4-10-membered ring structure, including bridged or fused rings, and whose ring structures include one to three heteroatoms, such as nitrogen, oxygen, and sulfur. Where possible, heterocyclic rings may be linked to the adjacent radical through carbon or nitrogen. Examples of heterocyclic groups include, but are not limited to, pyrrolidine, piperidine, morpholine, morpholine-one, thiomorpholine, piperazine, oxetane, azetidine, thietane dioxide, tetrahydrofuran or dihydrofuran etc.

Cycloalkyl, cycloalkenyl, heterocyclic, groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted. In some embodiments, the aryl is a $C_4$-$C_{10}$ aryl. Examples of optionally substituted aryl are phenyl, substituted phenyl, napthyl and substituted naphthyl.

The term "heteroaryl", as used herein, refers to aromatic carbocyclic groups containing one or more heteroatoms (O, S, or N) within a ring. A heteroaryl group, unless indicated otherwise, can be monocyclic or polycyclic. A heteroaryl group may additionally be substituted or unsubstituted. The heteroaryl groups of this disclosure can also include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is 4- to 12-membered heteroaryl. In yet other embodiments, the heteroaryl is a mono or bicyclic 4- to 10-membered heteroaryl.

The term "substituted" refers to substitution by independent replacement of one, two, or three or more of the hydrogen atoms with substituents including, but not limited to, and unless indicated otherwise, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —$NO_2$, —$N_3$, —CN, —$NH_2$, oxo, thioxo, —$NHR_x$, —$NR_xR_x$, dialkylamino, -diarylamino, -diheteroarylamino, —$OR_x$, —$C(O)R_y$, —$C(O)C(O)R_y$, —$OCO_2R_y$, —$OC(O)R_y$, $OC(O)C(O)R_y$, —$NHC(O)R_y$, —$NHCO_2R_y$, —$NHC(O)C(O)R_y$, $NHC(S)NH_2$, —$NHC(S)NHR_x$, —$NHC(NH)NH_2$, —$NHC(NH)NHR_x$, —$NHC(NH)R_x$, —$C(NH)NHR_x$, and ($C$=$NR_x$)$R_x$; —$NR_xC(O)R_x$, —$NR_xC(O)N(R_x)_2$, —$NRxCO_2R_y$, —$NRxC(O)C(O)R_y$, —$NR_xC(S)NH_2$, —$NR_xC(S)NHR_x$, —$NR_xC(NH)NH_2$, —$NR_xC(NH)NHR_x$, —$NR_xC(NH)R_x$, —$C(NRx)NHR_x$—$S(O)R_y$, —$NHSO_2R_x$, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -polyalkoxyalkyl, -polyalkoxy, -methoxymethoxy, -methoxyethoxy, —SH, —S—$R_x$, or -methylthiomethyl, wherein $R_x$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl and -heterocyclic and —$R_y$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl, -heterocyclic, —$NH_2$, —NH—$C_1$-$C_{12}$ alkyl, —NH—$C_2$-$C_{12}$ alkenyl, —NH—$C_2$-$C_{12}$-alkynyl, —NH—$C_3$-$C_{12}$ cycloalkyl, —NH-aryl, —NH-heteroaryl and —NH-heterocyclic. It is understood that the aryls, heteroaryls, alkyls, and the like can be further substituted.

The terms "halo" or "halogen" as used herein refer to F, Cl, Br, or I.

The term "haloalkyl" as used herein refers to an alkyl group having 1 to (2n+1) substituent(s) independently selected from F, Cl, Br or I, where n is the maximum number of carbon atoms in the alkyl group. It will be understood that haloalkyl is a specific example of an optionally substituted alkyl.

The terms "hydroxy" and "hydroxyl" as used herein refers to the radical —OH.

As will be understood by the skilled artisan, "H" is the symbol for hydrogen, "N" is the symbol for nitrogen, "S" is the symbol for sulfur, "O" is the symbol for oxygen. "Me" is an abbreviation for methyl.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009. Where a particular compound is described or depicted, it is intended to encompass that chemical structure as well as tautomers of that structure.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

The compounds disclosed herein can exist in solvated as well as unsolvated forms with pharmaceutically acceptable solvents such as water, ethanol, and the like, and it is intended that the disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the disclosure may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the disclosure can generally be prepared by following procedures analogous to those disclosed in the examples herein by substituting an isotopically labeled reagent for a non-isotopically labeled reagent. The term "pharmaceutically acceptable salt(s)" as used herein refers to salts of acidic or basic groups that may be present in a disclosed compounds used in disclosed compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

Also included in the present disclosure are methods that include administering prodrugs of the compounds described herein, or a pharmaceutical composition thereof or method of use of the prodrug.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as ($C_{1-8}$)alkyl, ($C_{2-12}$)alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_{1-2}$)alkylamino($C_{2-3}$)alkyl (such as β-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino($C_{2-3}$)alkyl.

Similarly, if a compound of the disclosure contains an alcohol functional group, a prodrug can be formed by the replacement of the hydrogen atom of the alcohol group with a group such as ($C_{1-6}$)alkylcarbonyloxymethyl, 1-(($C_{1-6}$)alkylcarbonyloxy)ethyl, 1-methyl-1-(($C_{1-6}$)alkylcarbonyloxy)ethyl ($C_{1-6}$)alkoxycarbonyloxymethyl, N—($C_{1-6}$)alkoxycarbonylaminomethyl, succinoyl, ($C_{1-6}$)alkylcarbonyl, α-amino($C_{1-4}$)alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplício, et al., *Molecules* 2008, 13, 519 and references therein The disclosure additionally includes use of clathrates of the compounds described herein, pharmaceutical compositions comprising the clathrates, and methods of use of the clathrates. In some embodiments, the disclosure is directed to clathrates of a disclosed compound of e.g., Formula (IIIa), (III), or (IV), or a pharmaceutical composition thereof topically labeled reagent.

The disclosure additionally encompasses embodiments wherein one or more of the nitrogen atoms in a disclosed compound are oxidized to N-oxide.

Representative and exemplary synthetic routes for the preparation of compounds described herein are shown in the schemes below and throughout the Examples section. As will be understood by the skilled artisan, diastereomers can be separated from the reaction mixture using column chromatography.

Schemes 1 and 2

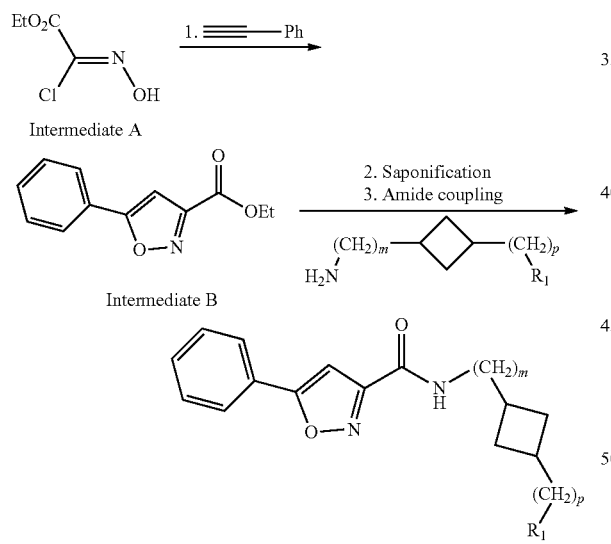

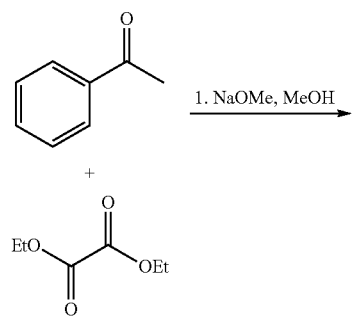

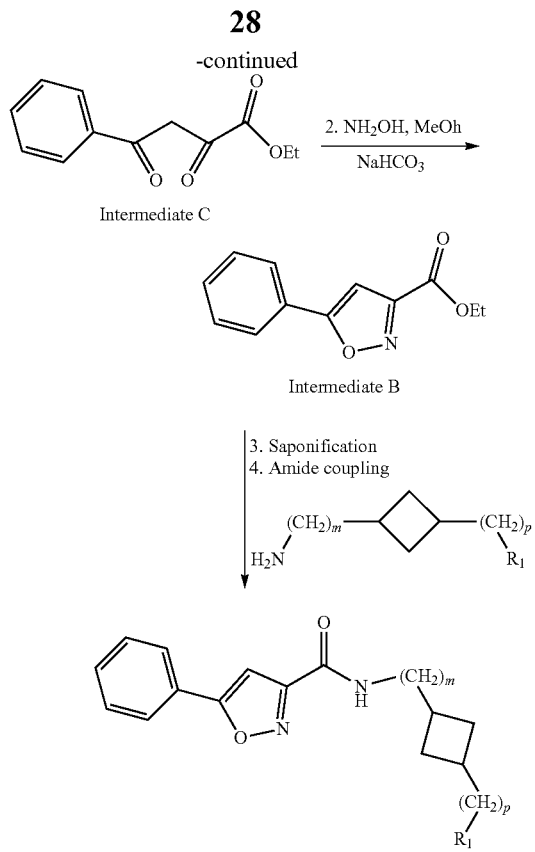

Scheme 3

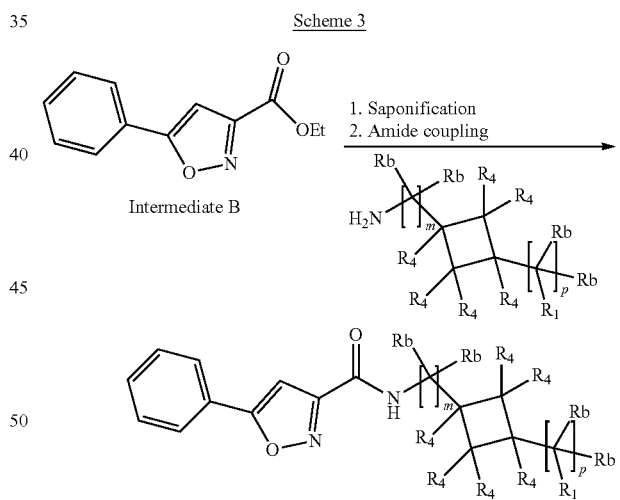

Compounds of the disclosure can also be prepared using methods described in the literature, including, but not limited to, *J. Med. Chem.* 2011, 54 (13), 4350-64; *Russian Journal of Organic Chemistry*, 2011, 47 (8), 1199-1203; U.S. Patent Application Publication No. 2009/0036451 A1; WO2008/046072 A2, and U.S. Pat. No. 4,336,264, the contents of each of which are expressly incorporated by reference herein.

Methods of Use

The disclosure is in part directed to a method of enhancing (e.g., increasing) CFTR activity in a subject (e.g., a subject suffering from any one or more of the conditions described herein) comprising administering a compound of the disclosure in an effective amount. The disclosure also encompasses a method of treating a patient suffering from a condition associated with CFTR activity comprising administering to said patient an effective amount of a compound described herein. In certain embodiments, the disease is cystic fibrosis.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a method of treatment, an "effective amount" of the therapeutic agent that is sufficient to ameliorate of one or more symptoms of a disorder and/or prevent advancement of a disorder, cause regression of the disorder and/or to achieve a desired effect.

The term "modulating" encompasses increasing, enhancing, inhibiting, decreasing, suppressing, and the like. The terms "increasing" and "enhancing" mean to cause a net gain by either direct or indirect means. As used herein, the terms "inhibiting" and "decreasing" encompass causing a net decrease by either direct or indirect means.

For example, CFTR activity in a patient may be enhanced after administration of a compound described herein when there is an increase in the CFTR activity as compared to that in the absence of the administration of the compound. CFTR activity encompasses, for example, chloride channel activity of the CFTR, and/or other ion transport activity (for example, $HCO_3^-$ transport). In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). Contemplated patients treated by disclosed methods may have a CFTR mutation(s) from one or more classes, such as without limitation, Class I CFTR mutations, Class II CFTR mutations, Class III CFTR mutations, Class IV CFTR mutations, Class V CFTR mutations, and Class VI CFTR mutations. Contemplated subject (e.g., human subject) CFTR genotypes include, without limitation, homozygote mutations (e.g., ΔF508/ΔF508 and R117H/R117H) and compound heterozygote mutations (e.g., ΔF508/G551D; ΔF508/A455E; ΔF508/G542X; Δ508F/W1204X; R553X/W1316X; W1282X/N1303K, 591Δ18/E831X, F508del/R117H/N1303K/3849+10kbC>T; Δ303K/384; and DF508/G178R).

In certain embodiments a patient may have a Class I mutation, e.g., a G542X; a Class II/I mutation, e.g., a ΔF508/G542X compound heterozygous mutation. In other embodiments, the mutation is a Class III mutation, e.g., a G551D; a Class II/Class III mutation, e.g., a ΔF508/G551D compound heterozygous mutation. In still other embodiments, the mutation is a Class V mutation, e.g., a A455E; Class II/Class V mutation, e.g., a ΔF508/A455E compound heterozygous mutation. Of the more than 1000 known mutations of the CFTR gene, ΔF508 is the most prevalent mutation of CFTR which results in misfolding of the protein and impaired trafficking from the endoplasmic reticulum to the apical membrane (Dormer et al. (2001). *J Cell Sci* 114, 4073-4081; http://www.genet.sickkids.on.ca/app). In certain embodiments, ΔF508 CFTR activity is enhanced (e.g., increased). In certain embodiments, ΔF508 CFTR activity and/or G542X CFTR activity and/or G551D CFTR activity and/or A455E CFTR activity is enhanced (e.g., increased). An enhancement of CFTR activity can be measured, for example, using literature described methods, including for example, Ussing chamber assays, patch clamp assays, and hBE Ieq assay (Devor et al. (2000), Am J Physiol Cell Physiol 279 (2): C461-79; Dousmanis et al. (2002), J Gen Physiol 119 (6): 545-59; Bruscia et al. (2005), PNAS 103 (8): 2965-2971).

Also provided herein are methods of treating a patient suffering from a condition associated with CFTR activity, including conditions associated with deficient CFTR activity. In some embodiments, the disclosure is directed to a method of treating a condition associated with deficient or decreased CFTR activity comprising administering an effective amount of a disclosed compound of (e.g., a disclosed formula, e.g., Formula (Ia) or (Ib)) that enhances CFTR activity. Non-limiting examples of conditions associated with deficient CFTR activity are cystic fibrosis, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), chronic sinusitis, dry eye disease, protein C deficiency, Aβ-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome.

In some embodiments, disclosed methods of treatment that include administering a disclosed compound to a patient may further comprise administering an additional therapeutic agent. For example, in an embodiment, provided herein is a method of administering a disclosed compound and at least one additional therapeutic agent. In certain aspects, the disclosure is directed to a method comprising administering a disclosed compound, and at least two additional therapeutic agents. Additional therapeutic agents include, for example, mucolytic agents, bronchodilators, antibiotics, anti-infective agents, anti-inflammatory agents, ion channel modulating agents (e.g., ENaC inhibitors), therapeutic agents used in gene therapy, CFTR correctors, and CFTR potentiators, or other agents that modulates CFTR activity. In some embodiments, at least one additional therapeutic agent is selected from the group consisting of a CFTR corrector and a CFTR potentiator. Non-limiting examples of CFTR correctors and potentiators include VX-770 (Ivacaftor), VX-809 (3-(6-(1-(2,2-difluorobenzo[d][1,3]dioxol-5-yl)cyclopropanecarboxamido)-3-methylpyridin-2-yl)benzoic acid, VX-661 (1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), VX-983, and Ataluren (PTC124) (3-[5-(2-fluorophenyl)-1,2,4-oxadiazol-3-yl]benzoic acid), FDL169, GLPG1837/ABBV-974 (for example, a CFTR potentiator), GLPG2222 (for example, a corrector); and compounds described in, e.g., WO2014/144860 and 2014/176553, hereby incorporated by reference. Non-limiting examples of modulators include QBW-251, QR-010, NB-124, and compounds described in, e.g., WO2014/045283; WO2014/081821, WO2014/081820, WO2014/152213; WO2014/160440, WO2014/160478, US2014027933; WO2014/0228376, WO2013/038390, WO2011/113894, WO2013/038386; and WO2014/180562, of which the disclosed modulators in those publications are contemplated as additional therapeutic agents and incorporated by reference. Non-limiting examples of anti-inflammatory agents include N6022 (3-(5-(4-(1H-imidazol-1-yl)phenyl)-1-(4-carbamoyl-2-methylphenyl)-¹H-pyrrol-2-yl) propanoic acid), CTX-4430, N1861, N1785, and N91115.

In some embodiments, the methods described herein can further include administering an additional therapeutic agent or administering at least two additional CFTR therapeutic agents. In some embodiments, the methods described herein can further include administering an additional CFTR modulator or administering at least two additional CFTR modulators. In certain embodiments, at least one CFTR modulator is a CFTR corrector (e.g., VX-809, VX-661, VX-983, GLPG2222 and) or potentiator (e.g., ivacaftor, genistein and GLPG1837). In certain of these embodiments, one of the at least two additional therapeutic agents is a CFTR corrector (e.g., VX-809, VX-661 and VX-983) and the other is a CFTR potentiator (e.g., ivacaftor and genistein). In certain of these embodiments, one of the at least two additional therapeutic agents is a CFTR corrector (e.g., GLPG2222) and the other is a CFTR potentiator (e.g., GLPG1837). In certain of these embodiments, one of the at least two additional therapeutic agents is a CFTR corrector (e.g., VX-809 or VX-661) and the other is a CFTR potentiator (e.g., ivacaftor). In certain of these embodiments, at least one CFTR modulator is an agent that enhances read-through of stop codons (e.g., NB124 or ataluren).

Accordingly, in another aspect, this disclosure provides a method of treating a condition associated with deficient or decreased CFTR activity (e.g., cystic fibrosis), which includes administering to a subject in need thereof (e.g., a human patient in need thereof) an effective amount of a disclosed compound and at least one or two additional CFTR therapeutic agent(s) (e.g., at least one or two additional CFTR therapeutic agents, e.g., in which one of the at least one or two additional therapeutic agents is optionally a CFTR corrector or modulator (e.g., VX-809, VX-661, VX-983, GLPG2222, NB124, ataluren) and/or the other is a CFTR potentiator (e.g., ivacaftor, genistein, and GLPG1837); e.g., one of the at least two additional therapeutic agents is GLPG2222, and the other is GLPG1837; or one of the at least two additional therapeutic agents is VX-809 or VX-661, and the other is a ivacaftor). In certain embodiments, the subject's CFTR genotype includes, without limitation, one or more Class I CFTR mutations, one or more Class II CFTR mutations, one or more Class III CFTR mutations, one or more Class IV CFTR mutations, or one or more Class V CFTR mutations, or one or more Class VI CFTR mutations. In certain embodiments, the subject's CFTR genotype includes, without limitation, one or more homozygote mutations (e.g., ΔF508/ΔF508 or R117H/R117H) and/or one or more compound heterozygote mutations (e.g., ΔF508/G551D; ΔF508/A455E; ΔF508/G542X; Δ508F/W1204X; R553X/W1316X; W1282X/N1303K; F508del/R117H; N1303K/3849+10kbC>T; ΔF508/R334W; DF508/G178R, and 591Δ18/E831X). In certain embodiments, the subject's CFTR genotype includes a Class I mutation, e.g., a G542X Class I mutation, e.g., a ΔF508/G542X compound heterozygous mutation. In other embodiments, the subject's CFTR genotype includes a Class III mutation, e.g., a G551D Class III mutation, e.g., a ΔF508/G551D compound heterozygous mutation. In still other embodiments, the subject's CFTR genotype includes a Class V mutation, e.g., a A455E Class V mutation, e.g., a ΔF508/A455E compound heterozygous mutation. In certain embodiments, ΔF508 CFTR activity and/or G542X CFTR activity and/or G551D CFTR activity and/or A455E activity is enhanced (e.g., increased). In certain embodiments, the enhancement in activity (e.g., increase in activity) provided by the combination of the disclosed compound and one or two additional therapeutic agents is greater than additive when compared to the enhancement in activity provided by each therapeutic component individually.

| Class | Effect on CFTR protein | Example of mutation |
|---|---|---|
| I | Shortened protein | W1282X Instead of inserting the amino acid tryptophan (W), the protein sequence is prematurely stopped (indicated by an X). |
| II | Protein fails to reach cell membrane | ΔF508 A phenylalanine amino acid (F) is deleted |
| III | Channel cannot be regulated properly | G551D A "missense" mutation: instead of a glycine amino acid (G), aspartate (D) is added |
| IV | Reduced chloride conductance | R117H Missense |
| V | Reduced due to incorrect splicing of gene | 3120 + 1G > A Splice-site mutation in gene intron 16 |
| VI | Reduced due to protein instability | N287Y a A –>T at 991 |

| Genotype | Description | Possible Symptoms |
|---|---|---|
| Δ508F/Δ508F | homozygote | Severe lung disease, pancreatic insufficient |
| R117H/R117H | homozygote | Congenital bilateral absence of the vas deferens; No lung or pancreas disease |
| WT/Δ508F | heterozygote | Unaffected |
| WT/3120 + 1 G > A | heterozygote | Unaffected |
| Δ508F/W1204X | compound heterozygote | No lung disease, pancreatic insufficient |
| R553X and W1316X | compound heterozygote | Mild lung disease, pancreatic insufficient |
| 591Δ18/E831X | compound heterozygote | No lung or pancreas disease, nasal polyps |

For example, provided herein is a method of treating a patient for e.g., cystic fibrosis, wherein the patient has one or more of the following mutations in the CFTR gene: G1244E, G1349D, G178R, G551S, S1251N, S1255P, S549N, S549R, G970R, or R117H, and/or e.g., a patient with one or two copies of the F508del mutation, or one copy of the ΔF508 mutation and a second mutation that results in a gating effect in the CFTR protein (e.g., a patient that is heterozygous for ΔF508 and G551D mutation), a patient with one copy of the ΔF508 mutation and a second mutation that results in residual CFTR activity, or a patient with one copy of the ΔF508 mutation and a second mutation that results in residual CFTR activity, comprising administering an effective amount of a disclosed compound. As described herein, such exemplary methods (e.g., of a patient having one or mutations such as those described above) may include, for example, administering to such patient a combination therapy, e.g., administering (simultaneously or sequentially) an effective amount of ivacaftor to said patient and an effective amount of disclosed compound that may act as an amplifier. Such administration may result, for example, in increased chloride transport in human bronchial epithelial cells with e.g., one or two copies of mutations, e.g., ΔF508 mutation, as compared to administration of ivacaftor alone. Another contemplated combination therapy that includes a disclosed compound may also include an effective amount of a readthrough agent (e.g., ataluren, NB124) and an effective amount of disclosed compound that may act as an amplifier.

The phrase "combination therapy," as used herein, refers to an embodiment where a patient is co-administered a disclosed compound, a CFTR potentiator agent (e.g., ivacaftor) and optionally, one or more CFTR corrector agent(s) (e.g., VX-661 and/or lumacaftor) as part of a specific treatment regimen intended to provide the beneficial effect from the co-action of these therapeutic agents. For example, a beneficial effect of a combination may include, but is not limited to, pharmacokinetic or pharmacodynamic co-action resulting from the combination of therapeutic agents. For example, administration of a disclosed compound with ivacaftor alone or with a CFTR corrector agent (e.g., lumacaftor or VX-661) may result in a level of function (e.g., as measured by chloride activity in HBE cells or patients that have a ΔF508 mutation, that achieves clinical improvement (or better) as compared to the chloride activity level in cells or patients with a G551D mutation receiving ivacaftor alone, or ivacaftor and a corrector agent (lumacaftor or VX-661; or for example, administration of a disclosed compound with ivacaftor alone or ivacaftor with a CFTR corrector agent (e.g., lumacaftor or VX-661) may result in a level of function (e.g., as measured by chloride activity in HBE cells or patients that have a A455E mutation, that achieves clinical improvement (or better) as compared to the chloride activity level at e.g., 50% or more of wild type cells; or upon administration of a disclosed compound and ivacaftor to a patient (e.g. having a G551D class III mutation) may show e.g., about two times or more improved activity of ivacaftor as compared to administration of ivacaftor alone. Administration of disclosed therapeutic agents in combination typically is carried out over a defined time period (usually a day, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner Substantially simultaneous administration can be accomplished, for example, by administering to the subject a single tablet or capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, inhalational routes, intravenous routes, intramuscular routes, and direct absorption through mucous membrane tissues. The therapeutic agents can be administered by the same route or by different routes. For example, a first therapeutic agent of the combination selected may be administered by intravenous injection or inhalation or nebulizer while the other therapeutic agents of the combination may be administered orally. Alternatively, for example, all therapeutic agents may be administered orally or all therapeutic agents may be administered by intravenous injection, inhalation or nebulization.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by a day, days or even weeks.

The components of a disclosed combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

The disclosure also encompasses the treatment of a condition associated with a dysfunction in proteostasis in a subject comprising administering to said subject an effective amount of a disclosed compound that enhances, improves or restores proteostasis of a protein. Proteostasis refers to protein homeostasis. Dysfunction in protein homeostasis is a result of protein misfolding, protein aggregation, defective protein trafficking or protein degradation. For example, the disclosure encompasses administering a compound of a disclosed formula, e.g., Formula (Ia) or (Ib) that corrects protein misfolding, reduces protein aggregation, corrects or restores protein trafficking and/or affects protein degradation for the treatment of a condition associated with a dysfunction in proteostasis. In some aspects of the disclosure, a compound of Formula (Ia) or (Ib) that corrects protein misfolding and/or corrects or restores protein trafficking is administered. In cystic fibrosis, the mutated or defective enzyme is the cystic fibrosis transmembrane conductance regulator (CFTR). One of the most common mutations of this protein is ΔF508 which is a deletion (A) of three nucleotides resulting in a loss of the amino acid phenylalanine (F) at the 508th (508) position on the protein. As described above, mutated cystic fibrosis transmembrane conductance regulator exists in a misfolded state and is characterized by altered trafficking as compared to the wild type CFTR. Additional exemplary proteins of which there can be a dysfunction in proteostasis, for example that can exist in a misfolded state, include, but are not limited to, glucocerebrosidase, hexosamine A, aspartylglucosaminidase, α-galactosidase A, cysteine transporter, acid ceramidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, TDP-43, superoxide dismutase (SOD), Aβ peptide, tau protein transthyretin and insulin. The disclosed compounds may be used to restore proteostasis (e.g., correct folding and/or alter trafficking) of the proteins described above.

Protein conformational diseases contemplated herein encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to, neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tautopathies (progressive supranuclear palsy, corticobasal degeneration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease, Lewy body dementia (LBD) and multiple system atrophy (SMA). Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. In another embodiment, the misfolded protein is alpha-1 anti-trypsin.

In a further embodiment methods are provided to treat a protein conformation disease such as loss of function disorder, comprising administering to a patient suffering from same a disclosed compound. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In another embodiment, the disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, the disease associated with a dysfunction in proteostasis is diabetes and/or complications of diabetes, including, but not limited to, diabetic retinopathy, cardiomyopathy, neuropathy, nephropathy, and impaired wound healing.

In a further embodiment, the disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration.

In yet additional embodiments, the method of the disclosure is directed to treating a disease associated with a dysfunction in proteostasis, wherein the disease affects the respiratory system, pancreas and/or the kidneys. For example, provided herein are methods of treating polycystic kidney disease and/or other kidney pathologies, comprising administering a disclosed compound. In certain additional embodiments, the methods of the disclosure encompass treating a condition selected from the group consisting of polyendocrinopathy/hyperinsulinemia, diabetes mellitus, Charcot-Marie Tooth syndrome, Pelizaeus-Merzbacher disease, and Gorham's Syndrome.

Additional conditions associated with a dysfunction of proteostasis include hemoglobinopathies, inflammatory diseases, intermediate filament diseases, drug-induced lung damage and hearing loss. The disclosure also encompasses methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage). The disclosure additionally encompasses methods for treating hearing loss, such as noise-induced hearing loss, aminoglycoside-induced hearing loss, and cisplatin-induced hearing loss.

Additional conditions include those associated with a defect in protein trafficking and that can be treated according to methods of the disclosure include: PGP mutations, hERG trafficking mutations, nephrongenic diabetes insipidus mutations in the arginine-vasopressin receptor 2, persistent hyperinsulinemic hypoglycemia of infancy (PHH1) mutations in the sulfonylurea receptor 1, and α1AT.

In an embodiment, a method of enhancing cystic fibrosis transmembrane conductance regulator (CFTR) activity in a subject in need thereof is provided, which includes administering to said subject an effective amount of a disclosed compound, e.g., having the Formula (IIIa) or (IIIb):

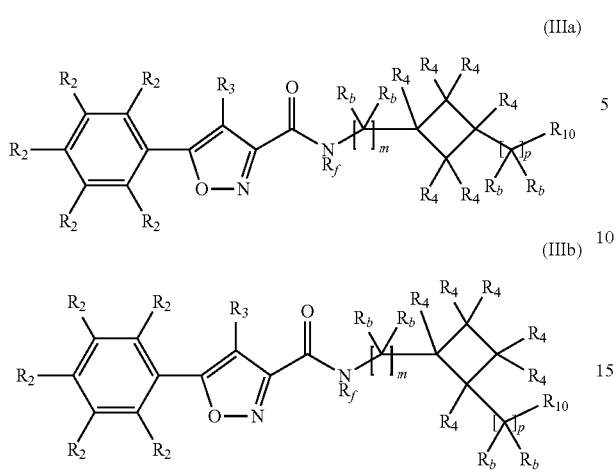

or a pharmaceutically acceptable salt, solvate, clathrate or prodrug thereof, wherein:

$R_{10}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, optionally substituted heterocyclic and optionally substituted heteroaryl;

each $R_2$ is independently selected from the group consisting of hydrogen, halo, CN, and optionally substituted $C_1$-$C_{10}$ alkyl;

$R_3$ is hydrogen or fluoro;

each $R_4$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, optionally substituted heterocyclic and optionally substituted heteroaryl; alternatively, two geminal $R_4$ groups are taken together with the carbon atom to which they are attached to form a spiro $C_3$-$C_{12}$ cycloalkyl, a spiro $C_3$-$C_{12}$ cycloalkenyl, a spiro heterocyclic, a spiro aryl or spiro heteroaryl, each optionally substituted; or yet alternatively, two vicinal $R_4$ groups are taken together with the carbon atoms to which they are attached to form a fused, optionally substituted cyclic group selected from the group consisting of $C_4$-$C_8$ cycloalkyl, $C_4$-$C_8$ cycloalkenyl, 4- to 8-membered heterocyclic, substituted aryl and heteroaryl, each optionally substituted; or further alternatively, two $R_4$ groups attached to non-adjacent carbon atoms are taken together with the carbon atoms to which they are attached to form a bridged cyclic group selected from the group consisting of $C_4$-$C_8$ cycloalkyl, $C_4$-$C_8$ cycloalkenyl, and 4- to 8-membered heterocyclic, each optionally substituted;

each $R_b$ is independently selected from the group consisting of hydrogen, halo, optionally substituted $C_1$-$C_{10}$ alkyl, and optionally substituted $C_3$-$C_6$ cycloalkyl, or two geminal $R_b$ groups are independently taken together with the carbon atom to which they are attached to form an optionally substituted heterocyclic or an optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl;

$R_e$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

$R_f$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

m is 0, 1 or 2;

each n is independently 0, 1 or 2; and p is 0, 1 or 2.

In a further aspect, a method of identifying a candidate agent that increases CFTR activity is provided, which includes: (i) contacting a cell that expresses a CFTR protein with the candidate agent and a disclosed compound; (ii) measuring the CFTR activity in the cell in the presence of the candidate agent and the disclosed compound; and (iii) comparing the CFTR activity to that in the absence of the test agent, wherein an increase in CFTR activity in the presence of the test agent indicates that the agent increases CFTR activity. In certain embodiments, the cell expresses a mutant CFTR protein. In certain embodiments, CFTR activity is measured by measuring chloride channel activity of the CFTR, and/or other ion transport activity. In certain of these embodiments, the method is high-throughput. In certain of these embodiments, a candidate agent is a CFTR corrector or a CFTR potentiator.

Compositions

Provided herein in an embodiment, are pharmaceutical compositions comprising a pharmaceutically acceptable carrier or excipient and a compound described herein, and methods of administering such compositions. For example, a disclosed compound, or a pharmaceutically acceptable salt, solvate, clathrate or prodrug thereof, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. A pharmaceutical composition comprising a disclosed compound or a pharmaceutically acceptable salt, solvate, clathrate or prodrug, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, preferably about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present disclosure, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The disclosure is illustrated by the following examples which are not meant to be limiting in any way.

EXEMPLIFICATION

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as "intermediates" herein are contemplated as compounds of the invention.

Example 1: N-trans-3-(5-(hydroxymethyl)-1H-1,2,3-triazol-1-yl)cyclobutyl)-5-phenylisoxazole-3-carboxamide and N-trans-3-(4-(hydroxymethyl)-1H-1,2,3-triazol-1-yl)cyclobutyl)-5-phenylisoxazole-3-carboxamide

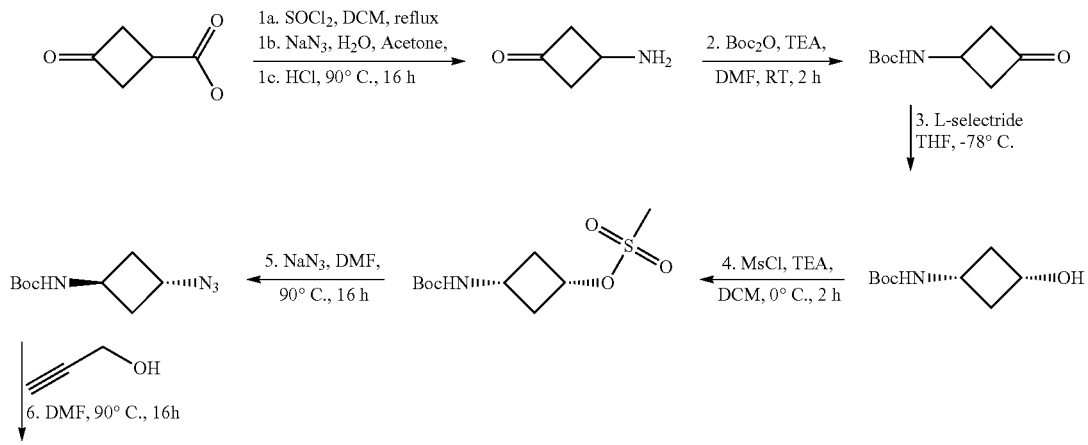

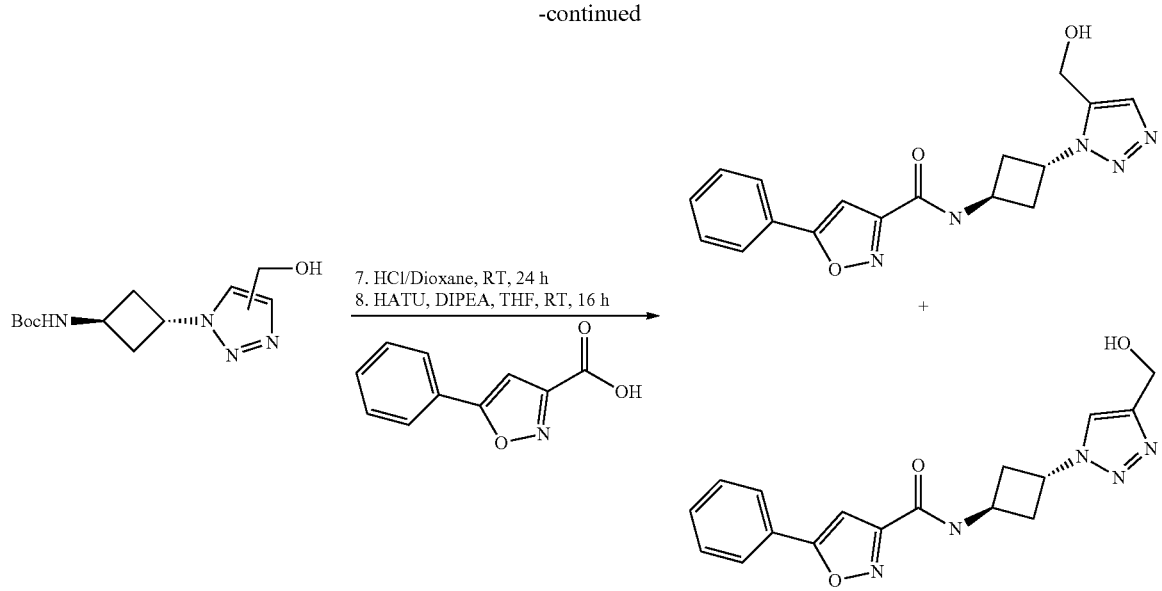

Step 1: 3-Amino-cyclobutan-1-one

SOCl$_2$ (15.6 g, 131.46 mmol) was added dropwise to an ice-cooled solution of 3-oxocyclobutane carboxylic acid (5.0 g, 43.82 mmol) in dry DCM (30 mL) and the reaction mixture was refluxed for 3 h. The reaction mixture was cooled to room temperature and the volatiles were removed under reduced pressure to get the crude compound which was azeotropically distilled with toluene (20 mL×2) to remove acidic traces. The crude compound was dissolved in dry acetone (15 mL) and to the resulting solution was added a solution of NaN$_3$ (5.69 g, 87.64 mmol) in water (20 mL) at 0° C. over 30 min. The reaction mixture was stirred for 1 h at 0° C. and crushed ice was added to the reaction mixture. The aq. phase was extracted with ether (3×50 mL), dried over sodium sulfate and concentrated to ~¼th volume. Then the reaction mixture was added to toluene (70 mL) and heated to 90° C., until evolution of N$_2$ ceased (~30 min). To the resulting reaction mixture was added 20% HCl (50 mL) at 0° C. and the reaction mixture was gently heated to 90° C. for 16 h. Organic layer was separated off and washed with water (50 mL). The aqueous layer was concentrated under vacuum to get the compound (5 g, crude) as a brown solid. $^1$H-NMR (400 MHz, CDCl$_3$) δ 8.75 (br, 3H), 3.92-3.86 (m obscured by solvent signal, 2H), 3.38-3.31 (m, 3H).

Step 2: tert-butyl (3-oxocyclobutyl) Carbamate

TEA (29.72 g, 293.73 mmol) was added dropwise to a solution of 3-aminocyclobutan-1-one (5.0 g, 58.74 mmol) and Boc$_2$O (25.64 g, 117.49 mmol) in DMF (80 mL) and the reaction mixture was stirred at room temperature for 2 h. After complete consumption of starting material as indicated by TLC, the reaction mixture was diluted with water (100 mL) and extracted with diethyl ether (70 mL×6). Combined organic layer was washed with brine (100 mL×2) and dried over Na$_2$SO$_4$. The solvent was removed under reduced pressure to get the crude compound which was purified by silica gel (100-200) column chromatography using 30% ethyl acetate in n-hexane to afford the product (5.3 g, 65% after two steps) as an off-white solid. $^1$H-NMR (400 MHz, CDCl$_3$) δ 4.91 (br, 1H), 4.25 (br, 1H), 3.41-3.34 (m, 2H), 3.07-3.00 (m, 2H), 1.44 (s, 9H).

Step 3: tert-butyl cis-3-hydroxycyclobutyl)carbamate a solution of L-Selectride (1M solution in THF) (8.053 mL, 8.05 mmol) was added dropwise over a period of 20 min to a solution of tert-butyl (3-oxocyclobutyl)carbamate (1.0 g, 5.40 mmol) in THF (25 mL) under N$_2$ atmosphere at −78° C. and the reaction mixture was stirred for 1 h at −78° C. To the resulting reaction mixture was added a solution of NaOH (3.25 g) in water (4 mL) over a period of 10 min followed by 30% aqueous H$_2$O$_2$ (3 mL) over a period of 20 min. The reaction mixture was allowed to warm to room temperature and diluted with ethyl acetate (100 mL). The organic layer was separated off and washed with 10% aq. Na$_2$SO$_3$ (40 mL) followed by brine (40 mL). The organic layer dried over Na$_2$SO$_4$ and concentrated under reduced pressure to get the crude compound which was further purified by neutral alumina column chromatography using 50% ethyl acetate in n-hexane as eluent to afford the desired compound. The compound was washed with n-hexane to get the product (0.750 g, 74%) as white solid. m. p. 119° C. (lit. value 117° C.). $^1$H NMR (400 MHz, CDCl$_3$) δ 4.63 (br, 1H), 4.03-3.96 (m, 1H), 3.66-3.64 (m, 1H), 2.76-2.72 (m, 2H), 1.91 (br, 1H), 1.79-1.76 (m, 2H), 1.42 (s, 9H).

Step 4: cis-3-((tert-butoxycarbonyl)amino)cyclobutyl methanesulfonate triethylamine (1.0 g, 9.93 mmol) was added to a cold (−10° C.) solution of tert-butyl (cis-3-hydroxycyclobutyl) carbamate (0.62 g, 3.31 mmol) in DCM (30 mL) followed by dropwise addition of methanesulfonyl chloride (0.45 g, 3.97 mmol) and the reaction mixture was stirred at −10° C. for 2 h. The reaction mixture was diluted with DCM (100 mL) and washed with water (5 mL) followed by dilute citric acid (30 mL) and brine (30 mL). The organic layer was dried over Na$_2$SO$_4$, concentrated under reduced pressure to get the product (0.800 g, crude) as white solid which was used as such in next step without further purification. ¹H NMR (400 MHz, CDCl₃) δ 4.73-4.66 (m, 2H), 3.85-3.80 (m, 1H), 2.98 (s, 3H), 2.93-2.86 (m, 2H), 2.20-2.13 (m, 2H), 1.42 (s, 9H).

Step 5: tert-butyl (trans-3-azidocyclobutyl) Carbamate

NaN₃ (0.49 g, 7.54 mmol) was added to a solution of cis-3-((tert-butoxycarbonyl) amino) cyclobutyl methanesulfonate (0.8 g, 3.01 mmol) in dry DMF (20 mL) and the mixture was heated at 85° C. for 16 h. The reaction mixture was diluted with water (40 mL) and the aqueous phase was extracted with ethyl acetate (50 mL×3). Combined organic layer was washed with brine (50 mL×4) and dried over Na₂SO₄. The solvent was removed under reduced pressure to get the crude product (0.73 g) as an off-white solid. Although DMF was present in the crude according to ¹H-NMR, it was used as such in the next step without further purification.

Step 6: tert-butyl trans-3-(5-(hydroxymethyl)-1H-1,2,3-triazol-1-yl)cyclobutyl)carbamate and tert-butyl (trans-3-(4-(hydroxymethyl)-1H-1,2,3-triazol-1-yl) cyclobutyl)carbamate a solution of tert-butyl trans-3-azidocyclobutyl)carbamate (0.98 g, 4.62 mmol) in DMF (5 mL) and propargyl alcohol (1.29 g, 23.08 mmol) was heated at 100° C. in a sealed tube for 16 h. The mixture was diluted with water (30 mL) and the aqueous phase was extracted with ethyl acetate (25 mL×7). Combined organic layer was dried over Na₂SO₄ and solvent was removed under reduced pressure to get the crude compound which was further purified by neutral alumina column chromatography using 80% ethyl acetate in n-hexane as eluent to afford a fraction of 5-isomer enriched (4/1 ratio of isomers 5/4, 0.350 g, 28%) as an off-white solid and elution with 5% methanol in DCM afforded a fraction of 4-isomer enriched (1/3 ratio of isomers 5/4, 0.52 g, 42%) as an off-white solid. LC-MS: (M+H)⁺=269.1

N-trans-3-(5-(hydroxymethyl)-1H-1,2,3-triazol-1-yl) cyclobutyl)-5-phenylisoxazole-3-carboxamide Step 7a: (1-trans-3-aminocyclobutyl)-1H-1,2,3-triazol-5-yl)methanol A suspension of a mixture of (1-((trans-3-aminocyclobutyl)-1H-1,2,3-triazol-5/4-yl)methanol isomers (4/1 ratio, 0.35 g, 1.30 mmol) and 4M HCl in dioxane (30 mL) was stirred at room temperature for 24 h. Volatiles were removed under reduced pressure to get compound (0.35 g, crude) as a white solid.

Step 8a: N-trans-3-(5-(hydroxymethyl)-1H-1,2,3-triazol-1-yl)cyclobutyl)-5-phenylisoxazole-3-carboxamide DIPEA (0.47 g, 3.64 mmol) and HATU (0.554 g, 1.45 mmol) were added sequentially to a solution of 5-phenylisoxazole-3-carboxylic acid (0.230 g, 1.21 mmol) in THF (15 mL) and the reaction mixture was stirred for 30 min. The mixture of amine isomers from step 7a was added (0.204 g, 1.21 mmol) to the reaction mixture and stirred at room temperature for 16 h. The reaction mixture was diluted with water (30 mL) and the aqueous phase was extracted with ethyl acetate (30 mL×3). Combined organic layer was dried over Na₂SO₄ and concentrated under reduced pressure to get crude compound which was purified by neutral alumina column chromatography. Elution with 2.5% MeOH in DCM as eluent afforded the desired compound which was further washed with ethyl acetate (2 mL×2) to obtain N-((trans-3-(5-(hydroxymethyl)-1H-1,2,3-triazol-1-yl)cyclobutyl)-5-phenylisoxazole-3-carboxamide (0.110 g).

Yield: 24% over two steps
Appearance: white solid
Analytical data: ¹H-NMR (400 MHz, CDCl₃) δ 9.38 (d, 1H, J=7.3 Hz), 7.96-7.93 (m, 2H), 7.64 (s, 1H), 7.62-7.52 (m, 3H), 7.40 (s, 1H), 5.44-5.41 (t, 1H, J=5.5 Hz), 5.24-5.17 (m, 1H), 4.80-4.73 (m, 1H), 4.55 (d, 1H, J=5.5 Hz), 2.89-2.84 (m, 2H), 2.81-2.76 (m, 2H).
LC-MS: (M+H)⁺=340.0
HPLC purity: 97.5% at 220 nm and 97.2% at 254 nm.

N-((trans-3-(4-(hydroxymethyl)-1H-1,2,3-triazol-1-yl) cyclobutyl)-5-phenylisoxazole-3-carboxamide Step 7b (1-trans-3-aminocyclobutyl)-1H-1,2,3-triazol-4-yl) methanol: A suspension of a mixture of (1-(trans-3-aminocyclobutyl)-1H-1,2,3-triazol-5/4-yl)methanol isomers (1/3 ratio, 0.52 g, 1.93 mmol) and 4M HCl in dioxane (30 mL) was stirred at room temperature for 24 h. Volatiles were removed under reduced pressure to get compound (0.52 g, crude) as a white solid.

Step 8b: N-trans-3-(4-(hydroxymethyl)-1H-1,2,3-triazol-1-yl)cyclobutyl)-5-phenylisoxazole-3-carboxamide DIPEA (0.650 g, 5.074 mmol) and HATU (0.771 g, 2.03 mmol) were added sequentially to a solution of 5-phenylisoxazole-3-carboxylic acid (0.320 g, 1.69 mmol) in THF (15 mL) and the reaction mixture was stirred for 30 min. The mixture of amine isomers from step 7b was added (0.284 g, 1.69 mmol) to the reaction mixture and stirred at room temperature for 16 h. The reaction mixture was diluted with water (30 mL) and the aqueous phase was extracted with ethyl acetate (30 mL×3). Combined organic layer was dried over Na₂SO₄ and concentrated under reduced pressure to get crude compound which was purified by neutral alumina column chromatography. Elution with 2.5% MeOH in DCM as eluent afforded the desired compound which was further washed with ethyl acetate (2 mL×2) to obtain N-((trans-3-(4-(hydroxymethyl)-1H-1,2,3-triazol-1-yl)cyclobutyl)-5-phenylisoxazole-3-carboxamide (0.270 g, 41% over two steps).

Yield: 41% over two steps
Appearance: white solid
Analytical data: ¹H-NMR (400 MHz, CDCl₃) δ 9.39-9.37 (d, 1H, J=7.3 Hz), 8.16 (s, 1H), 7.96-7.93 (m, 2H), 7.59-7.53 (m, 3H), 7.39 (s, 1H), 5.27-5.22 (m, 1H), 5.20-5.17 (t, 1H, J=5.6 Hz), 4.75-4.69 (m, 1H), 4.53-4.51 (d, 1H, J=5.6 Hz), 2.84-2.76 (m, 4H).
LC-MS: (M+H)⁺=339.9
HPLC purity: 99.4% at 220 nm and 99.7% at 254 nm.

Example 2: N-cis-3-(5-(hydroxymethyl)-1H-1,2,3-triazol-1-yl) cyclobutyl)-5-phenylisoxazole-3-carboxamide and N-cis-3-(4-(hydroxymethyl)-1H-1,2,3-triazol-1-yl) cyclobutyl)-5-phenylisoxazole-3-carboxamide

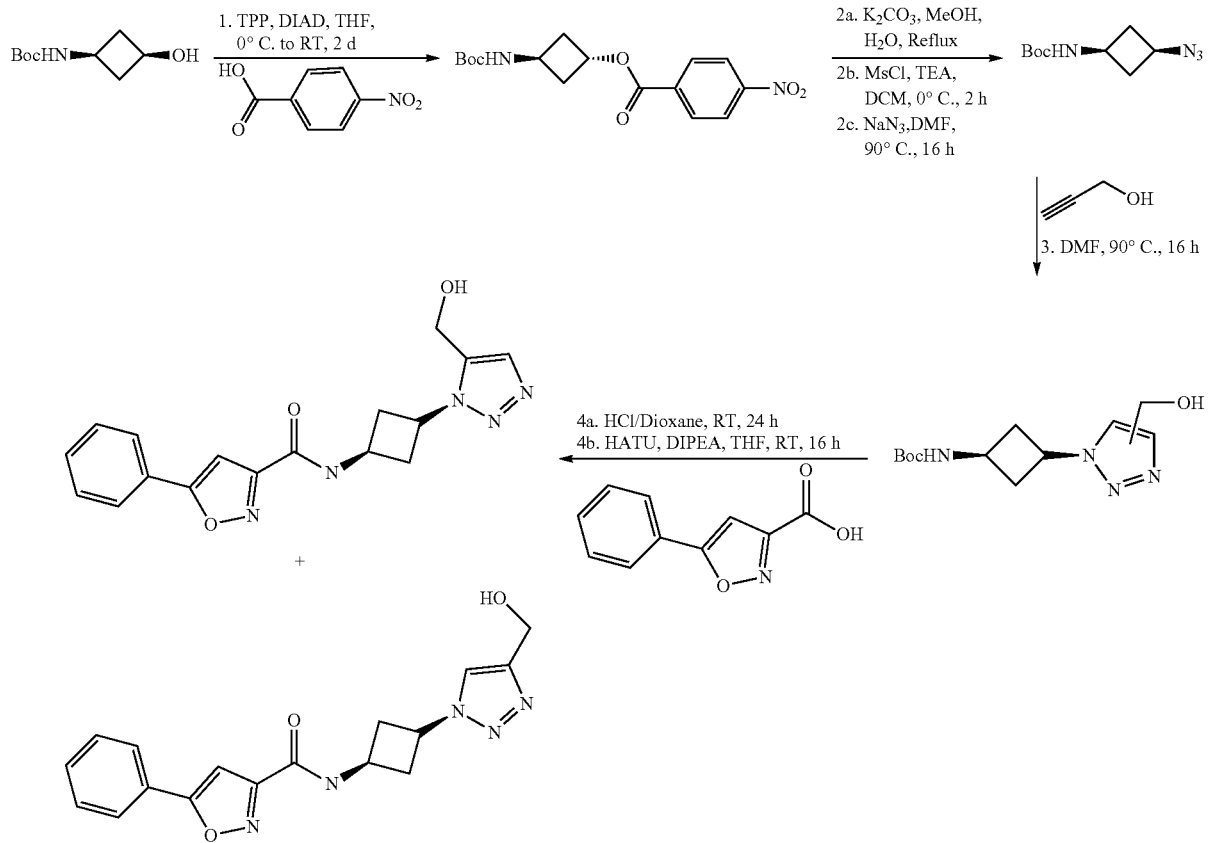

Step 1: trans-3-((tert-butoxycarbonyl)amino)cyclobutyl 4-nitrobenzoate

To an ice-cooled solution of tert-butyl (cis-3-hydroxycyclobutyl)carbamate (1.5 g, 80.11 mmol) and 4-nitrobenzoic acid (1.47 g, 88.12 mmol) in dry THF (60 mL) was added triphenyl phosphine (3.15 g, 12.01 mmol) followed by dropwise addition of DIAD (8.09 g, 40.05 mmol) and the reaction mixture was stirred at room temperature for 2 days. Solvent was removed under reduced pressure to get the crude compound which was purified by silica gel (100-200 mesh) column chromatography. Elution with 50% ethyl acetate in n-hexane followed by washing with diethyl ether (4 mL×2) gave the product (2.3 g, 85%) as a white solid. $^1$H-NMR (400 MHz, CDCl$_3$) δ 8.29-8.27 (q, 2H, J=8.92 Hz), 8.21-8.19 (q, 2H, J=8.92 Hz), 5.37-5.32 (m, 1H), 4.77 (br, 1H), 4.41-4.38 (m, 1H), 2.64-2.58 (m, 2H), 2.47-2.40 (m, 2H), 1.44 (s, 9H); LC-MS: (M+H)$^+$=336.8.

Step 2a: Trans-tert-butyl-3-hydroxycyclobutyl carbamate trans-3-((tert-butoxycarbonyl) amino) cyclobutyl 4-nitrobenzoate was added (2.3 g, 68.38 mmol) to a suspension of K$_2$CO$_3$ (1.41 g, 10.25 mmol) in MeOH (50 mL) and water (10 mL) and the reaction mixture was heated to reflux for 2 h. The reaction mixture was cooled and filtered through celite bed. Filtrate was concentrated under reduced pressure to get the crude product (4.2 g, crude) as an off-white solid which was used as such without further purification.

Step 2b: trans-3-((tert-butoxycarbonyl)amino)cyclobutyl methanesulfonate triethyl amine (6.8 g, 67.29 mmol) was added to a suspension of trans-tert-butyl-3-hydroxycyclobutyl carbamate (4.2 g, 22.43 mmol) in DCM (100 mL) followed by dropwise addition of methanesulfonyl chloride (3.08 g, 26.91 mmol) at −10° C. and the reaction mixture was stirred at −10° C. for 2 h. The reaction mixture was diluted with DCM (100 mL) and washed with water (50 mL) followed by brine (30 mL). The organic layer was dried over sodium sulfate and concentrated under reduced pressure to obtain the crude product (3.4 g, crude) as a yellow solid which was used as such in next step without purification.

Step 2c: cis-tert-butyl (3-azidocyclobutyl)carbamate sodium azide (2.08 g, 32.035 mmol) was added to a solution of trans-3-((tert-butoxycarbonyl)amino)cyclobutyl methanesulfonate (3.4 g, 12.81 mmol) in dry DMF (20 mL) at room temperature and the reaction mixture was heated at 85° C. for 16 h. The crude reaction mixture was diluted with water (50 mL) and the aqueous phase was extracted with ethyl acetate (50 mL×3). The combined organic layer was washed with brine (50 mL×4) and dried over Na$_2$SO$_4$. The solvent was removed under reduced pressure to give the crude compound which was purified by neutral alumina column chromatography using 10% MeOH in DCM as eluent to afford the product (1.0 g, 68% after two steps) as a white solid. $^1$H NMR (400 MHz, CDCl$_3$) δ 4.66 (br, 1H), 3.86-3.84 (m, 1H), 3.57-3.53 (m, 1H), 2.76-2.69 (m, 2H), 1.92-1.85 (m, 2H), 1.42 (s, 9H).

Step 3: cis-[3-(4/5-Hydroxymethyl-[1,2,3]triazol-1-yl)-cyclobutyl]-carbamic acid tert-butyl ester a mixture of cis-tert-butyl (3-azidocyclobutyl)carbamate (0.280 g, 1.32 mmol) and propargyl alcohol (0.221 g, 3.96 mmol) in DMF (5 mL) was heated at 100° C. in a sealed tube for 16 h. Solvent was removed under reduced pressure to get crude compound which was purified by neutral alumina column chromatography using 5% methanol in DCM as eluent to obtain a mixture of 4/5 regioisomers (0.30 g, 84%) as a viscous oil. This mixture was used as such in the next reaction. LC-MS: (M+H)$^+$=269.0.

Step 4a: (1-cis-3-aminocyclobutyl)-1H-1,2,3-triazol-4/5-yl)methanol (A)

A suspension of cis-[3-(4/5-hydroxymethyl-[1,2,3]triazol-1-yl)-cyclobutyl]-carbamic acid tert-butyl ester (0.30 g, 1.12 mmol) in 4M HCl in dioxane (30 mL) was stirred at room temperature for 24 h. Volatiles were removed under reduced pressure to get the crude mixture (0.30 g, crude) as off-white solid which was used as such in next step without further purification. As per $^1$H-NMR, it is a 50:50 mixture of two regioisomers.

Step 4b: N-(cis-3-(5-(hydroxymethyl)-1H-1,2,3-triazol-1-yl)cyclobutyl)-5-phenylisoxazole-3-carboxamide and N-(cis-3-(4-(hydroxymethyl)-1H-1,2,3-triazol-1-yl)cyclobutyl)-5-phenylisoxazole-3-carboxamide DIPEA (0.69 g, 3.64 mmol) was added to a solution of 5-phenylisoxazole-3-carboxylic acid (0.337 g, 1.78 mmol) in THF (10 mL) followed by HATU (0.813 g, 2.14 mmol) and the reaction mixture was stirred for 30 min. The amine (A) (0.300 g) was added to the mixture and the reaction mixture was stirred at room temperature for 16 h. The reaction mixture was diluted with water (30 mL) and the aqueous phase was extracted with ethyl acetate (30 mL×3). The combined organic layer was dried over Na$_2$SO$_4$ and concentrated under reduced pressure to get the crude mixture which was purified by preparative HPLC to get the two regioisomers:

N-(cis-3-(5-(hydroxymethyl)-1H-1,2,3-triazol-1-yl)cyclobutyl)-5-phenylisoxazole-3-carboxamide (0.040 g)

Appearance: pale pink solid
Analytical data: $^1$H-NMR (400 MHz, CDCl$_3$) δ 9.30 (d, 1H, J=7.4 Hz), 7.92-7.89 (m, 2H), 7.59 (s, 1H), 7.55-7.51 (m, 3H), 7.35 (s, 1H), 5.42 (t, 1H, J=5.5 Hz), 4.81-4.73 (m, 1H), 4.54 (d, 2H, J=5.5 Hz), 4.39-4.30 (m, 1H), 2.86-2.77 (m, 4H).
LC-MS: (M+H)$^+$=339.9
HPLC purity: 99.04% at 220 nm and 99.35% at 254 nm.

N-(cis-3-(4-(hydroxymethyl)-1H-1,2,3-triazol-1-yl)cyclobutyl)-5-phenylisoxazole-3-carboxamide (0.040 g)

Appearance: white solid
Analytical data: $^1$H-NMR (400 MHz, CDCl$_3$) δ 9.26 (d, 1H, J=8.32 Hz), 8.21 (s, 1H), 7.96-7.93 (m, 2H), 7.56-7.54 (m, 3H), 7.39 (s, 1H), 5.22 (t, 1H, J=5.5 Hz), 4.99-4.91 (m, 1H), 4.54 (d, 2H, J=5.5 Hz), 4.46-4.41 (m, 1H), 2.95-2.88 (m, 2H), 2.72-2.64 (m, 2H).
LC-MS: (M+H)$^+$=340.0
HPLC purity: 96.69% at 220 nm and 97.09% at 254 nm.
Yield: 22% over two steps.

Example 3: N-Cis-3-(4-((S)-1-hydroxyethyl)-1H-1,2,3-triazol-1-yl)cyclobutyl)-5-phenylisoxazole-3-carboxamide and N-cis-3-(5-((S)-1-hydroxyethyl)-1H-1,2,3-triazol-1-yl)cyclobutyl)-5-phenylisoxazole-3-carboxamide were prepared by the procedure described in example 2 using (S)-3-butyn-2-ol.

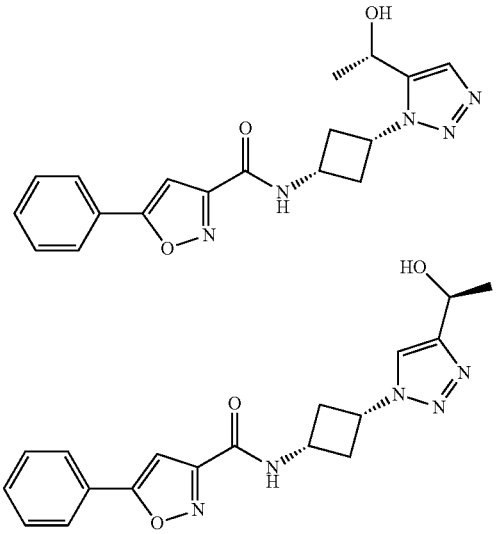

Yield: 57% over last 2 steps

N-Cis-3-(5-((S)-1-hydroxyethyl)-1H-1,2,3-triazol-1-yl)cyclobutyl)-5-phenylisoxazole-3-carboxamide
Appearance: pale pink solid Analytical data: $^1$H-NMR (400 MHz, CDCl$_3$) δ 9.34 (d, 1H, J=7.5 Hz), 7.95-7.92 (m, 2H), 7.61 (s, 1H), 7.59-7.54 (m, 3H), 7.38 (s, 1H), 5.51 (d, 1H, J=5.9 Hz), 4.91-4.85 (m, 2H), 4.40-4.34 (m, 1H), 2.88-2.80 (m, 4H), 1.43 (d, 3H, J=6.5 Hz).
LC-MS: (M+H)$^+$=354.0
HPLC purity: 99.84% at 220 nm and 99.80% at 254 nm N-Cis-3-(4-((S)-1-hydroxyethyl)-1H-1,2,3-triazol-1-yl)cyclobutyl)-5-phenylisoxazole-3-carboxamide
Appearance: white solid 1H-NMR (400 MHz, CDCl$_3$) δ 9.26 (d, 1H, J=8.4 Hz), 8.18 (s, 1H), 7.95-7.93 (m, 2H), 7.59-7.53 (m, 3H), 7.40 (s, 1H), 5.30 (d, 1H, J=4.8 Hz), 4.96-4.92 (m, 1H), 4.86-4.80 (m, 1H), 4.47-4.41 (m, 1H), 2.95-2.88 (m, 2H), 2.71-2.64 (m, 2H), 1.41 (d, 3H, J=6.5 Hz).
LC-MS: (M+H)$^+$=354.1
HPLC purity: 99.53% at 220 nm and 99.54% at 254 nm.

Example 4: N-((trans-3-(5-(hydroxymethyl)-1,3,4-thiadiazol-2-yl)cyclobutyl)methyl)-5-phenylisoxazole-3-carboxamide and N-((cis-3-(5-(hydroxymethyl)-1,3,4-thiadiazol-2-yl)cyclobutyl)methyl)-5-phenylisoxazole-3-carboxamide

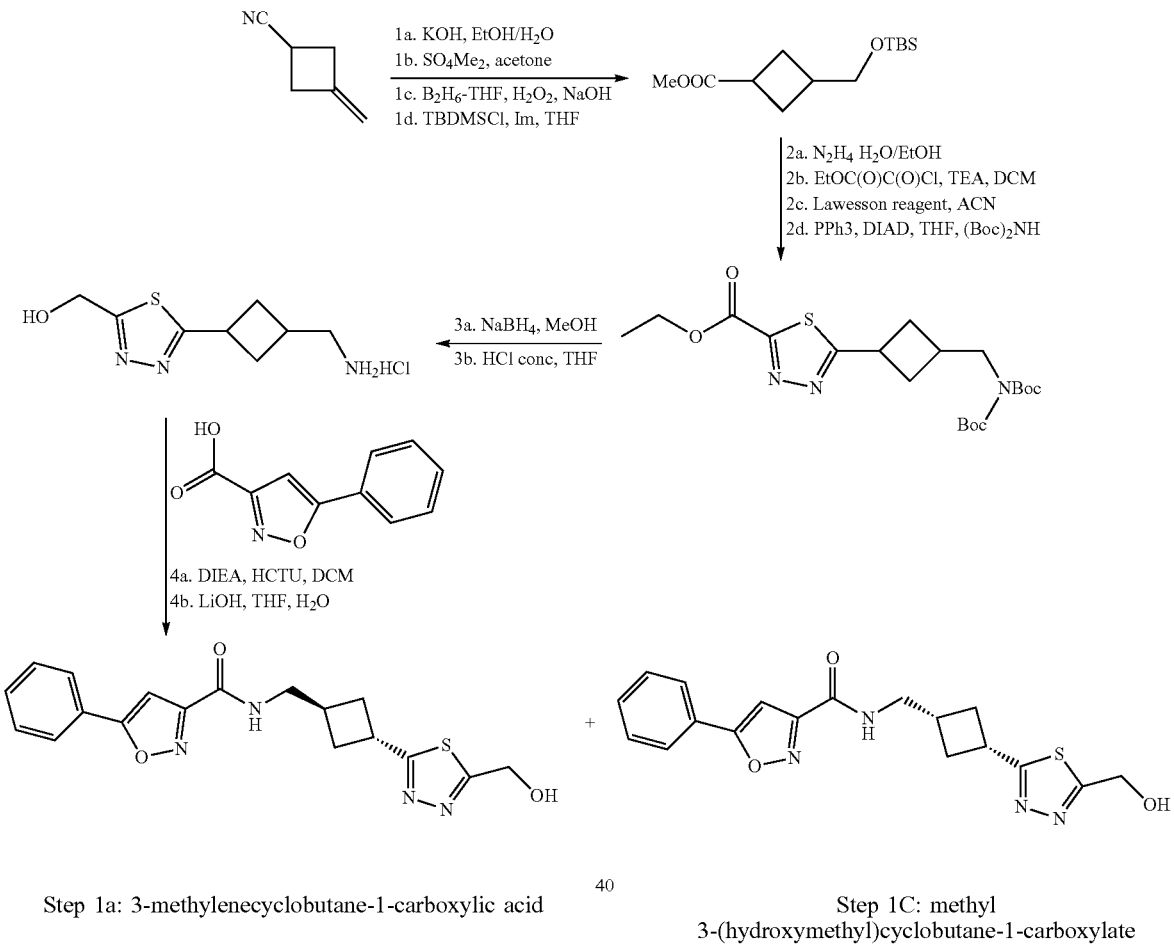

Step 1a: 3-methylenecyclobutane-1-carboxylic acid

To a solution of 3-methylidenecyclobutane-1-carbonitrile (6 g, 64.43 mmol, 1.00 eq.) in H₂O/EtOH (40/40 mL), was added potassium hydroxide (15 g, 267.33 mmol, 4.00 eq.) in several batches at 105° C. in 30 min. The resulting solution was stirred for 2 hours at 105° C. The resulting solution was diluted with water (200 mL) and the pH was adjusted to 2 with conc. hydrogen chloride aqueous (12 M). The resulting solution was extracted with ethyl acetate (2×200 mL) and the organic layers combined. The resulting mixture was washed with brine (2×200 mL), dried over anhydrous sodium sulfate and concentrated under vacuum to give of 3-methylidenecyclobutane-1-carboxylic acid as yellow oil (7 g, 97%).

Step 1b: methyl 3-methylenecyclobutane-1-carboxylate potassium carbonate (61.5 g, 444.98 mmol, 2.00 eq.) and dimethyl sulfate (33 g, 261.63 mmol, 1.20 eq.) were added to a solution of 3-methylidenecyclobutane-1-carboxylic acid (25 g, 222.96 mmol, 1.00 eq.) in acetone (300 mL). The resulting solution was stirred for 2 hours at 60° C. The resulting solution was diluted with water (700 mL) and then extracted with ethyl acetate (2×500 mL) and the organic layers combined. The resulting mixture was washed with brine (2×500 mL), dried over anhydrous sodium sulfate and concentrated under vacuum. This resulted in 30 g (crude) of methyl 3-methylidenecyclobutane-1-carboxylate as yellow oil.

Step 1C: methyl 3-(hydroxymethyl)cyclobutane-1-carboxylate a solution of borane-THF (56 mL, 0.80 eq.) was added dropwise over 30 min to a cold (−10° C.) solution of methyl 3-methylidenecyclobutane-1-carboxylate (10 g, 79.27 mmol, 1.00 eq.) in THF (100 mL). The resulting solution was stirred for 3 hours at 25° C. The mixture was cooled to −10° C. and methanol (20 mL) was added slowly and the mixture was stirred for 30 min at 25° C. The reaction mixture was cooled to −10° C. and H₂O₂ (9 g, 79.41 mmol, 1.00 eq., 30%) was added dropwise (5 min) followed by dropwise addition of sodium hydroxide aqueous (12.5 mL) at −10° C. The resulting solution was stirred for 3 hours at 25° C. The reaction was then quenched by the addition of Na₂SO₃ aqueous. The resulting solution was diluted with water (300 mL) and then extracted with ethyl acetate (2×300 mL) and the organic layers combined. The resulting mixture was washed with brine (2×300 mL), dried over anhydrous sodium sulfate and concentrated under vacuum to give methyl 3-(hydroxymethyl)cyclobutane-1-carboxylate as colorless oil (6.6 g, 58%).

Step 1d: methyl 3-(((tert-butyldimethylsilyl)oxy)methyl)cyclobutane-1-carboxylate imidazole (5.4 g, 79.41 mmol, 2.00 eq.) and TBDMSCl (9.4 g, 62.38 mmol, 1.50 eq.) were added to a solution of methyl 3-(hydroxymethyl)cyclobutane-1-carboxylate (5 g, 34.68 mmol, 1.00 eq.) in tetrahydrofuran (100 mL) and the resulting solution was stirred for 16 hours at 40° C. The mixture was diluted with water (200 mL) and then extracted with ethyl acetate (3×200 mL) and the organic layers were combined. The resulting mixture was washed with brine (2×300 mL), dried over anhydrous sodium sulfate and concentrated under vacuum to give methyl 3-[[(tert-butyldimethylsilyl)oxy]methyl]cyclobutane-1-carboxylate as a yellow oil (8 g, 89%).

Step 2a: 3-(((tert-butyldimethylsilyl)oxy)methyl)cyclobutane-1-carbohydrazide hydrazine hydrate (20 mL) was added to a solution of methyl 3-[[(tert-butyldimethylsilyl)oxy]methyl]cyclobutane-1-carboxylate (8 g, 30.96 mmol, 1.00 eq.) in ethanol (100 mL). The resulting solution was stirred for 2 hours at 80° C., diluted with water (300 mL) and then extracted with ethyl acetate (2×300 mL) and the organic layers combined. The resulting mixture was washed with brine (2×200 mL), dried over anhydrous sodium sulfate and concentrated under vacuum to give 3-[[(tert-butyldimethylsilyl)oxy]methyl]cyclobutane-1-carbohydrazide (7.5 g, 94%) as a yellow oil. LC-MS: (M+H)$^+$:259.1 [M+H]$^+$.

Step 2b: ethyl 2-(2-(3-(((tert-butyldimethylsilyl)oxy)methyl)cyclobutane-1-carbonyl)hydrazinyl)-2-oxoacetate ethyl 2-chloro-2-oxoacetate (8.87 g, 64.97 mmol, 1.10 eq.) was added dropwise (in 10 min) to a solution of 3-[[(tert-butyldimethylsilyl)oxy]methyl]cyclobutane-1-carbohydrazide (15.3 g, 59.20 mmol, 1.00 eq.) and TEA (9 g, 88.94 mmol, 1.50 eq.) in dichloromethane (200 mL) at 0° C. The resulting solution was stirred for 1 hour at 25° C., diluted with dichloromethane (300 mL) and it was then washed with brine (2×200 mL), dried over anhydrous sodium sulfate and concentrated under vacuum. The residue was applied onto a silica gel column and eluted with petroleum ether/ethyl acetate (2:1) to give ethyl 2-[(3-[[(tert-butyldimethylsilyl)oxy]methyl]cyclobutyl)formohydrazido]-2-oxoacetate (15 g, 71%) as a yellow oil. LC-MS: 359.0 [M+H]$^+$.

Step 2c: ethyl 5-(3-(hydroxymethyl)cyclobutyl)-1,3,4-thiadiazole-2-carboxylate Lawesson reagent (17 g, 42.03 mmol, 1.00 eq.) was added to a solution of ethyl 2-(2-(3-(((tert-butyldimethylsilyl)oxy)methyl)cyclobutane-1-carbonyl)hydrazinyl)-2-oxoacetate (15 g, 41.84 mmol, 1.00 eq.) in ACN (150 mL) and the solution was stirred for 2 hours at 50° C. The reaction mixture was diluted with water (300 mL), extracted with ethyl acetate (2×300 mL) and the organic layers combined. The resulting mixture was washed with brine (2×200 mL), dried over anhydrous sodium sulfate and concentrated under vacuum. The residue was purified by silica gel column with ethyl acetate/petroleum ether (2:1) followed by purification by Flash-Prep-HPLC using the following conditions (Intel-Flash-1): Column, C18 silica gel; mobile phase, X:H$_2$O Y:ACN=95/5 increasing to X:H$_2$O Y:ACN=40/60 within 50 min; Detector, UV 254 nm. This resulted in 3.4 g (34%) of ethyl 5-[3-(hydroxymethyl)cyclobutyl]-1,3,4-thiadiazole-2-carboxylate as a yellow oil. LC-MS: 243.2 [M+H]$^+$.

Step 2d: ethyl 5-(3-((bis((tert-butoxy)carbonyl)amino)methyl)cyclobutyl)-1,3,4-thiadiazole-2-carboxylate To a solution of ethyl 5-[3-(hydroxymethyl)cyclobutyl]-1,3,4-thiadiazole-2-carboxylate (1.8 g, 7.43 mmol, 1.00 eq.) in tetrahydrofuran (100 mL) was added triphenyl phosphine (3.9 g, 14.87 mmol, 2.00 eq.) in portions at 0° C. in 10 min. This was followed by the addition of DIAD (3 g, 14.78 mmol, 2.00 eq.) and di-tert-butyl iminodicarboxylate (2.4 g, 11.05 mmol, 1.50 eq.). The resulting solution was stirred for 3 hours at 25° C. and then diluted with water (200 mL). The resulting solution was extracted with ethyl acetate (3×200 mL) and the organic layers combined. The mixture was washed with brine (2×200 mL), dried over anhydrous sodium sulfate and concentrated under vacuum. The residue was purified by silica gel column using ethyl acetate/petroleum ether (1:5) to give the product (1.1 g, 33%) as a yellow solid. LC-MS: [M+H]$^+$ 442.3

Step 3a: tert-butyl [3-[5-(hydroxymethyl)-1,3,4-thiadiazol-2-yl]cyclobutyl]methyl N-[(tert-butoxy)carbonyl]carbamate NaBH$_4$ (310 mg, 8.19 mmol, 1.50 eq.) was added to a solution of ethyl-(3-((bis((tert-butoxy)carbonyl)amino)methyl)cyclobutyl)-1,3,4-thiadiazole-2-carboxylate (2.4 g, 5.42 mmol, 1.00 eq.) in methanol (50 mL), in portions at 0° C. in 10 min and the reaction mixture was then stirred for 1 hour at 25° C. The reaction was then quenched with water (200 mL). The resulting solution was extracted with ethyl acetate (2×200 mL) and the organic layers combined. The resulting mixture was washed with brine (2×200 mL), dried over anhydrous sodium sulfate and concentrated under vacuum to give the product (2 g, 92%) of as yellow oil. LC-MS: 400.0 [M+H]$^+$.

Step 3b: (5-(3-(aminomethyl)cyclobutyl)-1,3,4-thiadiazol-2-yl)methanol hydrochloride conc. hydrogen chloride aqueous (4 mL) was added to a solution of tert-butyl [3-[5-(hydroxymethyl)-1,3,4-thiadiazol-2-yl]cyclobutyl]methyl N-[(tert-butoxy)carbonyl]carbamate (2 g, 4.99 mmol, 1.00 eq.) in tetrahydrofuran (20 mL) and the solution was stirred for 16 hours at 25° C. The resulting mixture was concentrated under vacuum, the solid was washed with 20 mL of ethyl acetate to give the product (750 mg, 75%) as a yellow solid. LC-MS: 200.1 [M+H—HCl]$^+$.

Step 4a: (5-(3-((5-phenylisoxazole-3-carboxamido)methyl)cyclobutyl)-1,3,4-thiadiazol-2-yl)methyl 5-phenylisoxazole-3-carboxylate a solution of [5-[3-(aminomethyl)cyclobutyl]-1,3,4-thiadiazol-2-yl]methanol hydrogen chloride (750 mg, 3.17 mmol, 1.00 eq.), 5-phenyl-1,2-oxazole-3-carboxylic acid (860 mg, 4.55 mmol, 1.40 eq.), HCTU (1.59 g, 3.82 mmol, 1.20 eq.) and DIEA (1.66 g, 12.84 mmol, 3.00 eq.) in dichloromethane (50 mL) was stirred for 3 hours at 25° C. The resulting mixture was concentrated under vacuum. This resulted in 800 mg (crude) [5-(3-[[(5-phenyl-1,2-oxazol-3-yl)formamido]methyl]cyclobutyl)-1,3,4-thiadiazol-2-yl]methyl 5-phenyl-1,2-oxazole-3-carboxylate as a yellow oil. The crude product was used in the next step directly without further purification. LC-MS: 542.0 [M+H]$^+$.

Step 4b: N-((trans-3-(5-(hydroxymethyl)-1,3,4-thiadiazol-2-yl)cyclobutyl)methyl)-5-phenylisoxazole-3-carboxamide and N-((cis-3-(5-(hydroxymethyl)-1,3,4-thiadiazol-2-yl)cyclobutyl)methyl)-5-phenylisoxazole-3-carboxamide LiOH (142 mg, 5.93 mmol, 4.00 eq.) was added to a solution of [5-(3-[[(5-phenyl-1,2-oxazol-3-yl)formamido]methyl]cyclobutyl)-1,3,4-thiadiazol-2-yl]methyl 5-phenyl-1,2-oxazole-3-carboxylate (800 mg, 1.48 mmol, 1.00 eq.) in tetrahydrofuran/H₂O (20/5 mL) and the solution was stirred for 30 min at 25° C. The resulting solution was diluted with water (100 mL), extracted with ethyl acetate (2×100 mL) and the organic layers combined. The resulting mixture was washed with brine (2×100 mL) brine, dried over anhydrous sodium sulfate and concentrated under vacuum. The crude product was re-crystallized from petroleum ether/ethyl acetate in the ratio of 5:1. The solid was separated by Prep-SFC with the following conditions (prep SFC 350-2): Column, Phenomenex Lux 5μ Cellulose-3, 5*25 cm, 5 um; mobile phase, CO₂ (50%), methanol (50%); Detector, UV 220 nm.

5-phenyl-N-[[(trans-3-[5-(hydroxymethyl)-1,3,4-thiadiazol-2-yl]cyclobutyl]methyl]-1,2-oxazole-3-carboxamide Yield: 22%
Appearance: white solid Analytical data: ¹H NMR (300 MHz, DMSO-d₆, ppm): δ: 8.98-8.94 (m, 1H), 7.95-7.93 (m, 2H), 7.65-7.55 (m, 3H), 7.37 (s, 1H), 6.15-6.11 (m, 1H), 4.81-4.79 (d, J=6.0 Hz, 2H), 4.06-3.96 (m, 1H), 3.50-3.45 (m, 2H), 2.74-2.62 (m, 1H), 2.38-2.27 (m, 4H).

LC-MS: 371.3 [M+H]⁺

5-phenyl-N-[[(cis-3-[5-(hydroxymethyl)-1,3,4-thiadiazol-2-yl]cyclobutyl]methyl]-1,2-oxazole-3-carboxamide Yield: 21%
Appearance: white solid Analytical data: ¹H NMR (300 MHz, DMSO-d₆, ppm): δ: 8.92-8.90 (m, 1H), 7.95-7.92 (m, 2H), 7.64-7.54 (m, 3H), 7.39 (s, 1H), 6.13-6.09 (m, 1H), 4.79-4.77 (d, J=6.0 Hz, 2H), 3.87-3.75 (m, 1H), 3.35-3.31 (m, 3H), 2.73-2.61 (m, 2H), 2.10-2.1.99 (m, 2H).

LC-MS 371.3 [M+H]⁺

Example 5: N-((trans-3-((5-(hydroxymethyl)-1,3,4-thiadiazol-2-yl)methyl)cyclobutyl)-5-phenylisoxazole-3-carboxamide and N-((cis-3-((5-(hydroxymethyl)-1,3,4-thiadiazol-2-yl)methyl)cyclobutyl)-5-phenylisoxazole-3-carboxamide

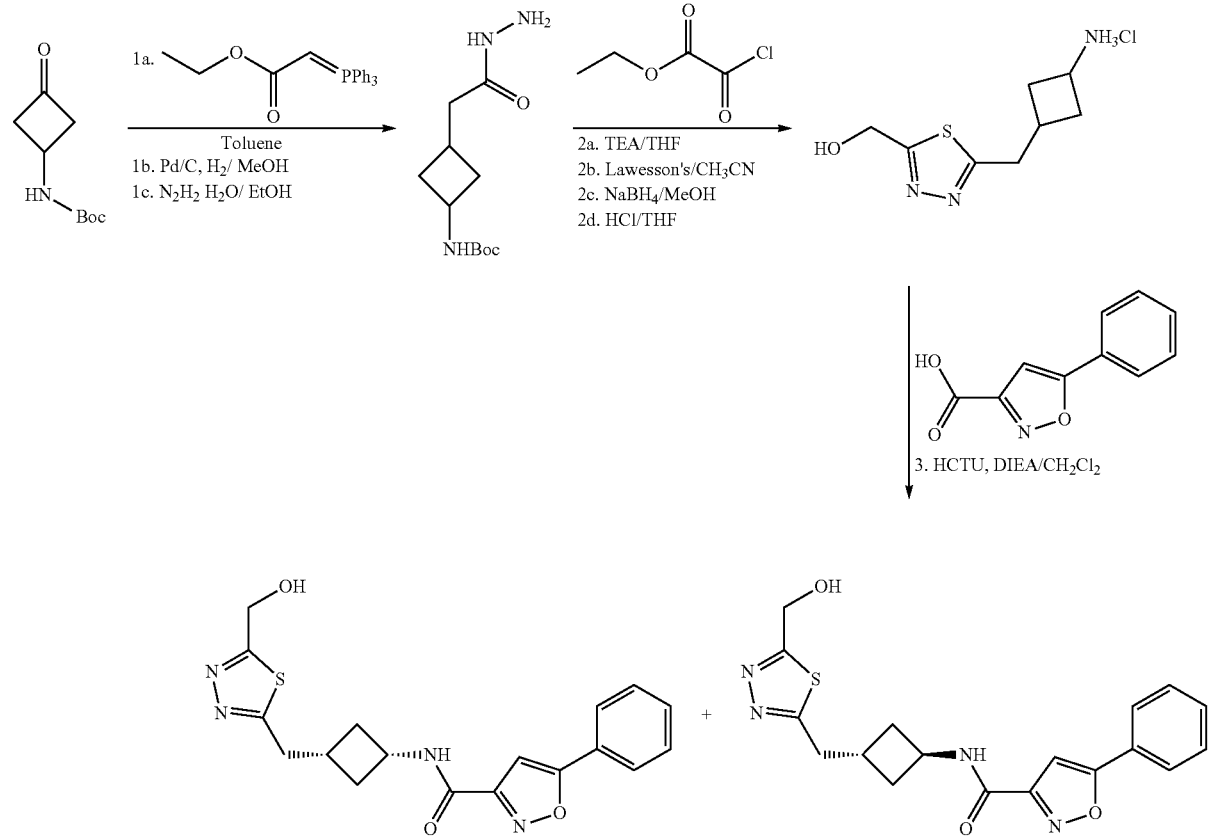

Step 1a: ethyl 2-(3-((tert-butoxycarbonyl)amino) cyclobutylidene)acetate a solution of tert-butyl N-(3-oxocyclobutyl) carbamate (8 g, 43.19 mmol, 1.00 eq.) and ethyl 2-(triphenyl-$\lambda^5$-phosphanylidene)acetate (16.8 g, 48.22 mmol, 1.10 eq.) in toluene (100 mL) was stirred for 2 hours at 100° C. The resulting mixture was concentrated under vacuum and the mixture was purified by silica gel column and eluted with ethyl acetate/petroleum ether (0-5%) to give crude (10.5 g) of ethyl 2-(3-[[(tert-butoxy)carbonyl]amino]cyclobutylidene) acetate as a white solid. LC-MS: 256 [M+H]$^+$.

Step 1b: ethyl 2-(3-[[(tert-butoxy)carbonyl]amino] cyclobutyl)acetate

Palladium carbon (210 mg) was added to a solution of ethyl 2-(3-[[(tert-butoxy)carbonyl]amino]cyclobutylidene) acetate (10.5 g, 41.13 mmol, 1.00 eq.) in methanol (150 mL), and the mixture was hydrogenated for 2 h at rt. The solids were filtered out and the mixture was concentrated under vacuum. This resulted in 10.6 g (crude) of ethyl 2-(3-[[(tert-butoxy)carbonyl]amino]cyclobutyl)acetate as a white solid. LC-MS: 258 [M+H]$^+$.

Step 1c: tert-butyl N-[3-[(hydrazine carbonyl)methyl]cyclobutyl]carbamate a solution of ethyl 2-(3-[[(tert-butoxy)carbonyl]amino] cyclobutyl)acetate (9.74 g, 37.85 mmol, 1.00 eq.) and hydrazine hydrate (11.4 mL) in ethanol (300 mL) was heated for 17 hours at 80° C. The resulting solution was diluted with water (500 mL) and then extracted with ethyl acetate (3×300 mL) and the combined organic layer was dried over anhydrous sodium sulfate and concentrated under vacuum. The crude product was re-crystallized from ethyl acetate/petroleum ether in the ratio of 1:2. This resulted in 6.88 g (crude) of tert-butyl N-[3-[(hydrazine carbonyl)methyl]cyclobutyl] carbamate as a white solid. LC-MS: 244 [M+H]$^+$.

Step 2a: ethyl 2-[2-(3-[[(tert-butoxy)carbonyl] amino]cyclobutyl)acetohydrazido]-2-oxoacetate ethyl 2-chloro-2-oxoacetate (4.74 g, 34.72 mmol, 1.20 eq.) was added dropwise to a cold solution (0° C.) of tert-butyl N-[3-[(hydrazine carbonyl)methyl]cyclobutyl]carbamate (7.04 g, 28.94 mmol, 1.00 eq.) and TEA (5.84 g, 57.71 mmol, 2.00 eq.) in tetrahydrofuran (150 mL). The resulting solution was stirred for 1 hour at room temperature, filtered and the resulting mixture was concentrated under vacuum. The residue was applied onto a silica gel column and eluted with ethyl acetate/petroleum ether (4:1) to give crude (9.5 g) ethyl 2-[2-(3-[[(tert-butoxy)carbonyl]amino] cyclobutyl)acetohydrazido]-2-oxoacetate as a yellow solid. LC-MS: 344 [M+H]$^+$.

Step 2b: ethyl 5-[(3-[[(tert-butoxy)carbonyl]amino] cyclobutyl)methyl]-1,3,4-thiadiazole-2-carboxylate a solution of ethyl 2-[2-(3-[[(tert-butoxy)carbonyl]amino] cyclobutyl)acetohydrazido]-2-oxoacetate (9.5 g, 27.67 mmol, 1.00 eq.) and Lawesson's reagent (11.19 g, 27.67 mmol, 1.00 eq.) in MeCN (200 mL) was heated 16 hours at 50° C. The reaction was then quenched by the addition of ice-water (300 mL). The resulting solution was extracted with ethyl acetate (4×200 mL). The combined organic layer was dried over anhydrous sodium sulfate and concentrated under vacuum to give crude (1.6 g) ethyl 5-[(3-[[(tert-butoxy)carbonyl]amino]cyclobutyl)methyl]-1,3,4-thiadiazole-2-carboxylate as a yellow solid. LC-MS: 342.2 [M+H]$^+$.

Step 2c: tert-butyl N-(3-[[5-(hydroxymethyl)-1,3,4-thiadiazol-2-yl]methyl]cyclobutyl)carbamate NaBH$_4$ (399 mg, 10.55 mmol, 3.00 eq.) was added in several batches to a cold solution (0° C.) of ethyl 5-[(3-[[(tert-butoxy)carbonyl]amino]cyclobutyl)methyl]-1,3,4-thiadiazole-2-carboxylate (1.2 g, 3.51 mmol, 1.00 eq.) in methanol (20 mL). The resulting solution was stirred for 1 hour at 0° C. and then quenched by the addition of water (3 mL). The mixture was filtered and then concentrated under vacuum to give crude (1.146 g) tert-butyl N-(3-[[5-(hydroxymethyl)-1,3,4-thiadiazol-2-yl]methyl]cyclobutyl)carbamate as a yellow solid. LC-MS: 300.1 [M+H]$^+$.

Step 2d: [5-[(3-aminocyclobutyl)methyl]-1,3,4-thiadiazol-2-yl]methanol hydrochloride a solution of tert-butyl N-(3-[[5-(hydroxymethyl)-1,3,4-thiadiazol-2-yl]methyl]cyclobutyl)carbamate (1.45 g, 4.84 mmol, 1.00 eq.) and concentrated hydrogen chloride aqueous (2 mL) in tetrahydrofuran (20 mL) was stirred for 16 hours at room temperature. The resulting mixture was concentrated under vacuum. This resulted in 980 mg (crude) of [5-[(3-aminocyclobutyl)methyl]-1,3,4-thiadiazol-2-yl] methanol hydrogen chloride salt as a yellow solid. LC-MS: 200.0 [M+H−HCl]+.

Step 3: N-(trans-3-((5-(hydroxymethyl)-1,3,4-thiadiazol-2-yl)methyl)cyclobutyl)-5-phenylisoxazole-3-carboxamide and N-(cis-3-((5-(hydroxymethyl)-1,3,4-thiadiazol-2-yl)methyl)cyclobutyl)-5-phenylisoxazole-3-carboxamide a solution of [5-[(3-aminocyclobutyl)methyl]-1,3,4-thiadiazol-2-yl]methanol hydrochloride (500 mg, 2.12 mmol, 1.00 eq., 99%), 5-phenyl-1,2-oxazole-3-carboxylic acid (481 mg, 2.54 mmol, 1.20 eq.), HCTU (1.061 g, 2.55 mmol, 1.20 eq.) and DIEA (1.09 g, 8.43 mmol, 1.20 eq.) in dichloromethane (30 mL) was stirred for 2 hours at room temperature. The resulting mixture was concentrated under vacuum. The crude product was purified by Prep-Flash with acetonitrile and water (0-46% within 40 min). The isomers were separated by Prep-SFC with the following conditions (prep SFC 350-2): Column, Phenomenex Lux 5μ Cellulose-4, 250*50 mm; mobile phase, CO$_2$ (50%), MeOH (0.2% DEA) (50%); Detector, UV 220 nm.

5-phenyl-N-[(cis-3-[[5-(hydroxymethyl)-1,3,4-thiadiazol-2-yl]methyl]cyclobutyl]-1,2-oxazole-3-carboxamide Yield: 37%
Appearance: off-white solid
Analytical data: $^1$H NMR (400 MHz, DMSO-d$_6$, ppm): δ: 9.06 (d, J=8.0 Hz, 1H), 7.94-7.92 (m, 2H), 7.58-7.54 (m, 3H), 7.35 (s, 1H), 6.14-6.11 (m, 1H), 4.80 (d, J=6.0 Hz, 2H), 4.35-4.33 (m, 1H), 3.19-3.17 (m, 2H), 2.43-2.33 (m, 3H), 1.99-1.93 (m, 2H).
LC-MS: 371.1 [M+H]$^+$ 5-phenyl-N-[(trans-3-[[5-(hydroxymethyl)-1,3,4-thiadiazol-2-yl]methyl]cyclobutyl]-1,2-oxazole-3-carboxamide Yield: 37%
Appearance: light yellow solid
Analytical data: $^1$H NMR (400 MHz, DMSO-$d_6$, ppm): δ: 9.14 (d, J=7.2 Hz, 1H), 7.94-7.92 (m, 2H), 7.56-7.54 (m, 3H), 7.36 (s, 1H), 6.14-6.11 (m, 1H), 4.80 (d, J=6.0 Hz, 2H), 4.63-4.55 (m, 1H), 3.33-3.28 (m, 2H), 2.51-2.49 (m, 1H), 2.33-2.31 (m, 2H), 2.14-2.13 (m, 2H).

Example 6: N-(trans-3-(5-((S)-1-hydroxyethyl)-1H-1,2,3-triazol-1-yl)cyclobutyl)-5-phenylisoxazole-3-carboxamide and N-(trans-3-(4-((S)-1-hydroxyethyl)-1H-1,2,3-triazol-1-yl)cyclobutyl)-5-phenylisoxazole-3-carboxamide were prepared by the procedure described in example 1 using (S)-3-butyne-2-ol instead of propargyl alcohol

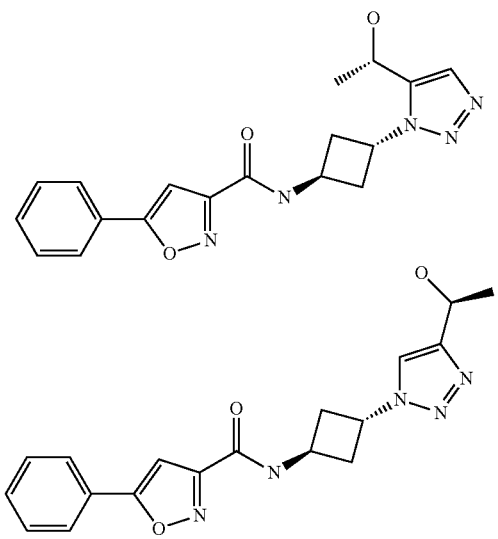

N-(trans-3-(5-((S)-1-hydroxyethyl)-1H-1,2,3-triazol-1-yl)cyclobutyl)-5-phenylisoxazole-3-carboxamide Appearance: white solid
Analytical data: $^1$H-NMR (400 MHz, DMSO) δ 9.40-9.39 (d, J=7.4 Hz, 1H), 7.96-7.94 (m, 2H), 7.62 (s, 1H), 7.59-7.54 (m, 3H), 7.40 (s, 1H), 5.49 (d, J=5.8 Hz, 1H), 5.32-5.28 (m, 1H), 4.86-4.75 (two overlapped multiplets, 2H), 2.90-2.83 (m, 2H), 2.83-2.76 (m, 2H), 1.43-1.42 (d, J=6.52 Hz, 3H).
LC-MS: (M+H)$^+$=354.0
HPLC purity: 99.9% at 220 nm and 99.89% at 254 nm.

N-(trans-3-(4-((S)-1-hydroxyethyl)-1H-1,2,3-triazol-1-yl)cyclobutyl)-5-phenylisoxazole-3-carboxamide Appearance: white solid
Analytical data: 1H-NMR (400 MHz, DMSO) δ 9.39-9.38 (d, J=7.3 Hz, 1H), 8.11 (s, 1H), 7.96-7.93 (m, 2H), 7.59-7.54 (m, 3H), 7.39 (s, 1H), 5.25-5.23 (m, 2H), 4.84-4.81 (m, 1H), 4.74-4.69 (m, 1H), 2.85-2.74 (m, 4H), 1.41 (d, J=6.52 Hz, 3H).
LC-MS: (M+H)$^+$=353.9
HPLC purity: 99.84% at 220 nm and 99.87% at 254 nm.

Example 7: N-(trans-3-(5-((R)-1-hydroxyethyl)-1H-1,2,3-triazol-1-yl)cyclobutyl)-5-phenylisoxazole-3-carboxamide and N-(trans-3-(4-((R)-1-hydroxyethyl)-1H-1,2,3-triazol-1-yl)cyclobutyl)-5-phenylisoxazole-3-carboxamide were prepared by the procedure described in example 1 using (R)-3-butyne-2-ol instead of propargyl alcohol

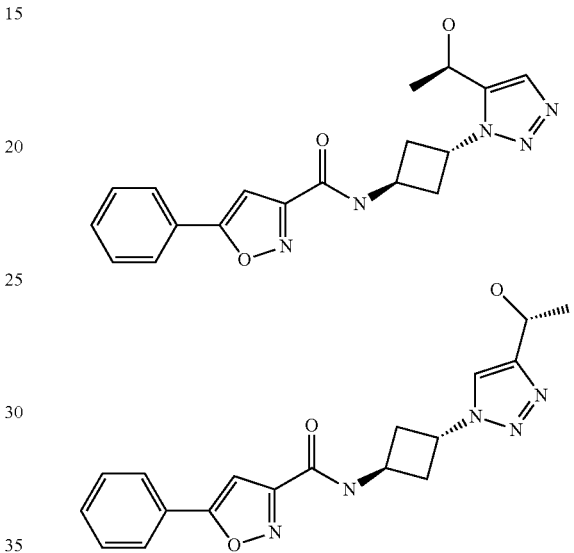

N-(trans-3-(5-((R)-1-hydroxyethyl)-1H-1,2,3-triazol-1-yl)cyclobutyl)-5-phenylisoxazole-3-carboxamide Appearance: Of white solid
Analytical data: $^1$H-NMR (400 MHz, DMSO) δ 9.37 (d, J=7.4 Hz, 1H), 7.93-7.91 (m, 2H), 7.60 (s, 1H), 7.55-7.51 (m, 3H), 7.38 (s, 1H), 5.46 (d, J=5.84 Hz, 1H), 5.30-5.22 (m, 1H), 4.82 (t, J=6.3 Hz, 2H), 4.76-4.71 (m, 1H), 2.87-2.82 (m, 2H), 2.78-2.71 (m, 2H), 1.40 (d, J=6.5 Hz, 3H).
LC-MS: (M+H)$^+$=354.1
HPLC purity: 94.46% at 200 nm, 95.18% at 220 nm and 95.14% at 254 nm N-(trans-3-(5-((R)-1-hydroxyethyl)-1H-1,2,3-triazol-1-yl)cyclobutyl)-5-phenylisoxazole-3-carboxamide Appearance: Of white solid
Analytical data: $^1$H-NMR (400 MHz, DMSO) 9.38 (d, J=7.3 Hz, 1H), 8.11 (s, 1H), 7.96-7.93 (m, 2H), 7.57-7.54 (m, 3H), 7.39 (s, 1H), 5.27-5.22 (m, 2H), 4.84-4.81 (m, 1H), 4.74-4.67 (m, 1H), 2.82-2.77 (m, 4H), 1.41 (d, J=6.5 Hz, 3H).
LC-MS: (M+H)$^+$=353.9
HPLC purity: 98.73% at 200 nm, 98.36% at 220 nm and 97.83% at 254 nm Example 8: N-(cis-3-(5-((R)-1-hydroxyethyl)-1H-1,2,3-triazol-1-yl)cyclobutyl)-5-phenylisoxazole-3-carboxamide and N-(cis-3-(4-((R)-1-hydroxyethyl)-1H-1,2,3-triazol-1-yl)cyclobutyl)-5-phenylisoxazole-3-carboxamide were prepared by the procedure described in example 2 using (R)-3-butyne-2-ol instead of propargyl alcohol

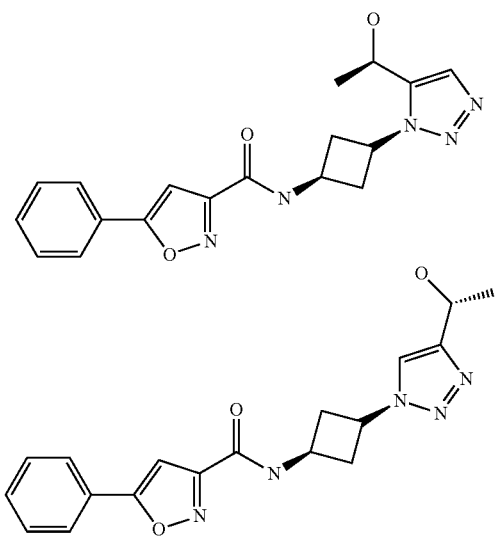

N-(cis-3-(5-((R)-1-hydroxyethyl)-1H-1,2,3-triazol-1-yl)cyclobutyl)-5-phenylisoxazole-3-carboxamide Appearance: off white solid Analytical data: $^1$H-NMR (400 MHz, CDCl$_3$): δ 7.80-7.76 (m, 2H), 7.56 (s, 1H), 7.50-7.45 (m, 3H), 7.38 (d, J=8.4 Hz, 1H), 6.95 (s, 1H), 5.01-4.96 (m, 1H), 4.93-4.87 (m, 1H), 4.64-4.58 (m, 1H), 3.16-3.05 (m, 2H), 2.96-2.87 (m, 2H), 2.23 (d, J=6.9 Hz, 1H).

LC-MS: (M+H)$^+$=353.9

HPLC purity: 99.48% at 200 nm, 99.76% at 220 nm and 99.55% at 254 nm

N-(cis-3-(4-((R)-1-hydroxyethyl)-1H-1,2,3-triazol-1-yl)cyclobutyl)-5-phenylisoxazole-3-carboxamide Appearance: off white solid Analytical data: $^1$H-NMR (400 MHz, CDCl$_3$): δ 7.80-7.77 (m, 2H), 7.60 (s, 1H), 7.51-7.46 (m, 3H), 7.30 (d, J=7.8 Hz, 1H), 6.95 (s, 1H), 5.11-5.08 (m, 1H), 4.82-4.78 (m, 1H), 4.54-4.50 (m, 1H), 3.17-3.10 (m, 2H), 2.86-2.78 (m, 2H), 2.41 (d, J=4.1 Hz, 1H), 1.60 (d obscured by solvent peak, 3H).

LC-MS: (M+H)$^+$=353.9

HPLC purity: 98.11% at 200 nm, 97.89% at 220 nm and 98.57% at 254 nm.

Example 9: Preparation of Intermediate I: N-trans-3-(hydrazinecarbonyl)cyclobutyl)-5-phenylisoxazole-3-carboxamide Hydrochloride

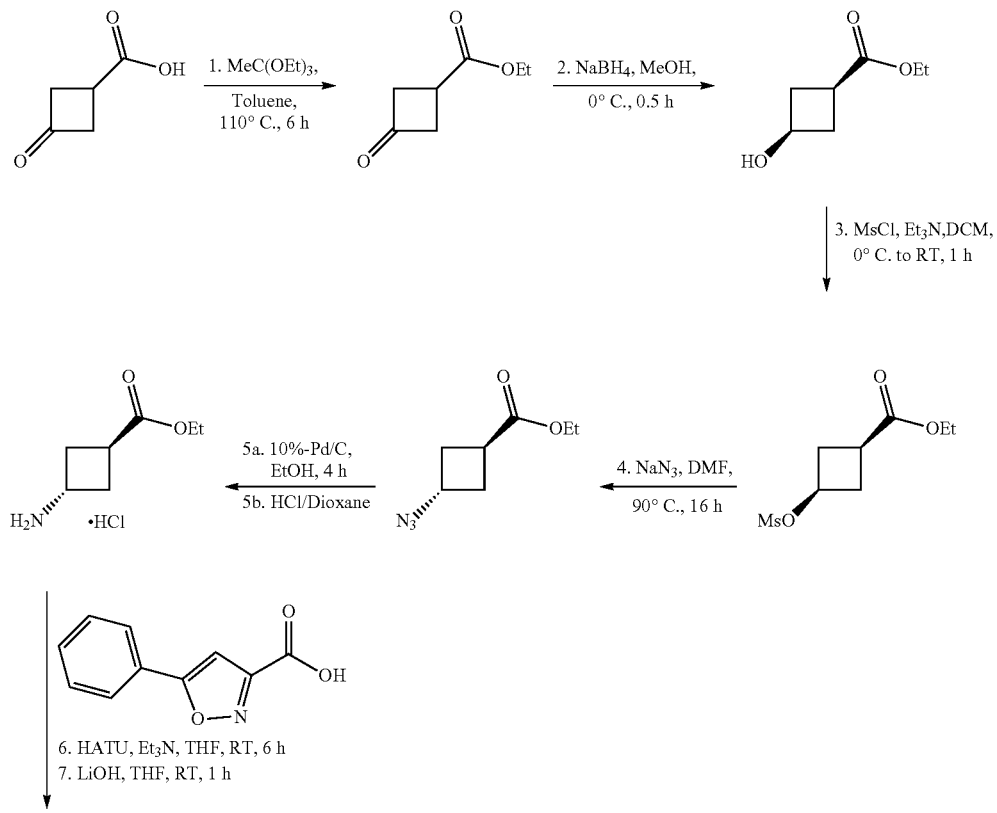

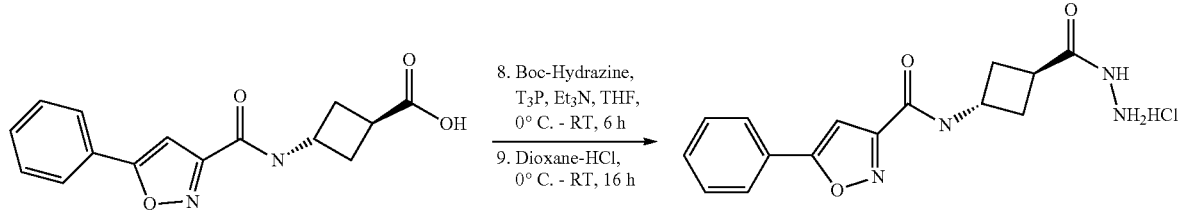

Step 1: ethyl 3-oxocyclobutane-1-carboxylate triethyl orthoacetate (21.31 g, 0.131 mol) was added to a solution of 3-oxocyclobutane-1-carboxylic acid (5.0 g, 0.043 mol) in toluene (100 mL) and the reaction mixture was refluxed for 6 h. The reaction mixture was quenched with a 1N HCl solution and the layers were separated off. The organic layer was washed with saturated $NaHCO_3$ solution (2×50 mL), brine (2×50 mL), dried over anhydrous sodium sulfate and concentrated under reduced pressure to get the product (5.3 g, 85%) as a yellow liquid. $^1$H NMR (400 MHz, $CDCl_3$): δ 4.23-4.17 (q, J=7.0 Hz, 2H), 3.44-3.37 (m, 2H), 3.32-3.16 (m, 3H), 1.30-1.26 (t, J=7.0 Hz, 3H).

Step 2: ethyl cis-3-hydroxycyclobutane-1-carboxylate sodium borohydride (1.55 g, 0.041 mol) was added to an iced cold solution of ethyl 3-oxocyclobutane-1-carboxylate (5.3 g, 0.037 mol) in methanol (75 mL) and the reaction mixture was stirred for 1 h. The reaction mixture was quenched with acetone (10 mL) and volatiles were removed under reduced pressure. The crude reaction mixture was suspended in $NaHCO_3$ solution (30 mL) and extracted with DCM (100 mL). The organic layer was washed with brine (30 mL), dried over anhydrous sodium sulfate and concentrated under reduced pressure to get the product (3.2 g, 59%) as a yellow oil. $^1$H NMR (400 MHz, $CDCl_3$): δ 4.20-4.09 (overlapped q and m, 3H), 3.68 (d, J=2.3 Hz, 1H), 2.62-2.54 (m, 3H), 2.20-2.10 (m, 2H), 1.26-1.22 (t, J=7.0 Hz, 3H); LC-MS: $[M+H]^+$ 145.1.

Step 3: ethyl cis-3-((methylsulfonyl)oxy)cyclobutane-1-carboxylate $Et_3N$ (8.96 mL, 0.0666 mol) was added to a solution of ethyl cis-3-hydroxycyclobutane-1-carboxylate (3.2 g, 0.0222 mol) in DCM (100 mL) followed by MsCl (3.03 g, 0.0266 mol) drop wise and the resulting reaction mixture was stirred at room temperature for 1 h. The reaction mixture was poured onto ice cold water (50 mL) and extracted with DCM. The organic layer was dried over anhydrous sodium sulfate and concentrated under reduced pressure to get the crude product (5.1 g) as a yellow oil. $^1$H NMR (400 MHz, $CDCl_3$): δ 4.95-4.88 (m, 1H), 4.17-4.12 (q, J=7.1 Hz, 2H), 3.71 (d, 1H), 2.98 (s, 3H), 2.74-2.66 (m, 3H), 2.60-2.59 (m, 2H), 1.27-1.25 (t, J=7.1 Hz, 3H); LC-MS: $[M+H]^+$ 223.0.

Step 4: ethyl trans-3-azidocyclobutane-1-carboxylate a mixture of sodium azide (2.98 g, 0.044 mol) and ethyl cis-3-((methylsulfonyl)oxy)cyclobutane-1-carboxylate (5.1 g, 0.022 mol) in DMF (25 mL) was heated to 90° C. for 16 h. The reaction mixture was poured onto water (70 mL) and extracted with ethyl acetate (2×100 mL). Combined organic layer was dried over anhydrous sodium sulfate and concentrated under reduced pressure to obtain crude product which was chromatographed on 230-400 mesh silica gel using 10% EtOAc in hexane as eluent to afford the product (3.8 g, 100% over two steps) as colorless liquid. $^1$H NMR (400 MHz, $CDCl_3$): δ 4.18-4.10 (m, 3H), 3.11-3.04 (m, 1H), 2.60-2.53 (m, 2H), 2.36-2.29 (m, 2H), 1.27-1.22 (t, J=7.1 Hz, 3H); LC-MS: $[M+H]^+$ 171.1.

Step 5a/b: ethyl trans-3-aminocyclobutane-1-carboxylate hydrochloride a mixture of ethyl trans-3-azidocyclobutane-1-carboxylate (3.8 g, 0.0221 mol) and 10% Pd/C (1.0 g) in ethanol (50 mL) was hydrogenated (50 psi) for 4 h at room temperature. The reaction mixture was filtered through a celite bed and the filtrate was concentrated under reduced pressure obtain the crude compound. The crude compound was treated with 4 M HCl in dioxane to afford HCl salt (3.8 g, 95%) as colorless viscous oil.

Step 6: ethyl trans-3-(5-phenylisoxazole-3-carboxamido)cyclobutane-1-carboxylate $Et_3N$ (5.6 mL, 42 mmol) and HATU (4.84 g, 13 mmol) were added to a mixture of ethyl trans-3-aminocyclobutane-1-carboxylate hydrochloride (1.89 g, 10 mmol) and 5-phenylisoxazole-3-carboxylic acid (2 g, 10 mmol) in THF (200 mL) at room temperature and the reaction mixture was stirred for 6 h at room temperature. Volatiles were removed under reduced pressure to get the crude compound. The reaction mixture was diluted with water (100 mL) and extracted using ethyl acetate (2×75 mL). Combined organic layer was washed with brine (50 mL), dried over anhydrous $Na_2SO_4$ and concentrated under reduced pressure. The mixture was purified by flash column chromatography using 30% EtOAc in hexane as eluent to give the product (2.65 g, 80%) as white solid. $^1$H NMR (400 MHz, CDCl3): δ 7.80-7.77 (m, 2H), 7.49-7.46 (m, 3H), 7.00 (d, J=7.2 Hz, 1H), 6.94 (s, 1H), 4.79-4.73 (m, 1H), 4.17 (q, J=7.1 Hz, 2H), 3.10-3.09 (m, 1H), 2.78-2.72 (m, 2H), 2.40-2.32 (m, 2H), 1.30-1.26 (t, J=7.2 Hz, 3H). LC-MS: $[M+H]^+$ 315.2

Step 7: trans-3-(5-phenylisoxazole-3-carboxamido)cyclobutane-1-carboxylic acid a solution of lithium hydroxide (0.66 g, 15 mmol) in water (20 mL) was added to a solution of ethyl trans-3-(5-phenylisoxazole-3-carboxamido)cyclobutane-1-carboxylate (2.5 g, 7.9 mmol) in THF (30 mL) and the reaction mixture was stirred for 1 h at room temperature. Volatiles were removed under reduced pressure and the crude compound was suspended in water (100 mL). The aq. layer was washed with diethyl ether (2×50 mL) and acidified with citric acid solution. The resulting reaction mixture was extracted with ethyl acetate (2×100 mL). Combined organic layer was dried over anhydrous sodium sulfate and concentrated under reduced pressure to afford the product (2 g, 92%) which was used as such in next step without further purification. $^1$H NMR (400 MHz, DMSO-$d_6$): δ 12.26 (br, 1H), 9.18-9.16 (d, J=7 Hz, 1H), 7.94-7.91 (m, 2H), 7.57-7.53 (m, 3H), 7.35 (s, 1H), 4.59-4.54 (m, 1H), 2.97-2.91 (m, 1H), 2.43-2.38 (m, 4H). LC-MS: [M−H]⁻ 284.9

Step 8: tert-butyl 2-trans-3-(5-phenylisoxazole-3-carboxamido)cyclobutane-1-carbonyl)hydrazine-1-carboxylate TEA (3.66 mL, 28.3 mmol) was added to a mixture of Boc-Hydrazine (1.49 g, 11 mmol) and trans-3-(5-phenylisoxazole-3-carboxamido)cyclobutane-1-carboxylic acid (2.7 g, 9.4 mmol) in THF (100 mL) followed by addition of T$_3$P (12 mL, 18.8 mol). The reaction mixture was stirred for 16 h at room temperature. Volatiles were removed under reduced pressure and the crude reaction mixture was diluted with water (100 mL). The reaction mixture was extracted with ethyl acetate (2×100 mL). Combined organic layer was washed with brine (100 mL), dried over anhydrous Na$_2$SO$_4$ and concentrated under reduced pressure to afford crude product which was further purified by flash column chromatography using 50% EtOAc in hexane as eluent to afford the product (3.3 g, 99%) as a white solid. $^1$H NMR (400 MHz, DMSO-$d_6$): δ 9.49 (s, 1H), 9.15-9.13 (d, J=7.8 Hz, 2H), 8.72 (s, 1H), 7.94-7.92 (m, 2H), 7.57-7.53 (m, 3H), 7.36 (s, 1H), 4.63-4.57 (m, 1H), 2.91-2.88 (m, 1H), 2.39-2.35 (m, 4H), 1.40 (s, 9H); LC-MS: [M−H]+ 399.1

Step 9: N-trans-3-(hydrazinecarbonyl)cyclobutyl)-5-phenylisoxazole-3-carboxamide hydrochloride 4 M HCl in dioxane (30 mL) was added to an ice cooled solution of tert-butyl 2-trans-3-(5-phenylisoxazole-3-carboxamido)cyclobutane-1-carbonyl)hydrazine-1-carboxylate (3.8 g, 9.5 mmol) in 1,4 dioxane (50 mL) and the reaction mixture was stirred at room temperature for 16 h. Volatiles were removed under reduced pressure and the crude compound was stirred in diethyl ether (100 mL). Solid was filtered and washed with hexane to afford the product (2.5 g, 78%) as an off white solid. $^1$H NMR (400 MHz, DMSO-$d_6$): δ 10.88 (s, 1H), 10.23 (br, 3H), 9.22-9.20 (d, J=7.9 Hz, 1H), 7.94-7.92 (m, 2H), 7.58-7.54 (m, 3H), 7.37 (s, 1H), 4.67-4.61 (m, 1H), 3.08-3.03 (m, 3H), 2.46-2.42 (m, 4H). LC-MS: [M+H]+ 301.0

Example 10: Preparation of N-(trans-3-(5-((R)-1-hydroxyethyl)-1,3,4-oxadiazol-2-yl)cyclobutyl)-5-phenylisoxazole-3-carboxamide

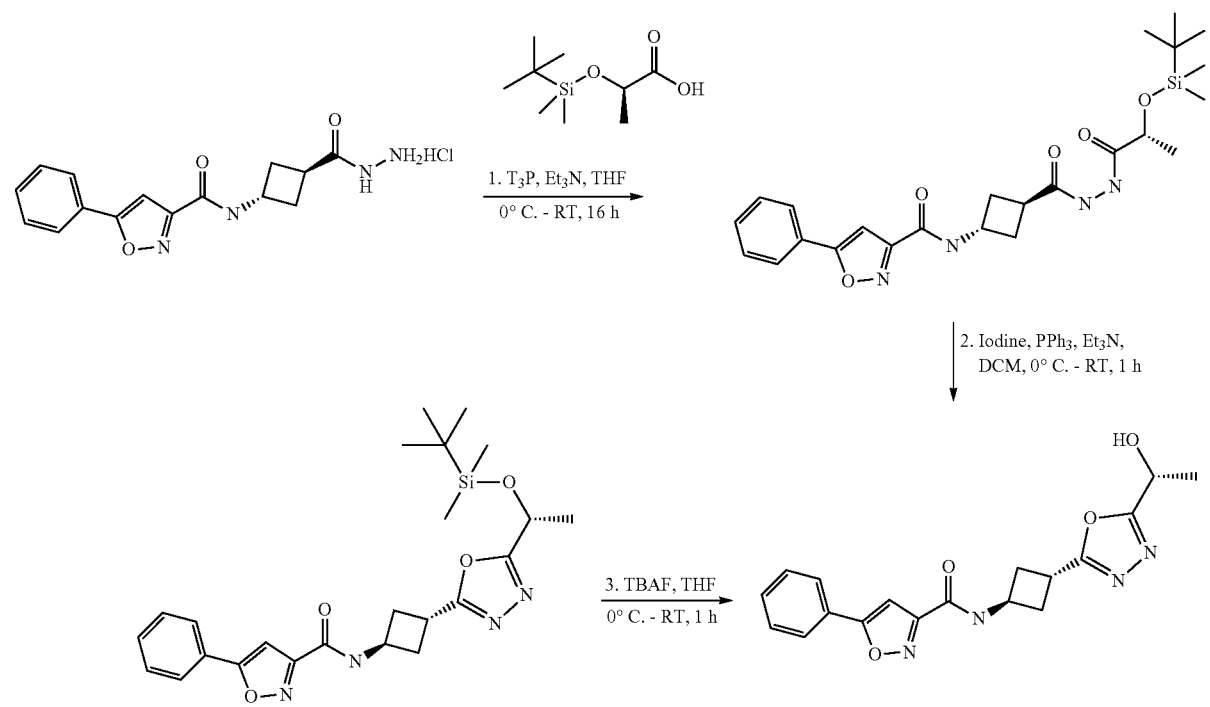

Step 1: N-(trans-3-(2-((R)-2-((tert-butyldimethylsilyl)oxy)propanoyl)hydrazine-1-carbonyl)cyclobutyl)-5-phenylisoxazole-3-carboxamide TEA (1.19 mL, 8.9 mmol) and T$_3$P (1.7 ml, 2.6 mmol) were sequentially added to an ice cooled solution of N-trans-3-(hydrazinecarbonyl)cyclobutyl)-5-phenylisoxazole-3-carboxamide hydrochloride (0.6 g, 1.7 mmol) and (R)-2-((tert-butyldimethylsilyl)oxy) propanoic acid (0.43 g, 2.1 mmol) in 1,4-dioxane (50 mL) were added and the reaction mixture was stirred for 16 h at room temperature. Volatiles were removed under reduced pressure and the crude reaction mixture was diluted with water (100 mL). The reaction mixture was extracted with ethyl acetate (3×50 mL). Combined organic layer was washed with brine (50 mL), dried over anhydrous Na$_2$SO$_4$ and concentrated under reduced pressure to afford crude compound which was further purified by flash column chromatography using 50% EtOAc in hexane as eluent to obtain product (0.3 g, 35%) as white solid. $^1$H NMR (400 MHz, DMSO-$d_6$): δ 9.83 (s, 1H), 9.44

(s, 1H), 9.16-9.14 (d, J=7.9 Hz, 1H), 7.94-7.92 (m, 2H), 7.58-7.53 (m, 3H), 7.34 (s, 1H), 4.65-4.59 (m, 1H), 4.29-4.24 (m, 1H), 3.01-2.94 (m, 1H), 2.40-2.37 (m, 4H), 1.28 (d, J=6.6 Hz, 3H), 0.88 (s, 9H), 0.09 (s, 6H). LC-MS: [M+H]⁺ 487.3.

Step 2: N-(trans-3-(5-((R)-1-((tert-butyldimethylsilyl)oxy)ethyl)-1,3,4-oxadiazol-2-yl)cyclobutyl)-5-phenylisoxazole-3-carboxamide a solution of triphenyl phosphine (0.32 g, 1.2 mmol) in DCM (20 mL) was added Iodine (0.31 g, 1.2 mmol) and the reaction mixture was stirred for 10 min. Then the reaction mixture was cooled to 0° C. To the resulting reaction mixture was added TEA (0.40 ml, 3.0 mmol) followed by addition of N-(trans-3-(2-((R)-2-((tert-butyldimethylsilyl)oxy)propanoyehydrazine-1-carbonyl)cyclobutyl)-5-phenylisoxazole-3-carboxamide (0.3 g, 0.6 mmol) and the reaction mixture was stirred for 1 h at room temperature. Volatiles were removed under reduced pressure and the crude reaction mixture was diluted with ethyl acetate. The precipitate thus obtained was filtered, filtrate concentrated and purified by flash column chromatography using 30% ethyl acetate in n-hexane as eluent to afford the product (0.180 g, 62%) as a off-white solid. ¹H NMR (400 MHz, CDCl3): δ 7.80-7.78 (m, 2H), 7.50-7.47 (m, 3H), 7.11-7.09 (d, J=7.3 Hz, 1H), 6.95 (s, 1H), 5.09-5.08 (m, 1H), 4.86-4.84 (m, 1H), 3.77-3.75 (m, 1H), 2.92-2.85 (m, 2H), 2.69-2.66 (m, 2H), 1.61 (d, J=6.6 Hz, 3H), 0.89 (s, 9H), 0.12 (s, 3H), 0.07 (s, 3H); LC-MS: [M+H]⁺ 454.8.

Step 3: N-(trans-3-(5-((R)-1-hydroxyethyl)-1,3,4-oxadiazol-2-yl)cyclobutyl)-5-phenylisoxazole-3-carboxamide TBAF (1 M solution in THF) (0.7 mL, 0.76 mmol) was added to an ice-cooled solution of N-(trans-3-(5-((R)-1-((tert-butyldimethylsilyl)oxy)ethyl)-1,3,4-oxadiazol-2-yl)cyclobutyl)-5-phenylisoxazole-3-carboxamide (0.180 g, 0.38 mmol) in THF (10 mL) was added and the reaction mixture was stirred for 1 h at room temperature. After completion of reaction, volatiles were removed under reduced pressure. The crude reaction mixture was diluted with water (30 mL) and the aq. phase was extracted with ethyl acetate (2×30 mL). Combined organic layer was washed with brine (20 mL), dried over anhydrous Na₂SO₄ and concentrated under reduced pressure to afford crude product which was triturated with diethyl ether (20 mL) and pentane (30 mL) to obtain N-(trans-3-(5-((R)-1-hydroxyethyl)-1,3,4-oxadiazol-2-yl)cyclobutyl)-5-phenylisoxazole-3-carboxamide (0.120 g).

Yield: 88%
Appearance: off-white solid
Analytical data: ¹H NMR (400 MHz, DMSO-d₆): δ 9.33 (d, J=7.7 Hz, 1H), 7.95-7.92 (m, 2H), 7.58-7.54 (m, 3H), 7.38 (s, 1H), 5.95 (d, J=5.6 Hz, 1H), 4.94-4.88 (m, 1H), 4.72-4.66 (m, 1H), 3.73-3.67 (m, 1H), 2.70-2.65 (m, 2H), 2.63-2.58 (m, 2H), 1.48-1.47 (d, J=6.6 Hz, 3H).
LC-MS: (M+H)⁺=355.0
HPLC purity: 99.68% at 200 nm and 99.66% at 254 nm.

Example 11: N-(trans-3-(5-((S)-1-hydroxyethyl)-1,3,4-oxadiazol-2-yl)cyclobutyl)-5-phenylisoxazole-3-carboxamide

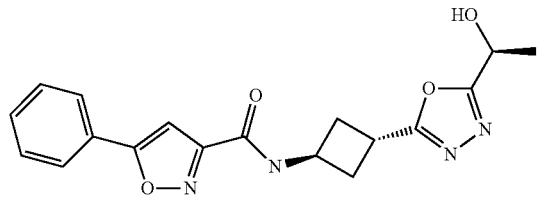 [SMILES: C[C@H](O)c1nnc([C@H]2C[C@H](NC(=O)c3cc(-c4ccccc4)on3)C2)o1]

This compound was prepared using a similar procedure as example 10 using (S)-2-((tert-butyldimethylsilyl)oxy)propanoic acid instead Appearance: white solid
Analytical data: ¹H NMR (400 MHz, DMSO-d₆): δ 9.34-9.32 (d, J=7.7 Hz, 1H), 7.95-7.92 (m, 2H), 7.58-7.53 (m, 3H), 7.38 (s, 1H), 5.96 (d, J=5.7 Hz, 1H), 4.94-4.88 (m, 1H), 4.72-4.66 (m, 1H), 3.73-3.66 (m, 1H), 2.70-2.63 (m, 2H), 2.62-2.60 (m, 2H), 1.48 (d, J=6.6 Hz, 3H).
LC-MS [M+H]⁺=355.2
HPLC purity: 99.47% at 254 nm and 98.78% at 220 nm.

Example 12: N-(trans-3-(5-(hydroxymethyl)-1,3,4-oxadiazol-2-yl)cyclobutyl)-5-phenylisoxazole-3-carboxamide

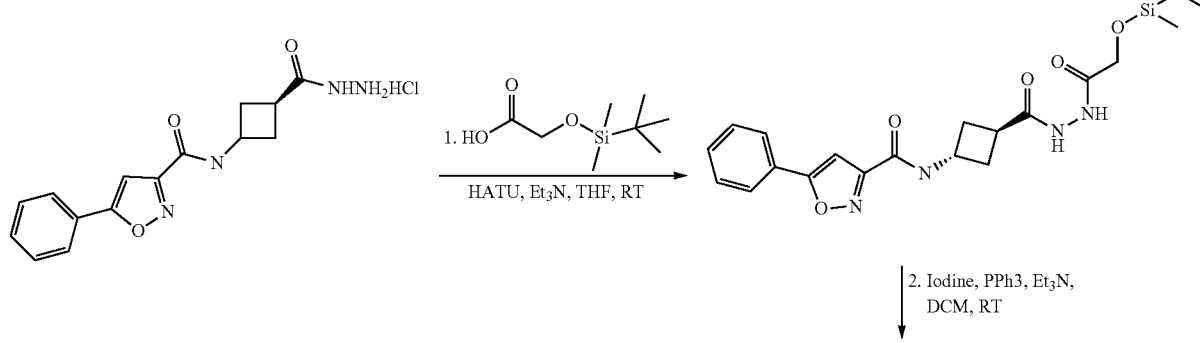

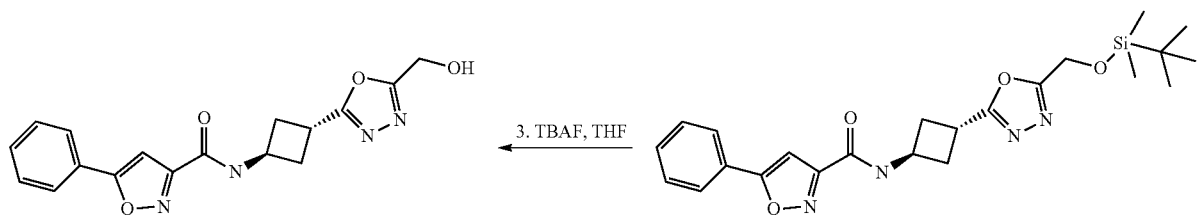

Step 1: N-(trans-3-(2-(2-((tert-butyldimethylsilyl)oxy)acetyl)hydrazine-1-carbonyl)cyclobutyl)-5-phenylisoxazole-3-carboxamide TEA (1.14 ml, 8.5 mmol) and HATU (0.77 g, 2.0 mmol) were added sequentially to a solution of N-trans-(3-(hydrazinecarbonyl)cyclobutyl)-5-phenylisoxazole-3-carboxamide hydrochloride (0.6 g, 1.7 mmol) and 2-((tert-butyldimethylsilyl)oxy)acetic acid (0.5 g, 2.6 mmol) in THF (50 mL). The reaction mixture was stirred for 4 h at room temperature, volatiles were removed under reduced pressure and the crude compound was diluted with water (100 mL). The aq. phase was extracted with ethyl acetate (3×50 mL). Combined organic layer was washed with brine (50 mL), dried over anhydrous $Na_2SO_4$ and concentrated under reduced pressure to afford crude compound which was further purified by flash column chromatography using 50% EtOAc in hexane as eluent to obtain the product (0.4 g, 47%) as off-white solid. $^1$H NMR (400 MHz, DMSO-$d_6$): δ 9.78 (s, 1H), 9.51 (s, 1H), 9.16-9.14 (m, 1H), 7.94-7.92 (m, 2H), 7.58-7.51 (m, 3H), 7.35 (s, 1H), 4.64-4.58 (m, 1H), 4.12 (s, 2H), 3.01-2.94 (m, 1H), 2.41-2.37 (m, 4H), 0.89-0.86 (s, 9H), 0.10 (s, 6H); LC-MS [M+H]$^+$ 473.3

Step 2: N-(trans-3-(5-(((tert-butyldimethylsilyl)oxy)methyl)-1,3,4-oxadiazol-2-yl)cyclobutyl)-5-phenylisoxazole-3-carboxamide a mixture of triphenyl phosphine (0.44 g, 1.7 mmol) and iodine (0.43 g, 1.7 mmol) in DCM (20 mL) was stirred for 10 min and then cooled to cooled to 0° C. To the resulting reaction mixture was added TEA (0.57 g, 4.2 mmol) and N-(trans-3-(2-(2-((tert-butyldimethylsilyl)oxy)acetyl)hydrazine-1-carbonyl)cyclobutyl)-5-phenylisoxazole-3-carboxamide (0.4 g, 0.84 mmol) sequentially and the reaction mixture was stirred for 1 h at room temperature. Volatiles were removed under reduced pressure and the crude reaction mixture was diluted with ethyl acetate. The precipitate thus formed was filtered, filtrate concentrated and purified by flash column chromatography using 30% ethyl acetate in n-hexane as eluent to afford the product (0.280 g, 73%) as an off-white solid. $^1$H NMR (400 MHz, CDCl3): δ 7.80-7.78 (m, 2H), 7.50-7.47 (m, 3H), 7.10-7.09 (d, J=7.3 Hz, 1H), 6.95 (s, 1H), 4.87-4.83 (m, 3H), 3.79-3.75 (m, 1H), 2.93-2.86 (m, 2H), 2.69-2.64 (m, 2H), 0.91 (s, 9H), 0.13 (s, 6H); LC-MS [M+H]$^{30}$ 454.8.

Step 3: N-(trans-3-(5-(hydroxymethyl)-1,3,4-oxadiazol-2-yl)cyclobutyl)-5-phenylisoxazole-3-carboxamide TBAF (1 M solution in THF) (1.2 mL, 1.2 mmol) was added to an ice-cooled solution of N-(trans-3-(5-(((tert-butyldimethylsilyl)oxy)methyl)-1,3,4-oxadiazol-2-yl)cyclobutyl)-5-phenylisoxazole-3-carboxamide (0.280 g, 0.61 m mol) in THF (10 mL) and the reaction mixture was stirred for 2 h at room temperature. Volatiles were removed under reduced pressure and the crude reaction mixture was diluted with water (30 mL). The aq. phase was extracted with ethyl acetate (2×30 mL). Combined organic layer was washed with brine (20 mL), dried over anhydrous $Na_2SO_4$ and concentrated under reduced pressure to afford crude product (0.180 g) which was triturated with diethyl ether (20 mL) and pentane (30 mL) to obtain the product (0.150 g).

Yield: 71%
Appearance: off-white solid
Analytical data: $^1$H NMR (400 MHz, DMSO-$d_6$): δ 9.34-9.32 (d, J=7.8 Hz, 1H), 7.95-7.92 (m, 2H), 7.58-7.53 (m, 3H), 7.38 (s, 1H), 5.89-5.86 (t, J=6.3 Hz, 1H), 4.73-4.67 (m, 1H), 4.63 (d, J=6.2 Hz, 2H), 3.73-3.68 (m, 1H), 2.70-2.68 (m, 2H), 2.63-2.59 (m, 2H).
LC-MS: [M+H]$^+$: 340.8
HPLC Purity: 99.79% at 269 nm, 99.74% at 254 nm and 99.58% at 220 nm.

Example 13: N-trans-3-(5-((R)-1-hydroxyethyl)-1,3,4-thiadiazol-2-yl)cyclobutyl)-5-phenylisoxazole-3-carboxamide

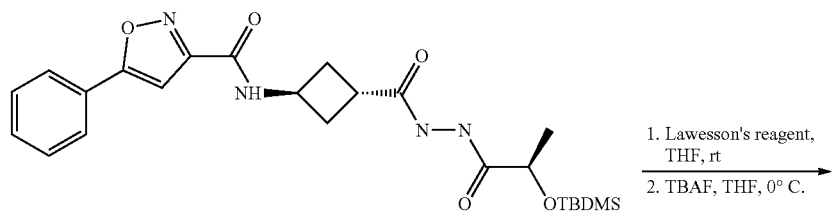

A

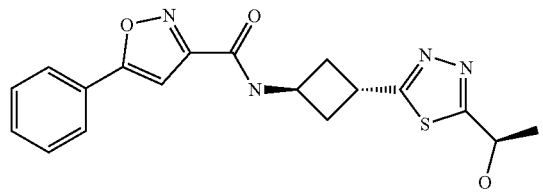

Step 1: N-trans-(3-(5-((1R)-1-((tert-butyl(methyl)silyl)oxy)ethyl)-1,3,4-thiadiazol-2-yl)cyclobutyl)-5-phenylisoxazole-3-carboxamide a solution of intermediate A (0.4 g, crude), which was prepared by the procedure described in step 1, example 12 using (R)-2-((tert-butyldimethylsilyl)oxy)propanoic acid, and Lawesson's reagent (0.499 g, 1.2 mmol) was stirred at room temperature for 3 h. Volatiles were removed under reduced pressure to obtain the crude compound which was purified by neutral alumina chromatography using 25% ethyl acetate in hexane to afford N-(trans-3-(5-((1R)-1-((tert-butyl(methyl)silyl)oxy)ethyl)-1,3,4-thiadiazol-2-yl)cyclobutyl)-5-phenylisoxazole-3-carboxamide (0.220 g, 34% over two steps) as white solid. $^1$H NMR (400 MHz, CDCl$_3$): δ 7.79-7.78 (m, 2H), 7.50-7.47 (m, 3H), 7.10 (d, J=7.2 Hz, 2H), 6.95 (s, 1H), 5.27-5.22 (m, 1H), 4.86-4.84 (m, 2H), 3.97-3.95 (m, 1H), 2.93-2.87 (m, 2H), 2.73-2.66 (m, 2H), 1.60 (t, J=6.4 Hz, 3H), 0.91 (s, 9H), 0.12 (s, 3H), 0.07 (s, 3H); LC-MS [M+H]$^+$ 485.3.

Step 2: N-trans-3-(5-((R)-1-hydroxyethyl)-1,3,4-thiadiazol-2-yl)cyclobutyl)-5-phenylisoxazole-3-carboxamide tetrabutylammonium fluoride (0.68 mL, 0.68 mmol, 1 M in THF) was added to a cold solution of N-(trans-3-(5-((1R)-1-((tert-butyl(methyl)silyl)oxy)ethyl)-1,3,4-thiadiazol-2-yl)cyclobutyl)-5-phenylisoxazole-3-carboxamide in THF (5 mL). The mixture was stirred at 0° C. for 2 h, the volatiles were removed under reduced pressure to get the crude compound which was suspended in water (10 mL) and extracted with ethyl acetate (2×10 mL). Combined organic layer was washed with water followed by brine, dried over anhydrous Na$_2$SO$_4$ and concentrated under reduced pressure to obtain the crude compound. The crude compound was further purified by combiflash using 2% MeOH in DCM as eluent to afford the product (0.110 g, 65%) as off white solid.

Analytical data: $^1$H NMR (400 MHz, CDCl$_3$): δ 7.79-7.78 (m, 2H), 7.51-7.46 (m, 3H), 7.12 (d, J=7.2 Hz, 1H), 6.95 (s, 1H), 5.30-5.28 (m, 1H), 4.88-4.82 (m, 1H), 4.02-3.96 (m, 1H), 2.94-2.87 (m, 2H), 2.80 (br, 1H), 2.73-2.68 (m, 2H), 1.69 (d, J=6.6 Hz, 3H).

LC-MS [M+H]$^+$ 371.1

HPLC purity: 97.80% at 220 nm and 98.69% at 254 nm.

Example 14: N-trans-3-(5-((S)-1-hydroxyethyl)-1,3,4-thiadiazol-2-yl)cyclobutyl)-5-phenylisoxazole-3-carboxamide was prepared by the procedure described in example 13 using (S)-2-((tert-butyldimethylsilyl)oxy)propanoic acid

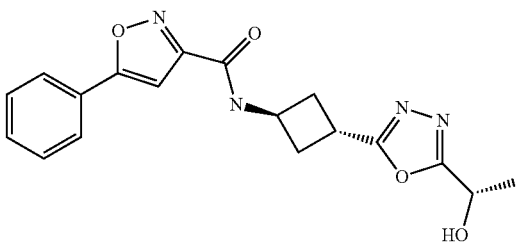 [SMILES: C[C@H](O)c1nnc([C@H]2C[C@H](NC(=O)c3cc(-c4ccccc4)on3)C2)o1]

Appearance: white solid

Analytical data: $^1$H NMR (400 MHz, CDCl$_3$): δ 7.80-7.77 (m, 2H), 7.50-7.47 (m, 3H), 7.13 (d, J=7.2 Hz, 1H), 6.95 (s, 1H), 5.33-5.27 (m, 1H), 4.88-4.82 (m, 1H), 4.02-3.96 (m, 1H), 2.91-2.87 (m, 2H), 2.84 (d, J=4.7 Hz, 1H), 2.73-2.70 (m, 2H), 1.69 (d, J=6.6 Hz, 3H).

LC-MS: [M+H]$^+$ 370.8

HPLC purity: 98.85% at 220 nm and 98.74% at 254 nm.

Example 15: Preparation of Intermediate II: 3-(dibenzylamino)cyclobutane-1-carbohydrazide

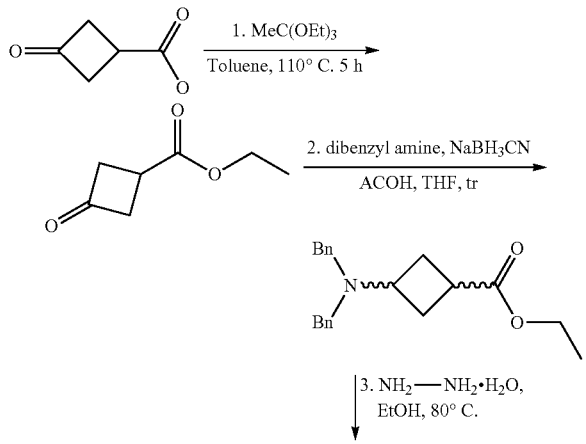

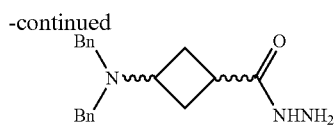

Step 1: ethyl 3-oxocyclobutane-1-carboxylate triethyl orthoacetate (24.25 g, 104 mmol) was added to a solution of 3-oxo-cyclobutanecarboxylic acid (5.0 g, 34.7 mmol) in toluene (100 mL) and the reaction mixture was heated to reflux for 5 h. The reaction mixture was cooled to 0° C. and quenched with 1N HCl. Organic layer was separated off and the aq. phase was extracted with ethyl acetate (2×20 mL). Combined organic layer was washed with saturated NaHCO$_3$ solution followed by water (50 mL) and dried over Na$_2$SO$_4$. Solvent removal under reduced pressure afforded the product (5.8 g, 93.5%) as a pale yellow oil. $^1$H NMR (400 MHz, CDCl$_3$): δ 4.20 (q, J=7.1 Hz, 2H), 3.44-3.37 (m, 2H), 3.31-3.17 (m, 3H), 1.28 (t, J=7.1 Hz, 3H).

Step 2: ethyl 3-(dibenzylamino)cyclobutane-1-carboxylate added dibenzyl amine (3.05 g, 15.4 mmol) was added to a solution of ethyl 3-oxocyclobutane-1-carboxylate (2.0 g, 14.4 mmol) in 10% THF in AcOH (50 mL) and the reaction mixture was stirred at room temperature for 20 min followed by addition of sodium cyanoborohydride (1.77 g, 28 mmol) portion wise. The mixture was stirred at room temperature for 12 h, volatiles were removed under reduced pressure and the crude compound was diluted with DCM (50 mL). DCM layer was washed with water and saturated NaHCO$_3$ solution, dried over Na$_2$SO$_4$ and concentrated under reduced pressure to get the crude compound. The crude compound was purified by combiflash using 10% ethyl acetate in hexane as eluent to afford the product (2.0 g, 44.4%) as colorless oil. $^1$H NMR (400 MHz, CDCl$_3$): δ 7.33-7.26 (m, 8H), 7.23-7.20 (m, 2H), 4.13-4.07 (m, 2H), 3.49 (s, 3H), 3.46 (s, 1H), 3.12-3.07 (m, 1H), 2.66-2.61 (m, 1H), 2.25-2.03 (m, 4H), 1.25-1.22 (t obscured by occluded EtOAc, 3H); LC-MS: [M+H]$^+$ 324.4

Step 3: 3-(dibenzylamino)cyclobutane-1-carbohydrazide hydrazine hydrate (0.99 mL, 30.9 mmol) was added to a solution of ethyl 3-(dibenzylamino)cyclobutane-1-carboxylate (2.0 g, 6.19 mmol) in EtOH (20 mL) and the reaction mixture was refluxed for 12 h. The volatiles were removed under reduced pressure and the crude compound was washed with hexane (2×20 mL). The residue thus obtained was dried under vacuum to get the product (1.8 g, 94.2%) as a white solid. $^1$H NMR (400 MHz, CDCl$_3$): δ 7.31-7.26 (m, 8H), 7.25-7.20 (m, 2H), 6.80 (s, 1H), 3.83 (br, 2H), 3.50 (s, 4H), 3.13-3.05 (m, 1H), 2.51-2.42 (m, 1H), 2.23-2.10 (m, 4H); LC-MS: [M+H]$^+$=309.9

Example 16: N-trans-3-(5-(hydroxymethyl)-1,3,4-thiadiazol-2-yl)cyclobutyl)-5-phenylisoxazole-3-carboxamide and N-cis-3-(5-(hydroxymethyl)-1,3,4-thiadiazol-2-yl)cyclobutyl)-5-phenylisoxazole-3-carboxamide

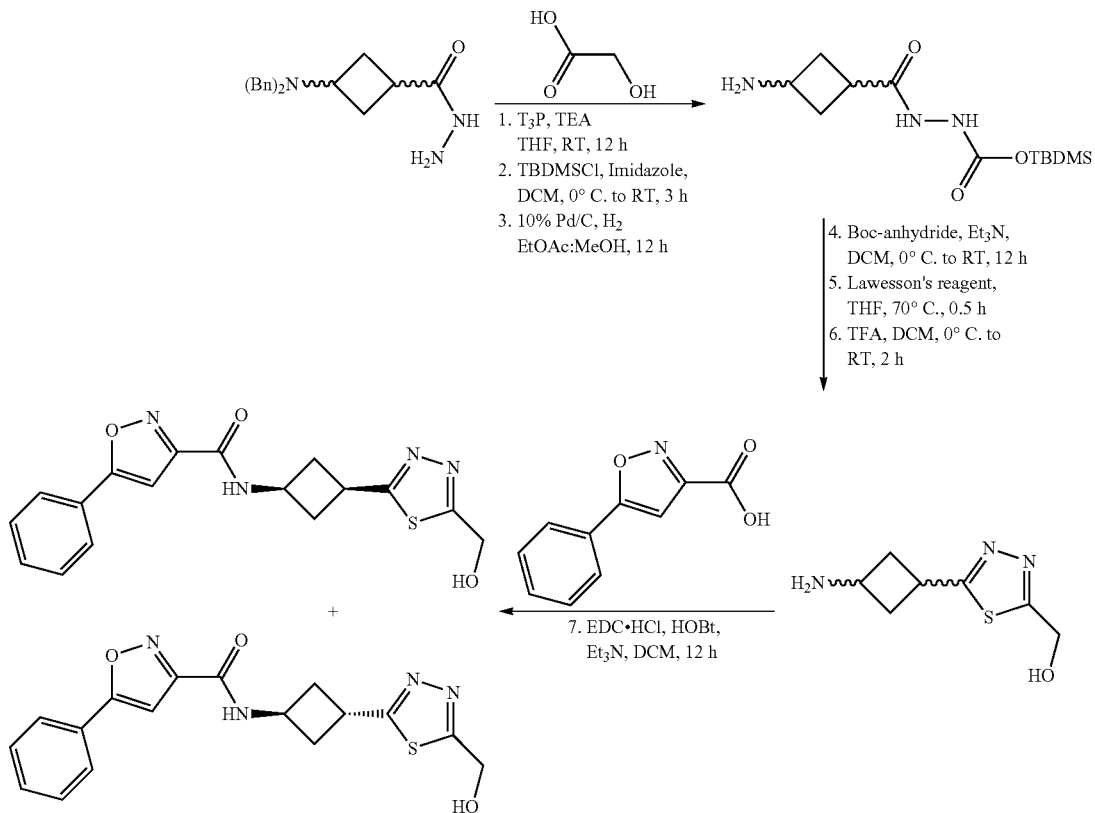

Step 1: 3-(dibenzylamino)-N'-(2-hydroxyacetyl) cyclobutane-1-carbohydrazide triethyl amine (2.7 mL, 19 mmol) was added to a solution of glycolic acid (0.5 g, 6.5 mmol) in DCM (20 mL) followed by T$_3$P (3.13 g, 9.8 mmol) and the reaction mixture was stirred for 10 min 3-(dibenzylamino)cyclobutane-1-carbohydrazide (2.23 g, 7.2 mmol) was added to the resulting reaction mixture and it was stirred at room temperature for 12 h. The reaction mixture was diluted with ice-water (20 mL) and the aq. phase was extracted with DCM (2×20 mL). Combined organic layer was washed with brine (20 mL), dried over Na$_2$SO$_4$ and concentrated under reduced pressure to get the crude compound. The crude compound was purified by combiflash using 3% MeOH in DCM as eluent to give the product (2.3 g, crude) as a white solid which was used as such in next step without further purification.

Step 2: N'-(2-((tert-butyldimethylsilyl)oxy)acetyl)-3-(dibenzylamino)cyclobutane-1-carbohydrazide imidazole (0.93 g, 13.7 mmol) was added to a solution of 3-(dibenzylamino)-N'-(2-hydroxyacetyl)cyclobutane-1-carbohydrazide (2.3 g, crude) in dry DMF (5 mL) and the reaction mixture was stirred for 10 minutes under N$_2$ atmosphere. The reaction mixture was cooled in an ice bath, and TBDMSCl (1.88 g, 12.5 mmol) was added and the resulting reaction mixture was stirred at room temperature for 3 h. The reaction mixture was quenched with water (10 mL) and extracted with ethyl acetate (3×50 mL). Combined organic layer was dried over Na$_2$SO$_4$ and concentrated under reduced pressure to get the crude compound. The mixture was purified by column chromatography using 30% ethyl acetate in hexane as eluent to get the product (2.0 g, 57% over two steps) as a white solid. $^1$H NMR (400 MHz, CDCl$_3$): δ 8.95 (d, J=5.9 Hz, 1H), 8.19 (d, J=6.6 Hz, 1H), 7.30-7.28 (m, 8H), 7.26-7.27 (m, 2H), 4.20 (s, 2H), 3.50 (s, 4H), 3.15-3.11 (m, 1H), 2.61-2.57 (m, 1H), 2.24-2.20 (m, 4H), 0.92 (s, 9H), 0.11 (s, 6H); LC-MS: [M+H]$^+$ 482.0

Step 3: 3-amino-N'-(2-((tert-butyldimethylsilyl)oxy) acetyl)cyclobutane-1-carbohydrazide 10% Pd-C (0.2 g) was added to a mixture of N-(2-((tert-butyldimethylsilyl)oxy)acetyl)-3-(dibenzylamino)cyclobutane-1-carbohydrazide (2.0 g, 4.15 mmol) in EtOAc-MeOH (30 mL) and the reaction mixture was stirred under H$_2$ atmosphere for 12 h at room temperature. The reaction mixture was filtered and washed with MeOH (2×10 mL). Filtrate was concentrated under reduced pressure to get the crude compound. The crude compound was purified by column chromatography using 20% MeOH in DCM as eluent to afford the product (0.8 g, 64.0%) as a white solid. $^1$H NMR (400 MHz, CDCl$_3$): δ 4.2 (s, 2H), 3.47-3.35 (m, 1H), 2.67-2.58 (m, 1H), 2.55-2.48 (m, 2H), 2.03-1.96 (m, 2H), 0.93 (s, 9H), 0.11 (s, 6H); LC-MS: [M+H]$^+$ 301.9.

Step 4: tert-butyl (3-(2-(2-((tert-butyldimethylsilyl) oxy)acetyl)hydrazine-1-carbonyl)cyclobutyl) carbamate triethyl amine (0.74 mL, 5.31 mmol) was added to an ice cooled solution of 3-amino-N'-(2-((tert-butyldimethylsilyl) oxy)acetyl)cyclobutane-1-carbohydrazide (0.8 g, 2.65 mmol) in DCM (10 mL). Boc-anhydride (0.91 mL, 3.98 mmol) was added to the mixture and the reaction mixture was stirred at room temperature for 12 h. The reaction was diluted with cold water (20 mL) and extracted with DCM (2×10 mL). Combined organic layer was dried over Na$_2$SO$_4$ and evaporated to dryness under vacuum to get the crude compound. The crude compound was purified by combiflash using 3% MeOH in DCM as eluent to afford the product (0.9 g, crude) as an off white solid. As per 1H-NMR, compound is not pure and used as such in next step.

Step 5: tert-butyl (3-(5-(((tert-butyldimethylsilyl) oxy)methyl)-1,3,4-thiadiazol-2-yl)cyclobutyl) Carbamate Lawesson's reagent (3.52 g, 8.7 mmol) was added to a solution of -butyl (3-(2-(2-((tert-butyldimethylsilyl)oxy) acetyl)hydrazine-1-carbonyl)cyclobutyl) carbamate (0.7 g, 1.74 mmol) in THF (10 mL) and the reaction mixture was heated to 70° C. for 30 min. The volatiles were removed under reduced pressure and the crude compound was purified by neutral alumina column chromatography using 15% EtOAc in hexane to afford the product (0.3 g, 32% over two steps) as white solid. $^1$H NMR (400 MHz, CDCl$_3$): δ 5.0 (s, 2H), 4.81-4.80 (br, 1H), 4.21 (m, 1H), 3.58-3.49 (m, 1H), 2.92-2.87 (m, 2H), 2.28-2.20 (m, 2H), 1.43 (s, 9H), 0.92 (s, 9H), 0.11 (s, 6H); LC-MS: [M+H]$^+$ 399.6.

Step 6: (5-(3-aminocyclobutyl)-1,3,4-thiadiazol-2-yl)methanol trifluoroacetic acid (0.171 g, 1.5 mmol) was added to an ice cooled solution of tert-butyl (3-(5-(((tert-butyldimethylsilyl)oxy)methyl)-1,3,4-thiadiazol-2-yl)cyclobutyl) carbamate (0.3 g, 7.5 mmol) in DCM (5 mL) and the reaction mixture was stirred at room temperature for 2 h. The volatiles were removed under reduced pressure to get the product (0.178 g, crude) as a white solid which was used as such in next step without further purification.

Step 7: N-trans-3-(5-(hydroxymethyl)-1,3,4-thiadiazol-2-yl)cyclobutyl)-5-phenylisoxazole-3-carboxamide and N-cis-3-(5-(hydroxymethyl)-1,3,4-thiadiazol-2-yl)cyclobutyl)-5-phenylisoxazole-3-carboxamide EDC.HCl (0.287 g, 1 mmol), HOBt (0.168 g, 11 mmol) were added to a solution of 5-phenylisoxazole-3-carboxylic acid (0.189 g, 1 mmol) in THF (5 mL), followed by addition of: (5-(3-aminocyclobutyl)-1,3,4-thiadiazol-2-yl)methanol (0.3 g, crude) and the mixture was stirred for 10 min. Triethyl amine (0.42 mL, 3 mmol) was added to the mixture and stir at room temperature for 12 h. The reaction mixture was diluted with cold water (20 mL) and extracted with DCM (2×10 mL). Combined organic layer was washed with brine and dried over Na$_2$SO$_4$ and concentrated under reduced pressure to get the crude compound. The crude compound was purified by prep HPLC to afford:

N-cis-3-(5-(hydroxymethyl)-1,3,4-thiadiazol-2-yl) cyclobutyl)-5-phenylisoxazole-3-carboxamide (0.05 g)

Yield: 11% over two steps
Appearance: off white solid.
Analytical data: $^1$H NMR (400 MHz, CDCl$_3$): δ 7.83-7.79 (m, 2H), 7.53-7.49 (m, 3H), 7.22-7.20 (br, 1H), 6.97 (s, 1H), 5.08 (s, 2H), 4.75-4.68 (m, 1H), 3.77-3.68 (m, 1H), 3.10-3.03 (m, 2H), 2.62 (br, 1H), 2.57-2.51 (m, 2H).
LC-MS: [M+H]$^+$ 356.8
HPLC purity: 99.19% at 220 nm and 99.11% at 254 nm.

N-trans-3-(5-(hydroxymethyl)-1,3,4-thiadiazol-2-yl)cyclobutyl)-5-phenylisoxazole-3-carboxamide (0.01 g)

Yield: 2% over two steps
Appearance: off white solid.
Analytical data: $^1$H NMR (400 MHz, CDCl$_3$): δ 7.80-7.78 (m, 2H), 7.50-7.47 (m, 3H), 7.11 (d, J=6.8 Hz, 1H), 6.95 (s, 1H), 5.07 (d, J=5.4 Hz, 2H), 4.88-4.83 (m, 1H), 4.02-3.98 (m, 1H), 2.95-2.88 (m, 2H), 2.76-2.69 (m, 2H), 2.51-2.48 (m, 1H).
LC-MS: [M+H]$^+$ 357.1
HPLC purity: 98.58% at 220 nm and 98.43% at 254 nm.

Example 17

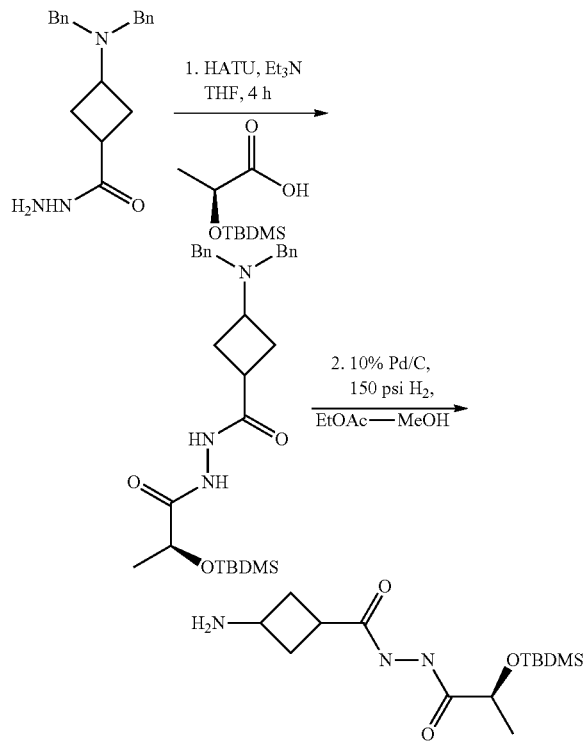

Step 1: (S)—N'-(2-((tert-butyldimethylsilyl)oxy)propanoyl)-3-(dibenzylamino)cyclobutane-1-carbohydrazide HATU (12.0 g, 31.6 mmol) was added to a solution of 2-((tert-butyldimethylsilyl)oxy)propanoic acid (4.3 g, 6.31 mmol) in THF (50 mL) followed by addition of 3-(dibenzylamino)cyclobutane-1-carbohydrazide (6.5 g, 6.31 mmol) and the reaction mixture was stirred for 10 min at room temperature. Triethyl amine (6.3 mL, 63.1 mmol) was added to the reaction mixture and stirring continued for 4 h at room temperature. The volatiles were removed under reduced pressure and the reaction mixture was quenched with ice-water (20 mL). The aq. phase was extracted with ethyl acetate (2×20 mL). Combined organic layer was washed with brine (20 mL), dried over Na$_2$SO$_4$ and concentrated under reduced pressure to get the crude compound. The crude compound was purified by combiflash using 15% ethyl acetate in hexane to obtain the product (6.2 g, 59.6%) as off white solid. $^1$H NMR (400 MHz, CDCl$_3$): δ 9.06 (d, J=6.2 Hz, 1H), 8.58 (d, J=6.4 Hz, 1H), 7.29-7.27 (m, 8H), 7.23-7.18 (m, 2H), 4.31 (q, J=6.7 Hz, 1H), 3.50 (s, 4H), 3.14-3.09 (m, 1H), 2.62-2.57 (m, 1H), 2.25-2.18 (m, 4H), 1.40 (d, J=6.7 Hz, 3H), 0.93 (s, 9H), 0.12-0.11 (two adjacent singlets, 6H); LC-MS: [M+H]$^+$ 496.0.

Step 2: (S)-3-amino-N'-(2-((tert-butyldimethylsilyl)oxy)propanoyl)cyclobutane-1-carbohydrazide a solution of (S)—N'-(2-((tert-butyldimethylsilyl)oxy)propanoyl)-3-(dibenzylamino)cyclobutane-1-carbohydrazide (6.2 g, 12.5 mmol) and 10% Pd-C (0.6 g) in EtOAc: MeOH (60:5 mL) was hydrogenated (150 psi) at 50° C. for 12 h. The reaction mixture was filtered, washed with MeOH (2×10 mL) and filtrate was evaporated to dryness under reduced pressure. The crude compound thus obtained was purified by 100-200 mesh silica gel using 20% MeOH in DCM as eluent to afford the product (2.5 g, crude) as white semisolid. $^1$H NMR (400 MHz, CDCl$_3$): δ 4.32 (q, J=6.7 Hz, 1H), 3.41-3.37 (m, 1H), 2.67-2.55 (m, 1H), 2.54-2.48 (m, 2H), 2.04-2.0 (m, 2H), 1.41 (d, J=6.7 Hz, 3H), 0.93 (s, 9H), 0.12-0.11 (two adjacent singlets, 6H); LC-MS: [M+H]$^+$ 315.7.

Example 18: N-cis-3-(5-((S)-1-hydroxyethyl)-1,3,4-thiadiazol-2-yl)cyclobutyl)-5-phenylisoxazole-3-carboxamide

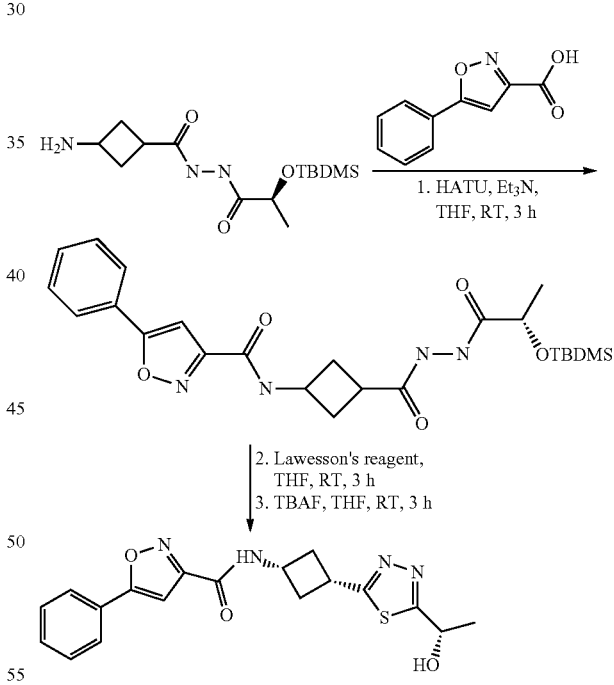

Step 1: (S)—N-(3-(2-(2-((tert-butyldimethylsilyl)oxy)propanoyl)hydrazine-1-carbonyl)cyclobutyl)-5-phenylisoxazole-3-carboxamide HATU (3.6 g, 9.5 mmol) was added to a solution of 5-phenylisoxazole-3-carboxylic acid (1.19 g, 6.3 mmol) in THF (20 mL) followed by addition of (S)-3-amino-N'-(2-((tert-butyldimethylsilyl)oxy)propanoyl)cyclobutane-1-carbohydrazide (2.0 g, 6.31 mmol). The reaction mixture was stirred for 10 minutes at room temperature and triethyl amine (2.67 mL, 19.0 mmol) was then added. The reaction mixture was stirred at room temperature for 3 h, volatiles were removed under reduced pressure and the reaction mixture was quenched with ice-water (20 mL). The aq. phase was extracted with ethyl acetate (3×20 mL). Combined organic layer was washed with brine (20 mL), dried over $Na_2SO_4$ and concentrated under reduced pressure to get the crude compound. The crude compound thus obtained was purified by combiflash using 45% ethyl acetate in hexane to get the product (2.2 g, 73.3%) as a white solid. $^1$H NMR (400 MHz, $CDCl_3$): δ 9.10-9.05 (m, 1H), 8.43-8.39 (m, 1H), 7.79-7.27 (m, 2H), 7.50-7.46 (m, 3H), 7.20-7.16 (m, 1H), 6.92 (s, 1H), 4.63-4.57 (m, 1H), 4.37-4.32 (m, 4H), 2.84-2.81 (m, 5H), 2.72-2.70 (m, 1H), 1.42 (d, J=6.6 Hz, 2H), 0.95 (s, 9H), 0.14 (s, 3H), 0.12 (s, 3H); LC-MS: [M+H]$^+$ 487.3.

Step 2: (S)—N-(3-(5-(1-((tert-butyldimethylsilyl)oxy)ethyl)-1,3,4-thiadiazol-2-yl)cyclobutyl)-5-phenylisoxazole-3-carboxamide Lawesson's reagent (2.7 g, 6.79 mmol) was added to a solution of (S)—N-(3-(2-(2-((tert-butyldimethylsilyl)oxy)propanoyl)hydrazine-1-carbonyl)cyclobutyl)-5-phenylisoxazole-3-carboxamide and the reaction mixture was stirred at room temperature for 3 h. Progress of the reaction was monitored by TLC. After completion, volatiles were removed under reduced pressure to obtain the crude compound which was further purified by neutral alumina column chromatography using 20% ethyl acetate in hexane to afford the product (1.3 g, 59%) as pale yellow oil. $^1$H NMR (400 MHz, $CDCl_3$): δ 7.82-7.80 (m, 2H), 7.52-7.50 (m, 3H), 7.17 (d, J=8.4 Hz, 1H), 6.97 (s, 1H), 5.29-5.26 (q, J=6.3 Hz, 1H), 4.75-4.71 (m, 1H), 3.71-3.66 (m, 1H), 3.07-3.02 (m, 2H), 2.52-2.47 (m, 2H), 1.62-1.56 (m, 3H), 0.91 (s, 9H), 0.15 (s, 3H), 0.10 (s, 3H); LC-MS: [M+H]$^+$ 485.5.

Step 3: N-cis-3-(5-((S)-1-hydroxyethyl)-1,3,4-thiadiazol-2-yl)cyclobutyl)-5-phenylisoxazole-3-carboxamide TBAF (4.0 mL, 4.0 mmol) was added to a solution of (S)—N-(3-(5-(1-((tert-butyldimethylsilyl)oxy)ethyl)-1,3,4-thiadiazol-2-yl)cyclobutyl)-5-phenylisoxazole-3-carboxamide (1.3 g, 2.68 mmol) in THF (10 mL) and the reaction mixture was stirred at room temperature for 3 h. The reaction mixture was diluted with cold water, filtered and the solid washed with water followed by hexane and dried under reduced pressure to get the crude compound. The crude compound was purified by prep HPLC to afford the product (0.2 g. 20.2%) as a white solid.

Analytical data: $^1$H NMR (400 MHz, $CDCl_3$): δ 7.80-7.77 (m, 2H), 7.49-7.46 (m, 3H), 7.20 (d, J=8 Hz, 1H), 6.94 (s, 1H), 5.28 (q, J=6.5 Hz, 1H), 4.71-4.46 (m, 1H), 3.70-3.63 (m, 1H), 3.06-2.99 (m, 2H), 2.86 (bs, 1H), 2.55-2.46 (m, 2H), 1.68 (d, J=6.6 Hz, 3H).

LC-MS: [M+H]$^+$ 371.2

HPLC purity: 98.09% at 220 nm and 98.44% at 254 nm.

Example 19: N-cis-3-(5-((R)-1-hydroxyethyl)-1,3,4-thiadiazol-2-yl)cyclobutyl)-5-phenylisoxazole-3-carboxamide

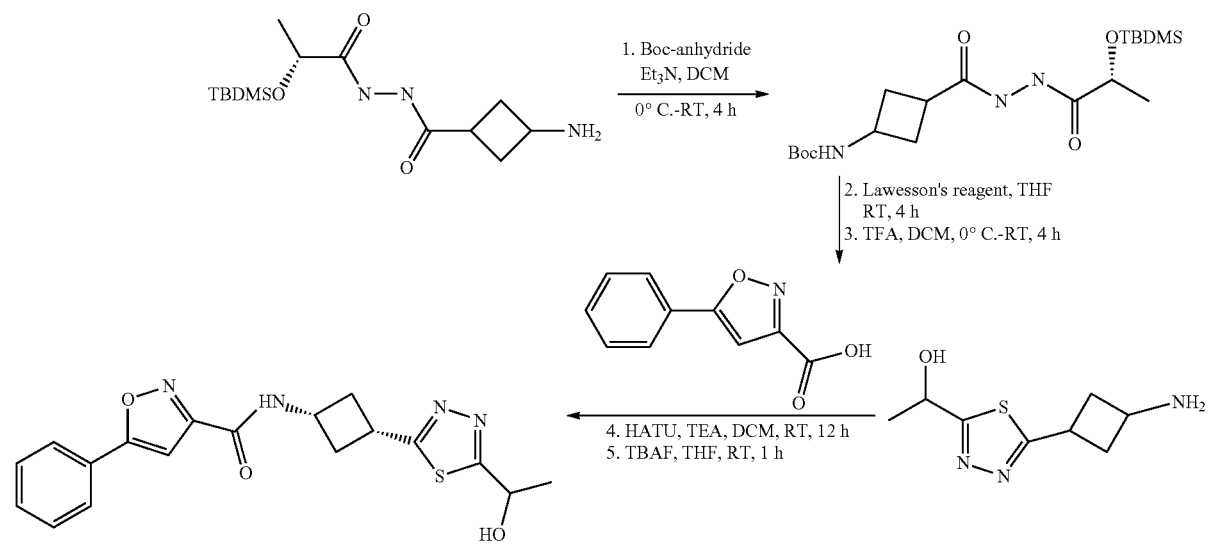

Step 1: tert-butyl (R)-(3-(2-(2-((tert-butyldimethylsilyl)oxy)propanoyl)hydrazine-1-carbonyl)cyclobutyl)carbamate triethyl amine (0.8 mL, 5.7 mmol) was added to a cold solution of (R)-3-amino-N'-(2-((tert-butyldimethylsilyl)oxy)propanoyl)cyclobutane-1-carbohydrazide (0.6 g, 1.9 mmol, prepared using procedure shown in example 17) in DCM (10 mL) followed by boc-anhydride (0.65 mL, 2.85 mmol) and the reaction mixture was stirred at room temperature for 4 h. The reaction mixture was diluted with cold water (20 mL) and extracted with DCM (2×20 mL). Combined organic layer was dried over $Na_2SO_4$ and evaporated to dryness under vacuum. The crude compound was purified by flash column chromatography using 20% ethyl acetate in hexane to afford the product (0.8 g, crude) as white solid which was used as such in next step. LC-MS: [M+H]$^+$ 415.9

Step 2: tert-butyl (R)-(3-(5-(1-((tert-butyldimethylsilyl)oxy)ethyl)-1,3,4-thiadiazol-2-yl)cyclobutyl)carbamate Lawesson's reagent (1.88 g, 4.6 mmol) was added to a solution of tert-butyl (R)-(3-(2-(2-((tert-butyldimethylsilyl)oxy)propanoyl)hydrazine-1-carbonyl)cyclobutyl)carbamate (0.8 g, crude) in THF (10 mL) and the reaction mixture stirred at room temperature for 4 h. The reaction mixture was purified by neutral alumina column chromatography using 15% ethyl acetate in hexane as eluent to afford the product (0.42 g, 22% over three steps) as a colorless oil. $^1$H NMR (400 MHz, CDCl$_3$): δ 5.21 (q, J=6.4 Hz, 1H), 4.81 (br, 1H), 4.22-4.20 (br, 1H), 3.56-3.47 (m, 1H), 2.91-2.84 (m, 2H), 2.28-2.18 (m, 2H), 1.56 (br obscured by solvent signal, 3H), 1.43 (s, 9H), 0.90 (s, 9H), 0.11 (s, 3H), 0.05 (s, 3H); LC-MS: [M+H]$^+$ 413.6.

Step 3: (R)-1-(5-(3-aminocyclobutyl)-1,3,4-thiadiazol-2-yl)ethan-1-ol trifluoroacetic acid (0.233 mL, 3.05 mmol) was added to a solution of tert-butyl (R)-(3-(5-(1-((tert-butyldimethylsilyl)oxy)ethyl)-1,3,4-thiadiazol-2-yl)cyclobutyl)carbamate (0.42 g, 1.06 mmol) in DCM (5 mL) and the reaction mixture was stirred at room temperature for 4 h. The volatiles were removed under reduced pressure to get the product (0.3 g, crude) as colorless oil which was used as such in next step without further purification. LC-MS: [M+H]$^+$ 314.7.

Steps 4 and 5: N-((1S,3s)-3-(5-((R)-1-hydroxyethyl)-1,3,4-thiadiazol-2-yl)cyclobutyl)-5-phenylisoxazole-3-carboxamide:

HATU (0.837 g, 2.2 mmol) was added to a solution of 5-phenylisoxazole-3-carboxylic acid (0.277 g, 1.4 mmol) in THF (5 mL) followed by addition of (R)-1-(5-(3-aminocyclobutyl)-1,3,4-thiadiazol-2-yl)ethan-1-ol (0.46 g, crude) and the resulting reaction mixture was stirred for 10 min. Triethyl amine (0.61 mL, 4.4 mmol) was added to the reaction mixture and stirring continued at room temperature for 12 h. Cold water (20 mL) was added to the mixture and then extracted with DCM (2×10 mL). Combined organic layer was washed with brine, dried over Na$_2$SO$_4$ and evaporated to dryness under vacuum. The crude compound was dissolved in THF (5 mL) and TBAF solution (1.2 mL, 1.2 mmol) was added and the reaction mixture was stirred for 1 h. After completion, the reaction mixture was quenched with cold water (20 mL) and extracted with DCM (2×5 mL). Combined organic layer was washed with brine and dried over Na$_2$SO$_4$ and evaporated to dryness under reduced pressure to get the crude compound which was purified by prep HPLC to afford 5-Phenyl-isoxazole-3-carboxylic acid {3-[5-((R)-1-hydroxy-ethyl)-[1, 3,4]thiadiazol-2-yl]-cyclobutyl}-amide (0.110 g, 15% over two steps) as an off white solid.

Analytical data: $^1$H NMR (400 MHz, CDCl$_3$): δ 7.78-7.76 (m, 2H), 7.50-7.46 (m, 3H), 7.20 (d, J=8 Hz, 1H), 6.94 (s, 1H), 5.28 (q, J=6.5 Hz, 1H), 4.71-4.65 (m, 1H), 3.72-3.63 (m, 1H), 3.05-2.99 (m, 2H), 2.85 (br, 1H), 2.53-2.46 (m, 2H), 1.68 (d, J=6.5 Hz, 3H).

LC-MS: [M+H]$^+$ 370.9

HPLC purity: 98.21% at 220 nm and 98.95% at 254 nm.

Example 20: N-cis-3-(hydrazinecarbonyl)cyclobutyl)-5-phenylisoxazole-3-carboxamide

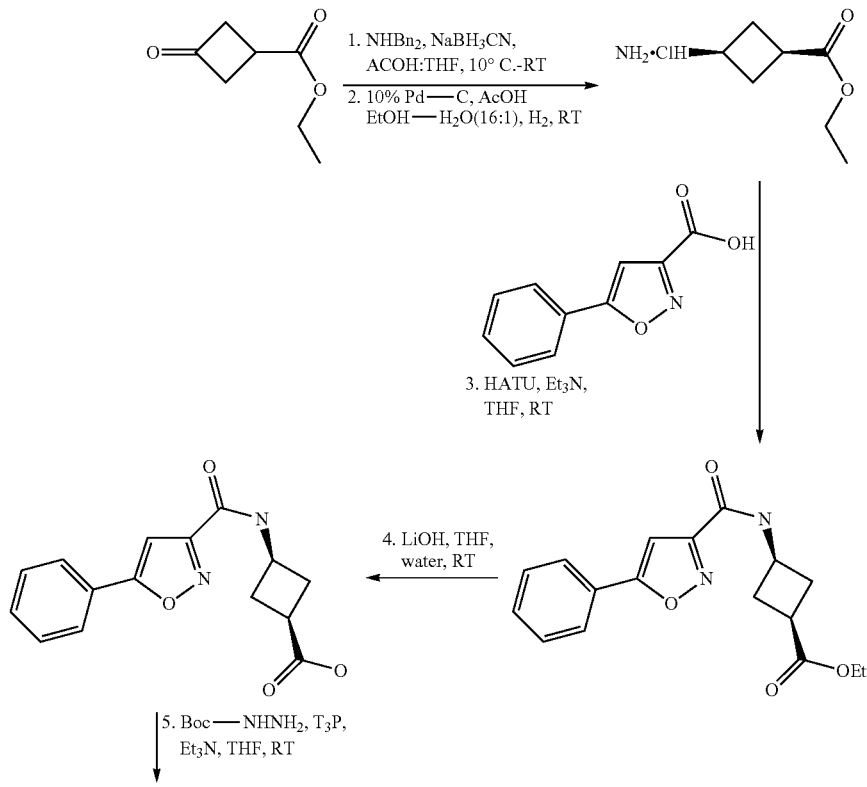

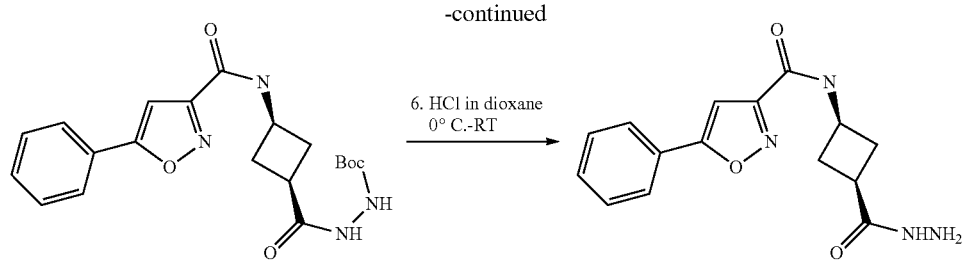

Step 1: ethyl cis-3-(dibenzylamino)cyclobutane-1-carboxylate dibenzyl amine (15.72 g, 79.69 mmol) and sodium cyanoborohydride (9.10 g, 144.9 mmol) were added sequentially to a solution of ethyl 3-oxocyclobutane-1-carboxylate (10.3 g, 72.45 mmol) in AcOH-THF (250 mL, 1:9) at 10° C. and the reaction mixture stirred at room temperature for 16 h. The volatiles were removed under reduced pressure and the crude reaction mixture was diluted with water. The aq. phase was extracted with DCM (50×3 mL). Combined organic layer was washed with sodium bicarbonate solution (50×2 mL) followed by brine (50 mL) and dried over anhydrous sodium sulfate. Volatiles were removed under reduced pressure to get the crude compound which was purified by combiflash chromatography using 7% ethyl acetate in n-hexane as eluent to give the product (15 g, 64.04%) as a colorless oil. 1H-NMR (400 MHz, CDCl$_3$) δ 7.32-7.27 (m, 8H), 7.24-7.20 (m, 2H), 4.10 (q, J=7.1 Hz, 2H), 3.50 (s, 4H), 3.13-3.08 (m, 1H), 2.66-2.62 (m, 1H), 2.25-2.04 (m, 4H), 1.24 (t, J=7.1 Hz, 3H); LC-MS: (M+H)$^+$=323.9.

Step 2: ethyl cis-3-aminocyclobutane-1-carboxylate hydrochloride acetic acid (1.77 mL, 30.91 mmol) was added to a solution of ethyl cis-3-(dibenzylamino)cyclobutane-1-carboxylate (10.0 g, 30.91 mmol) in EtOH:H$_2$O (510 mL) and the reaction mixture was degassed for 10 min. To the resulting reaction mixture was added Pd/C (3 g) and the reaction mixture was agitated in a Parr shaker under H$_2$ atmosphere for 16 h at room temperature. The reaction mixture was flittered through celite bed and washed with ethanol (2×100 mL). Filtrate was concentrated under reduced pressure to get the crude compound which was treated with 4M HCl in dioxane to get crude hydrochloride salt of compound 3. The crude compound was washed with diethyl ether to get as a mixture of cis and trans isomers (5 g). The mixture was dissolved in IPA (10 mL). After stirring for 1 h, the solution was cooled 0-5° C. and filtered. The solid was washed with cold IPA (2 mL) and dried under vacuum to get crude product (3.6 g, 81%) as off white solid. $^1$H-NMR (400 MHz, CDCl$_3$) δ 8.20 (br, 3H), 4.07 (q, J=7.1 Hz, 2H), 3.63-3.55 (m, 1H), 2.99-2.92 (m, 1H), 2.44-2.37 (m, 2H), 2.29-2.21 (m, 2H), 1.18 (t, J=7.1 Hz, 3H); LC-MS: (M+H)$^+$144.0.

Step 3: ethyl cis-3-(5-phenylisoxazole-3-carboxamido)cyclobutane-1-carboxylate Et$_3$N (5.3 mL, 0.04 mol) followed by HATU (9.16 g, 0.024 mol) were added to a solution of ethyl cis-3-aminocyclobutane-1-carboxylate hydrochloride (3.63 g, 0.020 mol) and 5-phenylisoxazole-3-carboxylic acid (4.20 g, 0.022 mol) in THF (150 mL) and the reaction mixture was stirred for 6 h at room temperature. Volatiles were removed under reduced pressure and the crude reaction mixture was diluted with water (100 mL). The aq. phase was extracted with ethyl acetate (200 mL). The organic layer was dried over anhydrous Na$_2$SO$_4$ and concentrated under reduced pressure to obtain the crude product. The crude compound was purified by silica gel column chromatography using 50% EtOAc in hexane as eluent to afford the product (5.02 g, 79%) as off white solid. $^1$H NMR (400 MHz, CDCl$_3$): δ 7.79-7.77 (m, 2H), 7.50-7.46 (m, 3H), 7.08 (d, J=8.0 Hz, 1H), 6.93 (s, 1H), 4.61-4.12 (m, 1H), 4.15 (q, J=7.1 Hz, 2H), 2.89-2.83 (m, 1H), 2.74-2.68 (m, 2H), 2.32-2.24 (m, 2H), 1.26 (t, J=7.2 Hz, 2H), LC-MS: [M+H]$^+$ 315.1.

Step 4: cis-3-(5-phenylisoxazole-3-carboxamido)cyclobutane-1-carboxylic acid lithium hydroxide monohydrate (0.800 g, 0.0190 mol) was added to a solution of ethyl cis-3-(5-phenylisoxazole-3-carboxamido)cyclobutane-1-carboxylate (5.0 g, 0.0159 mol) in THF—H$_2$O (200 mL, 1:1) and the reaction mixture was stirred at room temperature for 2 h. Volatiles were removed under reduced pressure and the crude reaction mixture was poured onto water (50 mL). The aq. phase was washed with ethyl acetate (2×10 mL) and the aq. layer was acidified with saturated citric acid solution. The precipitate thus obtained was filtered, washed with water and dried to afford the product (4.14 g, 90%) as a white solid. $^1$H NMR (400 MHz, DMSO-d$_6$): δ 12.14 (br, 1H), 9.11 (d, J=7.7 Hz, 1H), 7.93-7.91 (m, 2H), 7.58-7.53 (m, 3H), 7.34 (s, 1H), 4.40-4.29 (m, 1H), 2.80-2.73 (m, 1H), 2.50-2.42 (m, 2H), 2.40-2.32 (m, 2H); LC-MS: [M+H]$^+$ 287.1.

Step 5: tert-butyl 2-cis-3-(5-phenylisoxazole-3-carboxamido)cyclobutane-1-carbonyl)hydrazine-1-carboxylate Boc-hydrazine (2.2 g, 0.017 mol) was added to a solution of cis-3-(5-phenylisoxazole-3-carboxamido)cyclobutane-1-carboxylic acid (4.14 g, 0.0144 mol) in THF (100 mL) followed by the addition of Et$_3$N (5.81 mL, 0.043 mol) and T$_3$P in EtOAc (50%, 17.13 mL, 0.0288 mol) and the reaction mixture was stirred at room temperature for 12 h. Volatiles were removed under reduced pressure and the crude reaction mixture was poured onto water (100 mL). The aq. phase was extracted with ethyl acetate (2×100 mL). Combined organic layer was washed with saturated NaHCO$_3$ solution (2×100 mL), dried over anhydrous Na$_2$SO$_4$ and concentrated under reduced pressure to obtain the crude product. The crude compound was purified by silica gel column chromatography using 2% MeOH in EtOAc as eluent to afford the product (5.6 g, 96%) as a white solid. $^1$H NMR (400 MHz, DMSO-d$_6$): δ 9.50 (s, 1H), 9.14 (d, J=7.5 Hz, 1H), 8.70 (s, 1H), 7.93-7.90 (m, 2H), 7.64-7.53 (m, 3H), 7.34 (s, 1H), 4.37-4.31 (m, 1H), 2.72-2.67 (m, 1H), 2.40-2.38 (m, 2H), 2.34-2.29 (m, 2H), 1.39 (s, 9H); LC-MS: [M+H]$^+$ 400.9.

Step 6: N-cis-3-(hydrazinecarbonyl)cyclobutyl)-5-phenylisoxazole-3-carboxamide 4 M HCl in dioxane (40 mL) was added to a solution of tert-butyl 2-cis-3-(5-phenylisoxazole-3-carboxamido)cyclobutane-1-carbonyl)hydrazine-1-carboxylate (5.6 g, 0.0139 mol) in 1,4 dioxane (25 mL) and the resulting reaction mixture was stirred at room temperature for 4 h. Volatiles were removed under reduced pressure and the crude compound thus obtained was stirred in diethyl ether (100 mL). The precipitate was filtered, washed with hexane and dried to afford the product (5.4 g, crude) as off white solid. $^1$H NMR (400 MHz, DMSO-d$_6$): δ 10.92 (s, 1H), 10.26 (br, 2H), 9.20 (d, J=7.5 Hz, 1H), 7.93-7.91 (m, 2H), 7.58-7.53 (m, 2H), 7.36 (s, 1H), 4.41-4.35 (m, 1H), 2.87-2.83 (m, 1H), 2.49-2.41 (m, 2H), 2.39-2.29 (m, 2H); LC-MS: [M+H]$^+$ 300.9.

Example 21: N-cis-3-(5-(hydroxymethyl)-1,3,4-oxadiazol-2-yl)cyclobutyl)-5-phenylioxazole-3-carboxamide

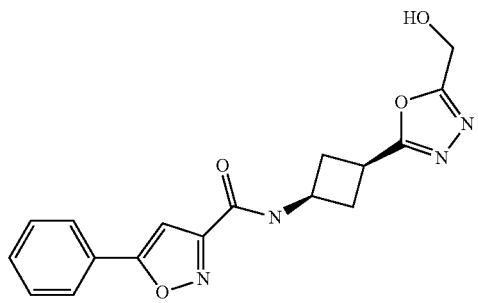 [SMILES: O=C(N[C@H]1C[C@@H](c2nnc(CO)o2)C1)c1cc(-c2ccccc2)on1]

N-cis-3-(5-(hydroxymethyl)-1,3,4-oxadiazol-2-yl)cyclobutyl)-5-phenylioxazole-3-carboxamide was prepared using a similar procedure described in example 12 using N-cis-3-(hydrazinecarbonyl)cyclobutyl)-5-phenylisoxazole-3-carboxamide as the starting material (example 20):

Appearance: off white solid

Analytical data: $^1$H-NMR (400 MHz, DMSO) δ 9.30 (d, J=7.7 Hz 1H), 7.94-7.91 (m, 2H), 7.58-7.53 (m, 3H), 7.37 (s, 1H), 5.86 (t, J=8 Hz, 1H), 4.61 (d, J=6.2 Hz, 2H), 4.56-4.50 (m, 1H), 3.53-3.46 (m, 1H) 2.72-2.66 (m, 2H), 2.54 (signal obscured by solvent signal, 2H).

LC-MS: [M+H]$^+$ 341

HPLC purity: 97.63% at 220 nm and 98.48% at 254 nm.

Example 22: N-cis-3-(5-((R)-1-hydroxyethyl)-1,3,4-oxadiazol-2-yl)cyclobutyl)-5-phenylisoxazole-3-carboxamide

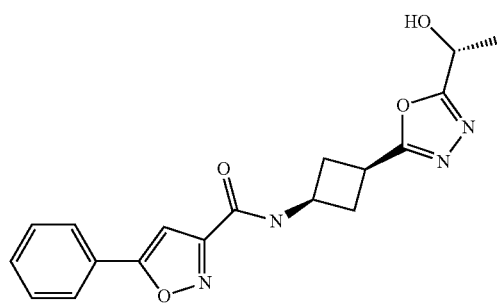 [SMILES: C[C@@H](O)c1nnc([C@H]2C[C@@H](NC(=O)c3cc(-c4ccccc4)on3)C2)o1]

N-cis-3-(5-((R)-1-hydroxyethyl)-1,3,4-oxadiazol-2-yl)cyclobutyl)-5-phenylisoxazole-3-carboxamide was prepared using a similar procedure described in example 12 using N-cis-3-(hydrazinecarbonyl)cyclobutyl)-5-phenylisoxazole-3-carboxamide as the starting material (example 20):

Appearance: off white solid

Analytical data: $^1$H-NMR (400 MHz, DMSO) δ 9.29 (d, J=7.9 Hz 1H), 7.93-7.91 (m, 2H), 7.58-7.53 (m, 3H), 7.37 (s, 1H), 5.94 (d, J=5.6 Hz, 1H), 4.92-4.86 (m, 1H), 4.59-4.48 (m, 1H), 3.53-3.47 (m, 1H), 2.72-2.65 (m, 2H), 2.54-2.59 (signal obscured by solvent signal, 2H), 1.46 (d, J=6.6 Hz, 3H).

LC-MS: [M+H]$^+$ 355.1

HPLC purity: 96.59% at 220 nm and 97.98% at 254 nm.

Example 23: N-cis-3-(5-((S)-1-hydroxyethyl)-1,3,4-oxadiazol-2-yl)cyclobutyl)-5-phenylisoxazole-3-carboxamide

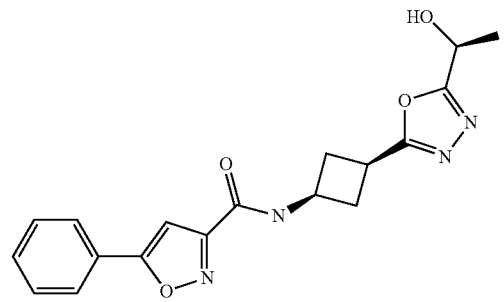 [SMILES: C[C@H](O)c1nnc([C@H]2C[C@@H](NC(=O)c3cc(-c4ccccc4)on3)C2)o1]

N-cis-3-(5-((S)-1-hydroxyethyl)-1,3,4-oxadiazol-2-yl)cyclobutyl)-5-phenylisoxazole-3-carboxamide was prepared using a similar procedure described in example 12 using N-cis-3-(hydrazinecarbonyl)cyclobutyl)-5-phenylisoxazole-3-carboxamide as the starting material (example 20).

Appearance: off white solid

Analytical data: $^1$H-NMR (400 MHz, DMSO) δ 9.29 (d, J=7.8 Hz 1H), 7.94-7.91 (m, 2H), 7.58-7.53 (m, 3H), 7.36 (s, 1H), 5.93 (d, J=5.6 Hz, 1H), 4.91-4.88 (m, 1H), 4.57-4.50 (m, 1H), 3.54-3.45 (m, 1H), 2.72-2.65 (m, 2H), 2.54-2.49 (m obscured by solvent signal, 2H), 1.46 (d, J=6.6 Hz, 3H).

LC-MS: [M+H]$^+$ 355.0

HPLC purity: 97.12% at 220 nm, 98.41% at 254 nm and 99.02% at 269 nm.

Example 24: N-cis-3-(5-((R)-1,2-dihydroxyethyl)-1,3,4-thiadiazol-2-yl)cyclobutyl)-5-phenylisoxazole-3-carboxamide

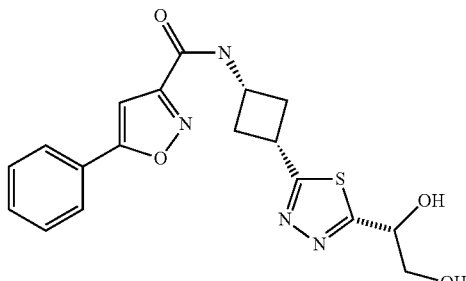

N-cis-3-(5-((R)-1,2-dihydroxyethyl)-1,3,4-thiadiazol-2-yl)cyclobutyl)-5-phenylisoxazole-3-carboxamide was prepared using a similar procedure described in example 12 using N-cis-3-(hydrazinecarbonyl)cyclobutyl)-5-phenylisoxazole-3-carboxamide as the starting material (example 20).

Appearance: off white solid

Analytical data: $^1$H NMR (400 MHz, DMSO-$d_6$): δ 9.27 (d, J=8.4 Hz, 1H), 7.94-7.92 (m, 2H), 7.58-7.54 (m, 3H), 7.37 (s, 1H), 6.32 (d, J=5.0 Hz, 1H), 5.07-5.04 (m, 1H), 4.92-4.89 (m, 1H), 4.54-4.52 (m, 1H), 3.73-3.68 (m, 2H), 3.67-3.57 (m, 1H), 2.81-2.75 (m, 2H), 2.50-2.42 (m, 1H).

LC-MS: [M+H]$^+$ 387.2

HPLC Purity: 98.16% at 269 nm and 97.06 at 254 nm.

Example 25: (1-cis-3-(5-phenylisoxazole-3-carboxamido)cyclobutyl)-1H-1,2,3-triazol-4-yl)methyl butylcarbamate

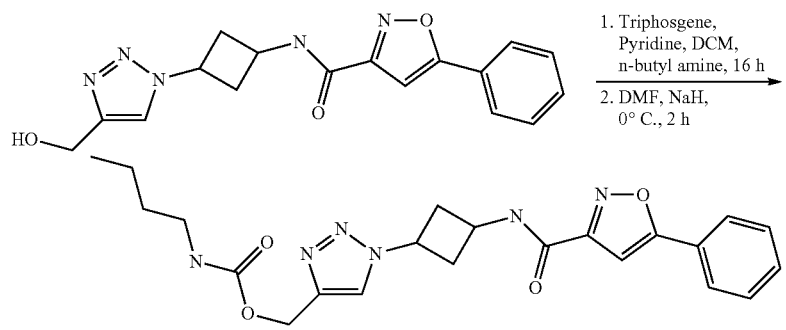

Step 1: N-butyl Carbamoyl Chloride solution of n-butyl amine (0.061 g, 0.84 mmol) and pyridine (0.266 g, 3.37 mmol) in DCM (10 mL) was added drop wise an ice-cooled solution of triphosgene (0.5 g, 1.68 mmol) in dry DCM (10 mL) under nitrogen atmosphere. The mixture was stirred for 16 h at 0° C. and filtered through a silica pad. The reaction mixture was eluted with DCM and concentrated under reduced pressure to get crude N-butyl carbamoyl chloride.

Step 2 to an ice cooled solution of N-cis-3-(4-(hydroxymethyl)-1H-1,2,3-triazol-1-yl)cyclobutyl)-5-phenylisoxazole-3-carboxamide (example 2: 0.07 g, 0.20 mmol) in DMF (2 mL) was added NaH (60%) (0.158 g, 0.41 mmol) portion wise and the reaction mixture were stirred at 0° C. for 10 min. To this resulting reaction mixture was added a solution of N-butyl carbamoyl chloride in DMF (2 mL) drop wise and the reaction mixture was stirred at 0° C. for 2 h. Progress of the reaction was monitored by TLC. After completion, the reaction mixture was diluted with water (15 mL) and extracted with ethyl acetate (15 mL×3). Combined organic layer was washed with brine, dried over anhydrous sodium sulfate and concentrated under reduced pressure to get the crude compound. The crude compound was purified by neutral alumina column chromatography using 1% MeOH in DCM as eluent to afford desired compound which was further washed with n-pentane (2 mL) followed by diethyl ether (2 mL×2) to get the product (0.025 g, 27.64%) as white solid.

Analytical data: $^1$H-NMR (400 MHz, CDCl$_3$) δ 9.27 (d, J=8.32 Hz, 1H), 8.32 (s, 1H), 7.95-7.93 (m, 2H), 7.54-7.59 (m, 3H), 7.39 (s, 1H), 7.20 (t, J=5.6 Hz, 1H), 5.04 (s, 2H), 5.01-4.93 (m, 1H), 4.46-4.40 (m, 1H), 3.00-2.88 (m, 4H), 2.69-2.66 (m, 2H), 1.38-1.29 (m, 2H), 1.27-1.20 (m, 2H), 0.85 (t J=7.2 Hz, 3H,).

LC-MS: (M+H)$^+$=439.2

HPLC purity: 94.93% at 254 nm, 94.74% at 200 nm and 93.79% at 220 nm.

Example 26: N-trans-3-(4-(R)-1-hydroxyethyl)-1H-pyrazol-1-yl)cyclobutyl)-5-phenylisoxazole-3-carboxamide and N-trans-3-(4-(S)-1-hydroxyethyl)-1H-pyrazol-1-yl)cyclobutyl)-5-phenylisoxazole-3-carboxamide

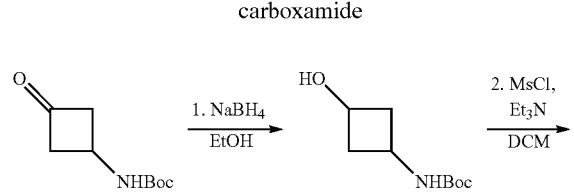

-continued

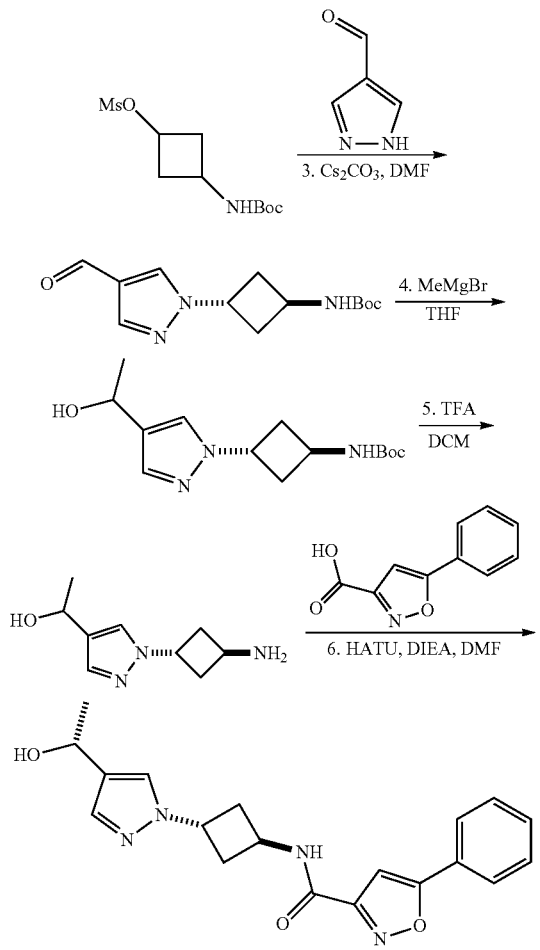

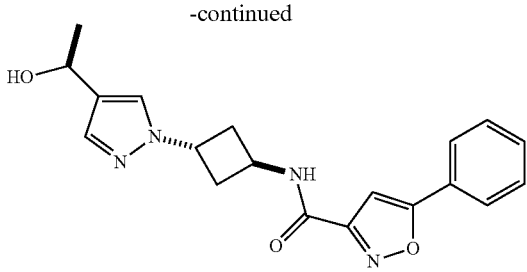

Step 1: tert-butyl (3-hydroxycyclobutyl)carbamate

NaBH$_4$ (1.02 g, 26.96 mmol, 0.50 eq.) was added slowly to a 0° C. solution of tert-butyl N-(3-oxocyclobutyl)carbamate (10 g, 53.99 mmol, 1.00 eq.) in ethanol (100 mL). The resulting solution was stirred for 1 hour at 25° C. and then concentrated under vacuum. This resulted in 9.9 g (98%) of tert-butyl N-(3-hydroxycyclobutyl)carbamate as a white solid.

Step 2: 3-((tert-butoxycarbonyl)amino)cyclobutyl methanesulfonate methanesulfonyl chloride (6.7 g, 58.49 mmol, 1.10 eq.) was added dropwise (5 min) to a 0° C. solution of tert-butyl N-(3-hydroxycyclobutyl)carbamate (9.9 g, 52.87 mmol, 1.00 eq.) and TEA (10.8 g, 106.73 mmol, 2.00 eq.) in dichloromethane (200 mL). The resulting solution was stirred for 3 hours at 25° C., the mixture was diluted with 400 mL of water. The resulting solution was extracted with dichloromethane (3×200 mL) and the organic layers combined. The resulting mixture was washed with brine (3×200 mL), dried over anhydrous sodium sulfate and concentrated under vacuum. This resulted in 11.4 g (81%) of tert-butyl N-[3-(methanesulfonyloxy)cyclobutyl]carbamate as a yellow solid.

Step 3: tert-butyl N-trans-3-(4-formyl-1H-pyrazol-1-yl)cyclobutyl]carbamate 1H-pyrazole-4-carbaldehyde (1.73 g, 18.00 mmol, 1.20 eq.) and Cs$_2$CO$_3$ (9.78 g, 30.02 mmol, 2.00 eq.) were added to a solution of tert-butyl N-[3-(methanesulfonyloxy)cyclobutyl]carbamate (4 g, 15.08 mmol, 1.00 eq.) in DMF (100 mL). The resulting solution was stirred for 16 hours at 80° C. and then diluted with 300 mL of water. The resulting solution was extracted with ethyl acetate (3×300 mL) and the organic layers combined. The resulting mixture was washed with brine (3×500 mL), dried over anhydrous sodium sulfate and concentrated under vacuum. The crude product was purified by Flash with the following conditions: Column, C18 silica gel; mobile phase, X:H$_2$O Y:ACN=70/30 increasing to X:H$_2$O Y:ACN=20/80 within 30 min; Detector, UV 254 nm. The isomers were separated by Prep-SFC with the following conditions (Prep SFC80-2): Column, Chiralpak IB, 2*25 cm, 5 um; mobile phase, CO$_2$ (80%), IPA (20%); Detector, UV 220 nm. This resulted in 1.2 g (30%) of tert-butyl N-trans-3-(4-formyl-1H-pyrazol-1-yl)cyclobutyl]carbamate as a white solid.

Step 4: tert-butyl N-trans-3-[4-(1-hydroxyethyl)-1H-pyrazol-1-yl]cyclobutyl]carbamate into a 100-mL round-bottom flask purged and maintained with an inert atmosphere of nitrogen, was placed a solution of tert-butyl N-trans-3-[4-formyl-1H-pyrazol-1-yl)cyclobutyl]carbamate (750 mg, 2.83 mmol, 1.00 eq.) in tetrahydrofuran (50 mL). This was followed by the addition of methyl magnesium bromide (3 mL, 3.00 eq., 3 mol/L) dropwise with stirring at 0° C. in 10 min. The resulting solution was stirred for 16 hours at 25° C. The reaction was then quenched by the addition of 100 mL of NH$_4$Cl aqueous. The resulting solution was extracted with ethyl acetate (3×100 mL) and the organic layers combined. The resulting mixture was washed with brine (2×200 mL), dried and concentrated under vacuum. This resulted in 600 mg (75%) of tert-butyl N-trans-3-[4-(1-hydroxyethyl)-1H-pyrazol-1-yl]cyclobutyl]carbamate as yellow oil.

Step 5: 1-[1-trans-3-aminocyclobutyl]-1H-pyrazol-4-yl]ethan-1-ol into a 50-mL round-bottom flask, was placed a solution of tert-butyl N-[(1r,3r)-3-[4-(1-hydroxyethyl)-1H-pyrazol-1-yl]cyclobutyl]carbamate (600 mg, 2.13 mmol, 1.00 eq.) in dichloromethane (15 mL) and trifluoroacetic acid (3 mL). The resulting solution was stirred for 2 hours at 25° C. The resulting mixture was concentrated under vacuum. This resulted in 226 mg (crude) of 1-[1-[trans-3-aminocyclobutyl]-1H-pyrazol-4-yl]ethan-1-ol as yellow oil.

Step 6: 5-phenyl-N-[trans-3-[4-[(1S and 1R)-1-hydroxyethyl]-1H-pyrazol-1-yl]cyclobutyl]-1,2-oxazole-3-carboxamide Into a 50-mL round-bottom flask, was placed a solution of 1-[1-[trans-3-aminocyclobutyl]-1H-pyrazol-4-yl]ethan-1-ol (226 mg, 1.25 mmol, 1.00 eq.) in DMF (5 mL). To the solution were added 5-phenyl-1,2-oxazole-3-carboxylic acid (282 mg, 1.49 mmol, 1.00 eq.), HATU (700 mg, 1.84 mmol, 1.50 eq.) and DIEA (560 mg, 4.33 mmol, 3.00 eq.). The resulting solution was stirred for 2 hours at 25° C. The resulting solution was diluted with 100 mL of water. The resulting solution was extracted with ethyl acetate (3×50 mL) and the organic layers combined. The resulting mixture was washed with brine (2×100 mL), dried and concentrated under vacuum. The residue was applied onto a silica gel column with ethyl acetate/petroleum ether (1:1). The pure isomers were separated by Chiral-Prep-HPLC with the following conditions (Prep-HPLC-004): Column, Phenomenex Lux 5u Cellulose-4 AXIA Packed, 250*21.2 mm, 5 um; mobile phase, Hex and IPA (hold 50.0% IPA in 15 min); Detector, UV 254/220 nm. This resulted in 39.6 mg (9%) of 5-phenyl-N-[trans-3-[4-[(1R)-1-hydroxyethyl]-1H-pyrazol-1-yl]cyclobutyl]-1,2-oxazole-3-carboxamide as a white solid and 39.4 mg (9%) of 5-phenyl-N-[trans-3-[4-[(1S)-1-hydroxyethyl]-1H-pyrazol-1-yl]cyclobutyl]-1,2-oxazole-3-carboxamide as a white solid:

Isomer 1:

Analytical data: $^1$H NMR (300 MHz, DMSO-d$_6$): δ 9.31-9.28 (d, J=7.2 Hz, 2H), 7.96-7.92 (m. 2H), 7.68 (s, 1H), 7.59-7.55 (m, 3H), 7.41 (s, 1H), 7.38 (s, 1H), 5.00-4.89 (m, 1H), 4.88-4.86 (d, J=4.8 Hz, 1H), 4.71-4.64 (m, 2H), 2.76-2.61 (m, 4H), 1.34-1.32 (d, J=6.3 Hz, 3H).

LC-MS: (M+H)$^+$=353

HPLC purity: 99.24 at 254 nm

Isomer 2:

Analytical data: $^1$H NMR (300 MHz, DMSO-d$_6$): δ 9.31-9.28 (d, J=7.5 Hz, 2H), 7.96-7.93 (m, 2H), 7.68 (s, 1H), 7.57-7.55 (m, 3H), 7.41 (s, 1H), 7.38 (s, 1H), 4.97-4.89 (m, 1H), 4.88-4.86 (d, J=4.8 Hz, 1H), 4.70-4.64 (m, 2H), 2.72-2.61 (m, 4H), 1.34-1.32 (d, J=6.6 Hz, 3H).

LC-MS: (M+H)+=353
HPLC purity: 99.74 at 254 nm.

Example 27: N-trans-3-(5-((R)-1-hydroxyethyl)-1H-pyrazol-1-yl)cyclobutyl)-5-phenylisoxazole-3-carboxamide and N-trans-3-(5-((S)-1-hydroxyethyl)-1H-pyrazol-1-yl)cyclobutyl)-5-phenylisoxazole-3-carboxamide

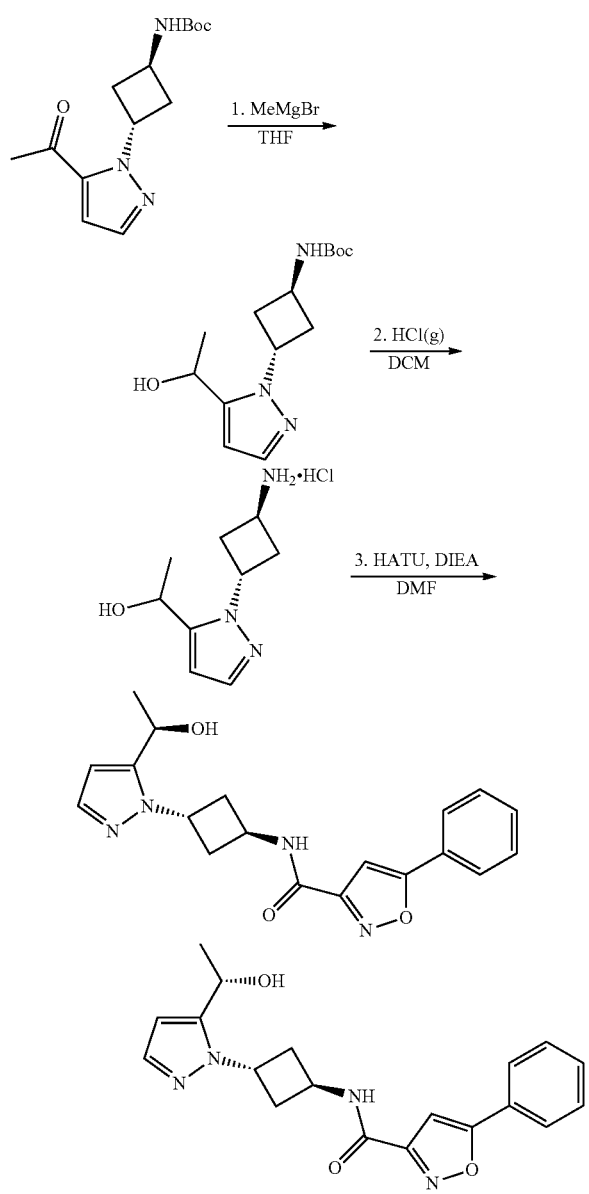

Step 1: tert-butyl N-[trans-3-[3-(1-hydroxyethyl)-1H-pyrazol-1-yl]cyclobutyl]carbamate Into a 50-mL, 3-necked round-bottom flask purged and maintained with an inert atmosphere of nitrogen, was placed a solution of tert-butyl N-[trans-3-(3-formyl-1H-pyrazol-1-yl)cyclobutyl]carbamate (486 mg, 1.83 mmol, 1.00 eq.) in tetrahydrofuran (10 mL). This was followed by the addition of MeMgBr (3M) (1.22 mL, 2.00 eq.) dropwise with stirring at 0° C. The resulting solution was stirred for 7 hours at room temperature. The reaction was then quenched by the addition of 10 mL of NH$_4$Cl aqueous. The resulting solution was extracted with ethyl acetate (3×10 mL) and the organic layers combined. The solution was dried over anhydrous sodium sulfate and concentrated under vacuum. The crude product was purified by Flash-Prep-HPLC with the following conditions (CombiFlash-1): Column, C18 silica gel; mobile phase, MeCN/H$_2$O=50:50 increasing to MeCN/H$_2$O=60:40 within 3 min; Detector, UV 254 nm. This resulted in 233 mg (45%) of tert-butyl N-[trans-3-[3-(1-hydroxyethyl)-1H-pyrazol-1-yl]cyclobutyl]carbamate as colorless oil.

Step 2: 1-[1-[trans-3-aminocyclobutyl]-1H-pyrazol-3-yl]ethan-1-ol hydrochloride into a 50-mL round-bottom flask, was placed a solution of tert-butyl N-[trans-3-[3-(1-hydroxyethyl)-1H-pyrazol-1-yl]cyclobutyl]carbamate (300 mg, 1.07 mmol, 1.00 eq.) in dichloromethane (10 mL) and hydrogen chloride gas was bubbled into the solution. The resulting solution was stirred for 5 hours at room temperature. The resulting solution was diluted with 20 mL of water. The resulting solution was washed with ethyl acetate (2×20 mL) and the aqueous layer was concentrated under vacuum. This resulted in 271 mg (crude) of 1-[1-[trans-3-aminocyclobutyl]-1H-pyrazol-3-yl]ethan-1-ol hydrochloride as yellow oil.

Step 3: 5-phenyl-N-[trans-3-[3-(1-hydroxyethyl)-1H-pyrazol-1-yl]cyclobutyl]-1,2-oxazole-3-carboxamide into a 50-mL round-bottom flask, was placed a solution of 5-phenyl-1,2-oxazole-3-carboxylic acid (177.7 mg, 0.94 mmol, 1.00 eq.), 1-[1-[trans-3-aminocyclobutyl]-1H-pyrazol-3-yl]ethan-1-ol hydrochloride (246 mg, 1.13 mmol, 1.20 eq.), HATU (428.8 mg, 1.13 mmol, 1.20 eq.) and DIEA (363.9 mg, 2.82 mmol, 3.00 eq.) in DMF (10 mL). The resulting solution was stirred for 2 hours at room temperature. The reaction was then quenched by the addition of 20 mL of water. The resulting solution was extracted with ethyl acetate (3×20 mL) and the organic combined layers were dried over anhydrous sodium sulfate and concentrated under vacuum. The residue was applied onto a Prep-TLC with ethyl acetate/petroleum ether (2:1). This resulted in 189 mg (57%) of 5-phenyl-N-[trans-3-[3-(1-hydroxyethyl)-1H-pyrazol-1-yl]cyclobutyl]-1,2-oxazole-3-carboxamide as a off-white solid.

The mixture (210 mg, 0.60 mmol, 1.00 eq.) was purified by Chiral-Prep-HPLC with the following conditions (Prep-HPLC-004): Column, Phenomenex Lux 5u Cellulose-4 AXIA Packed, 250*21.2 mm, 5 um; mobile phase, Hex and ethanol (hold 25.0% ethanol in 15 min); Detector, UV 254/220 nm. This resulted in 5-phenyl-N-[trans-3-[(1R or S)-1-hydroxyethyl]-1H-pyrazol-1-yl]cyclobutyl]-1,2-oxazole-3-carboxamide Isomer 1 (74 mg)
Appearance: white solid
Analytical data: $^1$H-NMR: (DMSO-d$_6$, 400 MHz): δ 9.30, 9.28 (d, J=8.0 Hz, 1H), 7.95-7.93 (m, 2H), 7.72, 7.71 (d, J=4.0 Hz, 1H), 7.58-7.54 (m, 3H), 7.37 (m, 1H), 6.19, 6.18 (d, J=4.0 Hz, 1H), 4.98-4.4.92 (m, 2H), 4.73-4.64 (m, 2H), 2.72-2.64 (m, 5H), 1.36, 1.34 (d, J=8.0 Hz, 3H).
LC-MS: (M+H)+=353
HPLC purity: 99.14% at 254 nm.

Isomer 2 (72 mg)
Appearance: white solid
Analytical data: $^1$H-NMR (DMSO-$d_6$, 300 MHz): δ 9.30, 9.28 (d, J=6.0 Hz, 1H), 7.96-7.93 (m, 2H), 7.73, 7.72 (d, J=3.0 Hz, 1H), 7.60-7.55 (m, 3H), 7.38 (s, 1H), 6.19, 6.18 (d, J=3.0 Hz, 1H), 4.99-4.92 (m, 2H), 4.74-4.63 (m, 2H), 2.78-2.65 (m, 5H), 1.37, 1.35 (d, J=6.0 Hz, 3H).
LC-MS: (M+H)$^+$=353
HPLC purity: 98.18% at 254 nm.

Example 28: N-(cis-3-(4-(hydroxymethyl)-1H-pyrazol-1-yl)cyclobutyl)-5-phenylisoxazole-3-carboxamide

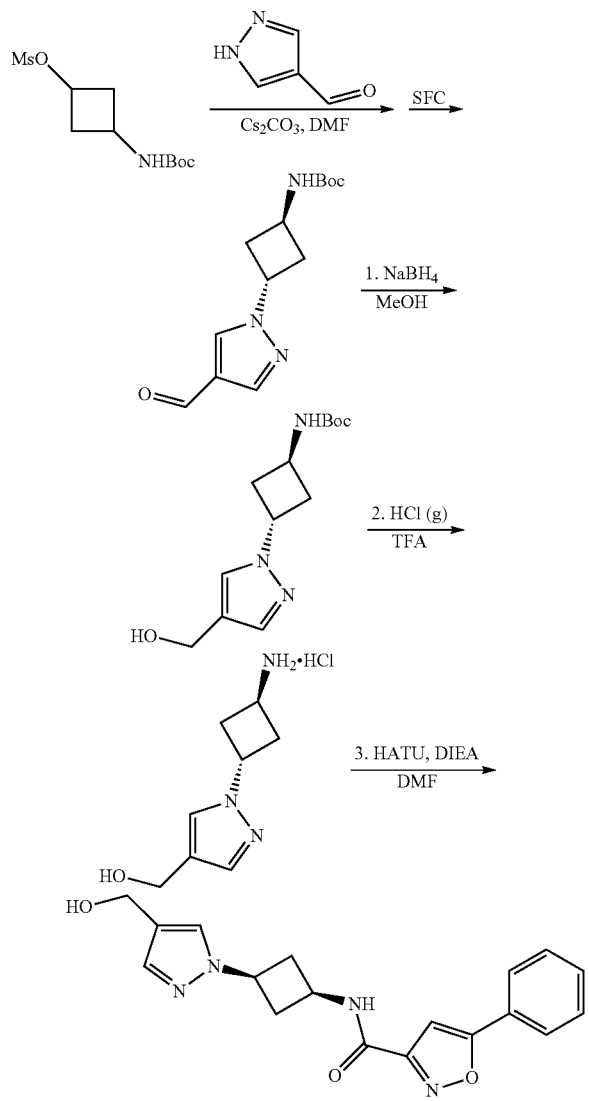

Tert-butyl N-[cis-3-(4-formyl-1H-pyrazol-1-yl)cyclobutyl]carbamate: into a 100-mL round-bottom flask, was placed a solution of tert-butyl N-[3-(methanesulfonyloxy)cyclobutyl]carbamate (2.65 g, 9.99 mmol, 1.00 eq.), 1H-pyrazole-4-carbaldehyde (1.152 g, 11.99 mmol, 1.20 eq.) and Cs$_2$CO$_3$ (6.52 g, 20.01 mmol, 2.00 eq.) in DMF (20 mL). The resulting solution was stirred for 4 h at room temperature. The reaction was then quenched by the addition of 100 mL of water. The resulting solution was extracted with 3×100 mL of ethyl acetate and the organic layers combined. The resulting mixture was washed with 100 mL of brine. The mixture was dried over anhydrous sodium sulfate and concentrated under vacuum. The crude product was purified by Flash-Prep-HPLC with the following conditions (CombiFlash-1): Column, C18 silica gel; mobile phase, MeCN/H$_2$O=60:40 increasing to MeCN/H$_2$O=70:30 within 3 min; Detector, UV 254 nm. The crude product purified by Prep-SFC with the following conditions (prep SFC 350-2): Column: Phenomenex Lux 5u Cellulose-4 250*50 mm; mobile Phase A: CO2:70, Mobile Phase B: MeOH—HPLC: 30; Flow rate: 150 mL/min; 254 nm; RT1: 4.53; RT2: 5.36. This resulted in 712 mg (54%) of tert-butyl N-[cis-3-(4-formyl-1H-pyrazol-1-yl)cyclobutyl]carbamate as a white solid.

Step 1: tert-butyl N-[cis-3-[4-(hydroxymethyl)-1H-pyrazol-1-yl]cyclobutyl]carbamate into a 50-mL round-bottom flask, was placed a solution of tert-butyl N-[cis-3-(4-formyl-1H-pyrazol-1-yl)cyclobutyl]carbamate (700 mg, 2.64 mmol, 1.00 eq.) in methanol (15 mL). This was followed by the addition of NaBH$_4$ (702.6 mg, 18.57 mmol, 7.04 eq.) in several batches at 0° C. The resulting solution was stirred for 30 min at room temperature. The reaction was then quenched by the addition of 50 mL of NH$_4$Cl (aq.). The resulting solution was extracted with ethyl acetate (50 mL×3) and the combined organic layers were dried over anhydrous sodium sulfate and concentrated under vacuum. This resulted in 819 mg (crude) of tert-butyl N-[cis-3-[4-(hydroxymethyl)-1H-pyrazol-1-yl]cyclobutyl]carbamate as an off-white solid.

Step 2: [1-[cis-3-aminocyclobutyl]-1H-pyrazol-4-yl]methanol hydrochloride into a 50-mL round-bottom flask, was placed a solution of tert-butyl N-[cis-3-[4-(hydroxymethyl)-1H-pyrazol-1-yl]cyclobutyl]carbamate (819 mg, 3.06 mmol, 1.00 eq.) in tetrahydrofuran (20 mL) and hydrogen chloride gas was bubbled in. The resulting solution was stirred for 3 hours at room temperature. The resulting solution was diluted with 20 mL of water. The resulting solution was extracted with ethyl acetate (2×20 mL) and the combined aqueous layer was concentrated under vacuum. This resulted in 855 mg (crude) of [1-[cis-3-aminocyclobutyl]-1H-pyrazol-4-yl]methanol hydrochloride as a off-white semi-solid.

Step 3: 5-phenyl-N-[cis-3-[4-(hydroxymethyl)-1H-pyrazol-1-yl]cyclobutyl]-1,2-oxazole-3-carboxamide into a 50-mL round-bottom flask, was placed a solution of [1-[cis-3-aminocyclobutyl]-1H-pyrazol-4-yl]methanol hydrochloride (408 mg, 2.00 mmol, 1.20 eq.) in DMF (10 mL). To the solution were added DIEA (645 mg, 4.99 mmol, 3.00 eq.), 5-phenyl-1,2-oxazole-3-carboxylic acid (315 mg, 1.67 mmol, 1.00 eq.) and HATU (760 mg, 2.00 mmol, 1.20 eq.). The resulting solution was stirred for 1 hour at room temperature. The reaction was then quenched by the addition of 20 mL of water. The resulting solution was extracted with ethyl acetate (3×20 mL) and the combined organic layers were dried over anhydrous sodium sulfate and concentrated under vacuum. The residue was applied onto a Prep-TLC with ethyl acetate/petroleum ether (2:1). This resulted in 63 mg (11%) of 5-phenyl-N-[cis-3-[4-(hydroxymethyl)-1H-pyrazol-1-yl]cyclobutyl]-1,2-oxazole-3-carboxamide.

Appearance: white solid

Analytical data: ¹HNMR (400 MHz, DMSO-d₆): δ 9.24, 9.22 (d, J=8.0 Hz, 1H), 7.95-7.92 (m, 2H), 7.80 (s, 1H), 7.59-7.53 (m, 3H), 7.38, 7.36 (d, J=8.0 Hz, 2H), 4.83-4.80 (t, J=6.0 Hz, 1H), 4.60-4.56 (m, 1H), 4.36-4.28 (m, 3H), 2.82-2.75 (m, 2H), 2.65-2.59 (m, 2H).

LC-MS: (M+H)⁺=339

HPLC purity: 99.94% at 254 nm.

Example 29: N-(trans-3-(4-(hydroxymethyl)-1H-pyrazol-1-yl)cyclobutyl)-5-phenylisoxazole-3-carboxamide

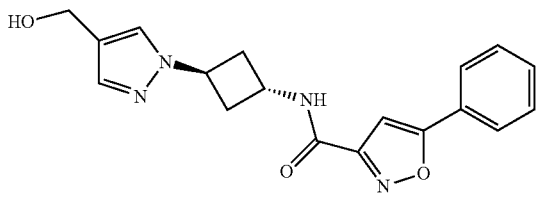 [SMILES: O=C(N[C@H]1C[C@H](n2cc(CO)cn2)C1)c1cc(-c2ccccc2)on1]

N-(trans-3-(4-(hydroxymethyl)-1H-pyrazol-1-yl)cyclobutyl)-5-phenylisoxazole-3-carboxamide was prepared using a similar procedure as shown in example 28 using tert-butyl N-[cis-3-(4-formyl-1H-pyrazol-1-yl)cyclobutyl]carbamate as the starting material.

Analytical data: ¹H NMR (400 MHz, DMSO-d₆): δ 9.31-9.29 (d, J=7.2 Hz, 1H), 7.95-7.93 (m, 2H), 7.72 (s, 1H), 7.60-7.55 (m, 3H), 7.43 (s, 1H), 7.37 (s, 1H), 4.97-4.93 (m, 1H), 4.69-4.67 (m, 1H), 4.34 (s, 2H), 2.75-2.63 (m, 4H).

HPLC purity: 99.7% at 254 nm.

Example 30: N-cis-3-(3-(hydroxymethyl)-1H-pyrazol-1-yl)cyclobutyl)-5-phenylisoxazole-3-carboxamide

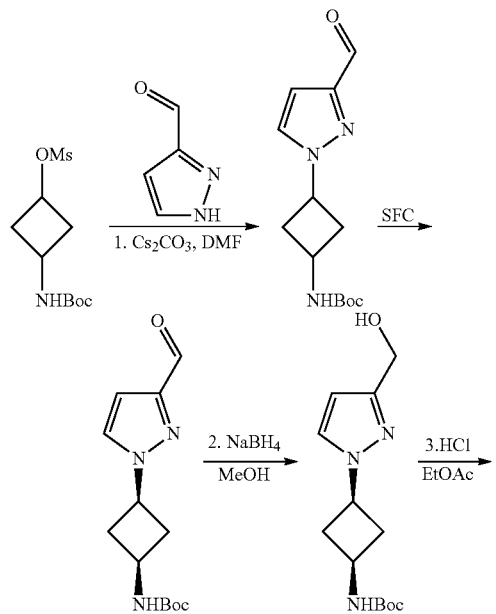

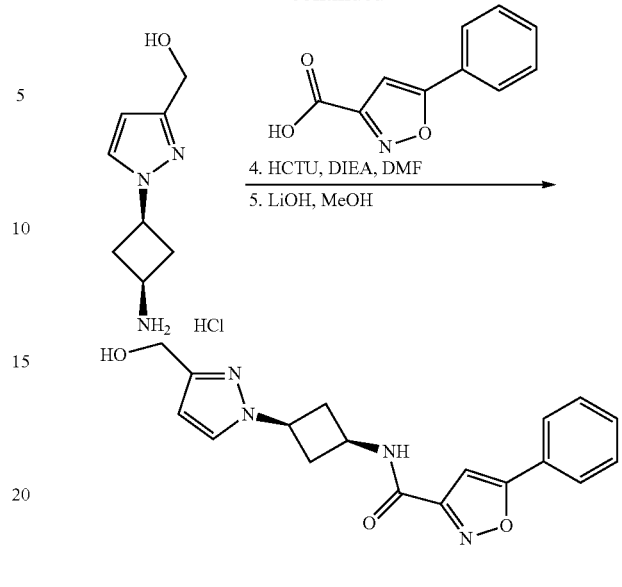

Step 1: tert-butyl N-[3-(3-formyl-1H-pyrazol-1-yl)cyclobutyl]carbamate into a 100-mL round-bottom flask, was placed a solution of tert-butyl N-[3-(methanesulfonyloxy)cyclobutyl]carbamate (2 g, 7.54 mmol, 1.00 eq.), 1H-pyrazole-3-carbaldehyde (725 mg, 7.55 mmol, 1.00 eq.) and Cs₂CO₃ (4.9 g, 15.04 mmol, 2.00 eq.) in DMF (40 mL). The resulting solution was stirred for 16 hours at 80° C. The reaction was then quenched by the addition of water. The resulting solution was extracted with of ethyl acetate and the organic layers combined. The resulting mixture was washed with brine, dried over anhydrous sodium sulfate and concentrated under vacuum. The residue was applied onto a silica gel column with ethyl acetate/hexane (1:4). This resulted in 1.9 g (95%) of tert-butyl N-[3-(3-formyl-1H-pyrazol-1-yl)cyclobutyl]carbamate as a white solid. LC-MS: (M+H)⁺=266. Mixture was purified by Prep-SFC with the following conditions (prep SFC 350-2): column, Chiralpak AS-H, 5*25 cm, 5 um; mobile phase, CO₂ (75%), methanol (25%); Detector, UV 220 nm. This resulted in 600 mg (32%) of tert-butyl N-[cis-3-(3-formyl-1H-pyrazol-1-yl)cyclobutyl]carbamate as yellow oil, and 760 mg (40%) of tert-butyl N-[trans-3-(3-formyl-1H-pyrazol-1-yl)cyclobutyl]carbamate as a white solid.

Step 2: tert-butyl N-[cis-3-[3-(hydroxymethyl)-1H-pyrazol-1-yl]cyclobutyl]carbamate into a 50-mL round-bottom flask, was placed a solution of tert-butyl N-[cis-3-(3-formyl-1H-pyrazol-1-yl)cyclobutyl]carbamate (600 mg, 2.26 mmol, 1.00 eq.) in methanol (5 mL). This was followed by the addition of NaBH₄ (86 mg, 2.34 mmol, 1.00 eq.), in portions. The resulting solution was stirred for 30 min at room temperature. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 600 mg (crude) of tert-butyl N-[cis-3-[3-(hydroxymethyl)-1H-pyrazol-1-yl]cyclobutyl]carbamate as a white solid. LC-MS: (M+H)⁺=268

Step 3: [1-[cis-3-aminocyclobutyl]-1H-pyrazol-3-yl] methanol hydrochloride into a 100-mL 3-necked round-bottom flask, was placed a solution of tert-butyl N-[cis-3-[3-(hydroxymethyl)-1H-pyrazol-1-yl]cyclobutyl]carbamate (600 mg, 2.24 mmol, 1.00 eq.) in ethyl acetate (5 mL). Hydrogen chloride gas was bubbled slowly into the solution. The resulting solution was stirred for 30 min at room temperature. The reaction was concentrated under vacuum. This resulted in 400 mg (88%) of [1-[cis-3-aminocyclobutyl]-1H-pyrazol-3-yl]methanol hydrochloride as a yellow syrup. LC-MS: (M+H)$^+$=168

Step 4: [1-[cis-3-(5-phenyl-1,2-oxazole-3-amido) cyclobutyl]-1H-pyrazol-3-yl]methyl 5-phenyl-1,2-oxazole-3-carboxylate into a 100-mL round-bottom flask, was placed a solution of [1-[cis-3-aminocyclobutyl]-1H-pyrazol-3-yl]methanol hydrochloride (400 mg, 1.96 mmol, 1.00 eq.), 5-phenyl-1,2-oxazole-3-carboxylic acid (745 mg, 3.94 mmol, 2.00 eq.), HCTU (983 mg, 2.36 mmol, 1.20 eq.) and DIEA (762 mg, 5.90 mmol, 3.00 eq.) in DMF (20 mL). The resulting solution was stirred for 2 hours at room temperature. The reaction was then quenched by the addition of water. The resulting solution was extracted with ethyl acetate and the organic layers combined. The resulting mixture was washed with brine, dried over anhydrous sodium sulfate and concentrated under vacuum. The crude residue was washed with 5 mL of methanol. This resulted in 400 mg (40%) of [1-[cis-3-(5-phenyl-1,2-oxazole-3-amido)cyclobutyl]-1H-pyrazol-3-yl]methyl 5-phenyl-1,2-oxazole-3-carboxylate as a white solid. LC-MS: (M+H)$^+$=510.

Step 5: 5-phenyl-N-[cis-3-[3-(hydroxymethyl)-1H-pyrazol-1-yl]cyclobutyl]-1,2-oxazole-3-carboxamide into a 50-mL round-bottom flask, was placed a solution of [1-[cis-3-(5-phenyl-1,2-oxazole-3-amido)cyclobutyl]-1H-pyrazol-3-yl]methyl 5-phenyl-1,2-oxazole-3-carboxylate (300 mg, 0.59 mmol, 1.00 eq.) in methanol/water (5 mL/5 mL). This was followed by the addition of LiOH (42 mg, 1.75 mmol, 3.00 eq.), in portions. The resulting solution was stirred for 30 min at room temperature. The reaction was then quenched by the addition of water. The resulting solution was extracted with ethyl acetate and the organic layers combined. The resulting mixture was washed with brine, dried over anhydrous sodium sulfate and concentrated under vacuum. The residue was applied onto a silica gel column with ethyl acetate/petroleum ether (1:1). This resulted in 120.7 mg (61%) of 5-phenyl-N-[cis-3-[3-(hydroxymethyl)-1H-pyrazol-1-yl]cyclobutyl]-1,2-oxazole-3-carboxamide as a white solid.

LC-MS: (M+H)$^+$=339.1

Analytical data: $^1$H NMR (300 MHz, DMSO-d$_6$, ppm): δ 9.25-9.22 (d, J=7.8 Hz, 1H), 7.95-7.94 (m, 2H), 7.93-7.92 (m, 1H), 7.77-7.55 (m, 3H), 7.38 (s, 1H), 6.22-6.21 (m, 1H), 4.99-4.95 (m, 1H), 4.63-4.52 (m, 1H), 4.42-4.40 (m, 2H), 4.34-4.26 (m, 1H), 2.82-2.76 (m, 2H), 2.66-2.56 (m, 2H).

HPLC purity: 98.8% at 254 nm.

Example 31: N-trans-3-(3-(hydroxymethyl)-1H-pyrazol-1-yl)cyclobutyl)-5-phenylisoxazole-3-carboxamide

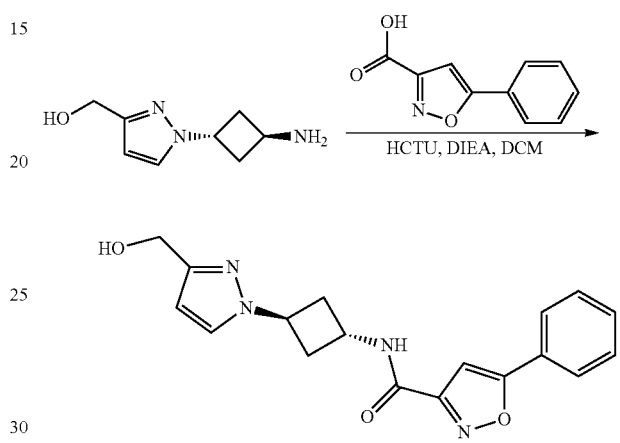

Into a 100-mL round-bottom flask, was placed a solution of [1-trans-3-aminocyclobutyl]-1H-pyrazol-3-yl]methanol (120 mg, 0.72 mmol, 1.00 eq., prepared using similar procedure as shown in example 29) in dichloromethane (5 mL). To the solution were added 5-phenyl-1,2-oxazole-3-carboxylic acid (163 mg, 0.86 mmol, 1.20 eq.) and HCTU (360 mg, 0.87 mmol, 1.20 eq.). This was followed by the addition of DIEA (278 mg, 2.15 mmol, 3.00 eq.) dropwise with stirring. The resulting solution was stirred for 1 hour at room temperature. The reaction was then quenched by the addition of water. The resulting solution was extracted with dichloromethane (3×50 mL). The organic layers were combined, dried and concentrated under vacuum. The crude product was purified by Prep-HPLC with the following conditions (Waters): Column, Bridget Prep C18 5 um OBDTM 19*100 mm; mobile phase, water with 0.05% NH$_4$HCO$_3$ and CH$_3$CN (40.0% CH$_3$CN up to 80.0% in 10 min, up to 95.0% in 1.5 min, down to 40.0% in 1.5 min); Detector, 254 nm. This resulted in 44.7 mg (18%) of 5-phenyl-N-trans-3-[3-(hydroxymethyl)-1H-pyrazol-1-yl]cyclobutyl]-1,2-oxazole-3-carboxamide as a white solid.

LC-MS: (M+H)$^+$=339

Analytical data: $^1$H NMR (400 MHz, DMSO-d$_6$): δ 9.32-9.30 (d, J=6.8 Hz, 1H), 7.95-7.94 (d, J=6.0 Hz, 2H), 7.74 (s, 1H), 7.57-7.55 (m, 3H), 7.38 (s, 1H), 6.20 (s, 1H), 5.02-4.99 (t, J=5.6 Hz, 1H), 4.96-4.95 (m, 1H), 4.71-4.65 (m, 1H), 4.44-4.42 (d, J=6.0 Hz, 2H), 2.75-2.63 (m, 4H).

HPLC purity: 98.8% at 254 nm.

Example 32: N-trans-3-(3-(hydroxymethyl)-1,2,4-oxadiazol-5-yl)cyclobutyl)-5-phenylisoxazole-3-carboxamide and N-cis-3-(3-(hydroxymethyl)-1,2,4-oxadiazol-5-yl)cyclobutyl)-5-phenylisoxazole-3-carboxamide was extracted with 3×100 mL of ethyl acetate and the organic layers combined and dried over anhydrous sodium sulfate and concentrated under vacuum. The residue was applied onto a silica gel column with ethyl acetate/petroleum ether (1:1). This resulted in 6 g (30%) of methyl 3-(1,3-dioxo-2,3-dihydro-1H-isoindol-2-yl)cyclobutane-1-car-

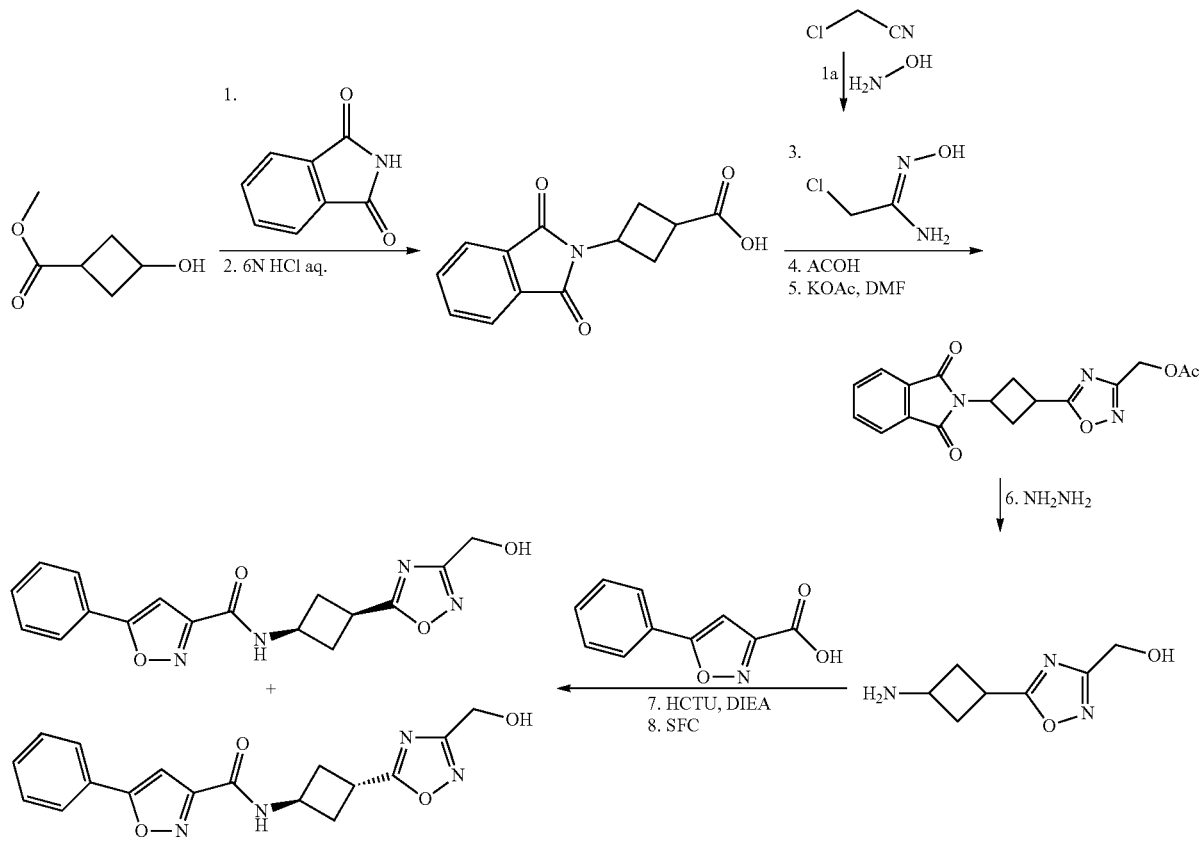

Step 1a: (Z)-2-chloro-N-hydroxyethenimidamide into a 100-mL round-bottom flask, was placed a solution of 2-chloroacetonitrile (8 g, 105.96 mmol, 1.00 eq.) in water (28 mL). To the solution were added $NH_2OH·HCl$ (7.36 g, 1.00 eq.) and $Na_2CO_3$ (5.6 g, 52.32 mmol, 0.50 eq.). The resulting solution was stirred for 1 hour at room temperature. The resulting solution was diluted with water. The resulting solution was extracted with ethyl acetate (3×100 mL) and the organic layer was dried and concentrated under vacuum. This resulted in 4 g (35%) of (Z)-2-chloro-N-hydroxyethenimidamide as a yellow solid. LC-MS: $(M+H)^+=109$.

Step 1: methyl 3-(1,3-dioxo-2,3-dihydro-1H-isoindol-2-yl)cyclobutane-1-carboxylate into a 1000-mL round-bottom flask, was placed a solution of methyl 3-hydroxycyclobutane-1-carboxylate (10 g, 76.88 mmol, 1.00 eq.) in tetrahydrofuran (500 mL), 2,3-dihydro-1H-isoindole-1,3-dione (13.2 g, 89.7 mmol, 1.20 eq.), triphenyl phosphine (23.6 g, 90.0 mmol, 1.20 eq.). This was followed by the addition of DEAD (21 g, 120.6 mmol, 1.50 eq.) dropwise with stirring. The resulting solution was stirred for 3 h at room temperature. The reaction was then quenched by the addition of water. The resulting solution boxylate as a white solid. $^1H$ NMR (300 MHz, $CDCl_3$): δ 7.85-7.81 (m, 2H), 7.75-7.70 (m, 2H), 5.09-5.03 (t, J=8.7 Hz, 1H), 3.32-3.29 (m, 1H), 3.18-3.10 (m, 2H), 2.67-2.59 (m, 2H), 1.31-1.24 (m, 3H). LC-MS: $(M+H)^+=260$.

Step 2: 3-(1,3-dioxo-2,3-dihydro-1H-isoindol-2-yl)cyclobutane-1-carboxylic acid into a 250-mL round-bottom flask, was placed a solution of methyl 3-(1,3-dioxo-2,3-dihydro-1H-isoindol-2-yl)cyclobutane-1-carboxylate (6 g, 23.14 mmol, 1.00 eq.) in dioxane (100 mL). To the solution was added 6N hydrogen chloride aqueous (30 mL). The resulting solution was stirred for 3 hours at 90° C. in an oil bath. The resulting mixture was concentrated under vacuum. This resulted in 5 g (crude) of 3-(1,3-dioxo-2,3-dihydro-1H-isoindol-2-yl)cyclobutane-1-carboxylic acid as a white solid. LC-MS: $(M+H)^+=246$.

Step 3: N-[(1E)-2-chloro-1-(hydroxyimino)ethyl]-3-(1,3-dioxo-2,3-dihydro-1H-isoindol-2-yl)cyclobutane-1-carboxamide into a 250-mL round-bottom flask, was placed a solution of 3-(1,3-dioxo-2,3-dihydro-1H-isoindol-2-yl)cyclobutane-1-carboxylic acid (5 g, 20.38 mmol, 1.00 eq.) in dichloromethane (100 mL). To the mixture were added (Z)-2- chloro-N-hydroxyethenimidamide (2.6 g, 24.00 mmol, 1.20 eq.), HATU (9.2 g, 38.16 mmol, 1.20 eq.) and DIEA (8 g, 60.36 mmol, 3.00 eq.) with stirring. The resulting solution was stirred for 2 hours at room temperature. The reaction was then quenched by the addition of water. The resulting solution was extracted with dichloromethane (3×100 mL) and the organic layer was dried over anhydrous sodium sulfate and concentrated under vacuum. The residue was applied onto a silica gel column with ethyl acetate/hexane (1:1). This resulted in 4.4 g (64%) of N-[(1E)-2-chloro-1-(hydroxyimino)ethyl]-3-(1,3-dioxo-2,3-dihydro-1H-isoindol-2-yl)cyclobutane-1-carboxamide as a white solid. LC-MS: [M+H]$^+$=336.

Step 4: 2-[3-[3-(chloromethyl)-1,2,4-oxadiazol-5-yl]cyclobutyl]-2,3-dihydro-1H-isoindole-1,3-dione into a 10-mL vial, was placed a solution of N-[(1E)-2-chloro-1-(hydroxyimino)ethyl]-3-(1,3-dioxo-2,3-dihydro-1H-isoindol-2-yl)cyclobutane-1-carboxamide (4 g, 11.92 mmol, 1.00 eq.) in AcOH (15 mL). The final reaction mixture was irradiated with microwave radiation for 30 min at 150° C. The resulting mixture was concentrated under vacuum. The residue was applied onto a silica gel column with ethyl acetate/hexane (1:1). This resulted in 2 g (53%) of 2-[3-[3-(chloromethyl)-1,2,4-oxadiazol-5-yl]cyclobutyl]-2,3-dihydro-1H-isoindole-1,3-dione as a white solid. LC-MS: [M+H]$^+$=318.

Step 5: [5-[3-(1,3-dioxo-2,3-dihydro-1H-isoindol-2-yl)cyclobutyl]-1,2,4-oxadiazol-3-yl]methyl Acetate into a 100-mL round-bottom flask, was placed a solution of 2-[3-[3-(chloromethyl)-1,2,4-oxadiazol-5-yl]cyclobutyl]-2,3-dihydro-1H-isoindole-1,3-dione (2 g, 6.60 mmol, 1.00 eq.) and potassium acetate (1.3 g, 13.22 mmol, 2.00 eq.) in DMF (50 mL). The resulting solution was stirred for 2 hours at 60° C. in an oil bath. The resulting mixture was concentrated under vacuum. The residue was applied onto a silica gel column with ethyl acetate/petroleum ether (1:1). This resulted in 1.4 g (62%) of [5-[3-(1,3-dioxo-2,3-dihydro-1H-isoindol-2-yl)cyclobutyl]-1,2,4-oxadiazol-3-yl]methyl acetate as yellow oil. LC-MS: [M+H]$^+$=342.

Step 6: [5-(3-aminocyclobutyl)-1,2,4-oxadiazol-3-yl]methanol into a 100-mL round-bottom flask, was placed a solution of [5-[3-(1,3-dioxo-2,3-dihydro-1H-isoindol-2-yl)cyclobutyl]-1,2,4-oxadiazol-3-yl]methyl acetate (1.4 g, 4.1 mmol, 1.00 eq.) in ethanol (40 mL). To the solution was added hydrazine (1 mL). The resulting solution was stirred for 3 hours at 60° C. in an oil bath. The solids were filtered out. The resulting mixture was concentrated under vacuum. This resulted in 1 g (crude) of [5-(3-aminocyclobutyl)-1,2,4-oxadiazol-3-yl]methanol as a white solid. LC-MS: [M+H]$^+$=170.

Step 7: N-[3-[3-(hydroxymethyl)-1,2,4-oxadiazol-5-yl]cyclobutyl]-5-phenyl-1,2-oxazole-3-carboxamide into a 250-mL round-bottom flask, was placed a solution of 5-phenyl-1,2-oxazole-3-carboxylic acid (1 g, 5.28 mmol, 1.10 eq.) in dichloromethane (100 mL). To the mixture were added [5-(3-aminocyclobutyl)-1,2,4-oxadiazol-3-yl]methanol (800 mg, 4.52 mmol, 1.00 eq.) and HATU (2.16 g, 8.96 mmol, 1.20 eq.). This was followed by the addition of DIEA (2 g, 14.5 mmol, 3.00 eq.) dropwise with stirring. The resulting solution was stirred for 1 hour at room temperature. The reaction was then quenched by the addition of water. The resulting solution was extracted with dichloromethane (3×100 mL) and the organic layer was dried over anhydrous sodium sulfate and concentrated under vacuum. The residue was applied onto a silica gel column with dichloromethane/methanol (50:1). This resulted in 1 g (62%) of N-[3-[3-(hydroxymethyl)-1,2,4-oxadiazol-5-yl]cyclobutyl]-5-phenyl-1,2-oxazole-3-carboxamide as a white solid. LC-MS: [M+H]$^+$=341.

Step 8: Separation by SFC the isomers (1 g) were separated by Chiral-Prep-HPLC with the following conditions (Prep-HPLC-032): Column, Repaired IA, 21.2*150 mm, 5 um; mobile phase, Hex and ethanol (hold 50.0% ethanol in 15 min); Detector, UV 254/220 nm. This resulted in 555 mg (37%) of 5-phenyl-N-[trans-3-[3-(hydroxymethyl)-1,2,4-oxadiazol-5-yl]cyclobutyl]-1,2-oxazole-3-carboxamide and 26.5 mg (3%) of 5-phenyl-N-[cis-3-[3-(hydroxymethyl)-1,2,4-oxadiazol-5-yl]cyclobutyl]-1,2-oxazole-3-carboxamide as a white solid.

5-Phenyl-N-[trans-3-[3-(hydroxymethyl)-1,2,4-oxadiazol-5-yl]cyclobutyl]-1,2-oxazole-3-carboxamide Analytical data: $^1$H NMR (300 MHz, DMSO-d$_6$): δ 9.34-9.31 (d, J=7.8 Hz, 1H), 7.96-7.93 (m, 2H), 7.78-7.75 (m, 3H), 7.60-7.55 (m, 3H), 7.38 (s, 1H), 5.72-5.68 (t, J=6.3 Hz, 1H), 4.81-4.70 (m, 1H), 4.57-4.55 (d, J=6.3 Hz, 2H), 3.81-3.75 (m, 1H), 2.78-2.71 (m, 2H), 2.68-2.58 (m, 2H).
HPLC purity: 99.27% at 254 nm.

5-Phenyl-N-[cis-3-[3-(hydroxymethyl)-1,2,4-oxadiazol-5-yl]cyclobutyl]-1,2-oxazole-3-carboxamide Analytical data: $^1$H-NMR (400 MHz, CD$_3$OD-d$_4$): δ 7.91-7.88 (m, 2H), 7.57-7.52 (m, 3H), 7.10 (s, 1H), 4.72-4.60 (m, 3H), 3.73-3.58 (m, 1H), 2.91-2.87 (m, 2H), 2.65-2.57 (m, 2H).
HPLC purity: 98.2% at 254 nm.

Example 33: N-(cis-3-(5-(hydroxymethyl)-1,2,4-oxadiazol-3-yl)cyclobutyl)-5-phenylisoxazole-3-carboxamide and N-(trans-3-(5-(hydroxymethyl)-1,2,4-oxadiazol-3-yl)cyclobutyl)-5-phenylisoxazole-3-carboxamide

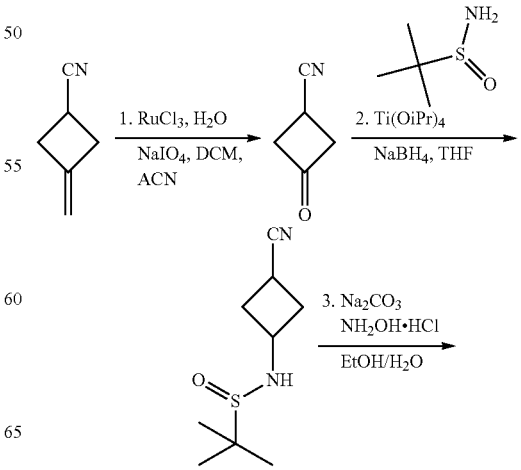

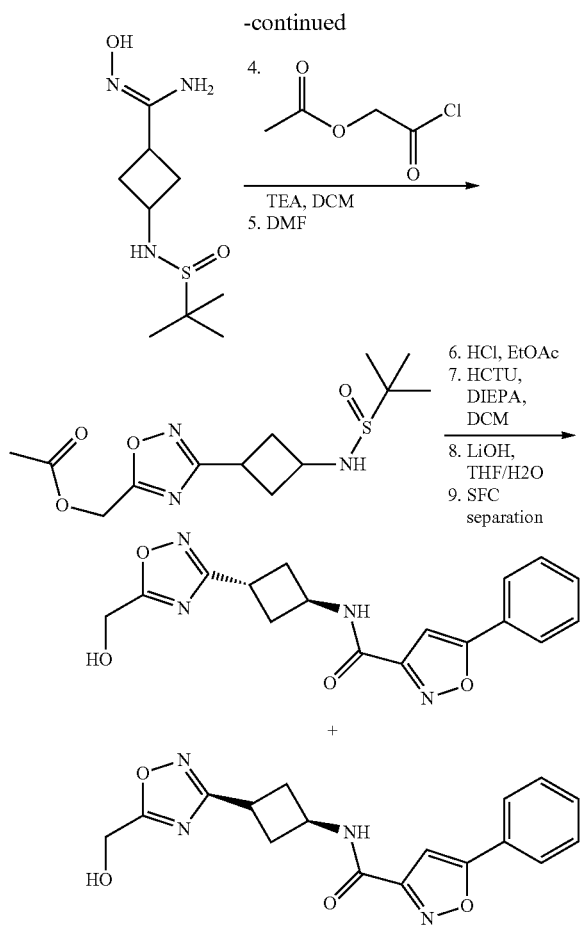

Step 1: Oxocyclobutane-1-carbonitrile into a 500-mL 3-necked round-bottom flask, was placed a solution of 3-methylidenecyclobutane-1-carbonitrile (1.5 g, 16.11 mmol, 1.00 eq.) and RuCl$_3$.H$_2$O (360 mg, 1.60 mmol, 0.10 eq.) in DCM/ACN/H$_2$O (60/60/90 mL). This was followed by the addition of sodium periodate (5.2 g, 24.31 mmol, 1.50 eq.), in portions at 10° C. in 15 min. The resulting solution was stirred for 2 hours at 25° C. The solids were filtered out. The resulting solution was extracted with dichloromethane (3×100 mL) and the organic layers combined. The resulting mixture was washed with brine (2×200 mL), dried over anhydrous sodium sulfate and concentrated under vacuum. The residue was applied onto a silica gel column with ethyl acetate/petroleum ether (1:1). This resulted in 1.1 g (72%) of 3-oxocyclobutane-1-carbonitrile as a yellow solid.

Step 2: N-(3-cyanocyclobutyl)-2-methylpropane-2-sulfinamide into a 500-mL round-bottom flask, was placed a solution of 3-oxocyclobutane-1-carbonitrile (4 g, 42.06 mmol, 1.00 eq.) tetra(propan-2-yloxy)titanium (14.16 g, 62.90 mmol, 1.50 eq.) and 2-methylpropane-2-sulfinamide (6.12 g, 50.49 mmol, 1.20 eq.) in tetrahydrofuran (200 mL). The resulting solution was stirred for 16 hours at 65° C. The reaction was cooled to 25° C. Then NaBH$_4$ (3.2 g, 84.60 mmol, 2.00 eq.) was added. The mixture was stirred for 2 hours at 25° C. The reaction was then quenched by the addition of 200 mL of water. The solids were filtered out and the resulting solution was extracted with ethyl acetate (2×200 mL) and the organic layers were combined. The resulting mixture was washed with brine (2×300 mL), dried over sodium sulfate and concentrated under vacuum. This resulted in 7.2 g (85%) of N-(3-cyanocyclobutyl)-2-methylpropane-2-sulfinamide as a yellow solid.

Step 3: (Z)—N-hydroxy-3-[(2-methylpropane-2-sulfinyl)amino]cyclobut-1-carboximidamide into a 500-mL round-bottom flask, was placed a solution of N-(3-cyanocyclobutyl)-2-methylpropane-2-sulfinamide (7.2 g, 35.95 mmol, 1.00 eq.) in ethanol/H$_2$O (200/70 mL). To the solution were added NH$_2$OH.HCl (5 g, 71.94 mmol, 2.00 eq.) and sodium carbonate (11.43 g, 107.84 mmol, 3.00 eq.). The resulting solution was stirred for 2 hours at 80° C. The resulting solution was diluted with 400 mL of water. The resulting solution was extracted with ethyl acetate (2×300 mL) and the organic layers combined. The resulting mixture was washed with brine (2×400 mL), dried over anhydrous sodium sulfate and concentrated under vacuum. This resulted in 5 g (60%) of (Z)—N-hydroxy-3-[(2-methylpropane-2-sulfinyl)amino]cyclobut-1-carboximidamide as yellow oil. LC-MS [M+H]$^+$=234.

Step 4: [[Z-hydroxyimino)([3-[(2-methylpropane-2-sulfinyl)amino]cyclobutyl])methyl]carbamoyl]methyl acetate into a 250-mL round-bottom flask, was placed a solution of (Z)—N-hydroxy-3-[(2-methylpropane-2-sulfinyl)amino]cyclobut-1-carboximidamide (3.7 g, 15.86 mmol, 1.00 eq.) in dichloromethane (mL). To the solution were added TEA (3.2 g, 31.62 mmol, 2.00 eq.) and 2-chloro-2-oxoethyl acetate (2.6 g, 19.04 mmol, 1.20 eq.). The resulting solution was stirred for 1 hour at 25° C. The resulting solution was diluted with 300 mL of H$_2$O and then it was extracted with ethyl acetate (2×500 mL) and the organic layers combined. The resulting mixture was washed with brine (2×500 mL), dried over anhydrous sodium sulfate and concentrated under vacuum. The residue was applied onto a silica gel column with ethyl acetate/petroleum ether (1:1). This resulted in 3.7 g (70%) of [[Z-hydroxyimino)([3-[(2-methylpropane-2-sulfinyl)amino]cyclobutyl])methyl]carbamoyl]methyl acetate as a yellow solid. LC-MS [M+H]$^+$=334.

Step 5: (3-[3-[(2-methylpropane-2-sulfinyl)amino]cyclobutyl]-1,2,4-oxadiazol-5-yl)methyl acetate into a 50-mL round-bottom flask, was placed a solution of [[(Z)-(hydroxyimino)([3-[(2-methylpropane-2-sulfinyl)amino]cyclobutyl])methyl]carbamoyl]methyl acetate (3.2 g, 9.60 mmol, 1.00 eq.) in DMF (20 mL). The resulting solution was stirred for 2 hours at 100° C. The mixture was concentrate and the crude product was purified by Flash-Prep-HPLC with the following conditions (IntelFlash-1): Column, C18; mobile phase, X: H2O Y:ACN=80/20 increasing to X:H$_2$O Y:ACN=20/80 within 20 min; Detector, UV 220 nm. This resulted in 1.2 g (40%) of (3-[3-[(2-methylpropane-2-sulfinyl)amino]cyclobutyl]-1,2,4-oxadiazol-5-yl)methyl acetate as a yellow solid. LC-MS [M+H]$^+$= 332.

Step 6: [3-(3-aminocyclobutyl)-1,2,4-oxadiazol-5-yl]methyl acetate into a 100-mL 3-necked round-bottom flask, was placed a solution of (3-[3-[(2-methylpropane-2-sulfinyl)amino]cyclobutyl]-1,2,4-oxadiazol-5-yl)methyl acetate (1.2 g, 3.80 mmol, 1.00 eq.) in ethyl acetate (50 mL). To the above solution, the HCl gas was introduced.

The resulting solution was stirred for 2 hours at 25° C. The resulting mixture was concentrated under vacuum. This resulted in 1.1 g (crude) of [3-(3-aminocyclobutyl)-1,2,4-oxadiazol-5-yl]methyl acetate as yellow oil. LC-MS: (M+H)$^+$=212.

Step 7: [3-[3-(3-phenyl-1,2-oxazole-5-amido)cyclobutyl]-1,2,4-oxadiazol-5-yl]methyl acetate into a 100-mL round-bottom flask, was placed a solution of [3-(3-aminocyclobutyl)-1,2,4-oxadiazol-5-yl]methyl acetate (1.1 g, 5.21 mmol, 1.00 eq.) in dichloromethane (50 mL). To the solution were added DIEA (2.02 g, 15.63 mmol, 3.00 eq.), HCTU (3.25 g, 7.80 mmol, 1.50 eq.) and 3-phenyl-1,2-oxazole-5-carboxylic acid (1.18 g, 6.24 mmol, 1.20 eq.). The resulting solution was stirred for 2 hours at 25° C. The resulting solution was diluted with 150 mL of H$_2$O, extracted with ethyl acetate (2×150 mL) and the organic layers combined. The resulting mixture was washed with brine (2×200 mL), dried over anhydrous sodium sulfate and concentrated under vacuum to give 1.5 g (crude) of [3-[3-(3-phenyl-1,2-oxazole-5-amido)cyclobutyl]-1,2,4-oxadiazol-5-yl]methyl acetate as yellow oil. LC-MS [M+H]$^+$= 383.

Step 8 into a 50-mL round-bottom flask, was placed a solution of [3-[3-(3-phenyl-1,2-oxazole-5-amido)cyclobutyl]-1,2,4-oxadiazol-5-yl]methyl acetate (1.5 g, 3.92 mmol, 1.00 eq.) in tetrahydrofuran/H$_2$O (12/4 mL). To the solution was added LiOH (480 mg, 20.04 mmol, 5.00 eq.) and the resulting solution was stirred for 1 hour at 25° C. The solution was diluted with 100 mL of H$_2$O and extracted with ethyl acetate (2×100 mL) and the organic layers combined. The resulting mixture was washed with brine (2×100 mL), dried over anhydrous sodium sulfate and concentrated under vacuum. The residue was applied onto a silica gel column with ethyl acetate/petroleum ether (1:2). The pure isomers were separated by Prep-SFC with the following conditions (prep SFC 350): Column, Phenomenex Lux 5 u Cellulose-3, 5*25 cm, 5 um; mobile phase, CO$_2$ (50%), methanol (50%); Detector, UV 220 nm. This resulted in 26 mg (2%) of 3-phenyl-N-[(trans-3-[5-(hydroxymethyl)-1,2,4-oxadiazol-3-yl]cyclobutyl]-1,2-oxazole-5-carboxamide (PH-PTS-002-0048-0) as a white solid and 565.1 mg (42%) of 3-phenyl-N-[cis-3-[5-(hydroxymethyl)-1,2,4-oxadiazol-3-yl]cyclobutyl]-1,2-oxazole-5-carboxamide as a white solid.

3-Phenyl-N-[(trans-3-[5-(hydroxymethyl)-1,2,4-oxadiazol-3-yl]cyclobutyl]-1,2-oxazole-5-carboxamide LC-MS: (M+H)$^+$=341
Analytical data: $^1$H NMR (400 MHz, CDCl$_3$): δ 7.83-7.81 (m, 2H), 7.54-7.50 (m, 2H), 7.16-7.14 (d, J=6.8 Hz 1H), 6.99 (s, 1H), 5.00-4.90 (m, 3H), 3.75-3.69 (m, 1H), 2.88-2.81 (m, 2H), 2.68-2.60 (m, 2H).
HPLC purity: 98.4% at 254 nm.

3-Phenyl-N-[(cis-3-[5-(hydroxymethyl)-1,2,4-oxadiazol-3-yl]cyclobutyl]-1,2-oxazole-5-carboxamide LC-MS: (M+H)$^+$=341
Analytical data: $^1$H NMR (300 MHz, DMSO-d$_6$): δ 9.26-9.23 (d, J=9.3 Hz, 1H), 7.95-7.92 (m, 2H), 7.60-7.51 (m, 3H), 7.36 (s, 1H), 5.99-5.95 (t, J=6.2 Hz, 1H), 4.72-4.70 (d, J=6.6 Hz, 2H), 4.56-4.45 (m, 1H), 3.45-3.34 (m, 1H), 2.69-2.60 (m, 2H), 2.50-2.40 (m, 2H).
HPLC purity: 99.3% at 254 nm.

Example 34: N-(trans-3-((5-((S)-1-hydroxyethyl)-1,3,4-thiadiazol-2-yl)methyl)cyclobutyl)-5-phenylisoxazole-3-carboxamide and N-(cis-3-((5-((S)-1-hydroxyethyl)-1,3,4-thiadiazol-2-yl)methyl)cyclobutyl)-5-phenylisoxazole-3-carboxamide

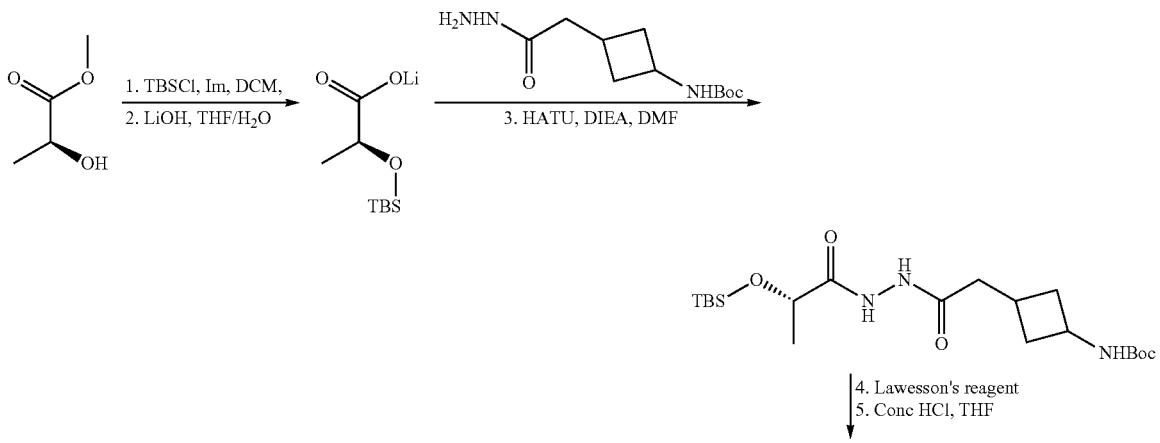

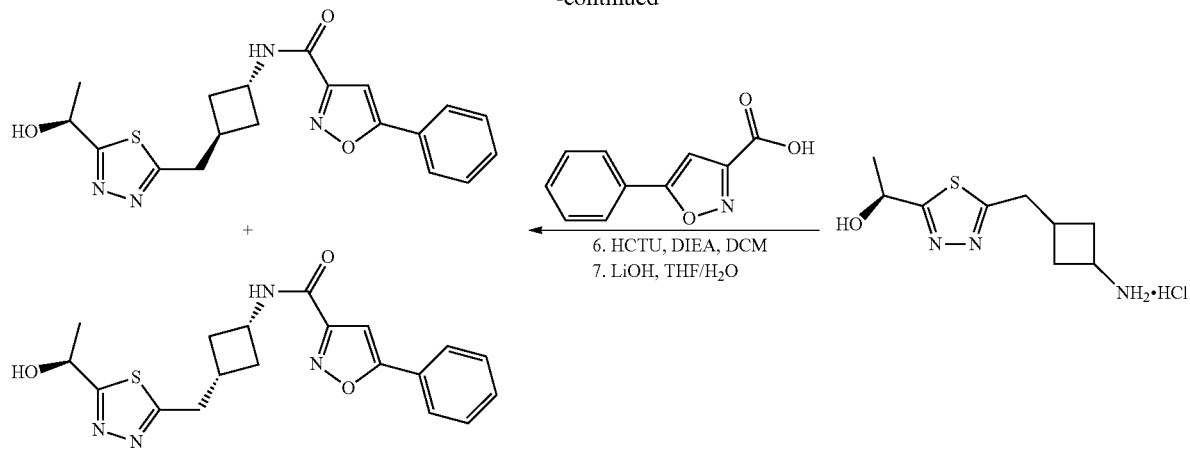

Tert-butyl (3-(2-hydrazinyl-2-oxoethyl)cyclobutyl)carbamate was prepared by the procedure described in example 5, step 1.

Step 1: methyl (S)-2-((tert-butyldimethylsilyl)oxy)propanoate a solution of methyl (2S)-2-hydroxypropanoate (5 g, 48.03 mmol, 1.00 eq.) and 1H-imidazole (4.9 g, 71.98 mmol, 1.50 eq.) in dichloromethane (100 mL) was placed into a 250-mL round-bottom flask. This was followed by the addition of a solution of tert-butyl(chloro)dimethylsilane (8.69 g, 57.66 mmol, 1.20 eq.) in dichloromethane (50 mL) dropwise with stirring at 0° C. The resulting solution was stirred for 2 hours at room temperature. The reaction was then quenched by the addition of 80 mL of water/ice and extracted with dichloromethane (3×50 mL). The resulting mixture was washed with brine (2×100 mL), dried over anhydrous sodium sulfate and concentrated under vacuum. This resulted in 8 g (76%) of methyl (2S)-2-[(tert-butyldimethylsilyl)oxy]propanoate as a colorless liquid.

Step 2: lithio (2S)-2-[(tert-butyldimethylsilyl)oxy]propanoate a solution of methyl (2S)-2-[(tert-butyldimethylsilyl)oxy]propanoate (7.2 g, 32.97 mmol, 1.00 eq.) in THF (50 mL) was placed in a 250 mL round bottom flask. This was followed by the addition of a solution of lithium hydroxide (1.67 g, 39.80 mmol, 1.20 eq.) in $H_2O$ (30 mL) dropwise with stirring. The resulting solution was stirred for 4 hours at room temperature. The resulting mixture was concentrated under vacuum. This resulted in 5.9 g (85%) of lithio (2S)-2-[(tert-butyldimethylsilyl)oxy]propanoate as a white solid.

Step 3: tert-butyl N-[3-[N-[(2S)-2-[(tert-butyldimethylsilyl)oxy]propanoyl]hydrazinecarbonyl]methyl)cyclobutyl]carbamate a solution of lithio (2S)-2-[(tert-butyldimethylsilyl)oxy]propanoate (5.9 g, 28.06 mmol, 1.00 eq.), tert-butyl N-[3-[(hydrazine carbonyl)methyl]cyclobutyl]carbamate (7.51 g, 30.87 mmol, 1.10 eq.) and HATU (16 g, 42.11 mmol, 1.50 eq.) in DMF (100 mL) were placed in a 250-mL round-bottom flask. This was followed by the addition of DIEA (10.9 g, 84.34 mmol, 3.00 eq.) dropwise with stirring at 0° C. The resulting solution was stirred for 4 hours at room temperature. The reaction was then quenched by the addition of 100 mL of water/ice and extracted with ethyl acetate (3×100 mL) and the organic layers combined. The resulting mixture was washed with brine (3×80 mL), dried over anhydrous sodium sulfate and concentrated under vacuum. The residue was applied onto a silica gel column with ethyl acetate/hexane (1:1). This resulted in 4.4 g (36%) of tert-butyl N-[3-([N-[(2S)-2-[(tert-butyldimethylsilyl)oxy]propanoyl]hydrazinecarbonyl]methyl)cyclobutyl]carbamate as off-white solid.

LC-MS: $(M+H)^+=430$.

Step 4: tert-butyl N-[3-([5-[(1S)-1-[(tert-butyldimethylsilyl)oxy]ethyl]-1,3,4-thiadiazol-2-yl]methyl)cyclobutyl]carbamate a solution of tert-butyl N-[3-([N-[(2S)-2-[(tert-butyldimethylsilyl)oxy]propanoyl]hydrazinecarbonyl]methyl)cyclobutyl]carbamate (4.4 g, 10.24 mmol, 1.00 eq.) and Lawesson reagent (6.2 g, 15.33 mmol, 1.50 eq.) in toluene (100 mL) were placed in a 250-mL round-bottom flask. The resulting solution was stirred for 2 hours at 80° C. in an oil bath. The reaction was then quenched by the addition of 50 mL of water/ice and extracted with ethyl acetate (3×80 mL) and the organic layers combined. The resulting mixture was washed with brine (2×50 mL), dried over anhydrous sodium sulfate and concentrated under vacuum. The residue was applied onto a silica gel column with ethyl acetate/petroleum ether (1:5). The crude product was purified by Flash-Prep-HPLC with the following conditions (CombiFlash-1): Column, C18 silica gel; mobile phase, $H_2O/CH_3CN=1:1$ increasing to $H_2O/CH_3CN=1:9$ within 30 min; Detector, UV 210 nm. This resulted in 2.1 g (48%) of tert-butyl N-[3-([5-[(1S)-1-[(tert-butyldimethylsilyl)oxy]ethyl]-1,3,4-thiadiazol-2-yl]methyl)cyclobutyl]carbamate as colorless oil. LC-MS: $(M+H)^+=428$.

Step 5: (1S)-1-[5-[(3-aminocyclobutyl)methyl]-1,3,4-thiadiazol-2-yl]ethan-1-ol hydrochloride a solution of tert-butyl N-[3-([5-[(1S)-1-[(tert-butyldimethylsilyl)oxy]ethyl]-1,3,4-thiadiazol-2-yl]methyl)cyclobutyl]carbamate (2.1 g, 4.91 mmol, 1.00 eq.) in THF (50 mL) was placed in a 100-mL round-bottom flask. To the mixture was added concentrated hydrogen chloride aqueous (5 mL). The resulting solution was stirred for 3 hours at room temperature. The resulting mixture was concentrated under vacuum. This resulted in 1.2 g (crude) of (1S)-1-[5-[(3-aminocyclobutyl)methyl]-1,3,4-thiadiazol-2-yl]ethan-1-ol hydrochloride as a colorless crude oil. LC-MS: (M+H)$^+$=214.

Step 6: (1S)-1-(5-[[3-(5-phenyl-1,2-oxazole-3-amido)cyclobutyl]methyl]-1,3,4-thiadiazol-2-yl) ethyl 5-phenyl-1,2-oxazole-3-carboxylate a solution of (1S)-1-[5-[(3-aminocyclobutyl)methyl]-1,3,4-thiadiazol-2-yl]ethan-1-ol hydrochloride (1.2 g, 4.80 mmol, 1.00 eq.), 5-phenyl-1,2-oxazole-3-carboxylic acid (2.36 g, 12.48 mmol, 2.60 eq.) and HCTU (6.0 g, 14.50 mmol, 3.00 eq.) in dichloromethane (50 mL) was placed in a 100-mL round-bottom flask. This was followed by the addition of DIEA (3.1 g, 23.99 mmol, 5.00 eq.) dropwise with stirring at 0° C. The resulting solution was stirred for 4 hours at room temperature. The reaction was then quenched by the addition of 50 mL of water/ice and extracted with dichloromethane (3×50 mL) and the organic layers combined. The resulting mixture was washed with brine (3×30 mL), dried over anhydrous sodium sulfate and concentrated under vacuum. The residue was applied onto a silica gel column with ethyl acetate/petroleum ether (2:1). This resulted in 2.1 g (79%) of (1S)-1-(5-[[3-(5-phenyl-1,2-oxazole-3-amido)cyclobutyl]methyl]-1,3,4-thiadiazol-2-yl)ethyl 5-phenyl-1,2-oxazole-3-carboxylate as a off-white solid. LC-MS: (M+H)$^+$=556.

Step 7: 5-phenyl-N-[(trans/cis-3-([5-[(1S)-1-hydroxyethyl]-1,3,4-thiadiazol-2-yl]methyl)cyclobutyl]-1,2-oxazole-3-carboxamide a solution of (1S)-1-(5-[[3-(5-phenyl-1,2-oxazole-3-amido)cyclobutyl]methyl]-1,3,4-thiadiazol-2-yl)ethyl 5-phenyl-1,2-oxazole-3-carboxylate (2.1 g, 3.78 mmol, 1.00 eq.) in THF (50 mL) was placed in a 100-mL round-bottom flask. To the solution was added a solution of lithium hydroxide (175 mg, 4.17 mmol, 1.10 eq.) in H$_2$O (5 mL). The resulting solution was stirred for 30 min at room temperature. The resulting solution was diluted with 50 mL of H$_2$O and extracted with ethyl acetate (3×50 mL) and the organic layers combined. The resulting mixture was washed with brine (2×30 mL), dried over anhydrous sodium sulfate and concentrated under vacuum. The isomers were separated by Prep-SFC with the following conditions (prep SFC 350-2): Column, Phenomenex Lux 5 u Cellulose-4 AXIA Packed, 250*21.2 mm, 5 um; mobile phase, CO$_2$ (50%), ethanol (50%); Detector, UV 220 nm. This resulted in 318.3 mg (22%) of 5-phenyl-N-[(trans-3-([5-[(1S)-1-hydroxyethyl]-1,3,4-thiadiazol-2-yl]methyl)cyclobutyl]-1,2-oxazole-3-carboxamide as a off-white solid and 511.3 mg (39%) of 5-phenyl-N-[cis-3-([5-[(1S)-1-hydroxyethyl]-1,3,4-thiadiazol-2-yl]methyl)cyclobutyl]-1,2-oxazole-3-carboxamide) as a off-white solid.

5-phenyl-N-[(trans-3-([5-[(1S)-1-hydroxyethyl]-1,3,4-thiadiazol-2-yl]methyl)cyclobutyl]-1,2-oxazole-3-carboxamide

LC-MS: (M+H)$^+$=385

Analytical data: $^1$H-NMR (300 MHz, DMSO-d$_6$): 9.14-9.12 (d, J=7.5 Hz, 1H), 7.95-7.92 (m, 2H), 7.60-7.53 (m, 3H), 6.24 (s, 1H), 5.09-5.02 (q, J=6.6 Hz, 1H), 4.62-4.54 (m, 1H), 3.29-3.26 (d, J=7.8 Hz, 2H), 2.69-2.59 (m, 1H), 2.38-2.28 (m, 2H), 2.17-2.09 (m, 2H), 1.49-1.47 (d, J=6.6 Hz, 3H).

HPLC purity: 99.4% at 254 nm 5-phenyl-N-[(cis-3-([5-[(1S)-1-hydroxyethyl]-1,3,4-thiadiazol-2-yl]methyl)cyclobutyl]-1,2-oxazole-3-carboxamide Analytical data: $^1$H-NMR (300 MHz, DMSO-d$_6$): δ 9.05-9.03 (d, J=8.1 Hz, 1H), 7.95-7.92 (m, 2H), 7.58-7.55 (m, 3H), 7.35 (s, 1H), 6.25 (s, 1H), 5.08-5.02 (q, J=6.6 Hz, 1H), 4.38-4.30 (m, 1H), 3.18-3.16 (d, J=7.2 Hz, 2H), 2.52-2.32 (m, 3H), 2.00-1.94 (m, 2H), 1.49-1.47 (d, J=6.6 Hz, 3H).

Example 35: 5-phenyl-N-[(trans-3-([5-[(1R)-1-hydroxyethyl]-1,3,4-thiadiazol-2-yl]methyl)cyclobutyl]-1,2-oxazole-3-carboxamide and 5-phenyl-N-[(cis-3-([5-[(1R)-1-hydroxyethyl]-1,3,4-thiadiazol-2-yl]methyl)cyclobutyl]-1,2-oxazole-3-carboxamide

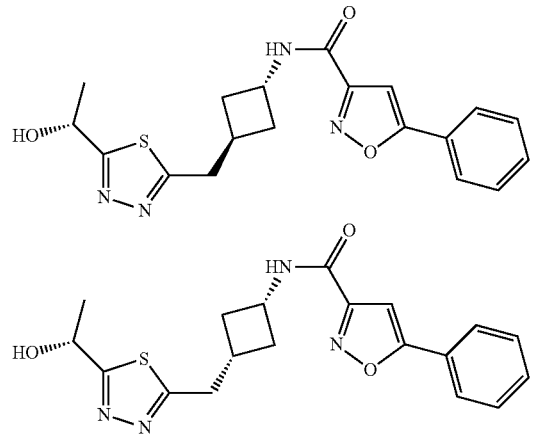

Compounds were prepared using the methodology shown in example 34 using methyl (R)-2-hydroxypropanoate in step 1.

5-phenyl-N-[(trans-3-([5-[(1R)-1-hydroxyethyl]-1,3,4-thiadiazol-2-yl]methyl)cyclobutyl]-1,2-oxazole-3-carboxamide

LC-MS: (M+H)$^+$=385

Analytical data: $^1$H NMR (300 MHz, DMSO-d$_6$): δ 9.14-9.12 (d, J=7.5 Hz, 1H), 7.95-7.92 (m, 2H), 7.60-7.54 (m, 3H), 7.36 (s, 1H), 6.25-6.24 (d, J=3.9 Hz, 1H), 5.07-5.04 (m, 1H), 4.62-4.54 (m, 1H), 3.29-3.26 (d, J=7.8 Hz, 2H), 2.65-2.58 (m, 1H), 2.38-2.28 (m, 2H), 2.17-2.10 (m, 2H), 1.49-1.47 (d, J=6.6 Hz, 3H).

HPLC purity: 98.8% at 254 nm.

5-phenyl-N-[(cis-3-([5[(1R)-1-hydroxyethyl]-1,3,4-thiadiazol-2-yl]methyl)cyclobutyl]-1,2-oxazole-3-carboxamide

LC-MS: (M+H)$^+$=385

Analytical data: $^1$H NMR (300 MHz, DMSO-d$_6$): 9.05-9.03 (d, J=8.1 Hz, 1H), 7.95-7.92 (m, 2H), 7.60-7.51 (m, 3H), 7.35 (s, 1H), 6.25-6.24 (d, J=5.1 Hz, 1H), 5.09-5.01 (m, 1H), 4.38-4.27 (m, 1H), 3.18-3.16 (d, J=6.9 Hz, 2H), 2.52-2.30 (m, 3H), 2.00-1.94 (m, 2H), 1.49-1.47 (d, J=6.6 Hz, 3H).

HPLC purity: 99.74% at 254 nm.

Example 36: N-trans-3-(2-hydroxyethyl)cyclobutyl)-5-phenylisoxazole-3-carboxamide and N-cis-3-(2-hydroxyethyl)cyclobutyl)-5-phenylisoxazole-3-carboxamide

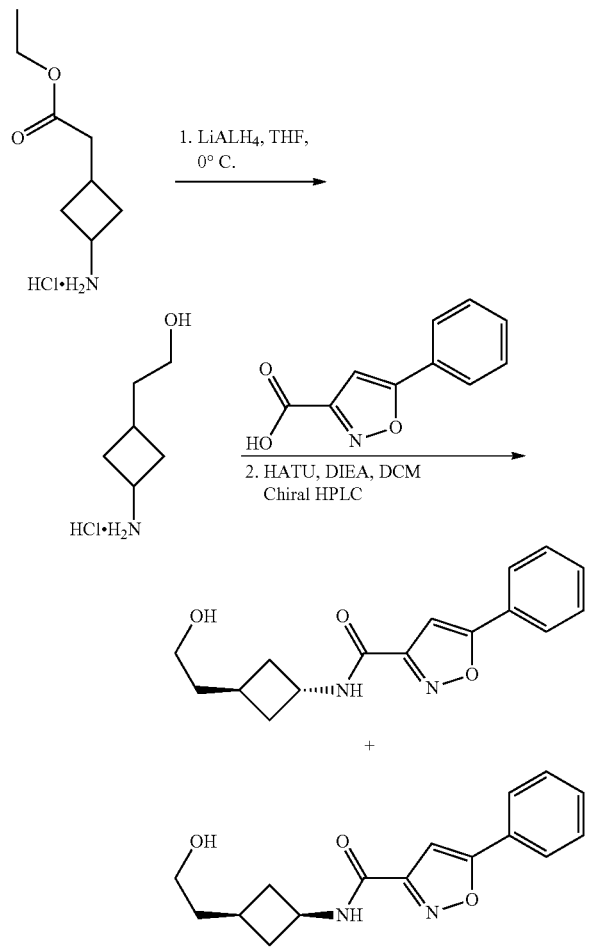

Step 1: 2-(3-aminocyclobutyl)ethan-1-ol hydrochloride a solution of ethyl 2-(3-aminocyclobutyl)acetate hydrochloride (2.5 g, 12.91 mmol, 1.00 eq.) in tetrahydrofuran (10 mL) was placed in a 100-mL round-bottom flask. This was followed by the addition of LiAlH$_4$ (2.4 g, 63.24 mmol, 4.90 eq.) in several batches at 0° C. The resulting solution was stirred for 1 hour at room temperature. The reaction was then quenched by the addition of 2 g of Na$_2$SO$_4$·H$_2$O. The solids were filtered out. The resulting mixture was concentrated under vacuum. This resulted in 1.8 g (crude) of 2-(3-aminocyclobutyl)ethan-1-ol hydrochloride as a yellow solid. LC-MS: (M+H)$^+$=152.

Step 2: N-[3-(2-hydroxyethyl)cyclobutyl]-5-phenyl-1,2-oxazole-3-carboxamide a solution of 5-phenyl-1,2-oxazole-3-carboxylic acid (850.5 mg, 4.50 mmol, 1.51 eq.) and 2-(3-aminocyclobutyl)ethan-1-ol hydrochloride (452 mg, 2.98 mmol, 1.00 eq.) in dichloromethane (25 mL) was placed in a 100-mL round-bottom flask. HATU (1.368 g, 3.60 mmol, 1.21 eq.) and DIEA (1.161 g, 8.98 mmol, 3.01 eq.) were added to the solution and stirred for 1 hour at room temperature. The resulting solution was diluted with 50 mL of water, extracted with chloromethane (3×30 mL) and the organic layers combined. The resulting mixture was dried over anhydrous sodium sulfate and concentrated under vacuum. The crude product was purified by Flash-Prep-HPLC with the following conditions (CombiFlash-1): Column, C18 silica gel; mobile phase, MeCN/H$_2$O=55:45 increasing to MeCN/H$_2$O=60:40 within 2 min; Detector, UV 254 nm to give 110 mg (13%) of N-[3-(2-hydroxyethyl)cyclobutyl]-5-phenyl-1,2-oxazole-3-carboxamide as a off-white solid. The isomers were separated by Chiral-Prep-HPLC using the following conditions (Prep-HPLC-009): Column, Repaired IA, 21.2*150 mm, 5 um; mobile phase, Hexane and ethanol (hold 20.0% ethanol in 20 min); Detector, UV 254/220 nm. This resulted in 23.8 mg (60%) of 5-phenyl-N-[trans-3-(2-hydroxyethyl)cyclobutyl]-1,2-oxazole-3-carboxamide as a white solid and 35.7 mg (70%) of 5-phenyl-N-[cis-3-(2-hydroxyethyl)cyclobutyl]-1,2-oxazole-3-carboxamide as a white solid.

N-trans-3-(2-hydroxyethyl)cyclobutyl)-5-phenylisoxazole-3-carboxamide

LC-MS: (M+H)$^+$=287

Analytical data: $^1$H NMR (CDCl$_3$, 400 MHz): δ 7.83-7.81 (m, 2H), 7.54-7.49 (m, 3H), 7.05-7.02 (m, 1H), 6.97 (s, 1H), 4.72-4.67 (m, 1H), 3.73-3.68 (t, J=10.0 Hz, 2H), 2.49-2.41 (m, 1H), 2.26-2.21 (m, 4H), 1.87-1.81 (m, 2H).

HPLC purity: 99.4% at 254 nm.

N-cis-3-(2-hydroxyethyl)cyclobutyl)-5-phenylisoxazole-3-carboxamide

LC-MS: (M+H)$^+$=287

Analytical data: $^1$H NMR (CDCl$_3$, 400 MHz): 7.83-7.80 (m, 2H), 7.54-7.49 (m, 3H), 7.02-6.93 (m, 3H), 4.50-4.44 (m, 1H), 3.67-3.63 (t, J=8.0 Hz, 2H), 2.68-2.62 (m, 2H), 2.22-2.13 (m, 1H), 1.76-1.66 (m, 4H).

HPLC purity: 99.0% at 254 nm.

Example 37: N-(cis-3-(methylsulfonamidomethyl)cyclobutyl)-5-phenylisoxazole-3-carboxamide

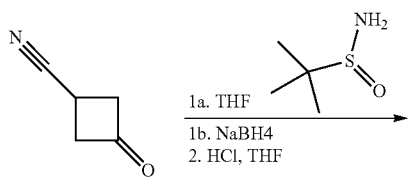

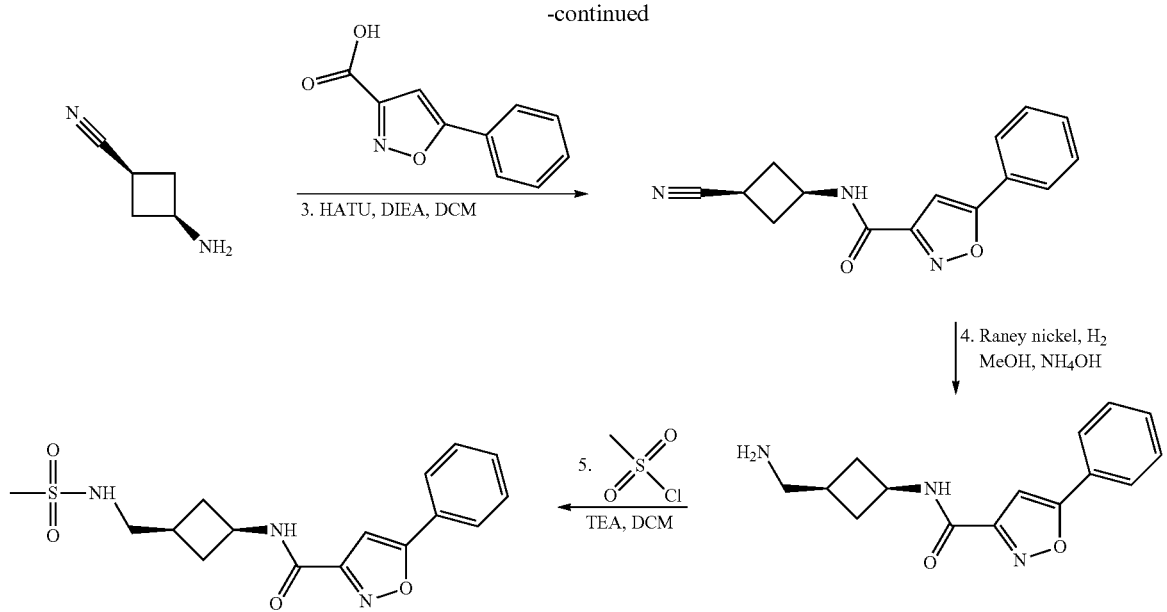

Step 1: N-(cis-3-cyanocyclobutyl)-2-methylpropane-2-sulfinamide a solution of 3-oxocyclobutane-1-carbonitrile (3.9 g, 41.01 mmol, 1.00 eq.) and 2-methylpropane-2-sulfinamide (4.97 g, 41.01 mmol, 1.00 eq.) in tetrahydrofuran (100 mL) was placed in a 250-mL 3-necked round-bottom flask and stirred for 16 hours at 70° C. After cooled to room temperature, NaBH$_4$ (780 mg, 20.53 mmol, 0.50 eq.) was added in portions and stirred for 30 min at room temperature. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 7.5 g (91%) of N-(cis-3-cyanocyclobutyl)-2-methylpropane-2-sulfinamide as a yellow solid. LC-MS: (M+H)$^+$=201.

Step 2: cis-3-aminocyclobutanecarbonitrile hydrochloride a solution of N-(cis-3-cyanocyclobutyl)-2-methylpropane-2-sulfinamide (1 g, 4.99 mmol, 1.00 eq.) in tetrahydrofuran (15 mL) was placed in a 100-mL round-bottom flask and concentrated hydrogen chloride (1 mL) was added. The resulting solution was stirred for 1 hour at room temperature and then concentrated under vacuum. This resulted in 440 mg (crude) of cis-3-aminocyclobutanecarbonitrile hydrochloride as a yellow solid.

Step 3: N-(cis-3-cyanocyclobutyl)-5-phenylisoxazole-3-carboxamide 3-aminocyclobutanecarbonitrile hydrochloride (440 mg, 4.58 mmol, 1.00 eq.), 5-phenyl-1,2-oxazole-3-carboxylic acid (866 mg, 4.58 mmol, 1.00 eq.) and HATU (2090 mg, 5.50 mmol, 1.20 eq.) in dichloromethane (18 mL) were placed in a 100-mL round-bottom flask. To the mixture was added DIEA (1773 mg, 13.72 mmol, 3.00 eq.) and the mixture was stirred for 2 hours at room temperature. The reaction was then quenched by the addition of water. The resulting solution was extracted with ethyl acetate and the organic layers combined. The resulting mixture was washed with brine, dried over anhydrous sodium sulfate and concentrated under vacuum. The residue was applied onto a silica gel column with ethyl acetate/petroleum ether (1:3) to give 600 mg (49%) of N-(cis-3-cyanocyclobutyl)-5-phenylisoxazole-3-carboxamide as a white solid. LC-MS: (M+H)$^+$=268.

Step 4: 5-phenyl-N-[cis-3-(aminomethyl)cyclobutyl]-1,2-oxazole-3-carboxamide a solution of N-(cis-3-cyanocyclobutyl)-5-phenylisoxazole-3-carboxamide (400 mg, 1.50 mmol, 1.00 eq.) and ammonia (0.1 mL) in methanol (10 mL) was placed in a 50-mL round-bottom flask and Raney Ni (40 mg) was added. The mixture was hydrogenated for 6 hours at 35° C. The solids were filtered out. The resulting mixture was concentrated under vacuum. This resulted in 180 mg (crude) of 5-phenyl-N-[cis-3-(aminomethyl)cyclobutyl]-1,2-oxazole-3-carboxamide as yellow green oil. LC-MS: (M+H)$^+$=272.

Step 5: 5-phenyl-N-[cis-3-(methanesulfonamidomethyl)cyclobutyl]-1,2-oxazole-3-carboxamide a solution of 5-phenyl-N-[cis-3-(aminomethyl)cyclobutyl]-1,2-oxazole-3-carboxamide (120 mg, 0.44 mmol, 1.00 eq.) and triethylamine (89 mg, 0.88 mmol, 2.00 eq.) in dichloromethane (3 mL) was placed in a 25-mL round-bottom flask and methanesulfonyl chloride (55 mg, 0.48 mmol, 1.10 eq.) was added. The resulting solution was stirred for 10 min at room temperature. The reaction was then quenched by the addition of water and extracted with ethyl acetate and the organic layers combined. The resulting mixture was washed with brine, dried over anhydrous sodium sulfate and concentrated under vacuum. The residue was applied onto a silica gel column with ethyl acetate/petroleum ether (1:2) to give 45.5 mg (29%) of 5-phenyl-N-[cis-3-(methanesulfonamidomethyl)cyclobutyl]-1,2-oxazole-3-carboxamide as a white solid.

LC-MS: (M+H)$^+$=350

Analytical data: $^1$H NMR (300 MHz, DMSO-d$_6$, ppm): δ 9.02-8.99 (d, J=7.8 Hz, 1H), 7.94-7.92 (m, 2H), 7.57-7.55 (m, 3H), 7.34 (s, 1H), 7.00-6.96 (t, J=5.7 Hz, 1H), 4.35-4.27 (m, 1H), 3.00-2.96 (m, 2H), 2.91-2.89 (m, 3H), 2.38-2.30 (m, 2H), 2.18-2.08 (m, 1H), 1.90-1.80 (m, 2H).

HPLC purity: 97.44% at 254 nm.

Example 38: N-(trans-3-(3-((S)-1-hydroxyethyl)-1,2,4-oxadiazol-5-yl)cyclobutyl)-5-phenylisoxazole-3-carboxamide and N-(trans-3-(3-((R)-1-hydroxyethyl)-1,2,4-oxadiazol-5-yl)cyclobutyl)-5-phenylisoxazole-3-carboxamide

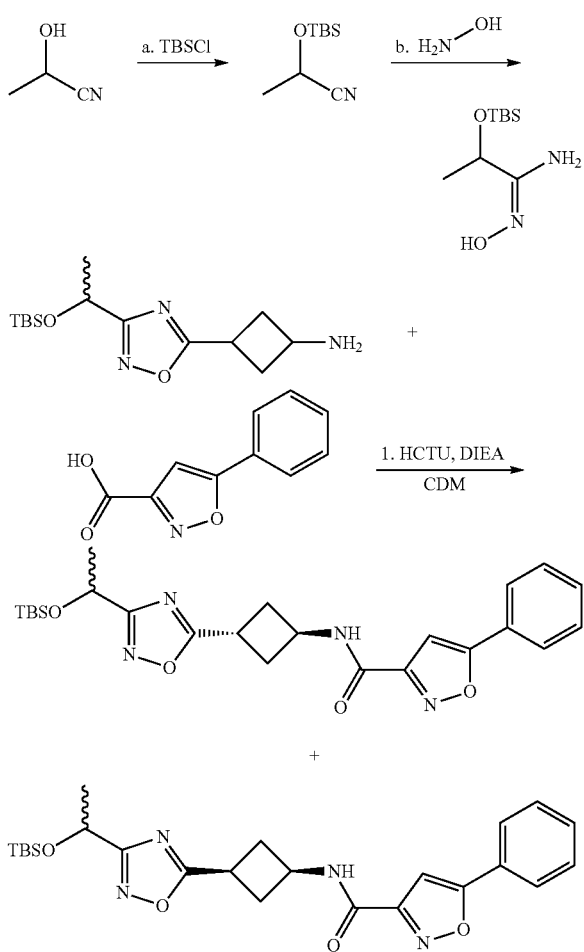

The compounds were prepared using a similar procedure as shown in example 32 using (E)-2-[(tert-butyldimethylsilyl)oxy]-N-hydroxypropimidamide as the starting material in step 3.

Preparation of (E)-2-((tert-butyldimethylsilyl)oxy)-N'-hydroxypropanimidamide

Step A: 2-[(tert-butyldimethylsilyl)oxy]propanenitrile: tert-butyl(chloro)dimethylsilane (6.3 g, 41.80 mmol, 1.50 eq.), imidazole (2.87 g, 42.16 mmol, 1.50 eq.) and 4-dimethylaminopyridine (400 mg, 3.27 mmol, 0.10 eq.) were added to a solution of 2-hydroxypropanenitrile (2 g, 28.14 mmol, 1.00 eq.) in dichloromethane (100 mL). The resulting solution was stirred for 3 hours at room temperature. The reaction was then quenched by the addition of water, extracted with ethyl acetate (3×50 mL) and the combined organic layers were dried over anhydrous sodium sulfate and concentrated under vacuum to give 4 g (crude) of 2-[(tert-butyldimethylsilyl)oxy]propanenitrile as colorless oil.

Step B: (E)-2-[(tert-butyldimethylsilyl)oxy]-N-hydroxypropimidamide: hydroxylamine hydrochloride (225 mg, 3.24 mmol, 2.00 eq.) and sodium methoxide (390 mg, 4.64 mmol, 3.00 eq.) was added to a solution of 2-[(tert-butyldimethylsilyl)oxy]propanenitrile (3 g, 16.19 mmol, 1.00 eq.) in methanol (100 mL). The resulting solution was stirred overnight at 70° C. in an oil bath. The reaction was then quenched by the addition of water. The resulting solution was extracted with ethyl acetate (3×50 mL) and the combined organic layers were dried over anhydrous sodium sulfate and concentrated under vacuum. The residue was applied onto a silica gel column with ethyl acetate/petroleum ether (1:2). This resulted in 2.4 g (68%) of (E)-2-[(tert-butyldimethylsilyl)oxy]-N-hydroxypropimidamide as a yellow solid. LC-MS: (M+H)$^+$=219.

Step 1: 5-phenyl-N-[cis-3-(3-[1-[(tert-butyldimethylsilyl)oxy]ethyl]-1,2,4-oxadiazol-5-yl)cyclobutyl]-1,2-oxazole-3-carboxamide and 5-phenyl-N-[trans-3-(3-[1-[(tert-butyldimethylsilyl)oxy]ethyl]-1,2,4-oxadiazol-5-yl)cyclobutyl]-1,2-oxazole-3-carboxamide to a solution of 3-(3-[1-[(tert-butyldimethylsilyl)oxy]ethyl]-1,2,4-oxadiazol-5-yl)cyclobutan-1-amine (1.5 g, 5.04 mmol, 1.00 eq.) in dichloromethane (100 mL) was added 5-phenyl-1,2-oxazole-3-carboxylic acid (1.13 g, 5.97 mmol, 1.20 eq.), HATU (2.28 g, 6.00 mmol, 1.20 eq.) and DIEA (1.93 g, 14.93 mmol, 3.00 eq.). The resulting solution was stirred for 1 hour at room temperature. The reaction was then quenched by the addition of water and extracted with ethyl acetate (3×50 mL) and the combined organic layers were dried over anhydrous sodium sulfate and concentrated under vacuum. The residue was applied onto a silica gel column with ethyl acetate/petroleum ether (1:50) to give 300 mg (13%) of 5-phenyl-N-[cis-3-(3-[1-[(tert-butyldimethylsilyl)oxy]ethyl]-1,2,4-oxadiazol-5-yl)cyclobutyl]-1,2-oxazole-3-carboxamide as a white solid. The solvent was changed to a mixture of with ethyl acetate/petroleum ether (1:20) to give 1.4 g (59%) of 5-phenyl-N-[trans-3-(3-[1-[(tert-butyldimethylsilyl)oxy]ethyl]-1,2,4-oxadiazol-5-yl)cyclobutyl]-1,2-oxazole-3-carboxamide as a white solid. LC-MS: (M+H)$^+$=469.

Step 2a: N-(trans-3-(3-((S)-1-hydroxyethyl)-1,2,4-oxadiazol-5-yl)cyclobutyl)-5-phenylisoxazole-3-carboxamide and N-(trans-3-(3-((R)-1-hydroxyethyl)-1,2,4-oxadiazol-5-yl)cyclobutyl)-5-phenylisoxazole-3-carboxamide

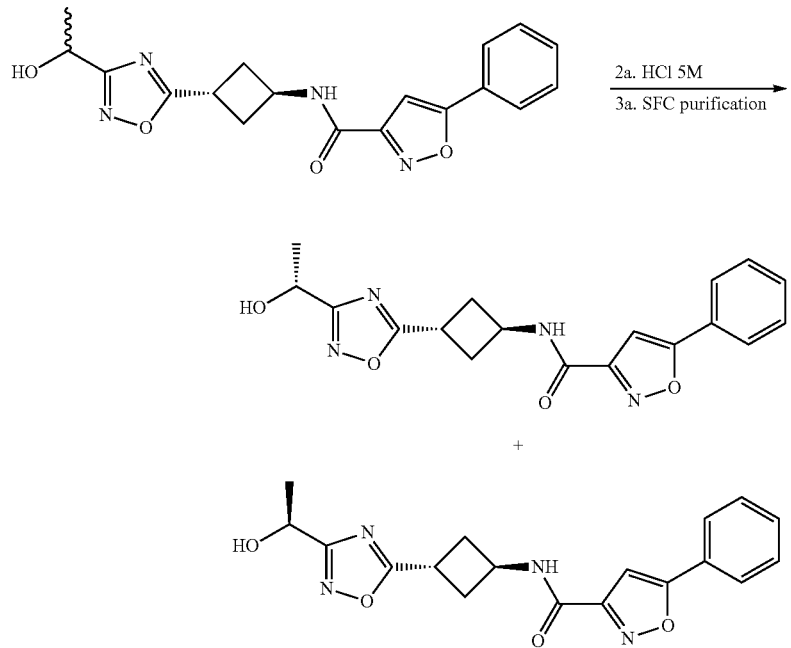

5M hydrogen chloride (15 mL) was added dropwise to a solution of 5-phenyl-N-[trans-3-(3-[1-[(tert-butyldimethylsilyl)oxy]ethyl]-1,2,4-oxadiazol-5-yl)cyclobutyl]-1,2-oxazole-3-carboxamide (1.4 g, 2.99 mmol, 1.00 eq.) in methanol (30 mL). The resulting solution was stirred for 1 hour at room temperature. The reaction was then quenched by the addition of water. The resulting solution was extracted with dichloromethane (3×50 mL) and the combined organic layers were dried over anhydrous sodium sulfate and concentrated under vacuum. The residue was applied onto a silica gel column with ethyl acetate/petroleum ether (1:1) to give 1.05 g (99%) of 5-phenyl-N-[trans-3-[3-(1-hydroxyethyl)-1,2,4-oxadiazol-5-yl]cyclobutyl]-1,2-oxazole-3-carboxamide as a white solid.

Step 3a: SFC Separation the pure isomers were separated by Prep-SFC with the following conditions (prep SFC 350): Column, Chiralpak IA SFC, 5*25 cm; mobile phase, $CO_2$ (50%), ACN/MeOH=1/1 (50%); Detector, UV: 220 nm. This resulted in:

Isomer I: 455 mg (41%) as a white solid
Analytical data: $^1$H NMR (400 MHz, DMSO-$d_6$): δ 9.33-9.31 (d, J=7.6 Hz, 1H), 7.95-7.93 (m, 2H), 7.59-7.52 (m, 3H), 7.38 (s, 1H), 5.72-5.71 (d, J=5.6 Hz, 1H), 4.87-4.82 (m, 1H), 4.80-4.71 (m, 1H), 3.80-3.74 (m, 1H), 2.76-2.71 (m, 2H), 2.68-2.60 (m, 2H).
HPLC purity: 99.35 at 254 nm.
Isomer II: 549 mg (50%) as a white solid
Analytical data: $^1$H NMR (400 MHz, DMSO-$d_6$): δ 9.33-9.31 (d, J=7.6 Hz, 1H), 7.95-7.93 (m, 2H), 7.59-7.52 (m, 3H), 7.38 (s, 1H), 5.72-5.71 (d, J=5.6 Hz, 1H), 4.86-4.81 (m, 1H), 4.80-4.71 (m, 1H), 3.80-3.74 (m, 1H), 2.76-2.71 (m, 2H), 2.68-2.60 (m, 2H).
HPLC purity: 99.5% at 254 nm.

Step 2b: N-(cis-3-(3-((S)-1-hydroxyethyl)-1,2,4-oxadiazol-5-yl)cyclobutyl)-5-phenylisoxazole-3-carboxamide and N-(cis-3-(3-((R)-1-hydroxyethyl)-1,2,4-oxadiazol-5-yl)cyclobutyl)-5-phenylisoxazole-3-carboxamide

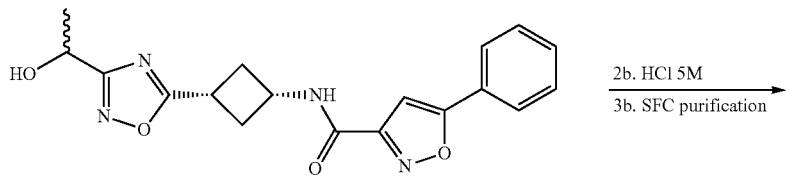

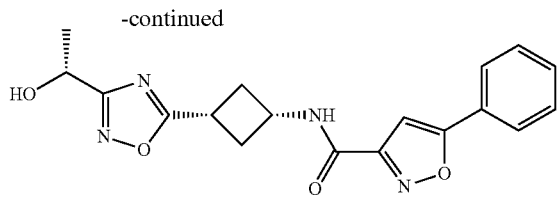

+

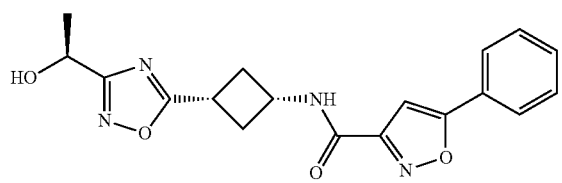

Step 2b 5M hydrogen chloride (5 mL) was added dropwise to a solution of 5-phenyl-N-[cis-3-(3-[1-[(tert-butyldimethylsilyl)oxy]ethyl]-1,2,4-oxadiazol-5-yl)cyclobutyl]-1,2-oxazole-3-carboxamide (300 mg, 0.64 mmol, 1.00 eq.) in methanol (20 mL). The resulting solution was stirred for 1 hour at room temperature and then quenched by the addition of water. The resulting solution was extracted with dichloromethane (3×20 mL) and the combined organic layers were dried over anhydrous sodium sulfate and concentrated under vacuum to give 140 mg (62%) of 5-phenyl-N-[cis-3-[3-(1-hydroxyethyl)-1,2,4-oxadiazol-5-yl]cyclobutyl]-1,2-oxazole-3-carboxamide as a white solid.

Step 3b: SFC Purification the pure isomers (140 mg, 0.40 mmol, 1.00 eq.) were separated by Chiral-Prep-HPLC using the following conditions (Prep-HPLC-009): Column, Repaired IA, 21.2*150 mm, 5 um; mobile phase, hexane and ethanol (hold 20.0% ethanol in 20 min); Detector, UV 254/220 nm to give:

Isomer I: 52.1 mg as a white solid
LC-MS: (M+H)$^+$=355
Analytical data: $^1$H NMR (400 MHz, DMSO-d$_6$): δ 9.28-9.26 (d, J=7.6 Hz, 1H), 7.94-7.91 (m, 2H), 7.58-7.53 (m, 3H), 7.36 (s, 1H), 5.68-5.66 (d, J=5.6 Hz, 1H), 4.84-4.78 (m, 1H), 4.58-4.52 (m, 1H), 3.59-3.54 (m, 1H), 2.76-2.71 (m, 2H), 2.68-2.60 (m, 2H), 1.42-1.40 (d, J=14.8 Hz, 3H).
HPLC purity: 97.9% at 254% nm
Isomer II: 49.7 mg (36%) as a white solid.
LC-MS: (M+H)$^+$=355

Example 39: 5-phenyl-N-[trans-3-([5-[(1R)-1-hydroxyethyl]-1,3,4-oxadiazol-2-yl]methyl)cyclobutyl]-1,2-oxazole-3-carboxamide and 5-phenyl-N-[cis-3-([5-[(1R)-1-hydroxyethyl]-1,3,4-oxadiazol-2-yl]methyl)cyclobutyl]-1,2-oxazole-3-carboxamide

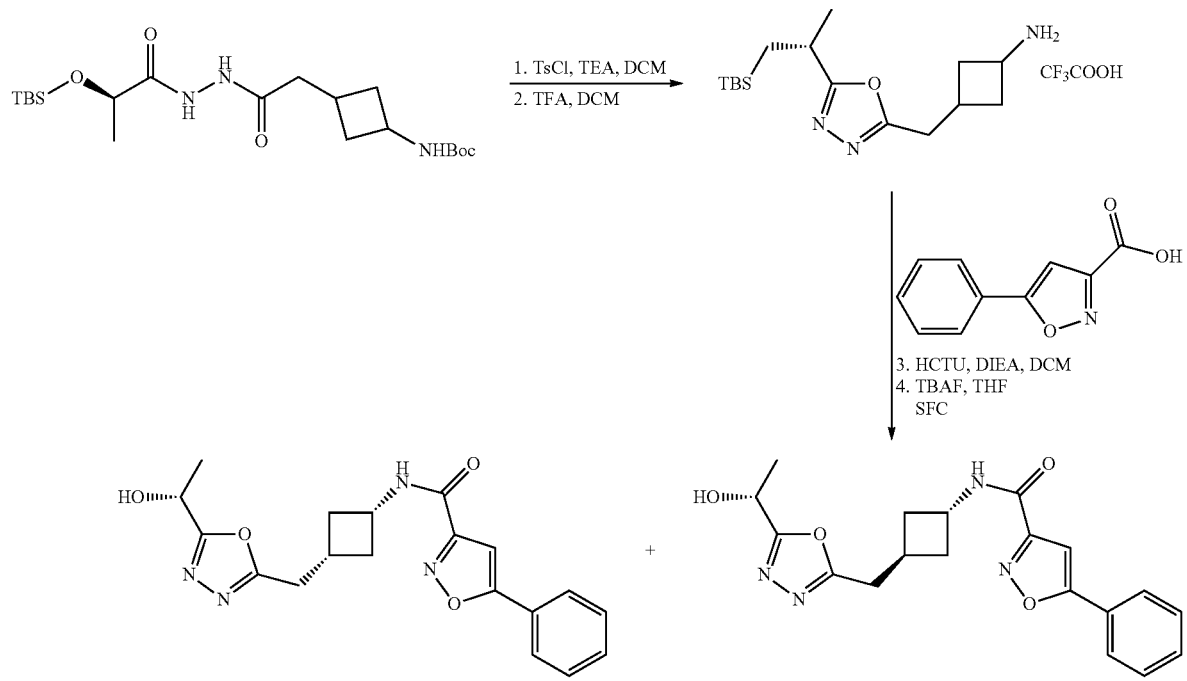

tert-butyl (R)-(3-(2-(2-(2-((tert-butyldimethylsilyl)oxy)propanoyl)hydrazinyl)-2-oxoethyl)cyclobutyl)carbamate was prepared following the procedure shown in example 34 (steps 1-3) using lithium (R)-2-((tert-butyldimethylsilyl)oxy)propanoate as the starting material.

Step 1: tert-butyl N-[3-([5-[(1R)-1-[(tert-butyldimethylsilyl)oxy]ethyl]-1,3,4-oxadiazol-2-yl]methyl)cyclobutyl]carbamate TEA (7 g, 69.18 mmol, 4.00 eq.) was added dropwise to a solution of tert-butyl N-[3-([N-[(2R)-2-[(tert-butyldimethylsilyl)oxy]propanoyl]hydrazinecarbonyl]methyl)cyclobutyl]carbamate (7.4 g, 17.22 mmol, 1.00 eq.) and 4-methylbenzene-1-sulfonyl chloride (9.85 g, 51.67 mmol, 3.00 eq.) in dichloromethane (100 mL). The resulting solution was stirred for 24 hours at room temperature. The reaction was then quenched by the addition of 100 mL of water/ice. The resulting solution was extracted with dichloromethane (3×100 mL) and the organic layers combined. The resulting mixture was washed with brine (2×50 mL), dried over anhydrous sodium sulfate and concentrated under vacuum. The residue was applied onto a silica gel column with ethyl acetate/petroleum ether (1:5) to give 4.3 g (61%) of tert-butyl N-[3-([5-[(1R)-1-[(tert-butyldimethylsilyl)oxy]ethyl]-1,3,4-oxadiazol-2-yl]methyl)cyclobutyl]carbamate as colorless oil. LC-MS: (M+H)$^+$=412.

Step 2: [3-([5-[(1R)-1-[(tert-butyldimethylsilyl)oxy]ethyl]-1,3,4-oxadiazol-2-yl]methyl)cyclobutyl]amino 2,2,2-trifluoroacetate trifluoroacetic acid (8 mL) was added to a solution of tert-butyl N-[3-([5-[(1R)-1-[(tert-butyldimethylsilyl)oxy]ethyl]-1,3,4-oxadiazol-2-yl]methyl)cyclobutyl]carbamate (3.2 g, 7.77 mmol, 1.00 eq.) in dichloromethane (50 mL). The resulting solution was stirred for 16 hours at room temperature and then concentrated under vacuum to give 3.2 g (97%) of [3-([5-[(1R)-1-[(tert-butyldimethylsilyl)oxy]ethyl]-1,3,4-oxadiazol-2-yl]methyl)cyclobutyl]amino 2,2,2-trifluoroacetate as colorless crude oil. LC-MS: (M+H)$^+$= 312.

Step 3: N-[3-([5-[(1R)-1-[(tert-butyldimethylsilyl)oxy]ethyl]-1,3,4-oxadiazol-2-yl]methyl)cyclobutyl]-5-phenyl-1,2-oxazole-3-carboxamide a solution of [3-([5-[(1R)-1-[(tert-butyldimethylsilyl)oxy]ethyl]-1,3,4-oxadiazol-2-yl]methyl)cyclobutyl]amino 2,2,2-trifluoroacetate (3 g, 7.08 mmol, 1.00 eq.), 5-phenyl-1,2-oxazole-3-carboxylic acid (2.68 g, 14.17 mmol, 2.00 eq.), HCTU (7.3 g, 17.65 mmol, 2.50 eq.) and DIEA (4.6 g, 35.59 mmol, 5.00 eq.) in dichloromethane (100 mL) was stirred for 3 hours at room temperature. The resulting solution was diluted with 100 mL of water, extracted with dichloromethane (3×100 mL) and the organic layers combined. The resulting mixture was washed with brine (3×50 mL), dried over anhydrous sodium sulfate and concentrated under vacuum. The residue was applied onto a silica gel column with ethyl acetate/petroleum ether (1:1) to give 2.7 g (79%) of N-[3-([5-[(1R)-1-[(tert-butyldimethylsilyl)oxy]ethyl]-1,3,4-oxadiazol-2-yl]methyl)cyclobutyl]-5-phenyl-1,2-oxazole-3-carboxamide as a white solid. LC-MS: (M+H)$^+$=483.

Step 4: N-[3-([5-[(1R)-1-hydroxyethyl]-1,3,4-oxadiazol-2-yl]methyl)cyclobutyl]-5-phenyl-1,2-oxazole-3-carboxamide TBAF (2 mL) in THF (2 mL) was added to a solution of N-[3-([5-[(1R)-1-[(tert-butyldimethylsilyl)oxy]ethyl]-1,3,4-oxadiazol-2-yl]methyl)cyclobutyl]-5-phenyl-1,2-oxazole-3-carboxamide (2.7 g, 5.59 mmol, 1.00 eq.) in THF (20 mL). The resulting solution was stirred for 1 hour at room temperature and then diluted with 50 mL of water. The resulting solution was extracted with dichloromethane (3×50 mL) and the combined organic layers were dried over anhydrous sodium sulfate and concentrated under vacuum. The residue was applied onto a silica gel column with ethyl acetate/petroleum ether (1:100). The crude product was purified by Flash-Prep-HPLC with the following conditions (CombiFlash-1): Column, C18 silica gel; mobile phase, H$_2$O/CH$_3$CN=9:1 increasing to H$_2$O/CH$_3$CN=1:1 within 30 min; Detector, UV 254 nm. This resulted in 1.8 g (88%) of N-[3-([5-[(1R)-1-hydroxyethyl]-1,3,4-oxadiazol-2-yl]methyl)cyclobutyl]-5-phenyl-1,2-oxazole-3-carboxamide as a off-white solid. LC-MS: (M+H)$^+$=369. The isomers were separated by Prep-SFC with the following conditions (prep SFC 350-2): Column, Phenomenex Lux, 5 u Cellulose-4 AXIA Packed, 250*21.2 mm, 5 um; mobile phase, CO$_2$ (50%), ethanol (0.2% DEA)(50%); Detector, UV 254 nm. This resulted in 460.2 mg (26%) of 5-phenyl-N-[trans-3-([5-[(1R)-1-hydroxyethyl]-1,3,4-oxadiazol-2-yl]methyl)cyclobutyl]-1,2-oxazole-3-carboxamide as a off-white solid and 749.4 mg (42%) of 5-phenyl-N-[cis-3-([5-[(1R)-1-hydroxyethyl]-1,3,4-oxadiazol-2-yl]methyl)cyclobutyl]-1,2-oxazole-3-carboxamide as a off-white solid.

5-phenyl-N-[trans-3-([5-[(1R)-1-hydroxyethyl]-1,3,4-oxadiazol-2-yl]methyl)cyclobutyl]-1,2-oxazole-3-carboxamide Analytical data: $^1$H NMR (400 MHz, CD$_3$OD): δ 7.90-7.87 (m, 2H), 7.56-7.50 (m, 3H), 7.09 (s, 1H), 5.04-4.99 (q, J=6.8 Hz, 1H), 4.70-4.63 (m, 1H), 3.17-3.15 (d, J=8 Hz, 2H), 2.88-2.79 (m, 1H), 2.48-2.41 (m, 2H), 2.35-2.30 (m, 2H), 1.61-1.59 (d, J=6.68 Hz, 3H).

HPLC purity: 98.6% at 254 nm.

5-phenyl-N-[cis-3-([5-[(1R)-1-hydroxyethyl]-1,3,4-oxadiazol-2-yl]methyl)cyclobutyl]-1,2-oxazole-3-carboxamide Analytical data: $^1$H NMR (400 MHz, CD$_3$OD): δ 7.89-7.87 (m, 2H), 7.56-7.50 (m, 3H), 7.08 (s, 1H), 5.04-4.99 (q, J=6.8 Hz, 1H), 4.49-4.41 (m, 1H), 3.07-3.05 (d, J=7.2 Hz, 2H), 2.66-2.50 (m, 3H), 2.05-1.96 (m, 2H), 1.61-1.59 (d, J=6.8 Hz, 3H).

HPLC purity: 100% at 254 nm.

Example 40: Preparation of N-((trans-3-((5-((S)-1-hydroxyethyl)-1,3,4-oxadiazol-2-yl)methyl)cyclobutyl)-5-phenylisoxazole-3-carboxamide and N-((cis-3-((5-((S)-1-hydroxyethyl)-1,3,4-oxadiazol-2-yl)methyl)cyclobutyl)-5-phenylisoxazole-3-carboxamide Compounds were prepared following the procedure shown in example 39, using tert-butyl (S)-(3-(2-(2-(2-((tert-butyldimethylsilyl)oxy)propanoyl)hydrazinyl)-2-oxoethyl)cyclobutyl)carbamate. Final products were purified by Chiral-Prep-HPLC with the following conditions (Prep-HPLC-009): Column, Chiral pak AS-H, 2*25 CM; mobile phase, hexane and IPA (hold 35.0% IPA in 22 min); Detector, UV 254/220 nm to give 201.8 mg (47%) of 5-phenyl-N-[trans-3-([5-[(1S)-1-hydroxyethyl]-1,3,4-oxadiazol-2-yl]methyl)cyclobutyl]-1,2-oxazole-3-carboxamide as a off-white solid and 81.9 mg (19%) of 5-phenyl-N-[cis-3-([5-[(1S)-1-hydroxyethyl]-1,3,4-oxadiazol-2-yl]methyl)cyclobutyl]-1,2-oxazole-3-carboxamide as a off-white solid.

N-((trans-3-((5-((S)-1-hydroxyethyl)-1,3,4-oxadiazol-2-yl)methyl)cyclobutyl)-5-phenylisoxazole-3-carboxamide LC-MS: (M+H)⁺=369
Analytical data: ¹H NMR (400 MHz, CD₃OD): δ 7.90-7.87 (m, 2H), 7.57-7.50 (m, 3H), 7.09 (s, 1H), 5.04-4.99 (q, J=6.8 Hz, 1H), 4.70-4.63 (m, 1H), 3.17-3.15 (d, J=8.0 Hz, 2H), 2.88-2.80 (m, 1H), 2.48-2.41 (m, 2H), 2.35-2.29 (m, 2H), 1.61-1.59 (d, J=6.8 Hz, 3H).
HPLC purity: 100% at 254 nm.

N-((cis-3-((5-((S)-1-hydroxyethyl)-1,3,4-oxadiazol-2-yl)methyl)cyclobutyl)-5-phenylisoxazole-3-carboxamide LC-MS: (M+H)⁺=369
Analytical data: ¹H NMR (400 MHz, CD₃OD): δ 7.89-7.87 (m, 2H), 7.56-7.50 (m, 3H), 7.08 (s, 1H), 5.04-4.99 (q, J=6.8 Hz, 1H), 4.49-4.41 (m, 1H), 3.07-3.05 (d, J=6.8 Hz, 2H), 2.66-2.50 (m, 3H), 2.03-1.96 (m, 2H), 1.61-1.59 (d, J=6.8 Hz, 3H).
HPLC purity: 100% at 254 nm.

Example 41: N-(trans-3-(5-((R)-1-hydroxyethyl)-1,2,4-oxadiazol-3-yl)cyclobutyl)-5-phenylisoxazole-3-carboxamide

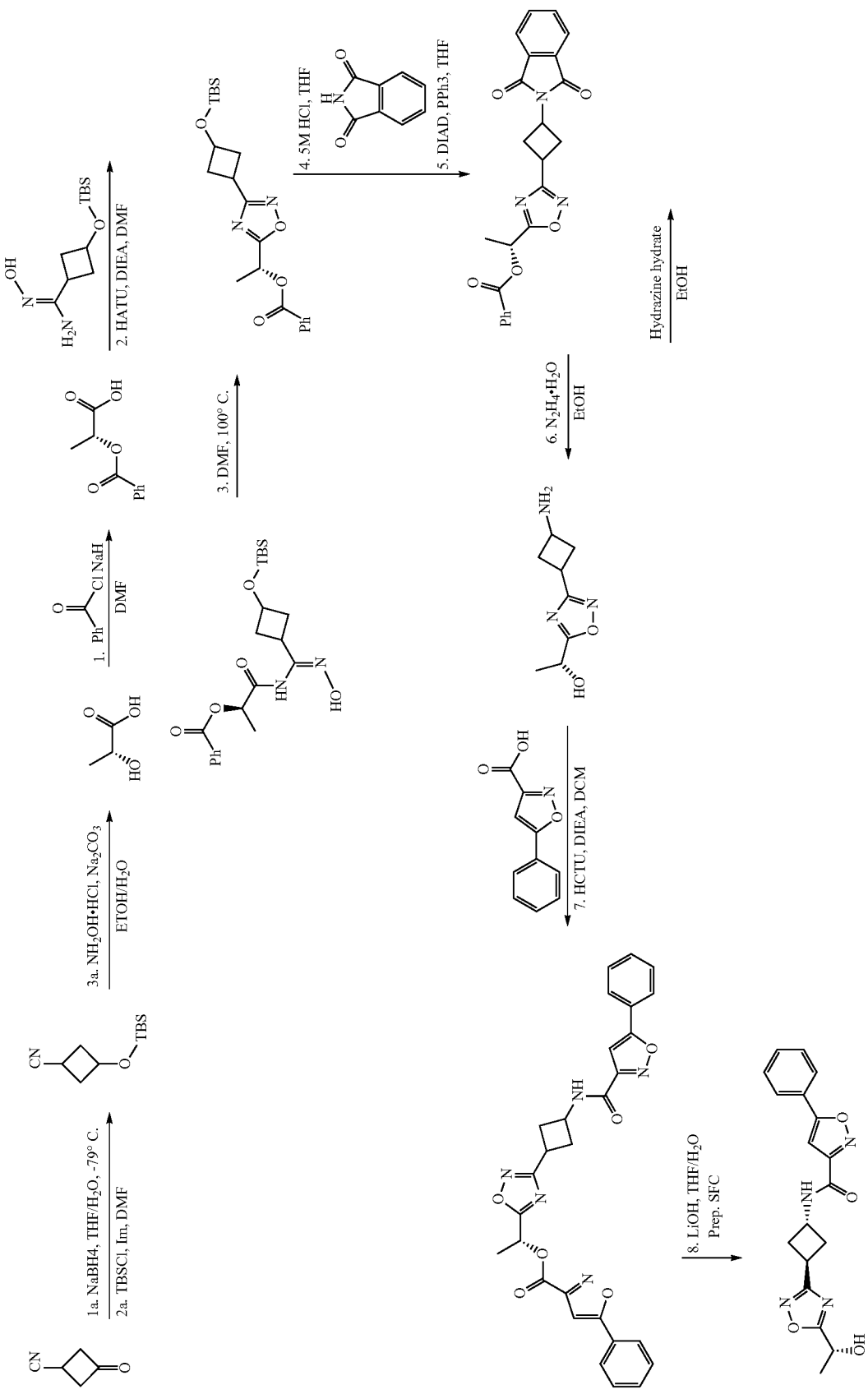

Step 1a: 3-hydroxycyclobutane-1-carbonitrile

NaBH$_4$ (2.4 g, 63.45 mmol, 0.50 eq.) was added slowly to a −70° C. solution of 3-oxocyclobutane-1-carbonitrile (12 g, 126.18 mmol, 1.00 eq., prepared according example 33, step 1) in THF (100 mL) and water (5 mL). The resulting solution was stirred for 1 hour at −70° C. in a liquid nitrogen bath. The reaction was then quenched by the addition of 50 mL of water/ice. The resulting solution was extracted with ethyl acetate (3×100 mL) and the organic layers combined. The resulting mixture was washed with brine (3×50 mL), dried over anhydrous sodium sulfate and concentrated under vacuum to give 8.13 g (66%) of 3-hydroxycyclobutane-1-carbonitrile as colorless oil.

Step 2a: 3-[(tert-butyldimethylsilyl)oxy]cyclobutane-1-carbonitrile tert-butyl(chloro)dimethylsilane (15.1 g, 100.18 mmol, 1.20 eq.) in dichloromethane (30 mL) was added dropwise to a 0° C. solution of 3-hydroxycyclobutane-1-carbonitrile (8.1 g, 83.41 mmol, 1.00 eq.) and 1H-imidazole (11.3 g, 165.99 mmol, 2.00 eq.) in dichloromethane (150 mL). The resulting solution was stirred for 1.5 hours at room temperature. The reaction was then quenched by the addition of 100 mL of water/ice and extracted with dichloromethane (3×100 mL) and the organic layers combined. The resulting mixture was washed with brine (3×80 mL), dried over anhydrous sodium sulfate and concentrated under vacuum to give 16.3 g (92%) of 3-[(tert-butyldimethylsilyl)oxy]cyclobutane-1-carbonitrile as colorless crude oil.

Step 3a: (E)-3-[(tert-butyldimethylsilyl)oxy]-N-hydroxycyclobut-1-carboximidamide sodium carbonate (18.49 g, 174.4 mmol, 2.30 eq.) and hydroxylamine hydrochloride (10.54 g, 151.66 mmol, 2.00 eq.) were added to a solution of 3-[(tert-butyldimethylsilyl)oxy]cyclobutane-1-carbonitrile (16 g, 75.83 mmol, 1.00 eq.) in ethanol (150 mL) and water (150 mL). The resulting solution was stirred for 20 hours at 80° C. in an oil bath. The resulting solution was diluted with 100 mL of water and extracted with ethyl acetate (3×100 mL) and the organic layers combined. The resulting mixture was washed with brine (2×100 mL), dried over anhydrous sodium sulfate and concentrated under vacuum to give 12.95 g (70%) of (E)-3-[(tert-butyldimethylsilyl)oxy]-N-hydroxycyclobut-1-carboximidamide as a off-white solid. LC-MS: (M+H)$^+$=245.

Step 1: (2R)-2-(benzoyloxy)propanoic acid benzoyl chloride (28 g, 199.19 mmol, 2.00 eq.) Was added dropwise to a 0° C. solution of (2R)-2-hydroxypropanoic acid (9 g, 99.91 mmol, 1.00 eq.) and sodium hydride (9.6 g, 240.02 mmol, 4.00 eq., 60%) in DMF (100 mL). The resulting solution was stirred for 2 hours at room temperature. The reaction was then quenched by the addition of 100 mL of water/ice. The resulting solution was washed with ethyl acetate (3×100 mL). The pH value of the aqueous layer was adjusted to 4 with hydrogen chloride aqueous (6 mol/L) and extracted with ethyl acetate (3×100 mL) and the organic layers combined. The resulting mixture was washed with brine (3×100 mL), dried over anhydrous sodium sulfate and concentrated under vacuum. The residue was applied onto a silica gel column with ethyl acetate/petroleum ether (1:2) to give 6.2 g (32%) of (2R)-2-(benzoyloxy)propanoic acid as colorless oil. LC-MS: (M+H)$^+$=193. $^1$H NMR (400 MHz, CDCl$_3$): δ 8.10-8.08 (m, 2H), 7.58-7.54 (m, 1H), 7.45-7.42 (m. 2H), 5.38-5.33 (m, 1H), 1.66-1.65 (d, J=6.8 Hz, 3H).

Step 2: (1R)-1-[[(1E)-[3-[(tert-butyldimethylsilyl)oxy]cyclobutyl](hydroxyimino)methyl]carbamoyl]ethyl benzoate DIEA (12 g, 92.85 mmol, 3.00 eq.) was added dropwise to a 0° C. solution of (E)-3-[(tert-butyldimethylsilyl)oxy]-N-hydroxycyclobut-1-carboximidamide (8.3 g, 33.96 mmol, 1.10 eq.), (2R)-2-(benzoyloxy)propanoic acid (6 g, 30.90 mmol, 1.00 eq.) and HATU (23.5 g, 61.84 mmol, 2.00 eq.) in DMF (100 mL). The resulting solution was stirred for 1.5 hours at room temperature. The reaction was then quenched by the addition of 100 mL of water/ice and extracted with ethyl acetate (3×100 mL) and the organic layers combined. The resulting mixture was washed with brine (3×100 mL), dried over anhydrous sodium sulfate and concentrated under vacuum. The residue was applied onto a silica gel column with ethyl acetate/petroleum ether (1:3) to give 6.25 g (48%) of (1R)-1-[[(1E)-[3-[(tert-butyldimethylsilyl)oxy]cyclobutyl](hydroxyimino)methyl]carbamoyl]ethyl benzoate as colorless oil. LC-MS: (M+H)$^+$=421.

Step 3: (1R)-1-(3-[3-[(tert-butyldimethylsilyl)oxy]cyclobutyl]-1,2,4-oxadiazol-5-yl)ethyl benzoate a solution of (1R)-1-[[(1Z)-[3-[(tert-butyldimethylsilyl)oxy]cyclobutyl](hydroxyimino)methyl] carbamoyl]ethyl benzoate (3.4 g, 8.08 mmol, 1.00 eq.) in DMF (15 mL) was stirred for 3 hours at 100° C. in an oil bath. The resulting solution was diluted with 50 mL of water and extracted with ethyl acetate (3×80 mL) and the organic layers combined. The resulting mixture was washed with brine (2×50 mL), dried over anhydrous sodium sulfate and concentrated under vacuum. The residue was applied onto a silica gel column with ethyl acetate/petroleum ether (1:6) to give 2.4 g (74%) of (1R)-1-(3-[3-[(tert-butyldimethylsilyl)oxy]cyclobutyl]-1,2,4-oxadiazol-5-yl)ethyl benzoate as colorless oil. LC-MS: (M+H)$^+$=403. $^1$H NMR (300 MHz, CDCl$_3$): δ 8.10-8.08 (m, 2H), 7.62-7.57 (m, 1H), 7.50-7.26 (m. 2H), 6.30-6.23 (m, 1H), 4.31-4.25 (m, 1H), 3.09-3.03 (m, 1H), 2.69-2.60 (m, 2H), 2.38-2.31 (m, 2H), 1.83-1.81 (d, J=6.6 Hz, 3H), 0.89 (s, 9H), 0.05 (s, 6H).

Step 4: (1R)-1-[3-(3-hydroxycyclobutyl)-1,2,4-oxadiazol-5-yl]ethyl benzoate 5M hydrogen chloride aqueous (2 mL) was added to a solution of (1R)-1-(3-[3-[(tert-butyldimethylsilyl)oxy]cyclobutyl]-1,2,4-oxadiazol-5-yl)ethyl benzoate (2.4 g, 5.95 mmol, 1.00 eq.) in Dioxane (30 mL). The resulting solution was stirred for 1 hour at room temperature. The resulting solution was diluted with 30 mL of water and extracted with ethyl acetate (3×50 mL) and the organic layers combined. The resulting mixture was washed with brine (3×20 mL), dried over anhydrous sodium sulfate and concentrated under vacuum. The residue was applied onto a silica gel column with ethyl acetate/petroleum ether (1:1) to give 1.63 g (95%) of (1R)-1-[3-(3-hydroxycyclobutyl)-1,2,4-oxadiazol-5-yl] ethyl benzoate as colorless oil. LC-MS: (M+H)$^+$=289. $^1$H NMR (300 MHz, CDCl$_3$): δ 8.11-8.08 (m, 2H), 7.63-7.60 (m, 1H), 7.47-7.44 (m. 2H), 6.31-6.24 (m, 1H), 4.34-4.30 (m, 1H), 3.21-3.13 (m, 1H), 2.83-2.74 (m, 2H), 2.35-2.25 (m, 2H), 1.84-1.82 (d, J=6.9 Hz, 3H).

Step 5: (1R)-1-[3-[3-(1,3-dioxo-2,3-dihydro-1H-isoindol-2-yl)cyclobutyl]-1,2,4-oxadiazol-5-yl]ethyl Benzoate DIAD (1.83 g, 9.05 mmol, 2.00 eq.) was dropwise to a solution of (1R)-1-[3-(3-hydroxycyclobutyl)-1,2,4-oxadiazol-5-yl]ethyl benzoate (1.3 g, 4.51 mmol, 1.00 eq.), 2,3-dihydro-1H-isoindole-1,3-dione (1.33 g, 9.04 mmol, 2.00 eq.) and triphenyl phosphine (2.37 g, 9.04 mmol, 2.00 eq.) in THF (50 mL) under $N_2$. The resulting solution was stirred for 2.5 hours at room temperature and concentrated under vacuum. The residue was applied onto a silica gel column with ethyl acetate/petroleum ether (1:5). The crude product was purified by Flash-Prep-HPLC with the following conditions (CombiFlash-1): Column, C18; mobile phase, $H_2O/CH_3CN=9:1$ increasing to $H_2O/CH_3CN=1:9$ within 30 min; Detector, UV 254 nm. This resulted in 1.3 g (69%) of (1R)-1-[3-[3-(1,3-dioxo-2,3-dihydro-1H-isoindol-2-yl)cyclobutyl]-1,2,4-oxadiazol-5-yl]ethyl benzoate as light yellow oil. LC-MS: $(M+H)^+=418$.

Step 6: (1R)-1-[3-(3-aminocyclobutyl)-1,2,4-oxadiazol-5-yl]ethan-1-ol hydrazine hydrate (5.4 g, 86.30 mmol, 30.00 eq., 80%) was added to a solution of (1R)-1-[3-[3-(1,3-dioxo-2,3-dihydro-1H-isoindol-2-yl)cyclobutyl]-1,2,4-oxadiazol-5-yl] ethyl benzoate (1.2 g, 2.87 mmol, 1.00 eq.) in ethanol (50 mL). The resulting solution was stirred for 3.5 hours at room temperature. The solids were filtered out and concentrated under vacuum to give 520 mg (99%) of (1R)-1-[3-(3-aminocyclobutyl)-1,2,4-oxadiazol-5-yl]ethan-1-ol as light yellow oil. LC-MS: $(M+H)^+=184$.

Step 7: (1R)-1-[3-[3-(5-phenyl-1,2-oxazole-3-amido)cyclobutyl]-1,2,4-oxadiazol-5-yl]ethyl 5-phenyl-1,2-oxazole-3-carboxylate DIEA (1.95 g, 15.09 mmol, 5.00 eq.) was added dropwise to a 0° C. solution of (1R)-1-[3-(3-aminocyclobutyl)-1,2,4-oxadiazol-5-yl]ethan-1-ol (520 mg, 2.84 mmol, 1.00 eq.), 5-phenyl-1,2-oxazole-3-carboxylic acid (1.14 g, 6.03 mmol, 2.00 eq.) and HCTU (3.1 g, 7.49 mmol, 2.50 eq.) in dichloromethane (60 mL). The resulting solution was stirred for 30 min at room temperature. The resulting solution was diluted with 50 mL of water/ice and extracted with dichloromethane (3×30 mL) and the organic layers combined. The resulting mixture was washed with brine (2×20 mL), dried over anhydrous sodium sulfate and concentrated under vacuum. The residue was applied onto a silica gel column with ethyl acetate/petroleum ether (1:1) to give 1.3 g (87%) of (1R)-1-[3-[3-(5-phenyl-1,2-oxazole-3-amido)cyclobutyl]-1,2,4-oxadiazol-5-yl]ethyl 5-phenyl-1,2-oxazole-3-carboxylate as light yellow oil. LC-MS: $(M+H)^+=526$.

Step 8: N-(3-[5-[(1R)-1-hydroxyethyl]-1,2,4-oxadiazol-3-yl]cyclobutyl)-5-phenyl-1,2-oxazole-3-carboxamide LiOH (115 mg, 2.74 mmol, 1.10 eq.) in $H_2O$ (10 mL) was added to a solution of (1R)-1-[3-[3-(5-phenyl-1,2-oxazole-3-amido)cyclobutyl]-1,2,4-oxadiazol-5-yl]ethyl 5-phenyl-1,2-oxazole-3-carboxylate (1.3 g, 2.47 mmol, 1.00 eq.) in THF (80 mL) and stirred for 30 min at room temperature. The resulting solution was diluted with 50 mL of $H_2O$ and extracted with ethyl acetate (2×20 mL) and the organic layers combined, dried over anhydrous sodium sulfate and concentrated under vacuum to give 850 mg (97%) of N-(3-[5-[(1R)-1-hydroxyethyl]-1,2,4-oxadiazol-3-yl]cyclobutyl)-5-phenyl-1,2-oxazole-3-carboxamide as a white solid. LC-MS: $(M+H)^+=355$. The isomers (850 mg) were separated by Prep-SFC using the following conditions (prep SFC 350-2): Column, Chiralpak AS-H, 5*25 cm, 5 um; mobile phase, $CO_2$ (50%), ethanol (0.2% DEA)(50%); Detector, UV 254 nm. This resulted in 679 mg (80%) of 5-phenyl-N-[trans-3-[5-[(1R)-1-hydroxyethyl]-1,2,4-oxadiazol-3-yl]cyclobutyl]-1,2-oxazole-3-carboxamide as white solid.

LC-MS: $(M+H)^+=355$

Analytical data: $^1$H NMR (300 MHz, DMSO-$d_6$): δ 9.29-9.26 (d, J=7.8 Hz, 1H), 7.95-7.92 (m, 2H), 7.58-7.53 (m, 3H), 7.37 (s, 1H), 6.10 (s, 1H), 5.03-4.96 (m, 1H), 4.83-4.72 (m, 1H), 3.64-3.55 (m, 1H), 2.72-2.62 (m, 2H), 2.52-2.46 (m, 2H), 1.51-1.49 (d, J=6.9 Hz, 3H).

HPLC purity: 99.2% at 254 nm.

Example 42: N-(trans-3-(5-((S)-1-hydroxyethyl)-1,2,4-oxadiazol-3-yl)cyclobutyl)-5-phenylisoxazole-3-carboxamide was prepared using a similar procedure as shown in example 42 where (2S)-2-hydroxypropanoic acid was used. The product was purified by Prep-SFC with the following conditions (prep SFC 350-2): Column, CHIRALPAK IC SFC, 5*25 cm, 5 um; mobile phase, $CO_2$ (50%), IPA (50%); Detector, UV 220 nm to give 282.4 mg (71%) 5-phenyl-N-[trans-3-[5-[(1S)-1-hydroxyethyl]-1,2,4-oxadiazol-3-yl]cyclobutyl]-1,2-oxazole-3-carboxamide as white solid.

LC-MS: $(M+H)^+=355$

Analytical data: $^1$H NMR (300 MHz, DMSO-$d_6$): δ 9.29-9.26 (d, J=7.8 Hz, 1H), 7.96-7.93 (m, 2H), 7.60-7.55 (m, 3H), 7.37 (s, 1H), 6.10-6.08 (d, J=5.7 Hz, 1H), 5.04-4.96 (m, 1H), 4.83-4.70 (m, 1H), 3.64-3.55 (m, 1H), 2.73-2.63 (m, 2H), 2.55-2.47 (m, 2H), 1.52-1.49 (d, J=6.9 Hz, 3H).

HPLC purity: 98.9% at 254 nm.

Example 43: 5-phenyl-N-[trans-3-[5-(1-methylazetidin-3-yl)-1,3,4-oxadiazol-2-yl]cyclobutyl]isoxazole-3-carboxamide

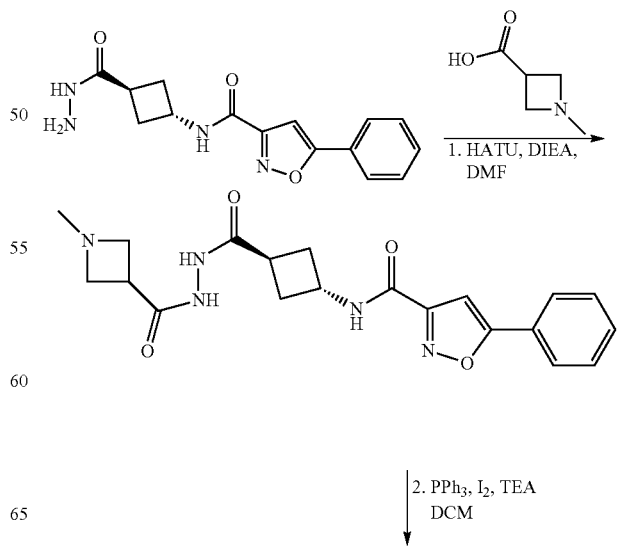

-continued

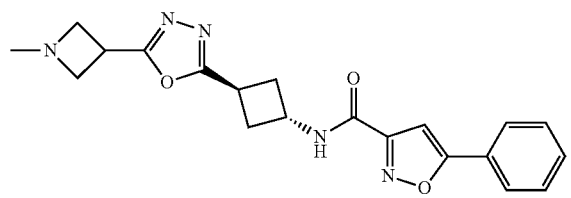

Step 1: 5-phenyl-N-[trans-3-[[(1-methylazetidin-3-yl) formohydrazido]carbonyl]cyclobutyl]isoxazole-3-carboxamide 1-methylazetidine-3-carboxylic acid (172.5 mg, 1.50 mmol, 1.50 eq.), HATU (456 mg, 1.20 mmol, 1.20 eq.) and DIEA (387 mg, 2.99 mmol, 3.00 eq.) were added to a solution of 5-phenyl-N-trans-3-(hydrazinecarbonyl)cyclobutyl]isoxazole-3-carboxamide (300 mg, 1.00 mmol, 1.00 eq., prepared according to example 20) in DMF (15 mL). The resulting solution was stirred for 3 hours at room temperature and then it was concentrated under vacuum. The crude product was purified by Flash-Prep-HPLC with the following conditions (IntelFlash-1): Column, C18; mobile phase, MeCN/$H_2$O=5:95 increasing to MeCN/$H_2$O=95:5 within 15 min; Detector, UV 254 nm. This resulted in 337 mg (85%) of 5-phenyl-N-[trans-3-[[(1-methylazetidin-3-yl)formohydrazido]carbonyl]cyclobutyl]isoxazole-3-carboxamide as a yellow solid. LC-MS (ES, m/z): [M+H]$^+$=398.

Step 2: 5-phenyl-N-[trans-3-[5-(1-methylazetidin-3-yl)-1,3,4-oxadiazol-2-yl]cyclobutyl]isoxazole-3-carboxamide $I_2$ (214 mg, 0.84 mmol, 1.44 eq.) was added to a solution of PPh$_3$ (221 mg, 0.84 mmol, 1.44 eq.) in dichloromethane (20 mL) at 0° C. Then TEA (340 mg, 3.36 mmol, 5.73 eq.) and 5-phenyl-N-[trans-3-[[(1-methylazetidin-3-yl)formohydrazido]carbonyl]cyclobutyl]isoxazole-3-carboxamide (233 mg, 0.59 mmol, 1.00 eq.) were added at 0° C., respectively. The resulting solution was stirred for 2 hours at room temperature. The resulting mixture was concentrated under vacuum. The residue was applied onto Prep-TLC with ethyl acetate/petroleum ether (1:1). The resulted crude product was purified by Prep-HPLC with the following conditions (waters): Column, XBridge Prep C18 OBD Column, 5 um, 19*150 mm; mobile phase, Water with 10 mmol NH$_4$HCO$_3$ and ACN (10.0% ACN up to 70.0% in 8 min); Detector, UV 254/220 nm. This resulted in 90 mg (40%) of 5-phenyl-N-[trans-3-[5-(1-methylazetidin-3-yl)-1,3,4-oxadiazol-2-yl]cyclobutyl]isoxazole-3-carboxamide as a white solid.

Analytical Data:

LC-MS (ES, m/z): [M+H]$^+$=380.2

1H NMR (300 MHz, DMSO-d$_6$): δ 9.31, 9.29 (d, J=7.5 Hz, 1H), 7.96-7.92 (m, 2H), 7.59-7.55 (m, 3H), 7.38 (s, 1H), 4.73-4.65 (q, J=8.1 Hz, 1H), 3.88-3.65 (m, 2H), 3.61-3.56 (m, 2H), 3.32-3.28 (m, 2H), 2.73-2.51 (m, 4H), 2.25 (s, 3H).

Example 44: 5-(4-fluorophenyl)-N-[trans-3-[5-[(1R)-1-hydroxyethyl]-1,3,4-oxadiazol-2-yl]cyclobutyl]isoxazole-3-carboxamide

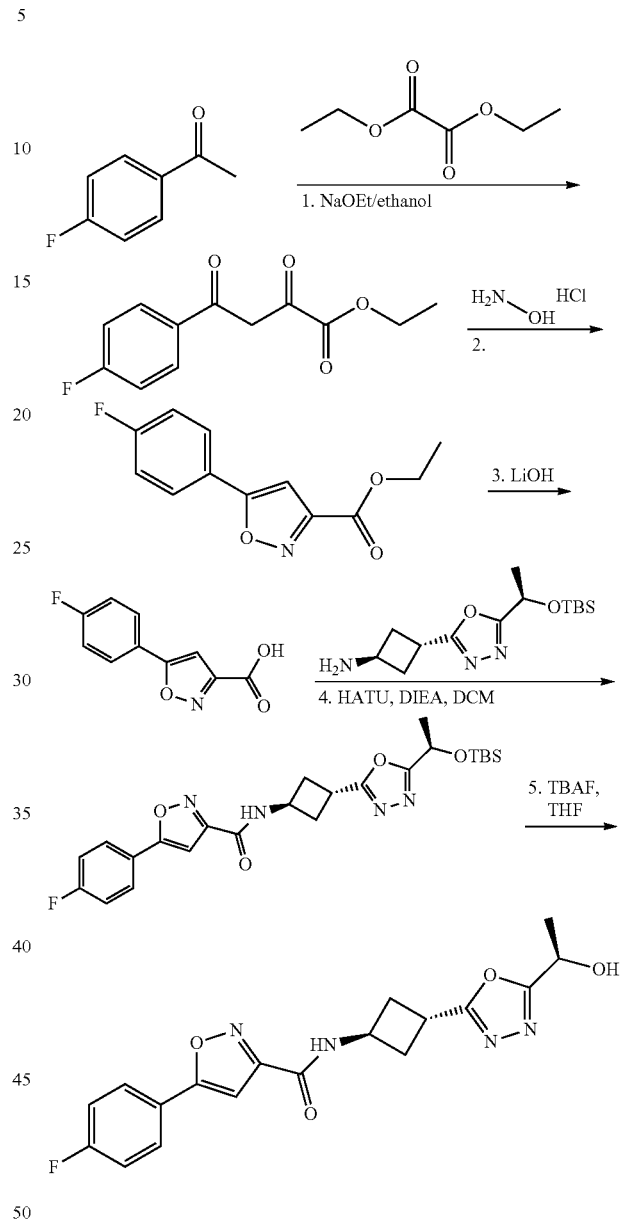

Step 1: ethyl 4-(4-fluorophenyl)-2,4-dioxobutanoate sodium ethoxide (20 mL, 2.00 eq.) was added to a solution of 1-(4-fluorophenyl)ethan-1-one (5 g, 36.20 mmol, 1.00 eq.) and diethyl oxalate (5.29 g, 36.20 mmol, 1.00 eq.) in ethanol (50 mL) at 0° C. The resulting solution was stirred for 5 hours at room temperature, diluted with 500 mL of water and the solids were collected by filtration. This resulted in 7 g (81%) of ethyl 4-(4-fluorophenyl)-2,4-dioxobutanoate as a yellow solid.

Step 2: ethyl 5-(4-fluorophenyl)isoxazole-3-carboxylate

NH$_2$OH HCl (2.92 g, 5.00 eq.) was added to a solution of ethyl 4-(4-fluorophenyl)-2,4-dioxobutanoate (2 g, 8.40 mmol, 1.00 eq.) in ethanol (20 mL). The resulting solution was stirred overnight at 90° C. in an oil bath. The solids were filtered and the resulting mixture was concentrated under vacuum. The residue was applied onto a silica gel column with ethyl acetate/petroleum ether (1:25). This resulted in 518 mg (26%) of ethyl 5-(4-fluorophenyl)isoxazole-3-carboxylate as a white solid. $^1$H NMR (400 MHz, CDCl$_3$): δ 7.85-7.81 (m, 2H), 7.23-7.19 (m, 2H), 6.90 (s, 1H), 4.53-4.47 (m, 2H), 1.49-1.45 (t, J=7.2 Hz, 3H).

Step 3: 5-(4-fluorophenyl)isoxazole-3-carboxylic acid lithium hydroxide (170 mg, 7.10 mmol, 3.00 eq.) in water (3 mL) was added to a solution of ethyl 5-(4-fluorophenyl)isoxazole-3-carboxylate (318 mg, 1.35 mmol, 1.00 eq.) in tetrahydrofuran (20 mL). The resulting solution was stirred overnight at room temperature. The pH of the solution was adjusted to 6 with hydrogen chloride aqueous, the solution was then extracted with ethyl acetate (3×150 mL) and the combined organic layers were dried over anhydrous sodium sulfate and concentrated under vacuum. This resulted in 403 mg (crude) of 5-(4-fluorophenyl)isoxazole-3-carboxylic acid as a white solid. LC-MS (ES, m/z): [M−1]$^-$=206.

Step 4: N-trans-(3-[5-[(1R)-1-[(tert-butyldimethylsilyl)oxy]ethyl]-1,3,4-oxadiazol-2-yl]cyclobutyl)-5-(4-fluorophenyl)isoxazole-3-carboxamide 5-(4-fluorophenyl)isoxazole-3-carboxylic acid (284 mg, 1.37 mmol, 1.20 eq.), HATU (652.5 mg, 1.50 eq.) and DIEA (443 mg, 3.00 eq.) were added to a solution of N-trans-3-5-[(1R)-1-[(tert-butyldimethylsilyl)oxy]ethyl]-1,3,4-oxadiazol-2-cyclobutan-1-amine (340 mg, 1.14 mmol, 1.00 eq.) in dichloromethane (6 mL). The resulting solution was stirred for 3 hours at room temperature. The reaction was then quenched by the addition of water. The resulting solution was extracted with ethyl acetate (3×100 mL) and the organic layers combined. The resulting mixture was washed with brine (3×100 mL), dried over anhydrous sodium sulfate and concentrated under vacuum to give 309 mg (56%) of N-trans-(3-[5-[(1R)-1-[(tert-butyldimethylsilyl)oxy]ethyl]-1,3,4-oxadiazol-2-yl]cyclobutyl)-5-(4-fluorophenyl)isoxazole-3-carboxamide as a solid. LC-MS (ES, m/z): [M+1]$^+$=487.

Step 5: 5-(4-fluorophenyl)-N-[trans-3-[5-[(1R)-1-hydroxyethyl]-1,3,4-oxadiazol-2-yl]cyclobutyl]isoxazole-3-carboxamide TBAF (1 mol/L in tetrahydrofuran, 1 mL) was added to solution of 5-(4-fluorophenyl)-N-[trans-3-[5-[(1R)-1-[(tert-butyldimethylsilyl)oxy]ethyl]-1,3,4-oxadiazol-2-yl]cyclobutyl]isoxazole-3-carboxamide (304 mg, 0.62 mmol, 1.00 eq.) in tetrahydrofuran (5 mL). The resulting solution was stirred for 3 hour at room temperature. The resulting mixture was concentrated under vacuum. The residue was applied onto a silica gel column with dichloromethane/methanol (50:1). This resulted in 129.7 mg (56%) of 5-(4-fluorophenyl)-N-[trans-3-[5-[(1R)-1-hydroxyethyl]-1,3,4-oxadiazol-2-yl]cyclobutyl]isoxazole-3-carboxamide as a white solid.

Analytical Data:
HPLC purity: 97.1% at 254 nm
LC-MS (ES, m/z): [M+1]$^+$=373.2
$^1$H NMR (400 MHz, DMSO-d$_6$): δ 9.33-9.31 (d, J=7.6 Hz, 1H), 8.04-8.00 (m, 2H), 7.44-7.38 (m, 3H), 5.95-5.94 (d, J=5.6 Hz, 1H), 4.95-4.89 (m, 1H), 4.73-4.67 (m, 1H), 3.73-3.69 (m, 1H), 2.73-2.66 (m, 2H), 2.64-2.50 (m, 2H), 1.50-1.48 (d, J=6.4 Hz, 3H).

Example 45: 5-phenyl-N-[trans-3-[5-[(1R)-1-methoxyethyl]-1,3,4-oxadiazol-2-yl]cyclobutyl]isoxazole-3-carboxamide

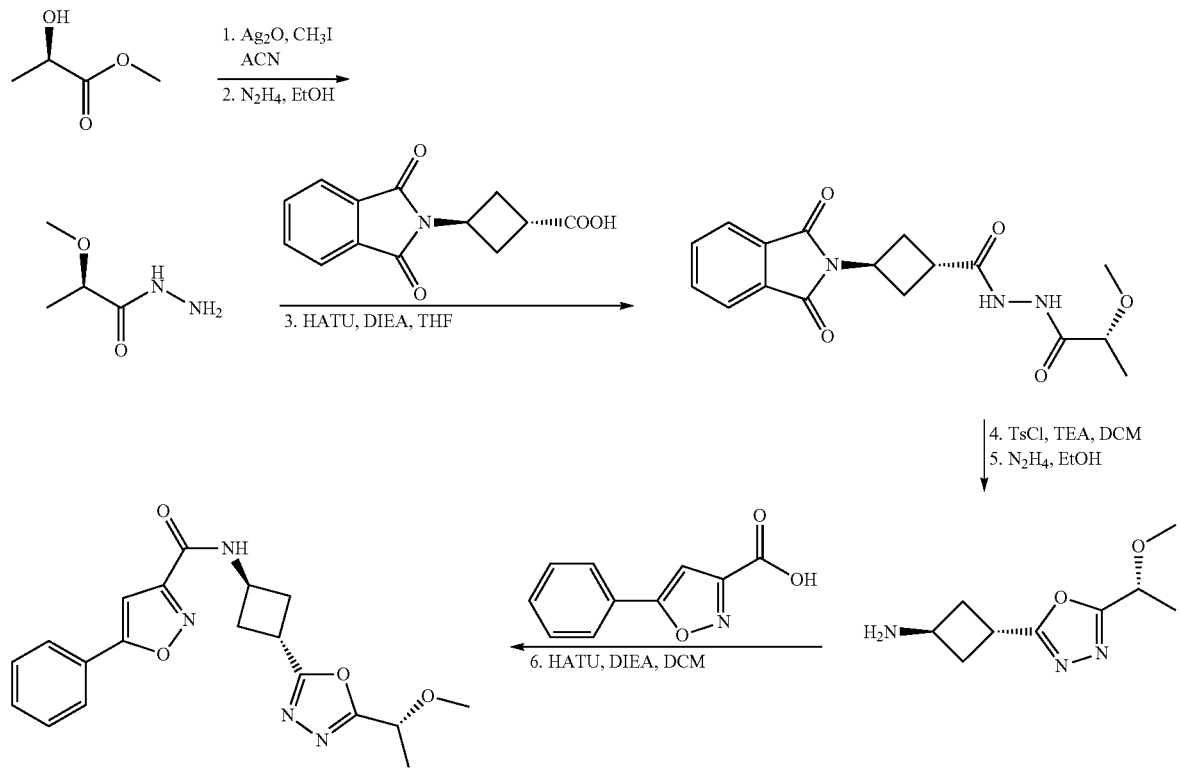

Step 1: methyl (2R)-2-methoxypropanoate

Ag₂O (6.1 g, 26.4 mmol, 1.10 eq.) was added to a solution of iodomethane (27.3 g, 192 mmol, 8.00 eq.) and methyl (2R)-2-hydroxypropanoate (2.5 g, 24 mmol, 1.00 eq.) in acetonitrile (30 mL) and the solution was stirred for 16 hours at 85° C. in an oil bath. The solids were filtered and the mixture was diluted with DCM (100 mL). The resulting mixture was washed with water (3×50 mL), dried over anhydrous sodium sulfate and concentrated under vacuum. This resulted in 2 g (70%) of methyl (2R)-2-methoxypropanoate as colorless oil.

¹H NMR (400 MHz, CDCl₃): δ 3.92-3.87 (m, 1H), 3.76 (s, 3H), 3.40 (s, 3H), 1.42-1.40 (d, J=6.8 Hz, 3H).

Step 2: (2R)-2-methoxypropanehydrazide a solution of methyl (2R)-2-methoxypropanoate (2 g, 16.93 mmol, 1.00 eq.) and hydrazine hydrate (5.3 g, 84.70 mmol, 5.00 eq.) in ethanol (50 mL) was stirred for 16 hours at 70° C. in an oil bath. The resulting mixture was concentrated under vacuum. This resulted in 2 g (crude) of (2R)-2-methoxypropanehydrazide as light yellow oil. LC-MS (ES, m/z): [M+1]⁺=119.

Step 3: (2R)-2-methoxy-N-[trans-3-(1,3-dioxo-2,3-dihydro-1H-isoindol-2-yl)cyclobutyl]carbonyl]propanehydrazide DIEA (3 g, 23.21 mmol, 3.00 eq.) was added to a solution of trans-3-(1,3-dioxo-2,3-dihydro-1H-isoindol-2-yl)cyclobutane-1-carboxylic acid (1.9 g, 7.75 mmol, 1.00 eq.), (2R)-2-methoxypropanehydrazide (1.37 g, 11.60 mmol, 1.50 eq.) and HATU (5.3 g, 13.95 mmol, 1.80 eq.) in THF (80 mL). The resulting solution was stirred for 1 hour at room temperature, it was then diluted with 100 mL of water/ice. The resulting solution was extracted with ethyl acetate (3×100 mL) and the organic layers combined. The resulting mixture was washed with brine (2×50 mL), dried over anhydrous sodium sulfate and concentrated under vacuum. The residue was applied onto a silica gel column with dichloromethane/methanol (30:10) to give 2.2 g (82%) of (2R)-2-methoxy-N-[trans-3-(1,3-dioxo-2,3-dihydro-1H-isoindol-2-yl)cyclobutyl]carbonyl]propanehydrazide as colorless oil. LC-MS (ES, m/z): [M+1]⁺=346.

Step 4: 2-[trans-3-[5-[(1R)-1-methoxyethyl]-1,3,4-oxadiazol-2-yl]cyclobutyl]-2,3-dihydro-1H-isoindole-1,3-dione a solution of TsCl (3.64 g, 19.09 mmol, 3.00 eq.) in dichloromethane (100 mL) was added dropwise to a cold solution of (2R)-2-methoxy-N-[trans-3-(1,3-dioxo-2,3-dihydro-1H-isoindol-2-yl)cyclobutyl]carbonyl]propanehydrazide (2.2 g, 6.37 mmol, 1.00 eq.) and TEA (3.22 g, 31.82 mmol, 5.00 eq.) in dichloromethane (50 mL) at 0° C. The resulting solution was stirred for 15 hours at room temperature, it was then washed with water (3×50 mL) and brine (1×50 mL), dried over anhydrous sodium sulfate and concentrated under vacuum. The crude product was purified by Flash-Prep-HPLC with the following conditions (IntelFlash-1): Column, C18; mobile phase, H₂O/CH₃CN=100:1 increasing to H₂O/CH₃CN=1:100 within 30 min; Detector, UV 254 nm. This resulted in 800 mg (38%) of 2-[trans-3-[5-[(1R)-1-methoxyethyl]-1,3,4-oxadiazol-2-yl]cyclobutyl]-2,3-dihydro-1H-isoindole-1,3-dione as colorless oil. LC-MS (ES, m/z): [M+1]⁺=328.

Step 5: trans-3-[5-[(1R)-1-methoxyethyl]-1,3,4-oxadiazol-2-yl]cyclobutan-1-amine a solution of 2-[trans-3-[5-[(1R)-1-methoxyethyl]-1,3,4-oxadiazol-2-yl]cyclobutyl]-2,3-dihydro-1H-isoindole-1,3-dione (800 mg, 2.44 mmol, 1.00 eq.) and hydrazine hydrate (3.06 g, 48.90 mmol, 20.00 eq., 80%) in ethanol (50 mL) was stirred for 4 hours at room temperature. The reaction mixture was filtered and then concentrated under vacuum. This resulted in 480 mg (crude) of trans-3-[5-[(1R)-1-methoxyethyl]-1,3,4-oxadiazol-2-yl]cyclobutan-1-amine as colorless oil. LC-MS (ES, m/z): [M+1]⁺=198.

Step 6: 5-phenyl-N-[trans-3-[5-[(1R)-1-methoxyethyl]-1,3,4-oxadiazol-2-yl]cyclobutyl]isoxazole-3-carboxamide DIEA (943 mg, 7.30 mmol, 3.00 eq.) was added dropwise to a cold solution of 5-phenylisoxazole-3-carboxylic acid (550 mg, 2.91 mmol, 1.20 eq.), trans-3-[5-[(1R)-1-methoxyethyl]-1,3,4-oxadiazol-2-yl]cyclobutan-1-amine (480 mg, 2.43 mmol, 1.00 eq.) and HATU (1.387 g, 3.65 mmol, 1.50 eq.) in dichloromethane (50 mL) at 0° C. The resulting solution was stirred for 1 hour at room temperature and then diluted with 50 mL of dichloromethane. The resulting mixture was washed with water (2×50 mL) and brine (1×50 mL), dried over anhydrous sodium sulfate and concentrated under vacuum. The residue was applied onto a silica gel column with ethyl acetate/petroleum ether (1:1) to give 628 mg (70%) of 5-phenyl-N-[trans-3-[5-[(1R)-1-methoxyethyl]-1,3,4-oxadiazol-2-yl]cyclobutyl]isoxazole-3-carboxamide as an off-white solid.

Analytical Data:
HPLC purity: 98.9% at 254 nm
LC-MS (ES, m/z): [M+1]⁺=369
¹H NMR (400 MHz, DMSO-d₆): 9.33-9.31 (d, J=7.6 Hz, 1H), 7.96-7.94 (t, J=5.6 Hz, 2H), 7.59-7.56 (m, 3H), 7.38 (s, 1H), 4.74-4.67 (m, 2H), 3.76-3.70 (m, 1H), 3.29 (s, 3H), 2.74-2.61 (m, 4H), 1.51-1.49 (d, J=6.8 Hz, 3H).

Example 46: (1R)-1-[5-[trans-3-(5-phenylisoxazole-3-amido)cyclobutyl]-1,3,4-oxadiazol-2-yl]ethyl acetate

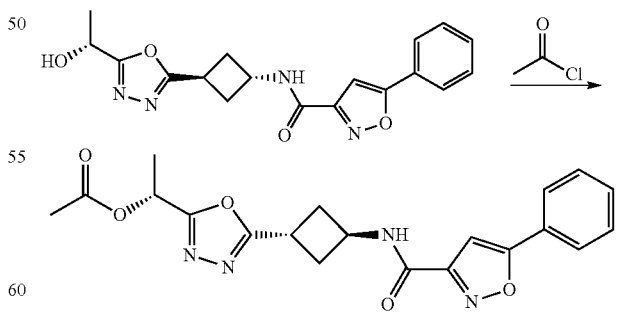

Acetyl chloride (60.3 mg, 0.77 mmol, 2.02 eq.) was added to a solution of 5-phenyl-N-[trans-3-[5-[(1R)-1-hydroxyethyl]-1,3,4-oxadiazol-2-yl]cyclobutyl]isoxazole-3-carboxamide (135 mg, 0.38 mmol, 1.00 eq.) and TEA (115.6 mg, 1.14 mmol, 3.00 eq.) in dichloromethane (10 mL). The resulting solution was stirred for 3 hours at room temperature and it was then concentrated under vacuum. The residue was applied onto a silica gel column with ethyl acetate/petroleum ether (1:1). The crude product was purified by Flash-Prep-HPLC with the following conditions (IntelFlash-1): Column, C18; mobile phase, MeCN/H2O=5:95 increasing to MeCN/H2O=95:5 within 20 min; Detector, UV 254 nm to give 65 mg (43%) of (1R)-1-[5-[trans-3-(5-phenylisoxazole-3-amido)cyclobutyl]-1,3,4-oxadiazol-2-yl] ethyl acetate as a white solid.

Analytical Data:

HPLC purity: 98.1% at 254 nm

LC-MS (ES, m/z): [M+H]+=397.1

$^1$H NMR (400 MHz, DMSO-d6, ppm): δ 9.32-9.31 (d, J=7.6 Hz, 1H), 7.96-7.94 (m, 2H), 7.59-7.56 (m, 3H), 7.38 (s, 1H), 6.05-6.00 (m, 1H), 4.72-4.66 (m, 1H), 3.73-3.70 (m, 1H), 2.73-2.60 (m, 4H), 2.11 (s, 3H), 1.63-1.61 (d, J=6.8 Hz, 3H).

Example 47: (R)-1-(5-(trans-3-(5-phenylisoxazole-3-carboxamido)cyclobutyl)-1,3,4-oxadiazol-2-yl) ethyl benzoate

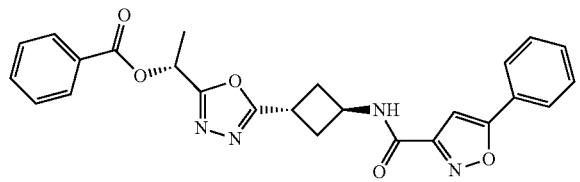 [SMILES: C[C@@H](OC(=O)c1ccccc1)c1nnc([C@H]2C[C@H](NC(=O)c3cc(-c4ccccc4)on3)C2)o1]

Compound was prepared using a similar procedure as described in example 46.

Yield: 66%

Analytical Data:

HPLC purity: 97.1% at 254 nm

Appearance: white solid

LC-MS (ES, m/z): [M+H]+=459.1

$^1$H NMR (400 MHz, DMSO-d$_6$, ppm): δ 9.31-9.29 (d, J=7.6 Hz, 1H), 8.03-8.01 (m, 2H), 7.96-7.94 (m, 2H), 7.73-7.70 (m, 1H), 7.59-7.53 (m, 5H), 7.38-7.36 (d, J=6.0 Hz, 1H), 6.33-6.28 (m, 1H), 4.74-4.64 (m, 1H), 3.76-3.70 (m, 1H), 2.73-2.63 (m, 4H), 1.78-1.76 (d, J=6.8 Hz, 3H).

Example 48: N-(trans-3-(5-((R)-1-isopropoxyethyl)-1,3,4-oxadiazol-2-yl)cyclobutyl)-5-phenylisoxazole-3-carboxamide

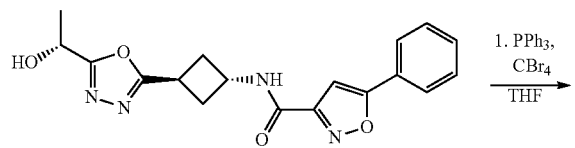

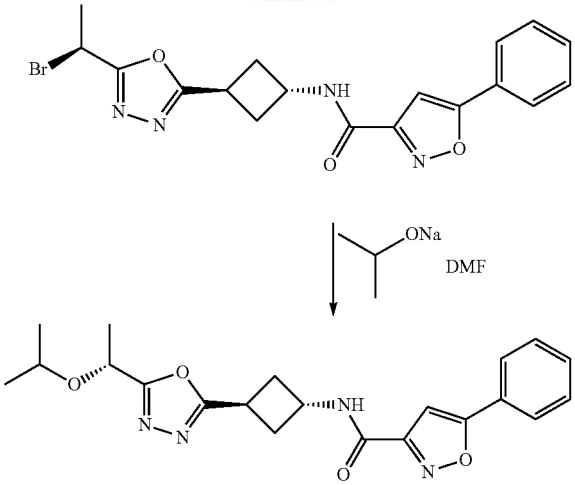

Step 1: 5-phenyl-N-[(trans-3-[5-[(1S)-1-bromoethyl]-1,3,4-oxadiazol-2-yl]cyclobutyl]isoxazole-3-carboxamide a solution of PPh$_3$ (1.66 g, 6.33 mmol, 1.50 eq.), CBr$_4$ (2.1 g, 6.33 mmol, 1.49 eq.) and 5-phenyl-N-[trans-3-[5-[(1R)-1-hydroxyethyl]-1,3,4-oxadiazol-2-yl]cyclobutyl]isoxazole-3-carboxamide (1.5 g, 4.23 mmol, 1.00 eq.) in tetrahydrofuran (50 mL) was stirred for 2 hours at room temperature. The resulting solution was diluted with dichloromethane, it washed with brine, dried over anhydrous sodium sulfate and concentrated under vacuum. The residue was applied onto a silica gel column with ethyl acetate/petroleum ether (1:5) to give 2.36 g (crude) of 5-phenyl-N-[(trans-3-[5-[(1S)-1-bromoethyl]-1,3,4-oxadiazol-2-yl]cyclobutyl]isoxazole-3-carboxamide as a white solid. LC-MS (ES, m/z): [M+H]+= 417.0.

Step 2: N-(trans-3-(5-((R)-1-isopropoxyethyl)-1,3,4-oxadiazol-2-yl)cyclobutyl)-5-phenylisoxazole-3-carboxamide a suspension of Na (1.1 g, 47.83 mmol, 1.00 eq.) in propan-2-ol (70 mL) was stirred overnight at 70° C. The resulting mixture was concentrated under vacuum to get 3.95 g (crude) of sodium propan-2-olate as a white solid. Into another 100-mL round-bottom flask, was placed a solution of 5-phenyl-N-[trans-3-[5-[(1S)-1-bromoethyl]-1,3,4-oxadiazol-2-yl]cyclobutyl]isoxazole-3-carboxamide (1 g, 2.40 mmol, 1.00 eq.) in DMF (30 mL). To the solution was added the freshly prepared sodium propan-2-olate (3.95 g, 48.13 mmol, 20.08 eq., crude). The resulting solution was stirred for 30 min at 50° C. The resulting mixture was concentrated under vacuum, the mixture was diluted with ethyl acetate and the resulting solution was washed with water and concentrated under vacuum. The residue was applied onto a Prep-TLC with ethyl acetate/petroleum ether (1:1) and the crude product was purified by Prep-HPLC using the following conditions (waters): Column, XBridge C18 OBD; mobile phase, water with 0.05% NH$_4$HCO$_3$ and CH$_3$CN (10% CH$_3$CN up to 70% CH$_3$CN in 10 min, up to 95% CH$_3$CN in 1.5 min, down to 10% CH$_3$CN in 1.5 min); Detector, UV 220&254 nm. 100 mg product was obtained. The crude product (100 mg) was purified by Chiral-Prep-HPLC with the following conditions (Prep-HPLC-032):

Column, Phenomenex Lux 5 u Cellulose-AXIA Packed, 250*21.2 mm, 5 um; mobile phase, hexane (0.2% DEA) and ethanol (hold 30.0% ethanol in 25 min); Detector, UV 254 nm. This resulted in 61 mg (6%) of 5-phenyl-N-[trans-3-[5-[(1R)-1-(propan-2-yloxy)ethyl]-1,3,4-oxadiazol-2-yl]cyclobutyl]isoxazole-3-carboxamide as a white solid.

Analytical Data:

HPLC purity: 99.8% at 254 nm

LC-MS (ES, m/z): [M+H]$^+$=397.1

$^1$H NMR (300 MHz, DMSO-d$_6$): δ 9.33-9.30 (d, J=7.8 Hz, 1H), 7.96-7.93 (m, 2H), 7.60-7.55 (m, 3H), 7.38 (s, 1H), 4.90-4.83 (m, 1H), 4.74-4.66 (m, 1H), 3.76-3.64 (m, 2H), 2.75-2.30 (m, 4H), 1.48-1.46 (d, J=6.6 Hz, 3H), 1.11-1.09 (d, J=6.0 Hz, 3H), 1.01-0.99 (d, J=6.0 Hz, 3H).

Example 49: N-(trans-3-(5-((R)-1-isobutoxyethyl)-1,3,4-oxadiazol-2-yl)cyclobutyl)-5-phenylisoxazole-3-carboxamide

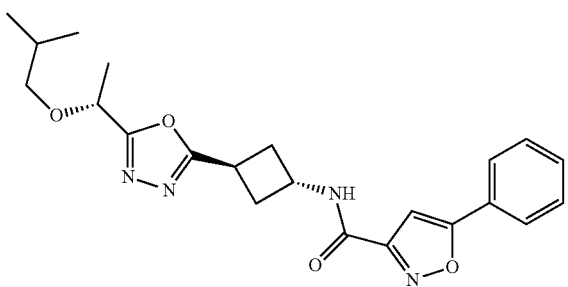 [SMILES: CC(C)CO[C@H](C)c1nnc([C@H]2C[C@H](NC(=O)c3cc(-c4ccccc4)on3)C2)o1]

The compound was prepared using a similar procedure as reported in example 48 using sodium 2-methylpropan-1-olate. The crude product was purified by Flash-Prep-HPLC with the following conditions (IntelFlash-1): Column, C18; mobile phase, MeCN/H$_2$O=5:95 increasing to MeCN/H$_2$O=95:5 within 20 min; Detector, UV 254 nm. 300 mg product was obtained. The crude product (300 mg) was purified by Prep-HPLC with the following conditions (1#-Pre-HPLC-005 (Waters)): Column, XBridge C18 OBD; mobile phase, water with 0.05% NH$_4$HCO$_3$ and CH$_3$CN (10% CH$_3$CN up to 70% CH$_3$CN in 10 min, up to 95% CH$_3$CN in 1.5 min, down to 10% CH$_3$CN in 1.5 min; Detector, UV 220&254 nm. 150 mg product was obtained. The crude product (150 mg) was purified by Chiral-Prep-HPLC with the following conditions (Prep-HPLC-004): Column, Phenomenex Lux, 5 u Cellulose-4 AXIA Packed, 250*21.2 mm, 5 um; mobile phase, hexane and ethanol (hold 30.0% ethanol in 30 min); Detector, UV 254 nm. This resulted in 41.9 mg (5%) of 5-phenyl-N-[trans-3-[5-[(1R)-1-(2-methylpropoxy)ethyl]-1,3,4-oxadiazol-2-yl]cyclobutyl]isoxazole-3-carboxamide as a white semi-solid.

Analytical Data:

LC-MS (ES, m/z): [M+H]$^+$=411.3

HPLC purity: 97.4% at 254 nm $^1$H NMR (300 MHz, CDCl$_3$): δ 7.82-7.79 (m, 2H), 7.50-7.48 (m, 3H), 7.21-7.18 (m, 1H), 6.97 (s, 1H), 4.82-4.67 (m, 2H), 3.57-3.45 (m, 1H), 3.28-3.17 (m, 2H), 3.02-2.92 (m, 2H), 2.56-2.46 (m, 2H), 1.91-1.82 (m, 1H), 1.61-1.59 (d, J=6.6 Hz, 3H), 0.91-0.86 (m, 6H) 2H), 2.56-2.46 (m, 2H), 1.91-77 (m, 1H), 1.61, 1.59 (d, J=6 Hz, 3H), 0.97-0.85 (m, 6H).

Example 50: Tert-butyl 3-(5-(trans-3-(5-phenylisoxazole-3-carboxamido)cyclobutyl)-1,3,4-oxadiazol-2yl)azetidine-1-carboxylate

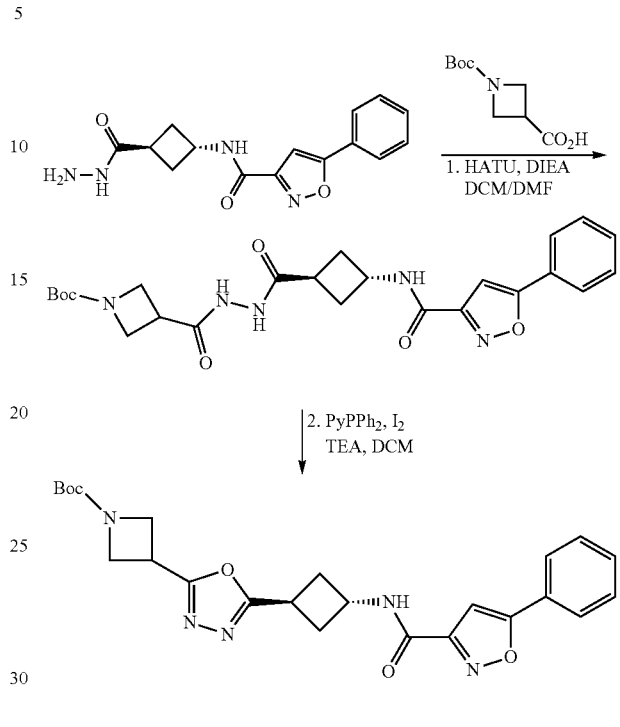

Step 1: tert-butyl 3-(N-[(trans-3-(5-phenylisoxazole-3-amido)cyclobutyl]carbonyl]hydrazinecarbonyl) azetidine-1-carboxylate 1-[(tert-butoxy)carbonyl]azetidine-3-carboxylic acid (402 mg, 2.00 mmol, 1.50 eq.), HATU (608 mg, 1.60 mmol, 1.20 eq.) and DIEA (516 mg, 3.99 mmol, 3.00 eq.) were added to a solution of 5-phenyl-N-[trans-3-(hydrazinecarbonyl)cyclobutyl]isoxazole-3-carboxamide (prepared according to example 9, 400 mg, 1.33 mmol, 1.00 eq.) in DMF (10 mL). The resulting solution was stirred for 2 hours at room temperature and the crude product was purified by Flash-Prep-HPLC with the following conditions (IntelFlash-1): Column, C18; mobile phase, MeCN/H$_2$O=5:95 increasing to MeCN/H$_2$O=95:5 within 10 min; Detector, UV 254 nm. This resulted in 400 mg (62%) of tert-butyl 3-(N-[[trans-3-(5-phenylisoxazole-3-amido)cyclobutyl]carbonyl]hydrazinecarbonyeazetidine-1-carboxylate as a white solid. LC-MS (ES, m/z): [M+H]$^+$=484.2.

$^1$H NMR (300 MHz, DMSO-d$_6$): δ 9.92-9.80 (m, 1H), 9.15-9.12 (d, J=7.8 Hz, 2H), 7.95-7.92 (m, 2H), 7.57-7.55 (m, 3H), 7.36 (s, 1H), 4.65-4.60 (m, 1H), 4.01-3.96 (m, 2H), 3.86 (br, 2H), 3.36-3.30 (m, 1H), 3.00-2.96 (m, 1H), 2.42-2.38 (t, J=7.5 Hz, 3H), 1.38 (s, 9H).

Step 2: tert-butyl 3-[5-[trans-3-(5-phenylisoxazole-3-amido)cyclobutyl]-1,3,4-oxadiazol-2-yl]azetidine-1-carboxylate 2-(diphenylphosphanyl)pyridine (308.7 mg, 1.17 mmol, 1.50 eq.) was added to solution of tert-butyl 3-(N-[trans-3-(5-phenylisoxazole-3-amido)cyclobutyl]carbonyl]hydrazinecarbonyl)azetidine-1-carboxylate (378 mg, 0.78 mmol, 1.00 eq.), I$_2$ (298.2 mg, 1.17 mmol, 1.50 eq.) and TEA (474.3 mg, 4.69 mmol, 6.00 eq.) in dichloromethane (30 mL) at 0° C. The resulting solution was stirred for 2 hours at room temperature and it was then concentrated under vacuum. The residue was applied onto a silica gel column with ethyl acetate/petroleum ether (2:1). The crude product was purified by Prep-HPLC with the following conditions (Waters): Column, XBridge Prep C18 OBD Column, 19*150 mm, 5 um; mobile phase, water with 0.05% NH$_4$HCO$_3$ and ACN (30.0% ACN up to 90.0% in 8 min); Detector, UV 254 nm. This resulted in 270 mg (74%) of tert-butyl 3-[5-[trans-3-(5-phenylisoxazole-3-amido)cyclobutyl]-1,3,4-oxadiazol-2-yl]azetidine-1-carboxylate as a white solid.

Analytical Data:

LC-MS (ES, m/z): [M+H-Boc]$^+$=366.2

HPLC purity: 99.2% at 254 nm $^1$H NMR (400 MHz, DMSO-d$_6$): δ 9.31-9.30 (d, J=7.6 Hz, 1H), 7.96-7.93 (m, 2H), 7.59-7.54 (m, 3H), 7.38 (s, 1H), 4.71-4.69 (m, 1H), 4.26 (s, 2H), 4.11-4.08 (m, 3H), 3.70-3.68 (m, 1H), 2.69-2.65 (m, 4H), 1.40 (s, 9H).

Example 51: Tert-butyl 3-(5-(trans-3-(5-phenylisoxazole-3-carboxamido)cyclobutyl)-1,3,4-oxadiazol-2-yl)azetidine-1-carboxylate

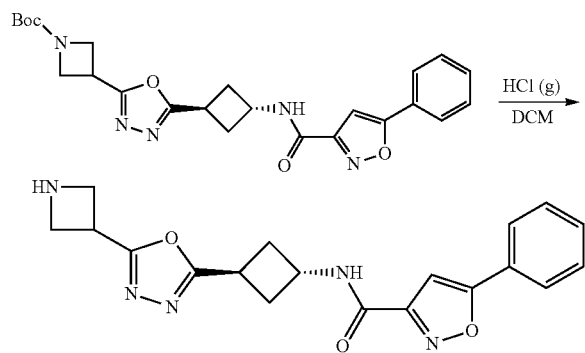

A solution of tert-butyl 3-[5-[trans-3-(5-phenylisoxazole-3-amido)cyclobutyl]-1,3,4-oxadiazol-2-yl]azetidine-1-carboxylate (200 mg, 0.43 mmol, 1.00 eq.) and hydrogen chloride (gas) in dichloromethane (10 mL) was stirred for 2 hours at room temperature. The resulting mixture was concentrated under vacuum and the crude product was purified by Prep-HPLC with the following conditions (Waters): Column, XBridge Prep C18 OBD Column, 5 um, 19*150 mm; mobile phase, Water with 0.05% NH$_4$HCO$_3$ and ACN (15.0% ACN up to 80.0% in 8 min); Detector, UV 254/220 nm. This resulted in 85 mg (54%) of 5-phenyl-N-[trans-3-[5-(azetidin-3-yl)-1,3,4-oxadiazol-2-yl]cyclobutyl]isoxazole-3-carboxamide as a white solid.

Analytical Data:

LC-MS (ES, m/z): [M+H]$^+$=366.1

HPLC purity: 98.5% at 254 nm $^1$H NMR (400 MHz, DMSO-d$_6$, ppm): δ 9.33-9.31 (d, J=7.6 Hz, 1H), 7.96-7.93 (m, 2H), 7.59-7.52 (m, 3H), 7.38 (s, 1H), 4.74-4.64 (m, 1H), 4.23-4.08 (m, 2H), 3.81-3.59 (m, 5H), 2.72-2.63 (m, 4H).

Example 52: N-(trans-3-(5-(oxetan-3-yl)-1,3,4-oxadiazol-2-yl)cyclobutyl)-5-phenylisoxazole-3-carboxamide

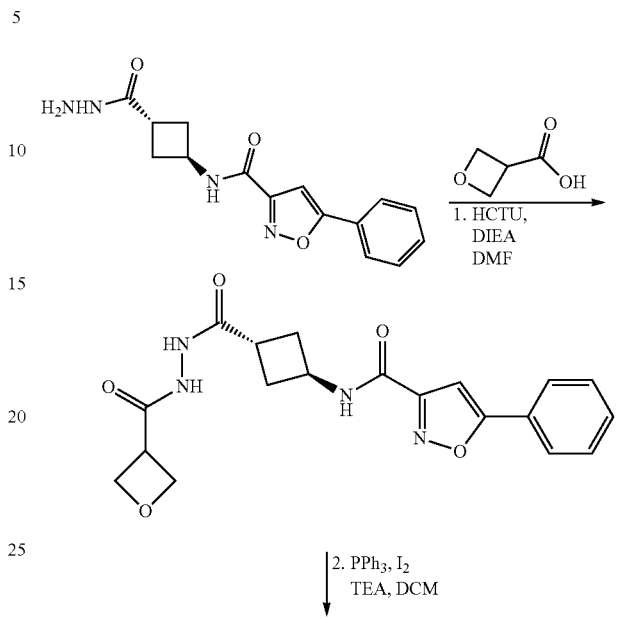

Step 1: 5-phenyl-N-[trans-3-[(oxetan-3-ylformohydrazido)carbonyl]cyclobutyl]isoxazole-3-carboxamide HCTU (1.16 g, 2.78 mmol, 2.00 eq.), oxetane-3-carboxylic acid (141 mg, 1.38 mmol, 1.00 eq.) and DIEA (537 mg, 4.16 mmol, 3.00 eq.) were added to a solution of 5-phenyl-N-[trans-3-(hydrazinecarbonyl)cyclobutyl]isoxazole-3-carboxamide (417 mg, 1.39 mmol, 1.00 eq.) in DMF (10 mL) and the mixture was stirred for 70 min at room temperature. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 0.3 g (56%) of 5-phenyl-N-[trans-3-[(oxetan-3-ylformohydrazido)carbonyl]cyclobutyl]isoxazole-3-carboxamide as an orange solid. LC-MS ES, m/z): [M+H]$^+$=385.1.

Step 2: 5-phenyl-N-[trans-3-[5-(oxetan-3-yl)-1,3,4-oxadiazol-2-yl]cyclobutyl]isoxazole-3-carboxamide I$_2$ (298 mg, 1.17 mmol, 1.50 eq.), TEA (473 mg, 4.67 mmol, 6.00 eq.) and 5-phenyl-N-[trans-3-[(oxetan-3-ylformohydrazido)carbonyl]cyclobutyl]isoxazole-3-carboxamide (270 mg, 0.70 mmol, 1.00 eq.) were added to a solution of triphenylphosphine (307 mg, 1.17 mmol, 1.50 eq.) in dichloromethane (5 mL). The resulting solution was stirred for 1 hour at room temperature and it was then quenched by the addition of 10 mL of water. The resulting solution was extracted with ethyl acetate (3×25 mL) and the organic layers combined. The resulting mixture was washed with brine (3×20 mL), dried over anhydrous sodium sulfate and concentrated under vacuum. The crude product was purified by Prep-HPLC with the following conditions (Waters): Column, X-Bridge Prep C18 OBD Column, 19*150 mm 5 um 13 nm; mobile phase, Water with 0.05% NH$_4$HCO$_3$ and ACN (20.0% ACN up to 70.0% in 8 min); Detector, UV 254/220 nm. This resulted in 63.5 mg (25%) of 5-phenyl-N-[trans-3-[5-(oxetan-3-yl)-1,3,4-oxadiazol-2-yl]cyclobutyl]isoxazole-3-carboxamide as a white solid.

Analytical Data:
LC-MS (ES, m/z): [M+H]$^+$=367.1
HPLC purity: 99.9% at 254 nm
$^1$H NMR (DMSO-d$_6$, 300 MHz): δ 9.32-9.29 (d, J=8.1 Hz, 1H), 7.96-7.93 (m, 2H), 7.59-7.55 (m, 3H), 7.38 (s, 1H), 4.95-4.90 (m, 2H), 4.83-4.78 (m, 2H), 4.74-4.53 (m, 2H), 3.72-3.68 (m, 1H), 2.70-2.65 (m, 4H).

Example 53: N-(trans-3-(1-methyl-1H-benzo[d]imidazol-2-yl)cyclobutyl)-5-phenylisoxazole-3-carboxamide

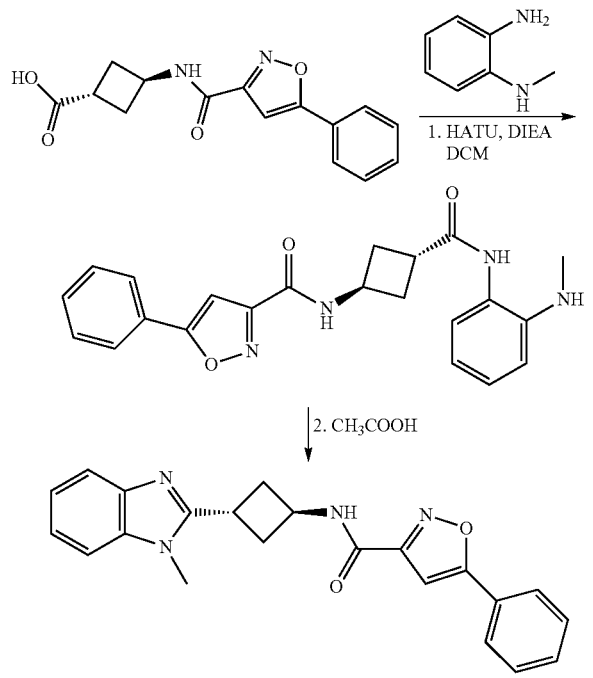

Step 1: 5-phenyl-N-[trans-3-[[2-(methylamino)phenyl]carbamoyl]cyclobutyl]isoxazole-3-carboxamide HATU (797 mg, 2.10 mmol, 1.20 eq.), 1-N-methylbenzene-1,2-diamine (426 mg, 3.49 mmol, 2.00 eq.) and DIEA (676 mg, 5.23 mmol, 3.00 eq.) were added to a solution of trans-3-(5-phenylisoxazole-3-amido)cyclobutane-1-carboxylic acid (500 mg, 1.75 mmol, 1.00 eq.) in dichloromethane (30 mL). The resulting solution was stirred for 6 hours at room temperature and it was then quenched by the addition of water. The resulting solution was extracted with dichloromethane and the organic layers combined. The resulting mixture was washed with brine, dried over anhydrous sodium sulfate and concentrated under vacuum. The residue was applied onto a silica gel column with ethyl acetate/petroleum ether (1:15) to give 200 mg (29%) of 5-phenyl-N-[trans-3-[[2-(methylamino)phenyl]carbamoyl]cyclobutyl]isoxazole-3-carboxamide as a white solid. LC-MS (ES, m/z): [M+H]$^+$=391.1.

Step 2: N-(trans-3-(1-methyl-1H-benzo[d]imidazol-2-yl)cyclobutyl)-5-phenylisoxazole-3-carboxamide solution of 5-phenyl-N-[trans-3-[[2-(methylamino)phenyl]carbamoyl]cyclobutyl]isoxazole-3-carboxamide (200 mg, 0.51 mmol, 1.00 eq.) in acetic acid (5 mL) was placed in a microwave reactor for 1 hour at 120° C. The reaction was then quenched by the addition of 10 mL of water and the resulting solution was extracted with ethyl acetate (3×15 mL) and the organic layers combined. The resulting mixture was washed with brine (3×20 mL), dried over anhydrous sodium sulfate and concentrated under vacuum. The crude product was purified by Prep-HPLC with the following conditions (Waters): Column, XBridge C18 OBD Prep Column, 5 um, 19 mm×250 mm; mobile phase, Water with 0.05% NH$_4$HCO$_3$ and ACN (30.0% ACN up to 75.0% in 8 min); Detector, UV 254 nm. The crude product was purified by Chiral-Prep-HPLC with the following conditions (Prep-HPLC-032): Column, CHIRALPAK IC, 2*25 cm, 5 um; mobile phase, hexane and ethanol (hold 40.0% ethanol in 15 min); Detector, UV 254/220 nm to give 41.5 mg (22%) of 5-phenyl-N-[trans-3-(1-methyl-1H-1,3-benzodiazol-2-yl)cyclobutyl]isoxazole-3-carboxamide as a white solid.

Analytical Data:
LC-MS (ES, m/z): [M+H]$^+$=373.2
HPLC purity: 99.5% at 254 nm
$^1$H NMR (CD$_3$OD-d$_4$, 400 MHz): δ 7.91-7.89 (m, 2H), 7.65-7.63 (m, 1H), 7.58-7.50 (m, 3H), 7.49-7.47 (m, 1H), 7.32-7.24 (m, 2H), 7.12 (s, 1H), 4.79-4.70 (m, 1H), 3.81 (s, 3H), 3.75-3.66 (m, 1H), 3.01-2.95 (m, 2H), 2.66-2.58 (m, 2H).

Example 54: 5-(2,4-difluorophenyl)-N-(trans-3-(5-((R)-1-hydroxyethyl)-1,3,4-oxadiazol-2-yl)cyclobutyl)isoxazole-3-carboxamide

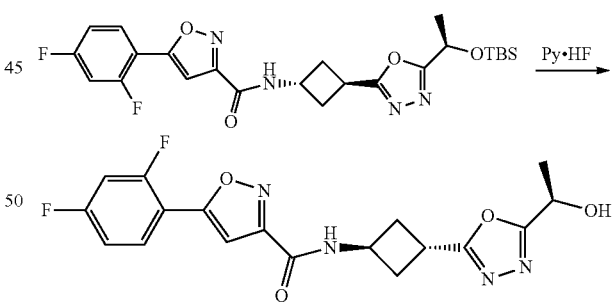

A solution of pyridine hydrogen fluoride (1 mL) and 5-(2,4-difluorophenyl)-N-[trans-3-[5-[(1R)-1-[(tert-butyldimethylsilyl)oxy]ethyl]-1,3,4-oxadiazol-2-yl]cyclobutyl]isoxazole-3-carboxamide (140 mg, 0.28 mmol, 1.00 eq., prepared according to example 44) in methanol (4 mL) was stirred for 2 hours at room temperature. The mixture was filtered and it was then concentrated under vacuum. The residue was applied onto a silica gel column with dichloromethane/methanol (50:1). The crude product was purified by Flash-Prep-HPLC with the following conditions (IntelFlash-1): Column, C18; mobile phase, H$_2$O/ACN=80:20 increasing to H$_2$O/ACN=20:80 within 20 min; Detector, UV 254 nm to give 23.4 mg (22%) of 5-(2,4-difluorophenyl)-N-[trans-3-[5-[(1S)-1-hydroxyethyl]-1,3,4-oxadiazol-2-yl]cyclobutyl]isoxazole-3-carboxamide as a white solid.
Analytical Data:
LC-MS (ES, m/z): [M+H]$^+$=391.2
HPLC purity: 98.8% at 254 nm
$^1$H NMR (400 MHz, DMSO-d$_6$): δ 9.36-9.35 (d, J=7.6 Hz, 1H), 8.08-8.07 (m, 1H), 7.61-7.59 (m, 1H), 7.36-7.34 (m, 1H), 7.18-7.17 (d, J=2.4 Hz, 1H), 5.96-5.94 (d, J=5.6 Hz, 1H), 4.94-4.90 (m, 1H), 4.70-4.69 (m, 1H), 3.73-3.71 (m, 1H), 2.70-2.62 (m, 4H), 1.49-1.48 (d, J=6.4 Hz, 3H).

Example 55: 5-(3-fluorophenyl)-N-(trans-3-(5-((R)-1-hydroxyethyl)-1,3,4-oxadiazol-2-yl)cyclobutyl)isoxazole-3-carboxamide

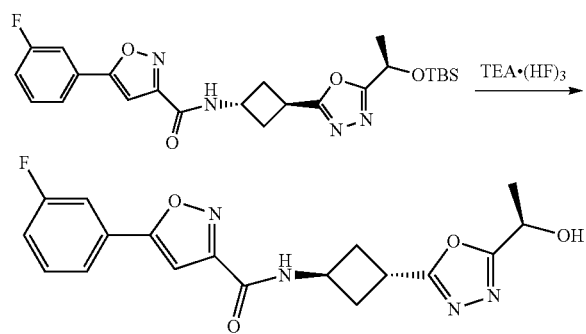

A solution of TEA.3HF (5 mL) and N-[trans-3-(5-[(1R)-[(tert-butyldimethylsilyl)oxy]ethyl]-1,3,4-oxadiazol-2-yl)cyclobutyl]-5-(3-fluorophenyl)isoxazole-3-carboxamide (500 mg, 1.03 mmol, 1.00 eq.) in methanol (20 mL) was stirred for 3 hours at room temperature. The resulting mixture was concentrated under vacuum and the crude product was purified by Flash-Prep-HPLC with the following conditions (IntelFlash-1): Column, C18; mobile phase, MeCN/water=20% increasing to MeCN/water=90% within 25 min; Detector, UV 254 nm to give 112.1 mg of 5-(3-fluorophenyl)-N-[trans-3-[5-(1-hydroxyethyl)-1,3,4-oxadiazol-2-yl]cyclobutyl]isoxazole-3-carboxamide as a white solid.
Analytical Data:
LC-MS (ES, m/z): [M+1]$^+$=373.1
HPLC purity: 98.5% at 254 nm
$^1$H NMR (DMSO-d$_6$, 300 MHz): δ 9.35-9.32 (d, J=7.8 Hz, 1H), 7.87-7.74 (m, 2H), 7.61-7.59 (m, 1H), 7.51 (s, 1H), 7.41-7.33 (m, 1H), 5.94-5.92 (d, J=5.7 Hz, 1H), 4.98-4.83 (m, 1H), 4.75-4.62 (m, 1H), 3.73-3.67 (m, 1H), 2.77-2.52 (m, 4H), 1.49-1.46 (d, J=6.6 Hz, 3H).

Example 56: 5-(2-fluorophenyl)-N-(trans-3-(5-((R)-1-hydroxyethyl)-1,3,4-oxadiazol-2-yl)cyclobutyl)isoxazole-3-carboxamide

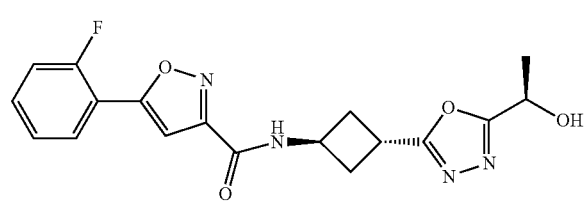 [SMILES: C[C@@H](O)c1nnc([C@H]2C[C@H](NC(=O)c3cc(-c4ccccc4F)on3)C2)o1]

The compound was prepared using the method methodology described in example 55. The crude product (150 mg) was purified by Flash-Prep-HPLC with the following conditions (IntelFlash-1): Column, C18 silica gel; mobile phase, H$_2$O/CH$_3$CN=85:15 increasing to H$_2$O/CH$_3$CN=15:85 within 20 min; Detector, UV 254 nm. This resulted in 59.3 mg (62%) of 5-(2-fluorophenyl)-N-[trans-3-[5-[(1R)-1-hydroxyethyl]-1,3,4-oxadiazol-2-yl]cyclobutyl]isoxazole-3-carboxamide as a white solid.
Analytical Data:
LC-MS (ES, m/z): [M+1]$^+$=373.0
HPLC purity: 98.6% at 254 nm
$^1$H NMR (DMSO-d$_6$, 400 MHz): δ 9.35 (d, J=7.6 Hz, 1H), 8.03-7.98 (m, 1H), 7.66-7.61 (m, 1H), 7.51-7.43 (m, 2H), 7.19-7.18 (d, J=2.8 Hz, 1H), 5.95 (d, J=5.6 Hz, 1H), 4.94-4.88 (m, 1H), 4.72-4.66 (m, 1H), 3.73-3.68 (m, 1H), 2.73-2.49 (m, 4H), 1.48 (d, J=6.4 Hz, 3H).

Example 57: 5-(4-hydroxyphenyl)-N-(trans-3-(5-((R)-1-hydroxyethyl)-1,3,4-oxadiazol-2-yl)cyclobutyl)isoxazole-3-carboxamide

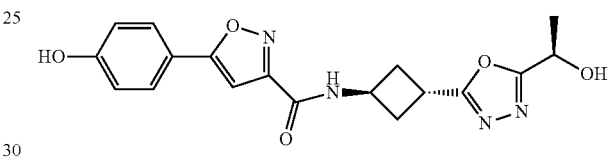

The compound was prepared using the method methodology described in example 54. The crude mixture was purified by Prep-HPLC with the following conditions (Waters): Column, XBridge C18 OBD Prep Column, 19 mm×250 mm; mobile phase, Water With 0.08% NH$_4$HCO$_3$ and CH$_3$CN (35% CH$_3$CN up to 70% CH$_3$CN in 10 min, up to 95% in 2 min and down to 35% in 2 min); Detector, UV 254. This resulted in 23 mg (46%) of N-(trans-3-[5-[(1R)-1-hydroxyethyl]-1,3,4-oxadiazol-2-yl]cyclobutyl)-5-(4-hydroxyphenyl)isoxazole-3-carboxamide as a white solid.
Analytical Data:
LC-MS (ES, m/z): [M+H]$^+$=371.1
HPLC purity: 100% at 254 nm
$^1$H NMR (400 MHz, DMSO-d$_6$): δ 10.15 (s, 1H), 9.26-9.24 (d, 1H, J=7.6 Hz), 7.77-7.75 (d, 2H, J=8.8 Hz), 7.12 (s, 1H), 6.92-6.90 (d, 2H, J=8.8 Hz), 5.95-5.94 (d, 1H, J=5.6 Hz), 4.93-4.89 (m, 1H), 4.71-4.65 (m, 1H), 3.73-3.69 (m, 1H), 2.68-2.60 (m, 4H), 1.49-1.48 (d, 3H, J=6.4 Hz).

Example 58: 5-(3-hydroxyphenyl)-N-(trans-3-(5-((R)-1-hydroxyethyl)-1,3,4-oxadiazol-2-yl)cyclobutyl)isoxazole-3-carboxamide

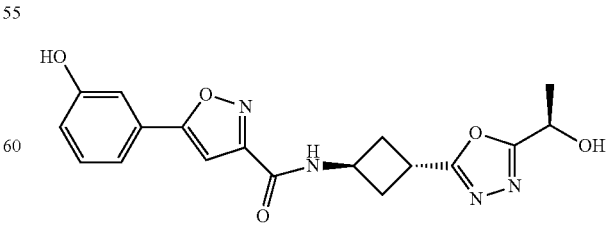

The compound was prepared using the method methodology described in example 54. The crude product was purified by Prep-HPLC with the following conditions (Waters): Column, XBridge C18 OBD Prep Column, 19 mm×250 mm; mobile phase, Water with 0.08% NH₄HCO₃ and CH₃CN (35% CH₃CN up to 70% CH₃CN in 10 min, up to 95% in 2 min and down to 35% in 2 min; Detector, 254 nm. This resulted in 36.6 mg (31%) of 5-(3-hydroxyphenyl)-N-[trans-3-[5-[(1S)-1-hydroxyethyl]-1,3,4-oxadiazol-2-yl]cyclobutyl]isoxazole-3-carboxamide as a white solid.

Analytical Data:

LC-MS (ES, m/z): [M+H]⁺=371.0

HPLC purity: 98.0% at 254 nm

¹H NMR (400 MHz, DMSO-d₆, ppm): δ 9.84 (s, 1H), 9.31~9.29 (d, 1H, J=7.6 Hz), 7.36~7.35 (d, 2H, J=5.2 Hz), 7.28 (s, 2H), 6.95~6.92 (m, 1H), 5.96~5.94 (d, 1H, J=5.6 Hz), 4.94~4.90 (m, 1H), 4.72~4.66 (m, 1H), 3.73~3.69 (m, 1H), 2.70~2.59 (m, 4H), 1.50~1.48 (d, 3H, J=6.4 Hz).

Example 59: 5-(3,4-difluorophenyl)-N-(trans-3-(5-((R)-1-hydroxyethyl)-1,3,4-oxadiazol-2-yl)cyclobutyl)isoxazole-3-carboxamide

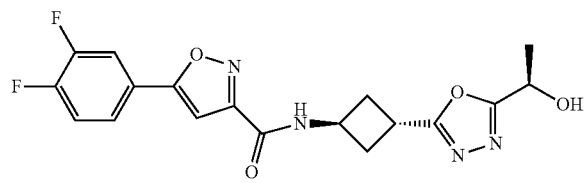 [SMILES: C[C@@H](O)c1nnc([C@H]2C[C@H](NC(=O)c3cc(-c4ccc(F)c(F)c4)on3)C2)o1]

The compound was prepared using the method methodology described in example 55. The mixture was purified by Prep-TLC with ethyl acetate/petroleum ether (1:1) to give 112 mg (94%) 5-(3,4-difluorophenyl)-N-(trans-3-(5-((R)-1-hydroxyethyl)-1,3,4-oxadiazol-2-yl)cyclobutyl)isoxazole-3-carboxamide as a white solid.

Analytical Data:

LC-MS (ES, ink): [M+H]⁺=391.1

HPLC purity: 98.8% at 254 nm

¹H NMR (400 MHz, DMSO-d₆): δ 9.36-9.34 (d, J=8.0 Hz, 1H), 8.12-8.08 (m, 1H), 7.84-7.83 (m, 1H), 7.69-7.62 (m, 1H), 7.46 (s, 1H), 5.95-5.94 (d, J=5.6 Hz, 1H), 4.95-4.90 (m, 1H), 4.74-4.64 (m, 1H), 3.73-3.68 (m, 1H), 2.73-2.60 (m, 4H), 1.49-1.48 (d, J=6.8 Hz, 3H).

Example 60: N-(trans-3-(5-((R)-1-(methylsulfonyl)ethyl)-1,3,4-oxadiazol-2-yl)cyclobutyl)-5-phenylisoxazole-3-carboxamide

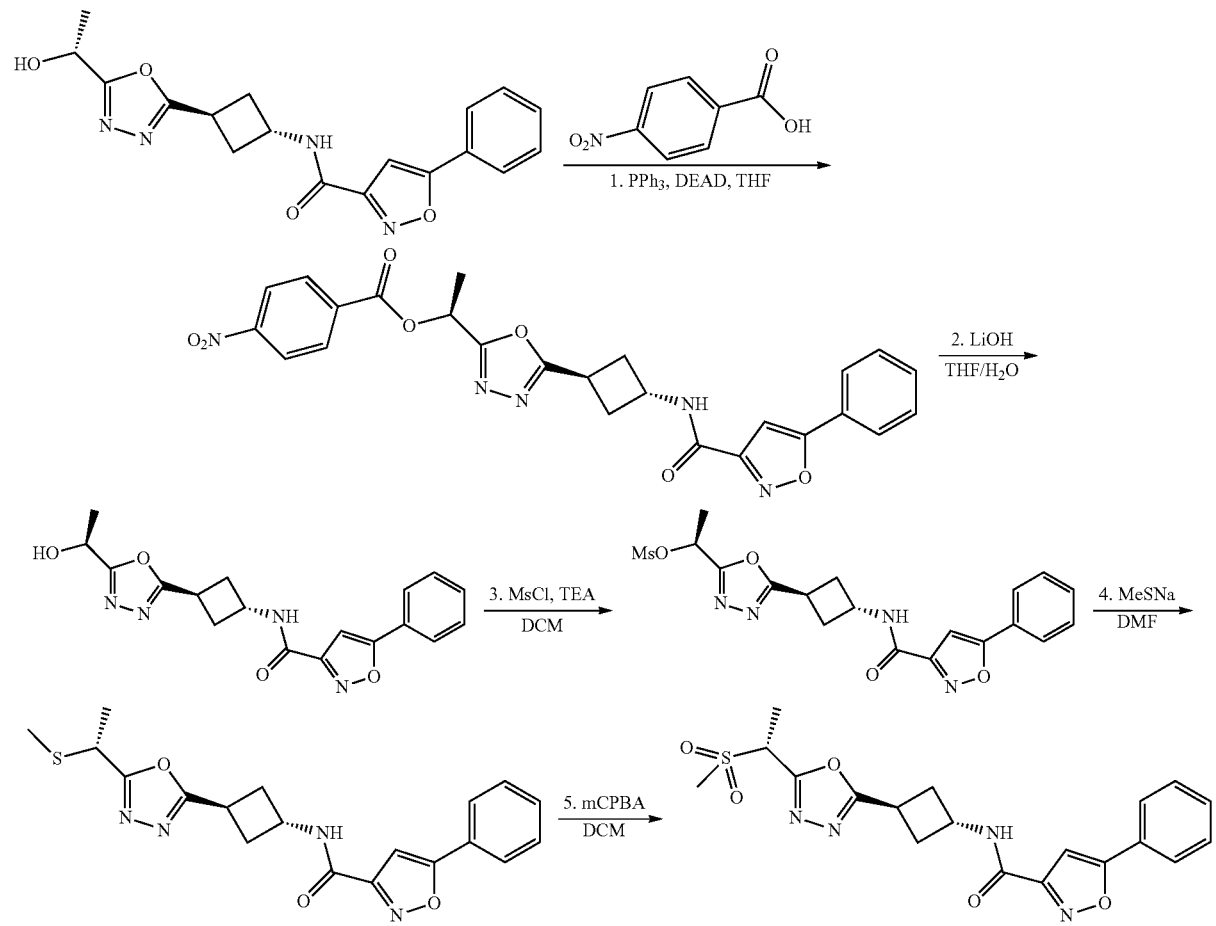

Step 1: (1S)-1-[5-[trans-3-(5-phenylisoxazole-3-amido)cyclobutyl]-1,3,4-oxadiazol-2-yl]ethyl 4-nitrobenzoate DEAD (30 g, 1.50 eq.) was added dropwise to a solution of 5-phenyl-N-[trans-3-[5-[(1R)-1-hydroxyethyl]-1,3,4-oxadiazol-2-yl]cyclobutyl]isoxazole-3-carboxamide (35 g, 98.77 mmol, 1.00 eq.), 4-nitrobenzoic acid (20 g, 119.68 mmol, 1.20 eq.) and triphenylphosphine (38.85 g, 148.12 mmol, 1.50 eq.) in tetrahydrofuran (500 mL). The resulting solution was stirred for 2 hours at room temperature. The resulting solution was diluted with 500 ml of ethyl acetate, washed with brine (2×200 mL) and concentrated under vacuum. The residue was applied onto a silica gel column with ethyl acetate/petroleum ether (1:4). This resulted in 43 g of (1S)-1-[5-[trans-3-(5-phenylisoxazole-3-amido)cyclobutyl]-1,3,4-oxadiazol-2-yl]ethyl 4-nitrobenzoate as a white solid. LC-MS (ES, m/z): [M+H]$^+$=504.1.

Step 2: 5-phenyl-N-[trans-3-[5-[(1S)-1-hydroxyethyl]-1,3,4-oxadiazol-2-yl]cyclobutyl]isoxazole-3-carboxamide solution of LiOH (8 g, 334.06 mmol, 2.00 eq.) in water (100 mL) was added to a solution of (1S)-1-[5-[trans-3-(5-phenylisoxazole-3-amido)cyclobutyl]-1,3,4-oxadiazol-2-yl]ethyl 4-nitrobenzoate (48 g, 95.34 mmol, 1.00 eq.) in tetrahydrofuran (600 mL). The resulting solution was stirred for 5 hours at room temperature and it was then concentrated under vacuum. The residue was dissolved in 200 mL of water. The pH value of the solution was adjusted to 1-2 with hydrogen chloride aqueous (2N). The solid was collected by filtration and dried to give 31 g (92%) of 5-phenyl-N-[trans-3-[5-[(1S)-1-hydroxyethyl]-1,3,4-oxadiazol-2-yl]cyclobutyl]isoxazole-3-carboxamide as a white solid. LC-MS (ES, m/z): [M+H]$^+$=355.0.

Step 3: (1S)-1-[5-[trans-3-(5-phenylisoxazole-3-amido)cyclobutyl]-1,3,4-oxadiazol-2-yl]ethyl methanesulfonate MsCl (14.5 g, 126.58 mmol, 1.50 eq.) was added dropwise to a cold solution of 5-phenyl-N-[trans-3-[5-[(1S)-1-hydroxyethyl]-1,3,4-oxadiazol-2-yl]cyclobutyl]isoxazole-3-carboxamide (31 g, 87.48 mmol, 1.00 eq.) and TEA (26 g, 256.94 mmol, 3.00 eq.) in dichloromethane (500 mL) at 0° C. The resulting solution was stirred for 5 hours in a water/ice bath. The resulting mixture was washed with water (3×100 mL), CuSO$_4$ aqueous (2×100 mL) and brine (2×50 mL). The resulting mixture was concentrated under vacuum to give 40 g (crude) of (1S)-1-[5-[trans-3-(5-phenylisoxazole-3-amido)cyclobutyl]-1,3,4-oxadiazol-2-yl]ethyl methanesulfonate as an off white solid. LC-MS (ES, m/z): [M+H]$^+$=433.0.

Step 4: 5-phenyl-N-[trans-3-[5-[(1R)-1-(methylsulfanyl)ethyl]-1,3,4-oxadiazol-2-yl]cyclobutyl]isoxazole-3-carboxamide sodium methanethiolate (13 g, 185.48 mmol, 2.00 eq.) was added to a solution of (1S)-1-[5-[trans-3-(5-phenylisoxazole-3-amido)cyclobutyl]-1,3,4-oxadiazol-2-yl]ethyl methanesulfonate (40 g, 92.50 mmol, 1.00 eq.) in DMF (200 mL). The resulting solution was stirred for 5 hours at 100° C. in an oil bath and it was then quenched by the addition of 100 mL of water. The resulting solution was extracted with ethyl acetate (3×100 mL) and the organic layers combined. The resulting mixture was washed with brine (2×20 mL) and concentrated under vacuum. This resulted in 32 g (crude) of 5-phenyl-N-[trans-3-[5-[(1R)-1-(methylsulfanyl)ethyl]-1,3,4-oxadiazol-2-yl]cyclobutyl]isoxazole-3-carboxamide as brown oil. LC-MS (ES, m/z): [M+H]$^+$=385.1.

Step 5: 5-phenyl-N-[trans-3-[5-[(1R)-1-methanesulfonylethyl]-1,3,4-oxadiazol-2-yl]cyclobutyl]isoxazole-3-carboxamide m-CPBA (58 g, 336.10 mmol, 4.00 eq.) was added to a solution of 5-phenyl-N-[trans-3-[5-[(1R)-1-(methylsulfanyl)ethyl]-1,3,4-oxadiazol-2-yl]cyclobutyl]isoxazole-3-carboxamide (32 g, 83.24 mmol, 1.00 eq.) in dichloromethane (500 mL). The resulting solution was stirred for 4 hours at 0° C. in a water/ice bath and it was then quenched with 300 mL of Na$_2$S$_2$O$_3$ aqueous. The separated organic layer was washed with NaHCO$_3$ aqueous (2×300 mL) and concentrated under vacuum. The residue was applied onto a silica gel column with dichloromethane/MeOH (20:1) to give 14.16 g (41%) of 5-phenyl-N-[(trans-3-[5-[(1R)-1-methanesulfonylethyl]-1,3,4-oxadiazol-2-yl]cyclobutyl]isoxazole-3-carboxamide as a light yellow solid.

Analytical Data:
LC-MS (ES, m/z): [M+H]$^+$=417.3
HPLC purity: 95.0% at 254 nm
$^1$H NMR (DMSO-d$_6$, 400 MHz): δ 9.33-9.31 (d, J=7.6 Hz, 1H), 7.96-7.93 (m, 2H), 7.59-7.54 (m, 3H), 7.38 (s, 1H), 5.18-5.13 (m, 1H), 4.73-4.67 (m, 1H), 3.77-3.73 (m, 1H), 3.16 (s, 3H), 2.75-2.60 (m, 4H), 1.74-1.72 (d, J=7.2 Hz, 3H).

Example 61: N-(trans-3-(5-cyclobutyl-1,3,4-oxadiazol-2-yl)cyclobutyl)-5-phenylisoxazole-3-carboxamide

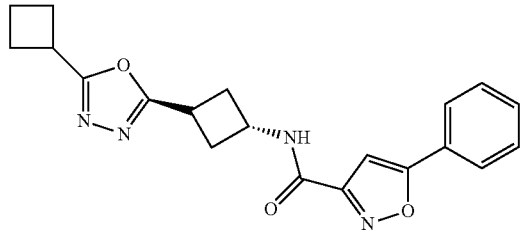

The compound was prepared according to the procedure shown in example 50.
Appearance: white solid
Analytical Data:
LC-MS (ES, m/z): [M+H]$^+$ 365.0
HPLC purity: 97.3% at 254 nm
$^1$H NMR (300 MHz, DMSO-d$_6$, ppm): δ 9.31-9.29 (m, 1H), 7.96-7.93 (m, 2H), 7.60-7.55 (m, 3H), 7.38 (s, 1H), 4.69-4.67 (m, 1H), 3.81-3.64 (m, 2H), 2.72-2.57 (m, 4H), 2.39-2.23 (m, 4H), 2.14-1.98 (m, 2H).

Example 62: N-(trans-3-(1H-imidazol-1-yl)cyclobutyl)-5-phenylisoxazole-3-carboxamide

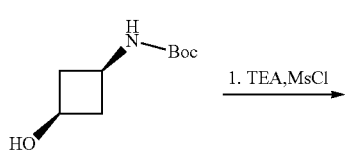

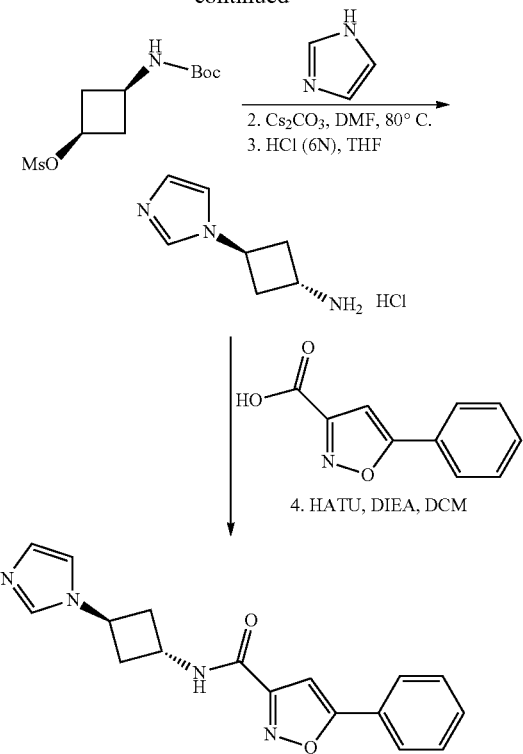

1H-imidazole (272 mg, 4.00 mmol, 2.00 eq.) and Cs₂CO₃ (1.956 g, 6.00 mmol, 3.01 eq.) in DMF (10 mL). was stirred overnight at 80° C. The resulting mixture was concentrated under vacuum, diluted with 100 mL of ethyl acetate and the mixture was washed with water (2×50 mL), dried over anhydrous sodium sulfate and concentrated under vacuum to give 230 mg (crude) of tert-butyl N-[trans-3-(1H-imidazol-1-yl)cyclobutyl]carbamate as yellow oil. LC-MS (ES, ink): [M+H]⁺=238.12.

Step 3: trans-3-(1H-imidazol-1-yl)cyclobutan-1-amine Hydrochloride 2N hydrogen chloride aqueous (10 mL) was added to a solution of tert-butyl N-[trans-3-(1H-imidazol-1-yl)cyclobutyl]carbamate (230 mg, 0.97 mmol, 1.00 eq.) in tetrahydrofuran (10 mL). The resulting solution was stirred for 4 hours at room temperature, concentrated under vacuum to give 0.4 g (crude) of trans-3-(1H-imidazol-1-yl)cyclobutan-1-amine hydrochloride as yellow oil. LC-MS (ES, m/z): [M+H]⁺=138.0.

Step 4: 5-phenyl-N-[trans-3-(1H-imidazol-1-yl)cyclobutyl]isoxazole-3-carboxamide trans-3-(1H-imidazol-1-yl)cyclobutan-1-amine hydrochloride (400 mg, 2.30 mmol, 0.70 eq.), HATU (1.507 g, 3.96 mmol, 1.20 eq.) and DIEA (1.279 g, 9.90 mmol, 3.00 eq.) were added to a solution of 5-phenylisoxazole-3-carboxylic acid (624 mg, 3.30 mmol, 1.00 eq.) in dichloromethane (30 mL). The resulting solution was stirred for 2 hours at room temperature and it was then concentrated under vacuum. The crude product was purified by Prep-HPLC with the following conditions (Waters): Column, XBridge BEH130 Prep C18 OBD Column, 19*150 mm 5 um 13 nm; mobile phase, water with 0.05% TFA and ACN (12.0% ACN up to 50.0% in 8 min); Detector, UV 254 nm. This resulted in 58 mg (6%) of 5-phenyl-N-[trans-3-(1H-imidazol-1-yl)cyclobutyl]isoxazole-3-carboxamide as a white solid.

Analytical Data:
LC-MS (ES, m/z): [M+H]⁺=309.2
HPLC purity: 99.4% at 254 nm
¹H NMR (300 MHz, DMSO-d₆, ppm): δ 9.28 (s, 1H), 7.98-7.93 (m, 3H), 7.51 (s, 1H), 7.60-7.56 (m, 3H), 7.37 (s, 1H), 5.20-5.11 (m, 1H), 4.69-4.60 (m, 1H), 2.91-2.45 (m, 4H).

Example 63: N-(3-(5-((R)-1-hydroxyethyl)-1,3,4-oxadiazol-2-yl)cyclohexyl)-5-phenylisoxazole-3-carboxamide Step 1: tert-butyl N-[trans-3-(methanesulfonyloxy)cyclobutyl]carbamate MsCl (5.386 g, 46.83 mmol, 2.00 eq.) was added dropwise to a cold solution of tert-butyl N-[trans-3-hydroxycyclobutyl]carbamate (4.379 g, 23.39 mmol, 1.00 eq.) and TEA (7.095 g, 70.12 mmol, 3.00 eq.) in dichloromethane (25 mL at 0° C. The resulting solution was stirred for 3 hours at room temperature and it was then diluted with 200 mL of dichloromethane. The resulting mixture was washed with water (2×100 mL), dried over anhydrous sodium sulfate and concentrated under vacuum. The crude product was recrystallized from dichloromethane/hexane in the ratio of 1:1 to give 5.548 g (89%) of tert-butyl N-[cis-3-(methanesulfonyloxy)cyclobutyl]carbamate as an off-white solid.

Step 2: tert-butyl N-[trans-3-(1H-imidazol-1-yl)cyclobutyl]carbamate a solution of tert-butyl N-[cis-3-(methanesulfonyloxy)cyclobutyl]carbamate (530 mg, 2.00 mmol, 1.00 eq.),

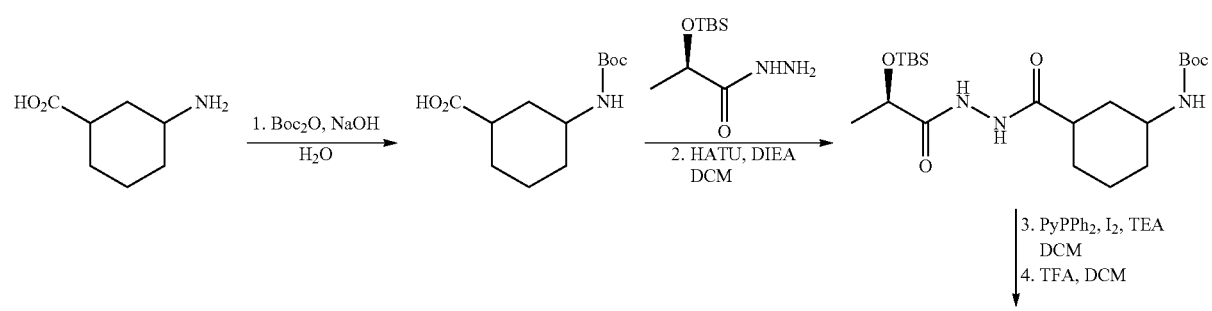

-continued

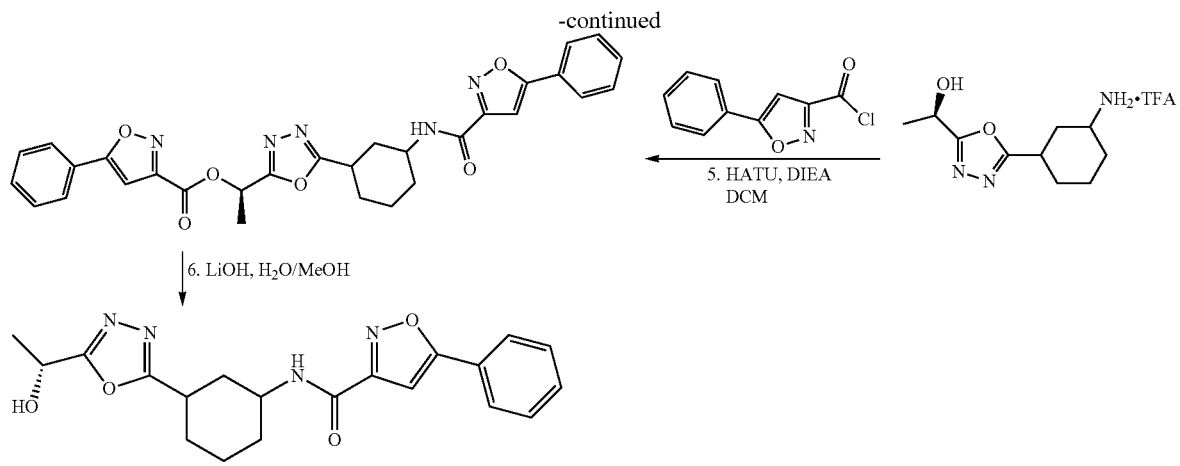

Step 1: 3-[[(tert-butoxy)carbonyl]amino]cyclohexane-1-carboxylic acid sodium hydroxide (1.6 g, 40.00 mmol, 2.00 eq.) and Boc$_2$O (5.232 g, 24.00 mmol, 1.20 eq.) were added to a solution of 3-aminocyclohexane-1-carboxylic acid (2.86 g, 19.97 mmol, 1.00 eq.) in water (50 mL) and the mixture was stirred for 3 hours at room temperature. The solids were collected by filtration to give 4.048 g (83%) of 3-[[(tert-butoxy)carbonyl]amino]cyclohexane-1-carboxylic acid as a white solid. LC-MS (ES, m/z): [M+H]$^+$=244.1.

Step 2: of tert-butyl N-(3-[N-[(2R)-2-[(tert-butyldimethylsilyl)oxy]propanoyl]hydrazinecarbonyl]cyclohexyl)carbamate (2R)-2-[(tert-butyldimethylsilyl)oxy]propanehydrazide (637 mg, 2.92 mmol, 1.20 eq.), HATU (1.111 g, 2.92 mmol, 1.20 eq.) and DIEA (943 mg, 7.30 mmol, 3.00 eq.) were added to solution of 3-[[(tert-butoxy)carbonyl]amino]cyclohexane-1-carboxylic acid (592 mg, 2.43 mmol, 1.00 eq.) in dichloromethane (30 mL). The resulting solution was stirred for 2 hours at room temperature and it was then concentrated under vacuum. The residue was applied onto a silica gel column with ethyl acetate/petroleum ether (1:5) to give 848 mg (79%) of tert-butyl N-(3-[N-[(2R)-2-[(tert-butyldimethylsilyl)oxy]propanoyl]hydrazinecarbonyl]cyclohexyl)carbamate as an off-white solid. LC-MS (ES, m/z): [M+H]$^+$=444.2.

Step 3: N-(3-[5-[(1R)-1-[(tert-butyldimethylsilyl)oxy]ethyl]-1,3,4-oxadiazol-2-yl]cyclohexyl)carbamate I$_2$ (833 mg, 3.28 mmol, 2.00 eq.), TEA (993 mg, 9.81 mmol, 6.00 eq.) and tert-butyl N-(3-[N-[(2R)-2-[(tert-butyldimethylsilyl)oxy]propanoyl]hydrazinecarbonyl]cyclohexyl)carbamate (726 mg, 1.64 mmol, 1.00 eq.) were added slowly (in several batches) to a cold solution of PyPPh$_2$ (862 mg, 3.28 mmol, 2.00 eq.) in dichloromethane (20 mL) at 0° C. The resulting solution was stirred for 2 hours at room temperature and it was then concentrated under vacuum. The residue was applied onto a silica gel column with ethyl acetate/petroleum ether (1:10) to give 549 mg (79%) of tert-butyl N-(3-[5-[(1R)-1-[(tert-butyldimethylsily)oxy]ethyl]-1,3,4-oxadiazol-2-yl]cyclohexyl)carbamate as yellow oil. LC-MS (ES, m/z): [M+H]$^+$=426.2.

Step 4: (1R)-1-(5-(3-aminocyclohexyl)-1,3,4-oxadiazol-2-yl)ethan-1-ol a solution of tert-butyl N-(3-[5-[(1R)-1-[(tert-butyldimethylsilyl)oxy]ethyl]-1,3,4-oxadiazol-2-yl]cyclohexyl)carbamate (549 mg, 1.29 mmol, 1.00 eq.) and trifluoroacetic acid (3 mL) in dichloromethane (10 mL) was stirred for 2 hours at room temperature. The resulting mixture was concentrated under vacuum to give 300 mg (crude) of (1R)-1-(5-(3-aminocyclohexyl)-1,3,4-oxadiazol-2-yl)ethan-1-ol as yellow oil. LC-MS (ES, m/z): [M−TFA+H]$^+$=212.3.

Step 5: (1R)-1-[5-[3-(5-phenylisoxazole-3-amido)cyclohexyl]-1,3,4-oxadiazol-2-yl]ethyl 5-phenylisoxazole-3-carboxylate 5-phenylisoxazole-3-carboxylic acid (275 mg, 1.45 mmol, 1.50 eq.), HATU (553 mg, 1.45 mmol, 1.50 eq.) and DIEA (376 mg, 2.91 mmol, 3.00 eq.) were added to a solution of (1R)-1-(5-(3-aminocyclohexyl)-1,3,4-oxadiazol-2-yl)ethan-1-ol (300 mg, 0.97 mmol, 1.00 eq.) in dichloromethane (20 mL). The resulting solution was stirred for 2 hours at room temperature and it was then concentrated under vacuum. The residue was applied onto a silica gel column with ethyl acetate/petroleum ether (1:5) to give 350 mg (65%) of (1R)-1-[5-[3-(5-phenylisoxazole-3-amido)cyclohexyl]-1,3,4-oxadiazol-2-yl]ethyl 5-phenylisoxazole-3-carboxylate as a white solid. LC-MS (ES, m/z): [M+H]$^+$=554.3.

Step 6: N-(3-[5-[(1R)-1-hydroxyethyl]-1,3,4-oxadiazol-2-yl]cyclohexyl)-5-phenylisoxazole-3-carboxamide a solution of (1R)-1-[5-[3-(5-phenylisoxazole-3-amido)cyclohexyl]-1,3,4-oxadiazol-2-yl]ethyl 5-phenylisoxazole-3-carboxylate (350 mg, 0.63 mmol, 1.00 eq.) and LiOH H$_2$O (133 mg, 3.17 mmol, 5.01 eq.) in methanol (20 mL)/water (3 mL) was stirred for 2 hours at 50° C. The resulting mixture was concentrated under vacuum, diluted with 50 mL of dichloromethane and it was then washed with brine (2×20 mL), dried over anhydrous sodium sulfate and concentrated under vacuum. The crude product was purified by Prep-HPLC with the following conditions (HPLC-10): Column, XBridge Shield RP18 OBD Column, 5 um, 19*150 mm; mobile phase, Water with 0.08% NH$_4$HCO$_3$ and ACN (20.0% ACN up to 70.0% in 8 min); Detector, UV 254/220 nm. This resulted in 86 mg (36%) of N-(3-[5-[(1R)-1-hydroxyethyl]-1,3,4-oxadiazol-2-yl]cyclohexyl)-5-phenylisoxazole-3-carboxamide as a white solid.
Analytical Data:
LC-MS (ES, m/z): [M+H]⁺=383.1
HPLC purity: 99.8% at 254 nm
¹H NMR (400 MHz, DMSO-d₆, ppm): δ 8.83-8.81 (d, J=8.4 Hz, 1H), 7.95-7.92 (m, 2H), 7.59-7.52 (m, 3H), 7.38 (s, 1H), 5.93-5.91 (d, J=5.6 Hz, 1H), 4.92-4.85 (m, 1H), 4.03-3.96 (m, 1H), 3.18-3.12 (m, 1H), 2.22-2.19 (m, 1H), 2.04-2.01 (m, 1H), 1.88-1.86 (m, 2H), 1.68-1.46 (m, 7H).

Example 64: N-(3-(4-(hydroxymethyl)-1H-1,2,3-triazol-1-yl)cyclohexyl)-5-phenylisoxazole-3-carboxamide and N-(3-(5-(hydroxymethyl)-1H-1,2,3-triazol-1-yl)cyclohexyl)-5-phenylisoxazole-3-carboxamide 1H-1,2,3-triazol-1-yl]cyclohexyl]carbamate. LC-MS (ES, m/z): [M+H]⁺=297.2.

Step 3: [1-(3-aminocyclohexyl)-1H-1,2,3-triazol-⅘-yl]methanol hydrogen chloride (3 mL) was added to a solution of mixture of tert-butyl N-[3-[⅘-(hydroxymethyl)-1H-1,2,3-triazol-1-yl]cyclohexyl]carbamate (582 mg, 1.96 mmol, 1.00 eq., crude) in 1,4-dioxane (10 mL). The resulting solution was stirred for 4 hours at room temperature and then it was concentrated under vacuum. This resulted in 637 mg of mixture of [1-(3-aminocyclohexyl)-1H-1,2,3-triazol-⅘-yl]methanol as a brown oil. LC-MS (ES, m/z): [M+H]⁺=197.1.

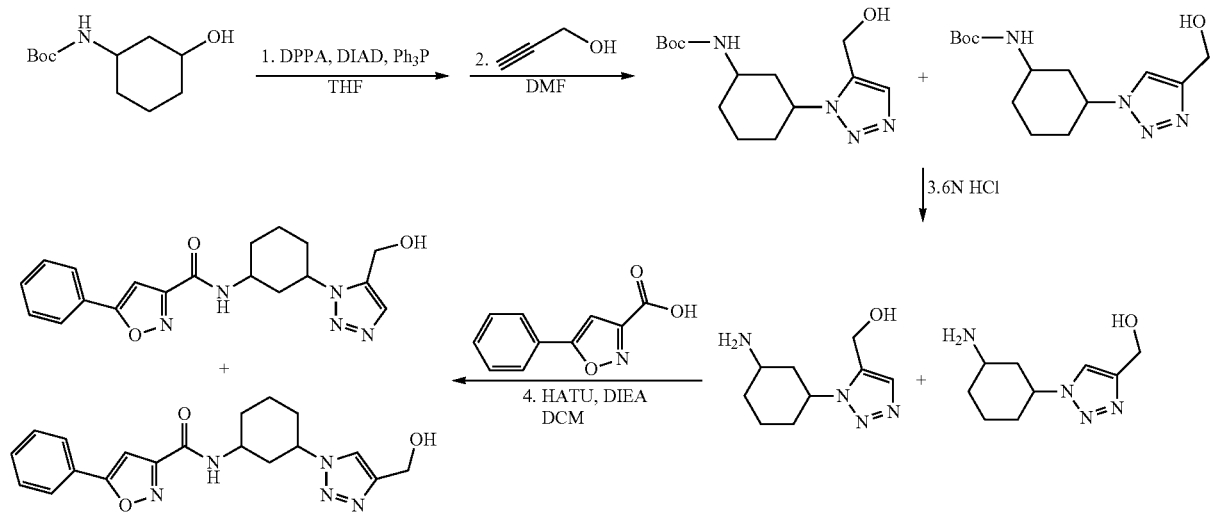

Step 1: tert-butyl N-(3-azidocyclohexyl)carbamate

DIAD (1.41 g, 6.97 mmol, 1.50 eq.), DPPA (1.53 g, 5.56 mmol, 1.20 eq.) and tert-butyl N-(3-hydroxycyclohexyl) carbamate (1 g, 4.64 mmol, 1.00 eq.) were added to a solution of PPh₃ (1.82 g, 6.94 mmol, 1.50 eq.) in tetrahydrofuran (30 mL). The resulting solution was stirred for 2 hours at room temperature, diluted with 50 mL of ethyl acetate and it was then washed with brine (2×30 mL) and concentrated under vacuum. The residue was applied onto a silica gel column with ethyl acetate/petroleum ether (1:20) to give 0.642 g (58%) of tert-butyl N-(3-azidocyclohexyl) carbamate as a light yellow solid.

Step 2: tert-butyl N-[3-[⅘-(hydroxymethyl)-1H-1,2,3-triazol-1-yl]cyclohexyl]carbamate a solution of tert-butyl N-(3-azidocyclohexyl)carbamate (642 mg, 2.67 mmol, 1.00 eq.) and prop-2-yn-1-ol (300 mg, 5.35 mmol, 2.00 eq.) in DMF (10 mL) was placed in a sealed tube and the solution was stirred for overnight at 100° C. in an oil bath. The resulting mixture was concentrated under vacuum. The residue was applied onto a silica gel column with ethyl acetate/petroleum ether (3:1). This resulted in 582 mg (crude) mixture of tert-butyl N-[3-[⅘-(hydroxymethyl)-

Step 4: N-[3-[5-(hydroxymethyl)-1H-1,2,3-triazol-1-yl]cyclohexyl]-5-phenylisoxazole-3-carboxamide and N-[3-[4-(hydroxymethyl)-1H-1,2,3-triazol-1-yl] cyclohexyl]-5-phenylisoxazole-3-carboxamide DIEA (1.26 g, 3.00 eq.), HATU (2.47 g, 2.00 eq.) and 5-phenylisoxazole-3-carboxylic acid (1.23 g, 6.5 mmol, 2.00 eq.) were added to a mixture of [1-(3-aminocyclohexyl)-1H-1,2,3-triazol-5-yl]methanol and [1-(3-aminocyclohexyl)-1H-1,2,3-triazol-4-yl]methanol (637 mg, 3.25 mmol, 1.00 eq.) in dichloromethane (100 mL). The resulting solution was stirred for 5 hours at room temperature and the reaction was then quenched by the addition of 40 mL of water. The resulting solution was extracted with dichloromethane (3×100 mL) and the combined organic layers were washed with brine (2×20 mL), dried over anhydrous sodium sulfate and concentrated under vacuum. The residue was applied onto a silica gel column with ethyl acetate (100%). This resulted in 25.9 mg (6%) of N-[3-[5-(hydroxymethyl)-1H-1,2,3-triazol-1-yl]cyclohexyl]-5-phenylisoxazole-3-carboxamide as an off-white solid and 36.4 mg (5%) of N-[3-[4-(hydroxymethyl)-1H-1,2,3-triazol-1-yl] cyclohexyl]-5-phenylisoxazole-3-carboxamide as an white solid.-

157

N-[3-[4-(hydroxymethyl)-1H-1,2,3-triazol-1-yl]cyclohexyl]-5-phenylisoxazole-3-carboxamide Analytical Data:

LC-MS (ES, m/z): [M+H]$^+$=368.1

$^1$H NMR (DMSO-d$_6$, 400 MHz): δ 8.82-8.80 (d, J=7.6 Hz, 1H), 8.05 (s, 1H), 7.95-7.93 (m, 2H), 7.58-7.54 (m, 3H), 7.37 (s, 1H), 5.18-5.15 (m, 1H), 4.93 (br, 1H), 4.53-4.50 (m, 2H), 4.31-4.25 (m, 1H), 2.38-2.30 (m, 1H), 2.18-2.11 (m, 1H), 1.97-1.95 (m, 2H), 1.73-1.71 (m, 4H).

N-[3-[5-(hydroxymethyl)-1H-1,2,3-triazol-1-yl]cyclohexyl]-5-phenylisoxazole-3-carboxamide Analytical Data:

LC-MS (ES, m/z): [M+H]$^+$=368.1

$^1$H NMR (DMSO-d$_6$, 400 MHz): δ 8.77-8.75 (d, J=7.6 Hz, 1H), 7.94-7.93 (m, 2H), 7.60-7.55 (m, 4H), 7.37 (s, 1H), 5.50-5.43 (m, 1H), 4.92-4.91 (m, 1H), 4.60-4.52 (m, 3H), 2.37-2.12 (m, 2H), 2.03-1.82 (m, 2H), 1.75 (br, 3H), 1.60-1.45 (m, 1H), 1.82-1.75 (m, 4H).

Example 65: N-[3-[5-(hydroxymethyl)-1,3,4-oxadiazol-2-yl]cyclopentyl]-5-phenylisoxazole-3-carboxamide

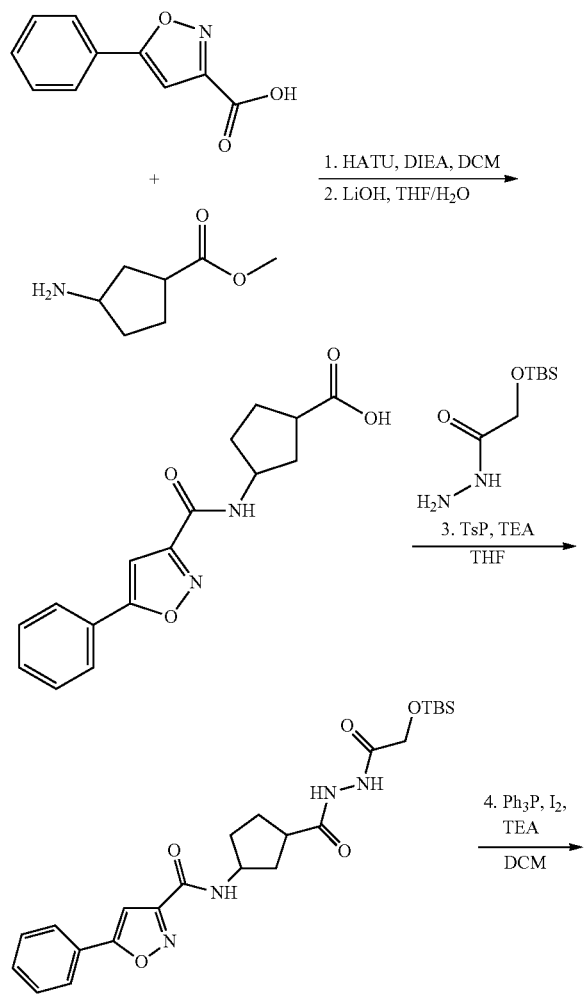

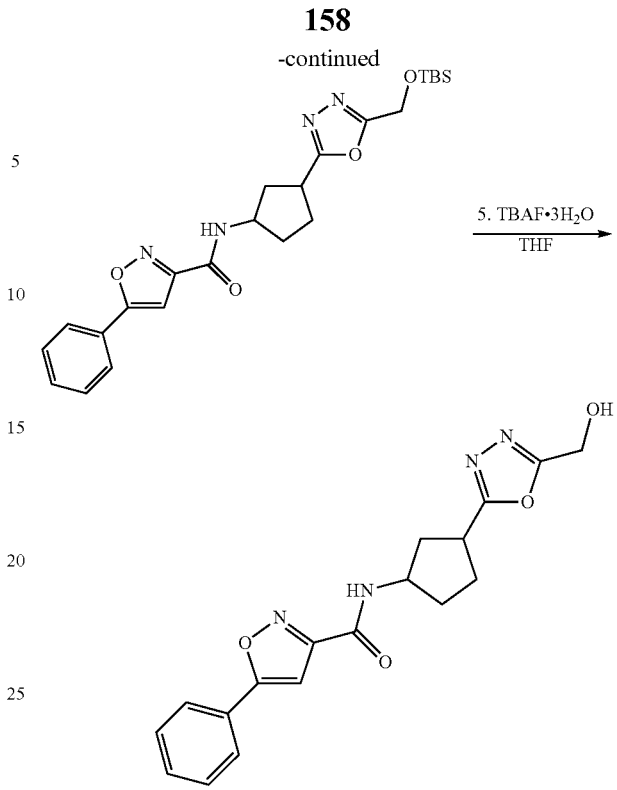

Step 1: methyl 3-(5-phenylisoxazole-3-carboxamido)cyclopentane-1-carboxylate into a 50-mL round-bottom flask, was placed a solution of methyl 3-aminocyclopentane-1-carboxylate (500 mg, 3.49 mmol, 1.00 eq.) in dichloromethane (10 mL) To the solution were added HATU (1.59 g, 4.18 mmol, 1.20 eq.), DIEA (1.6 g, 12.38 mmol, 3.50 eq.) and 5-phenylisoxazole-3-carboxylic acid (790 mg, 4.18 mmol, 1.20 eq.). The resulting solution was stirred for 2 hours at room temperature. The reaction was then quenched by the addition of water. The resulting solution was extracted with ethyl acetate and the combined organic layers were dried over anhydrous sodium sulfate and concentrated under vacuum. This resulted in 0.925 g (84%) of methyl 3-(5-phenylisoxazole-3-amido)cyclopentane-1-carboxylate as a light yellow solid. LC-MS (ES, m/z) [M+H]$^+$=315.1

Step 2: 3-(5-phenylisoxazole-3-amido)cyclopentane-1-carboxylic acid into a 50-mL round-bottom flask, was placed a solution of methyl 3-(5-phenylisoxazole-3-amido)cyclopentane-1-carboxylate (925 mg, 2.94 mmol, 1.00 eq.) in tetrahydrofuran/H$_2$O (10/1 mL). To the solution was added LiOH (354 mg, 14.78 mmol, 5.00 eq.). The resulting solution was stirred for 1 hour at room temperature. The resulting mixture was diluted with 50 mL of water. The resulting solution was washed with dichloromethane and the organic layers combined. The pH value of the aqueous layer was adjusted to 3 with hydrogen chloride aqueous (2 mol/L). The resulting solution was extracted with dichloromethane and the combined organic layers were dried over anhydrous sodium sulfate and concentrated under vacuum. This resulted in 0.7971 g (90%) of 3-(5-phenylisoxazole-3-amido)cyclopentane-1-carboxylic acid as a yellow solid. LC-MS (ES, m/z) [M+H]$^+$=301.1

Step 3: N-[3-([2-[(tert butyldimethylsilyl)oxy]acetohydrazido]carbonyl)cyclopentyl]-5-phenylisoxazole-3-carboxamide into a 250-mL round-bottom flask, was placed a solution of 3-(5-phenylisoxazole-3-amido)cyclopentane-1-carboxylic acid (2.8 g, 9.32 mmol, 1.00 eq.) in tetrahydrofuran (50 mL). To the solution were added T₃P (50%) (29.68 g, 5.00 eq.), TEA (4.71 g, 46.55 mmol, 5.00 eq.) and 2-[(tert-butyldimethylsilyl)oxy]acetohydrazide (2.4851 g, 12.16 mmol, 1.00 eq.). The resulting solution was stirred for 3 hours at 30° C. The reaction was then quenched by the addition of water. The resulting solution was extracted with dichloromethane and the combined organic layers were dried over anhydrous sodium sulfate. The solids were filtered out. The resulting mixture was concentrated under vacuum. The residue was applied onto a silica gel column with ethyl acetate/petroleum ether (10:9). This resulted in 1.12 g (25%) of N-[3-([2-[(tert-butyldimethylsilyl)oxy]acetohydrazido]carbonyl)cyclopentyl]-5-phenylisoxazole-3-carboxamide as a yellow solid. LC-MS (ES, m/z) [M+H]⁺= 487.2

Step 4: N-(3-(5-((tert-butyldimethylsilyloxy)methyl)-1,3,4-oxadiazol-2-yl)cyclopentyl)-5-phenylisoxazole-3-carboxamide into a 100-mL round-bottom flask purged and maintained with an inert atmosphere of nitrogen, was placed a solution of Ph₃P (2.83 g, 5.00 eq.) in dichloromethane (25 mL). To the solution were added I₂ (2.72 g, 5.00 eq.), TEA (1.31 g, 12.95 mmol, 6.00 eq.) and N-[3-([2-[(tert-butyldimethylsilyl)oxy]acetohydrazido]carbonyl)cyclopentyl]-5-phenylisoxazole-3-carboxamide (1.05 g, 2.16 mmol, 1.00 eq.). The resulting solution was stirred for 2 hours at 0° C. The reaction was then quenched by the addition of water. The resulting solution was extracted with dichloromethane and the combined organic layers were dried over anhydrous sodium sulfate and concentrated under vacuum. The residue was applied onto a silica gel column with ethyl acetate/petroleum ether (5:1). This resulted in 0.2 g (20%) of N-(3-(5-((tert-butyldimethylsilyloxy)methyl)-1,3,4-oxadiazol-2-yl)cyclopentyl)-5-phenylisoxazole-3-carboxamide as a light yellow solid. LC-MS (ES, m/z) [M+H]⁺=469.2

Step 5: N-[3-[5-(hydroxymethyl)-1,3,4-oxadiazol-2-yl]cyclopentyl]-5-phenylisoxazole-3-carboxamide into a 25-mL round-bottom flask, was placed N-[3-(5-[[(tert-butyldimethylsilyl)oxy]methyl]-1,3,4-oxadiazol-2-yl)cyclopentyl]-5-phenylisoxazole-3-carboxamide (468 mg, 1.00 mmol, 1.00 eq.), tetrahydrofuran (5 mL), TABF (0.27 g, 2.00 eq.). The resulting solution was stirred for 2 h at 0° C. The reaction was then quenched by the addition of water. The resulting solution was extracted with dichloromethane and the organic layers combined and dried over anhydrous sodium sulfate. The solids were filtered out. The resulting mixture was concentrated under vacuum. The residue was applied onto a silica gel column with dichloromethane/methanol (5:1). The crude product was purified by Prep-HPLC with the following conditions: Column: XBridge Prep C18 OBD Column 19*250 mm 10 um; Mobile Phase A: Water with 0.5% NH₄HCO₃, Mobile Phase B: ACN; Flow rate: 25 mL/min; Gradient: 20% B to 60% B in 10 min; 254/220 nm. This resulted in 43 mg (12%) of N-[3-[5-(hydroxymethyl)-1,3,4-oxadiazol-2-yl]cyclopentyl]-5-phenylisoxazole-3-carboxamide as a white solid.

Yield: 12%
Appearance: white solid
Analytical Data:
LC-MS (ES, M/Z): [M+1]⁺=355.1
¹H NMR: (DMSO-d₆, 300 MHz, ppm): δ 8.89 (d, J=8.1 Hz, 1H), 7.90-7.87 (m, 2H), 7.55-7.50 (m, 3H), 7.31 (s, 1H), 5.82-5.77 (m, 1H), 4.56 (d, J=6.0 Hz, 2H), 4.42-4.35 (m, 1H), 3.48-3.37 (m, 1H), 2.41-2.35 (m, 1H), 2.10-1.88 (m, 4H), 1.81-1.71 (m, 1H).

Example 65: N-(cis/trans-4-(5-(hydroxymethyl)-1,3,4-oxadiazol-2-yl)cyclohexyl)-5-phenylisoxazole-3-carboxamide

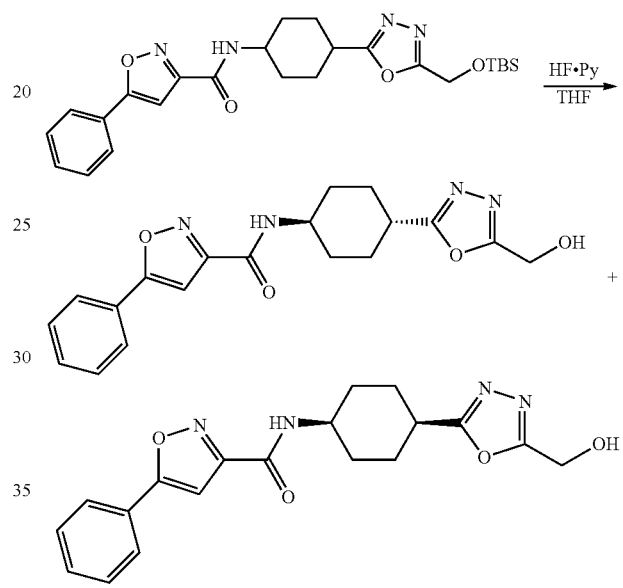

A solution of N-[4-(5-[[(tert-butyldimethylsilyl)oxy]methyl]-1,3,4-oxadiazol-2-yl)cyclohexyl]-5-phenylisoxazole-3-carboxamide (170 mg, 0.35 mmol, 1.00 eq., prepared using similar methodology as in example 64) in tetrahydrofuran (6 mL) and pyridine hydrofluoride (0.5 mL) was stirred for 1 hour at room temperature. The reaction was then quenched by the addition of water. The solids were collected by filtration and washed with ethyl acetate. This resulted in 37.8 mg (29%) of N-(cis/trans-4-(5-(hydroxymethyl)-1,3,4-oxadiazol-2-yl)cyclohexyl)-5-phenylisoxazole-3-carboxamide as a white solid. Then the resulting filtrate was extracted with ethyl acetate and the organic layers combined. The resulting mixture was washed with brine, dried over anhydrous sodium sulfate and concentrated under vacuum. The crude product was purified by Prep-HPLC with the following conditions (Waters): Column, X Bridge Prep C18 OBD Column, 19*250 mm, 10 um; mobile phase, Water with 0.05% NH₄HCO₃ and ACN (30.0% ACN up to 40.0% in 10 min); Detector, UV 254/220 nm. This resulted in 12 mg (10%) of 5-phenyl-N-[cis-4-[5-(hydroxymethyl)-1,3,4-oxadiazol-2-yl]cyclohexyl]-5-phenylisoxazole-3-carboxamide and 35 mg (29%) of 5-phenyl-N-[trans-4-[5-(hydroxymethyl)-1,3,4-oxadiazol-2-yl]cyclohexyl]-5-phenylisoxazole-3-carboxamide as a white solids.

5-phenyl-N-[trans-4-[5-(hydroxymethyl)-1,3,4-oxadiazol-2-yl]cyclohexyl]-5-phenylisoxazole-3-carboxamide
Yield: 29%
Appearance: white solid Analytical Data:
LC-MS (ES, m/z): [M+H]⁺=369.1
¹H NMR: (300 MHz, DMSO-d₆, ppm): δ 8.76-8.73 (d, 1H, J=8.1 Hz), 7.95-7.92 (m, 2H), 7.57-7.55 (m, 3H), 7.36 (s, 1H), 5.86-5.82 (t, 1H, J=6.0 Hz), 4.61-4.59 (d, 2H, J=6.0 Hz), 3.85-3.83 (m, 1H), 2.94-2.90 (m, 1H), 2.15-2.12 (m, 2H), 1.98-1.95 (m, 2H), 1.69-1.50 (m, 4H).

5-phenyl-N-[cis-4-[5-(hydroxymethyl)-1,3,4-oxadiazol-2-yl]cyclohexyl]-5-phenylisoxazole-3-carboxamide
Yield: 10%
Appearance: white solid
Analytical Data:
LC-MS (ES, m/z): [M+H]⁺=369.1
¹H NMR: (300 MHz, DMSO-d₆, ppm): δ 8.65-8.63 (d, 1H, J=7.5 Hz), 7.93-7.90 (m, 2H), 7.60-7.54 (m, 3H), 7.34 (s, 1H), 5.87-5.83 (t, 1H, J=6.0 Hz), 4.63-4.61 (d, 2H, J=6.3 Hz), 3.98-3.94 (m, 1H), 3.23-3.16 (m, 1H), 2.15-2.11 (m, 2H), 1.90-1.82 (m, 2H), 1.78-1.62 (m, 4H).

Example 66: 5-(3,4-dihydroxyphenyl)-N-(trans-3-(5-((R)-1-hydroxyethyl)-1,3,4-oxadiazol-2-yl)cyclobutyl)isoxazole-3-carboxamide

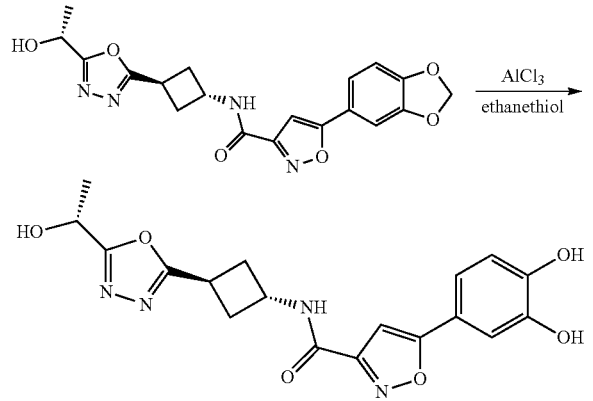

5-(benzo[d][1,3]dioxol-5-yl)-N-(trans-3-(5-((R)-1-hydroxyethyl)-1,3,4-oxadiazol-2-yl)cyclobutyl)isoxazole-3-carboxamide was prepared using the method methodology described in example 54. AlCl₃ (268 mg, 2.01 mmol, 4.00 eq.) was added slowly to a solution of 5-(2H-1,3-benzodioxol-5-yl)-N-[trans-3-[5-[(1R)-1-hydroxyethyl]-1,3,4-oxadiazol-2-yl]cyclobutyl]isoxazole-3-carboxamide (200 mg, 0.50 mmol, 1.00 eq.) in ethanethiol (5 mL) at 0° C. The resulting solution was stirred for 8 hours at room temperature, it was then quenched by the addition of 50 mL of water/ice. The solids were filtered and the mixture was concentrated under vacuum. The crude product was purified by Flash-Prep-HPLC with the following conditions (IntelFlash-1): Column, C18; mobile phase, H₂O:CH₃CN=100:1 increasing to H₂O:CH₃CN=1:100 within 20 min; Detector, UV 254 nm. This resulted in 92 mg (47%) of 5-(3,4-dihydroxyphenyl)-N-[trans-3-[5-[(1R)-1-hydroxyethyl]-1,3,4-oxadiazol-2-yl]cyclobutyl]isoxazole-3-carboxamide as a light yellow solid.

Analytical data: LC-MS (ES, m/z): [M+1]⁺=387
HPLC purity: 96.9% at 254 nm
¹H NMR (400 MHz, DMSO-d₆): δ 9.69 (s, 1H), 9.38 (s, 1H), 9.24-9.22 (d, J=7.6 Hz, 1H), 7.26-7.24 (dd, J=2.0 Hz, 2H), 7.1 (s, 1H), 6.75 (s, 1H), 5.95-5.94 (d, J=5.2 Hz, 1H), 4.94-4.89 (m, 1H), 4.71-4.65 (m, 1H), 3.73-3.67 (m, 1H), 2.72-2.57 (m, 4H), 1.49-1.48 (d, J=6.4 Hz, 3H).

Example 67: N-(trans-3-(1H-benzo[d]imidazol-1-yl)cyclobutyl)-5-phenylisoxazole-3-carboxamide

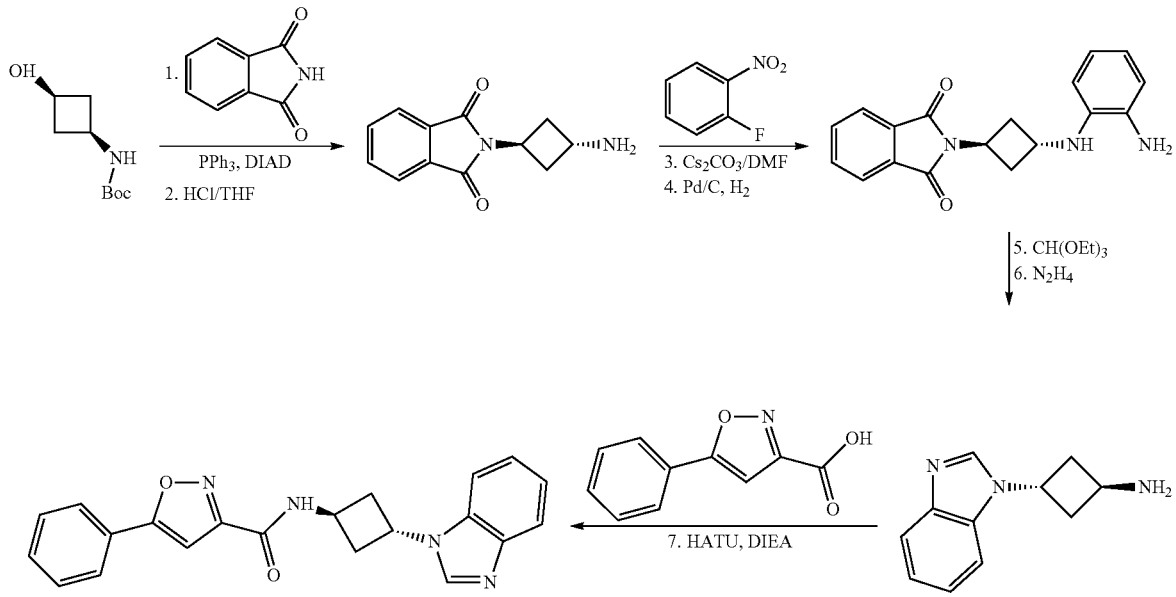

Step 1: tert-butyl N-[trans-3-(1,3-dioxo-2,3-dihydro-1H-isoindol-2-yl)cyclobutyl]carbamate triphenylphosphine (15.97 g, 60.89 mmol, 1.50 eq.), 2,3-dihydro-1H-isoindole-1,3-dione (7.17 g, 48.73 mmol, 1.20 eq.) and DIAD (12.31 g, 60.94 mmol, 1.50 eq.) were added to a solution of tert-butyl N-[cis-3-hydroxycyclobutyl]carbamate (7.6 g, 40.59 mmol, 1.00 eq.) in THF (100 mL). The solution was stirred for 2 hours at room temperature and it was then quenched by the addition of water. The resulting solution was extracted with ethyl acetate and the organic layers combined. The resulting mixture was washed with brine, dried over anhydrous sodium sulfate and concentrated under vacuum. The residue was applied onto a silica gel column with ethyl acetate/petroleum ether (1:15). This resulted in 3.5 g (27%) of tert-butyl N-[trans-3-(1,3-dioxo-2,3-dihydro-1H-isoindol-2-yl)cyclobutyl]carbamate as a white solid. LC-MS (ES, m/z): [M+H]$^+$=317.0.

Step 2: 2-[trans-3-aminocyclobutyl]-2,3-dihydro-1H-isoindole-1,3-dione concentrated hydrogen chloride (15 mL) was added to a solution of tert-butyl N-[trans-3-(1,3-dioxo-2,3-dihydro-1H-isoindol-2-yl)cyclobutyl]carbamate (2.5 g, 7.90 mmol, 1.00 eq.) in THF (20 mL) and the resulting solution was stirred overnight at room temperature. The resulting mixture was concentrated under vacuum. This resulted in 2.4 g (crude) of 2-[trans-3-aminocyclobutyl]-2,3-dihydro-1H-isoindole-1,3-dione as a white solid. LC-MS (ES, m/z): [M+H]$^+$=217.0.

Step 3: of 2-[trans-3-[(2-nitrophenyl)amino]cyclobutyl]-2,3-dihydro-1H-isoindole-1,3-dione a solution of 2-[trans-3-aminocyclobutyl]-2,3-dihydro-1H-isoindole-1,3-dione (600 mg, 2.77 mmol, 1.00 eq.), 1-fluoro-2-nitrobenzene (470 mg, 3.33 mmol, 1.20 eq.) and Cs$_2$CO$_3$ (2.72 g, 8.32 mmol, 3.00 eq.) in DMF (20 mL) was stirred for 3 hours at 90° C. The reaction was then quenched by the addition of water, extracted with ethyl acetate and the organic layers combined. The solution was dried over anhydrous sodium sulfate and concentrated under vacuum. The residue was applied onto a silica gel column with ethyl acetate/petroleum ether (1:2) to give 680 mg (73%) of 2-[trans-3-[(2-nitrophenyl)amino]cyclobutyl]-2,3-dihydro-1H-isoindole-1,3-dione as orange oil. LC-MS (ES, m/z): [M+H]$^+$=338.1.

Step 4: 2-[trans-3-[(2-aminophenyl)amino]cyclobutyl]-2,3-dihydro-1H-isoindole-1,3-dione Pd/C (20 mg 0 was added to a solution of 2-[trans-3-[(2-nitrophenyl)amino]cyclobutyl]-2,3-dihydro-1H-isoindole-1,3-dione (200 mg, 0.59 mmol, 1.00 eq.) in methanol (30 mL). The solution was degassed and back filled with hydrogen and it was stirred for 9 hours at room temperature. The solids were filtered out. The resulting mixture was concentrated under vacuum to give 230 mg (crude) of 2-[trans-3-[(2-aminophenyl)amino]cyclobutyl]-2,3-dihydro-1H-isoindole-1,3-dione as brown oil. LC-MS (ES, m/z): [M+H]$^+$=308.1.

Step 5: 2-[trans-3-(1H-1,3-benzodiazol-1-yl)cyclobutyl]-2,3-dihydro-1H-isoindole-1,3-dione solution of 2-[trans-3-[(2-aminophenyl)amino]cyclobutyl]-2,3-dihydro-1H-isoindole-1,3-dione (650 mg, 2.11 mmol, 1.00 eq.)), trimethoxymethane (450 mg, 4.24 mmol, 2.00 eq.) and 4-methylbenzene-1-sulfonic acid (73 mg, 0.42 mmol, 0.20 eq.) in toluene (4 mL) was irradiated with microwave radiation for 1 hour at 130° C. The reaction was then quenched by the addition of water, extracted with ethyl acetate and the organic layers combined. The resulting mixture was washed with brine, dried over anhydrous sodium sulfate and concentrated under vacuum to give 1.146 g (crude) of 2-[trans-3-(1H-1,3-benzodiazol-1-yl)cyclobutyl]-2,3-dihydro-1H-isoindole-1,3-dione as brown oil. LC-MS (ES, m/z): [M+H]$^+$=318.0.

Step 6: trans-3-(1H-1,3-benzodiazol-1-yl)cyclobutan-1-amine solution of 2-[trans-3-(1H-1,3-benzodiazol-1-yl)cyclobutyl]-2,3-dihydro-1H-isoindole-1,3-dione (540 mg, 1.70 mmol, 1.00 eq.) and NH$_2$NH$_2$.H$_2$O (320 mg, 6.40 mmol, 3.00 eq.) in ethanol (15 mL) was stirred overnight at room temperature. The solids were filtered out and then concentrated under vacuum. This resulted in 378 mg (crude) of trans-3-(1H-1,3-benzodiazol-1-yl)cyclobutan-1-amine as a brown solid. LC-MS (ES, m/z): [M+H]$^+$=188.1.

Step 7: 5-phenyl-N-[trans-3-(1H-1,3-benzodiazol-1-yl)cyclobutyl]isoxazole-3-carboxamide 5-phenylisoxazole-3-carboxylic acid (374 mg, 1.98 mmol, 1.00 eq.), HATU (902 mg, 2.37 mmol, 1.20 eq.) and DIEA (766 mg, 5.93 mmol, 3.00 eq.) were added to solution of trans-3-(1H-1,3-benzodiazol-1-yl)cyclobutan-1-amine (370 mg, 1.98 mmol, 1.00 eq.) in dichloromethane (5 mL) and the solution was stirred for overnight at room temperature. The reaction was then quenched by the addition of 10 mL of water, extracted with dichloromethane (3×15 mL) and the organic layers combined. The resulting mixture was washed with brine (3×25 mL), dried over anhydrous sodium sulfate and concentrated under vacuum. The crude product was purified by Prep-HPLC with the following conditions (HPLC-10): Column, X Bridge BEH130 Prep C18 OBD Column, 19×150 mm, 5 um 13 nm; mobile phase, Water with 0.05% NH$_4$HCO$_3$ and ACN (37% ACN up to 52% in 8 min); Detector, UV 254 nm. This resulted in 37.2 mg (5%) of 5-phenyl-N-[trans-3-(1H-1,3-benzodiazol-1-yl)cyclobutyl]isoxazole-3-carboxamide as a light yellow solid.

Analytical Data:
LC-MS (ES, m/z): [M+H]$^+$=359.2
HPLC purity: 98.9% at 254 nm
$^1$H NMR (CDCl$_3$, 400 MHz): δ 8.39 (s, 1H), 7.89-7.81 (m, 3H), 7.52-7.50 (m, 3H), 7.48-7.43 (m, 1H), 7.39-7.35 (m, 2H), 7.00 (s, 1H), 5.25-5.21 (m, 1H), 4.81-4.79 (br, 1H), 3.17-3.10 (m, 2H), 2.98-2.95 (m, 2H).

Example 68: N-(trans-3-(5-(1,1-dioxidothietan-3-yl)-1,3,4-oxadiazol-2-yl)cyclobutyl)-5-phenylisoxazole-3-carboxamide

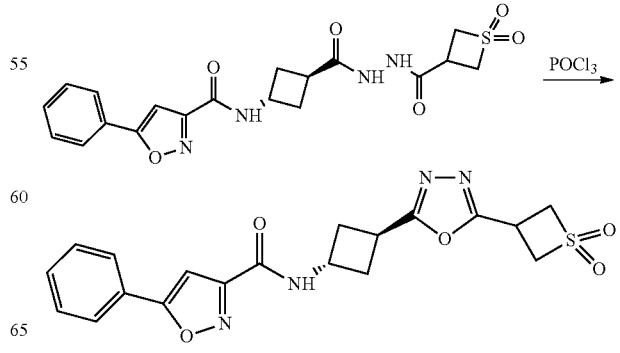

A solution of N-trans-3-(2-(1,1-dioxidothietane-3-carbonyl)hydrazine-1-carbonyl)cyclobutyl)-5-phenylisoxazole-3-carboxamide (170 mg, 0.39 mmol, 1.00 eq., prepared using a similar procedure as shown in example 52) in POCl$_3$ (5 mL, 1.00 eq.) was stirred for 3 hours at 100° C. The reaction was then quenched by the addition of sodium bicarbonate/ice, extracted with ethyl acetate and the organic layers combined. The resulting mixture was washed with sodium bicarbonate aqueous (1×50 mL), dried over anhydrous sodium sulfate and concentrated under vacuum. The crude product was purified by Prep-HPLC with the following conditions (HPLC-10): Column, XBridge BEH130 Prep C18 OBD Column, 19*150 mm, 5 um 13 nm; mobile phase, Water with NH$_4$HCO$_3$ (50 mmol/L) and ACN (40.0% ACN up to 55.0% in 12 min); Detector, UV 254 nm. This resulted in 54 mg (33%) of N-(trans-3-(5-(1,1-dioxidothietan-3-yl)-1,3,4-oxadiazol-2-yl)cyclobutyl)-5-phenylisoxazole-3-carboxamide as a white solid.

Analytical Data:
LC-MS (ES, m/z): [M+H]$^+$=415.1
HPLC purity: 98.3% at 254 nm
$^1$H NMR (DMSO-d$_6$, 400 MHz): δ 9.32-9.30 (d, J=7.6 Hz, 1H), 7.96-7.93 (m, 2H), 7.57-7.55 (m, 3H), 7.38 (s, 1H), 4.76-4.69 (m, 5H), 4.22-4.19 (m, 1H), 3.75-3.71 (m, 1H), 2.70-2.66 (m, 4H).

Example 69: N-(3-(4-(hydroxymethyl)-1H-1,2,3-triazol-1-yl)cyclopentyl)-5-phenylisoxazole-3-carboxamide and N-(3-(5-(hydroxymethyl)-1H-1,2,3-triazol-1-yl)cyclopentyl)-5-phenylisoxazole-3-carboxamide Step 1: tert-butyl N-(3-azidocyclopentyl)carbamate DIAD (1.5 g, 7.43 mmol, 1.50 eq.) was added dropwise to a solution of triphenylphosphine (1.972 g, 7.52 mmol, 1.50 eq.) in tetrahydrofuran (50 mL) at 10° C. in 5 min. The resulting solution was stirred for 20 min at 10° C. and then added DPPA (1.65 g, 6.00 mmol, 1.20 eq.), and a solution of tert-butyl N-(3-hydroxycyclopentyl)carbamate (1 g, 4.97 mmol, 1.00 eq.) in tetrahydrofuran (20 mL). The mixture was stirred for 1 hour at 25° C., and then diluted with 100 mL of H$_2$O. The resulting solution was extracted with ethyl acetate (2×100 mL) and the organic layers combined, washed with brine (2×100 mL), dried over anhydrous sodium sulfate and concentrated under vacuum. The residue was applied onto a silica gel column with ethyl acetate/petroleum ether (1:20) to give 785 mg (70%) of tert-butyl N-(3-azidocyclopentyl)carbamate as yellow oil.

Step 2: tert-butyl N-[3-[5-(hydroxymethyl)-1H-1,2,3-triazol-1-yl]cyclopentyl]carbamate and tert-butyl N-[3-[4-(hydroxymethyl)-1H-1,2,3-triazol-1-yl]cyclopentyl]carbamate a solution of tert-butyl N-(3-azidocyclopentyl)carbamate (785 mg, 3.47 mmol, 1.00 eq.) and prop-2-yn-1-ol (387 mg, 6.90 mmol, 2.00 eq.) in DMF (5 mL) was stirred for 16 hours at 100° C. The resulting mixture was concentrated under vacuum. The residue was applied onto a silica gel column with ethyl acetate/petroleum ether (2:1) to give 620 mg (63%) of a mixture of tert-butyl N-[3-[5-(hydroxymethyl)-1H-1,2,3-triazol-1-yl]cyclopentyl]carbamate and tert-butyl

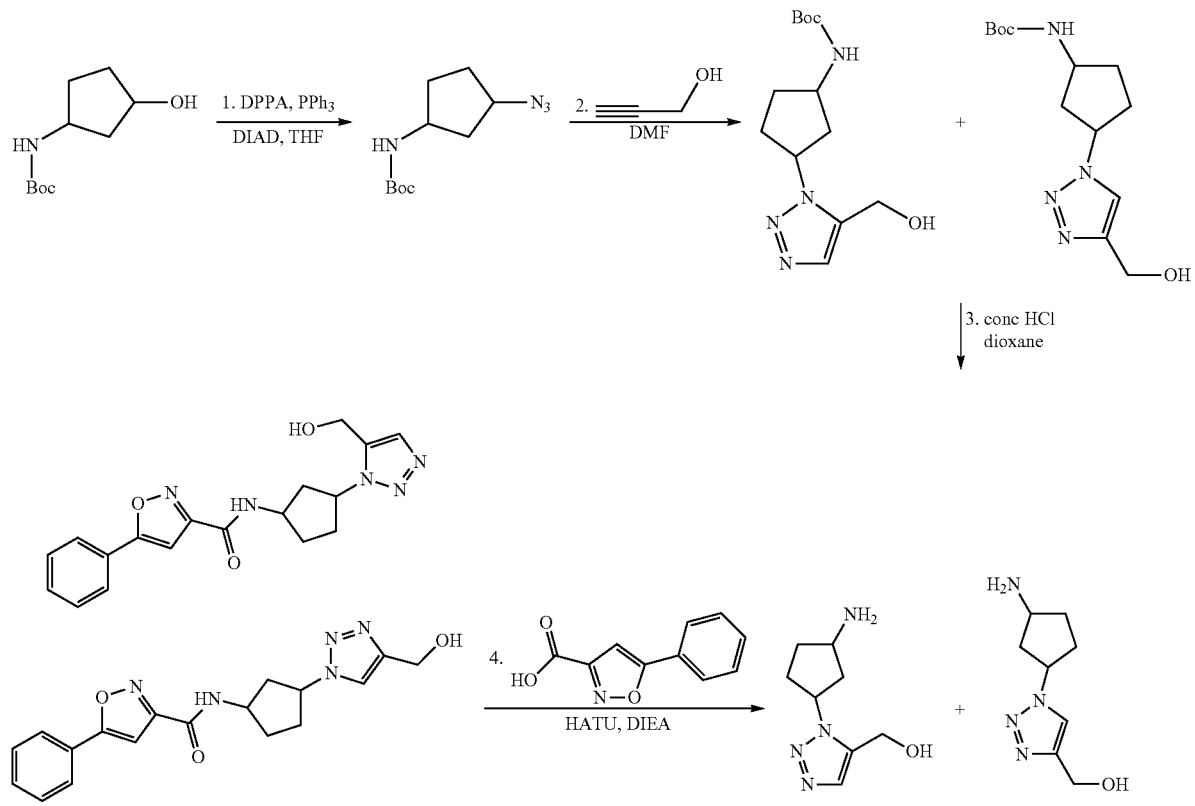

N-[3-[4-(hydroxymethyl)-1H-1,2,3-triazol-1-yl]cyclopentyl]carbamate as a yellow oil. LC-MS (ES, m/z): [M+H]+=283.2

Step 3: [1-(3-aminocyclopentyl)-1H-1,2,3-triazol-5-yl]methanol and [1-(3-aminocyclopentyl)-1H-1,2,3-triazol-4-yl]methanol concentrated hydrogen chloride (3 mL) was added to a solution of the mixture of tert-butyl N-[3-[5-(hydroxymethyl)-1H-1,2,3-triazol-1-yl]cyclopentyl]carbamate and tert-butyl N-[3-[4-(hydroxymethyl)-1H-1,2,3-triazol-1-yl]cyclopentyl]carbamate (620 mg, 2.20 mmol, 1.00 eq.) in 1,4-dioxane (10 mL) and the mixture was stirred for 3 hours at 25° C. The mixture was concentrated under vacuum. This resulted in 600 mg (crude) of a mixture of [1-(3-aminocyclopentyl)-1H-1,2,3-triazol-5-yl]methanol and [1-(3-aminocyclopentyl)-1H-1,2,3-triazol-4-yl]methanol as yellow oil. LC-MS (ES, m/z): [M+H]+=183.1.

Step 4: N-[3-[5-(hydroxymethyl)-1H-1,2,3-triazol-1-yl]cyclopentyl]-5-phenylisoxazole-3-carboxamide and N-[3-[4-(hydroxymethyl)-1H-1,2,3-triazol-1-yl]cyclopentyl]-5-phenylisoxazole-3-carboxamide

[1-(3-aminocyclopentyl)-1H-1,2,3-triazol-5-yl]methanol and [1-(3-aminocyclopentyl)-1H-1,2,3-triazol-4-yl]methanol (327 mg, 1.8 mmol, 1.20 eq.) were added to a solution of 5-phenylisoxazole-3-carboxylic acid (285 mg, 1.50 mmol, 1.00 eq.), HATU (855 mg, 2.25 mmol, 1.50 eq.) and DIEA (580 mg, 4.49 mmol, 3.00 eq.) in dichloromethane (10 mL) and the mixture was stirred for 3 hours at 25° C. The resulting solution was diluted with 100 mL of H$_2$O, extracted with ethyl acetate (2×100 mL) and the organic layers combined. The resulting mixture was washed with brine (2×100 mL), dried over anhydrous sodium sulfate and concentrated under vacuum. The crude product was purified by Prep-TLC (petroleum ether/ethyl acetate=1:2). This resulted in 54.2 mg (10%) of N-[3-[5-(hydroxymethyl)-1H-1,2,3-triazol-1-yl]cyclopentyl]-5-phenylisoxazole-3-carboxamide as a light yellow solid and 124.4 mg (23%) of N-[3-[4-(hydroxymethyl)-1H-1,2,3-triazol-1-yl]cyclopentyl]-5-phenylisoxazole-3-carboxamide as a white solid.

Analytical Data:
N-[3-[5-(hydroxymethyl)-1H-1,2,3-triazol-1-yl]cyclopentyl]-5-phenylisoxazole-3-carboxamide
LC-MS (ES, m/z): [M+H]+=354.3
$^1$H NMR (400 MHz, DMSO-d$_6$) δ 9.03-9.02 (d, J=7.6 Hz, 1H), 7.95-7.92 (m, 2H), 7.59-7.52 (m, 4H), 7.38 (s, 1H), 5.48-5.45 (t, J=5.6 Hz, 1H), 5.03-4.96 (m, 1H), 4.62-4.60 (d, J=5.6 Hz, 2H), 4.49-4.43 (q, J=7.6 Hz, 1H), 2.60-2.57 (m, 1H), 2.26-2.21 (m, 3H), 2.14-2.04 (m, 1H), 2.00-1.93 (m, 1H).

N-[3-[4-(hydroxymethyl)-1H-1,2,3-triazol-1-yl]cyclopentyl]-5-phenylisoxazole-3-carboxamide
LC-MS (ES, m/z): [M+H]+=354.3
$^1$H NMR (400 MHz, DMSO-d$_6$) δ 9.06 (d, J=7.8 Hz, 1H), 8.10 (s, 1H), 7.97-7.92 (m, 2H), 7.63-7.52 (m, 3H), 7.39 (s, 1H), 5.19 (t, J=5.6 Hz, 1H), 5.03 (q, J=7.6 Hz, 1H), 4.53 (d, J=5.7 Hz, 2H), 4.47 (q, J=7.6 Hz, 1H), 2.64 (dd, J=14.3, 6.7 Hz, 1H), 2.29-1.86 (m, 5H).

Example 70

Compounds A-T below are prepared using one or more of the above procedures"

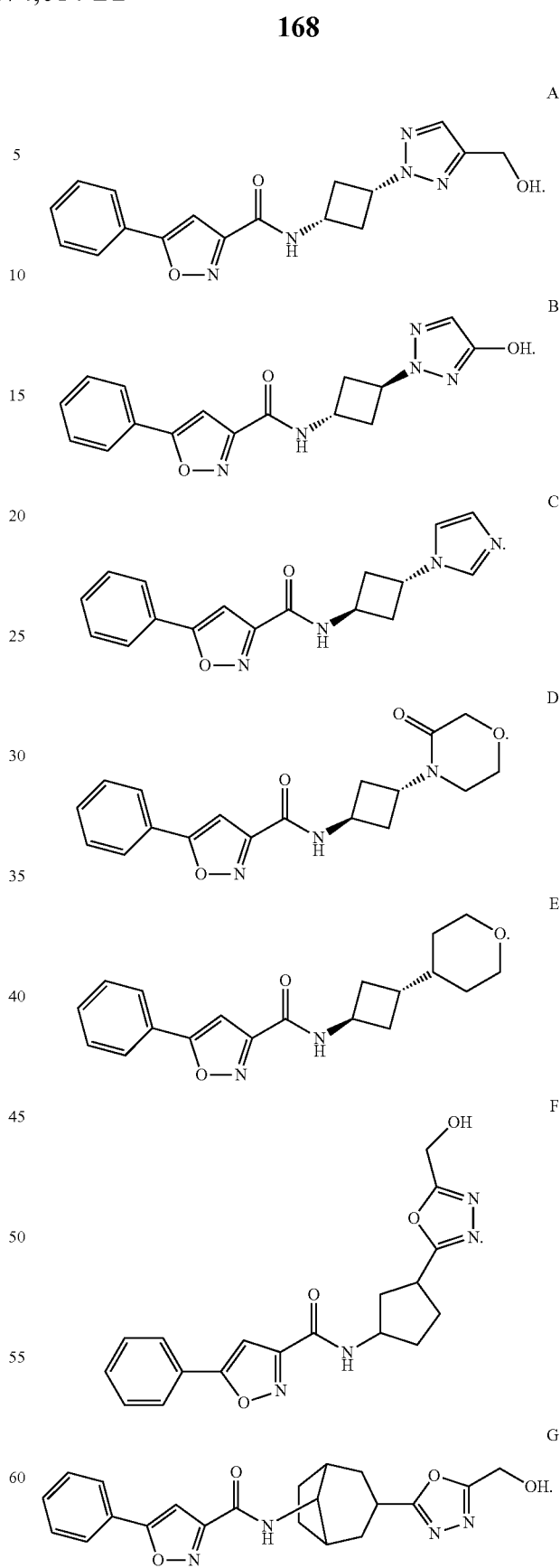

169
-continued
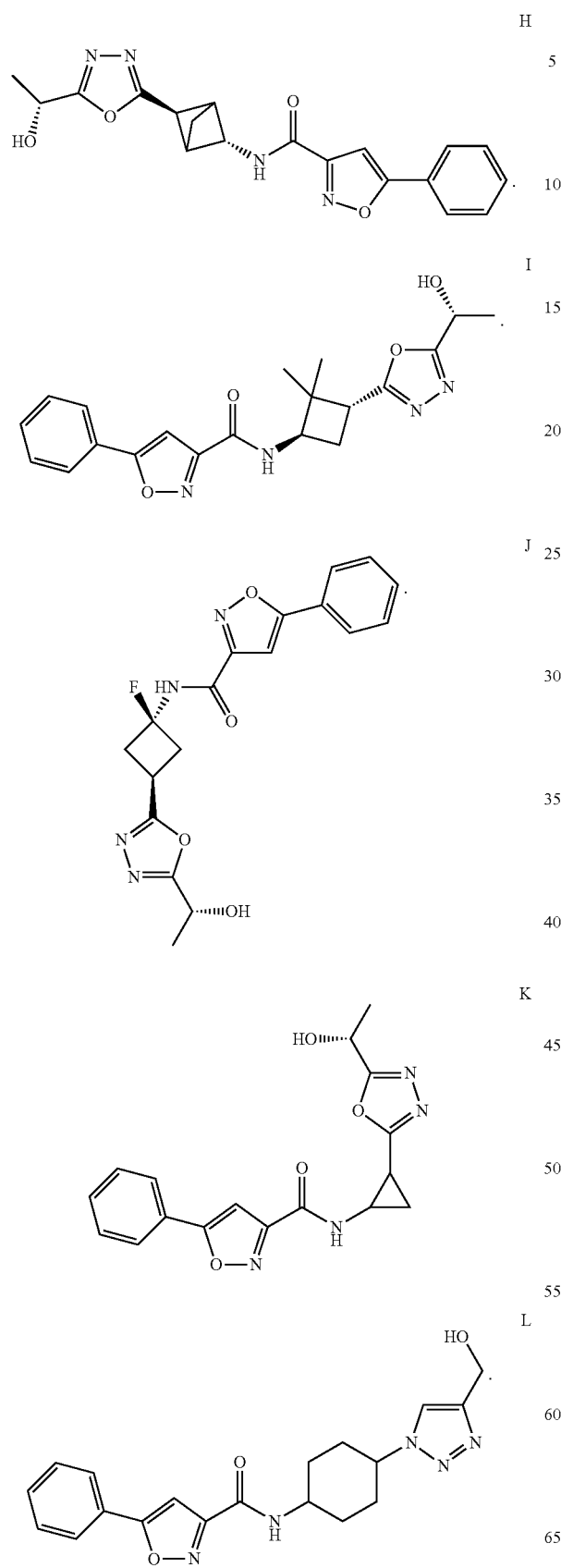
170
-continued
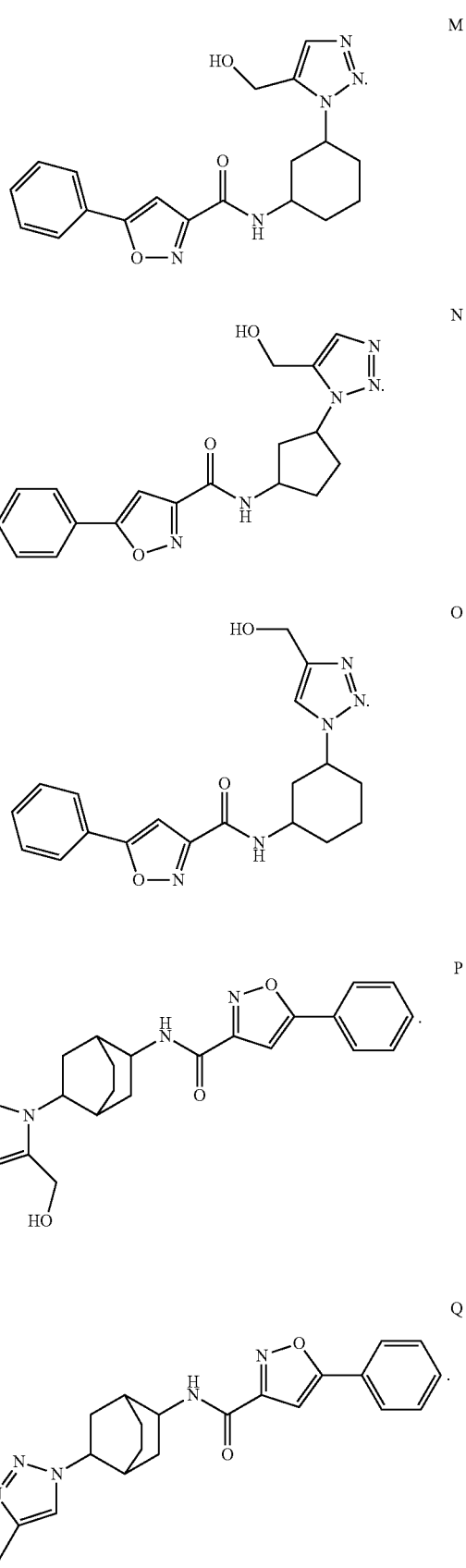

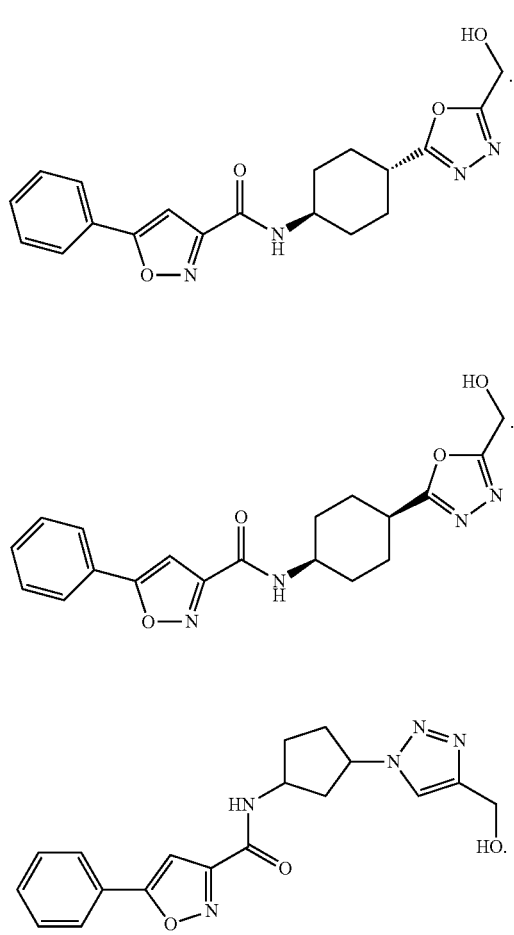

Example 71: CFTR Activity Assays i. Ussing Measurements

As discussed above, Ussing measurements can be used to measure CFTR activity. In this method, primary lung epithelial cells (hBEs) homozygous for the Cystic Fibrosis-causing ΔF508 mutation were differentiated for a minimum of 4 weeks in an air-liquid interface on SnapWell filter plates prior to the Ussing measurements. Cells were apically mucus-washed for 30 minutes prior to treatment with compounds. The basolateral media was removed and replaced with media containing the compound of interest diluted to its final concentration from DMSO stocks. Treated cells were incubated at 37° C. and 5% $CO_2$ for 24 hours. At the end of the treatment period, the cells on filters were transferred to the Ussing chamber and equilibrated for 30 minutes. The short-circuit current was measured in voltage clamp-mode ($V_{hold}$=0 mV), and the entire assay was conducted at a temperature of 36° C.-36.5° C. Once the voltages stabilized, the chambers were clamped, and data was recorded by pulse readings every 5 seconds. Following baseline current stabilization, the following additions were applied and the changes in current and resistance of the cells was monitored:
1. Benzamil to the apical chamber to inhibit ENaC sodium channel 2. Forskolin to both chambers to activate ΔF508-CFTR by phosphorylation.

3. Genistein to both chambers to potentiate ΔF508-CFTR channel opening.

4. CFTRinh-172 to the apical chamber to inhibit ΔF508-CFTR Cl-conductance.

The inhabitable current (that current that is blocked by CFTRinh-172) is measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation were differentiated for a minimum of 4 weeks in an air-liquid interface on Costar 24 well HTS filter plates prior to the equivalent current (Ieq) measurements. Cells were apically mucus-washed for 30 minutes 24 h prior to treatment with compounds. The basolateral media was removed and replaced with media containing the compound of interest diluted to its final concentration from DMSO stocks. Treated cells were incubated at 37° C. and 5% $CO_2$ for 24 hours. At the end of the treatment period, the media was changed to the Ieq experimental solution for 30 minutes before the experiment and plates are maintained in a $CO_2$-free incubator during this period. The plates containing the cells were then placed in pre-warmed heating blocks at 36° C.±0.5 for 15 minutes before measurements are taken. The transepithelial voltage ($V_T$) and conductance ($G_T$) were measured using a custom 24 channel current clamp (TECC-24) with 24 well electrode manifold. The Ieq assay measurements were made following additions with standardized time periods:

1. The baseline $V_T$ and $G_T$ values were measured for approximately 20 minutes.

2. Benzamil was added to block ENaC for 15 minutes.

3. Forskolin plus VX-770 (ivacaftor) were added to maximally activate ΔF508-CFTR for 27 minutes.

4. Bumetanide was added to inhibit the $NaK_2Cl$ cotransporter and shut-off secretion of chloride.

The activity data captured was the area under the curve (AUC) for the traces of the equivalent chloride current. The AUC was collected from the time of the forskolin/VX-770 addition until the inhibition by bumetanide addition. Correction in response to compound treatment was scored as the increase in the AUC for compound-treated samples over that of vehicle-treated samples.

The results are shown below in Table A. (** indicates activity ≥200% of VX-809 (1 uM) with compound at 10 uM and VX-809 at 1 uM; * indicates activity 100-200% of VX-809 (1 uM) with compound at 10 uM and VX-809 at 1 uM. ## indicates activity ≥200% of VX-809 (3 uM) with compound at 10 uM and VX-809 at 3 uM; # indicates activity 100-200% of VX-809 (3 uM) with compound at 10 uM and VX-809 at 3 uM.

TABLE A

| Structure | Ieq (% VX-809) | Ussing (% VX-809) |
|---|---|---|
| | ++ * | ## |
| | ** | # |
| | ** | ## |
| | ++ * | ## |
| | ** | |
| | ** | |
| | ** | ## |
| | ** | ## |

TABLE A-continued

| Structure | Ieq (% VX-809) | Ussing (% VX-809) |
|---|---|---|
| | ** | ## |
| | ** | ## |
| | ** | |
| | ** | ## |
| | ** | ## |
| | ** | ## |
| | ** | ## |

TABLE A-continued
| Structure | Ieq (% VX-809) | Ussing (% VX-809) |
|---|---|---|
| 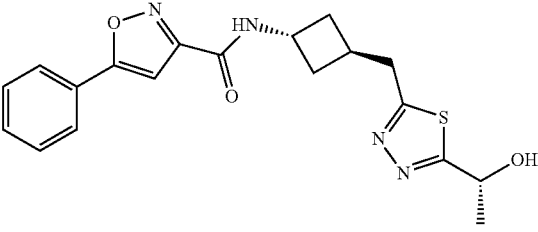 | ** | ## |
| 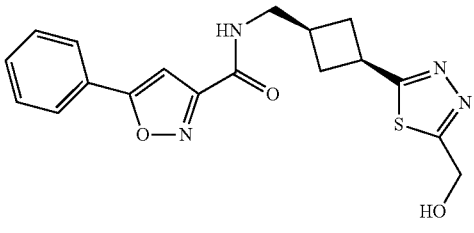 [SMILES: O=C(NC[C@H]1C[C@@H](c2nnc(CO)s2)C1)c1cc(-c2ccccc2)on1] | ** | |
| 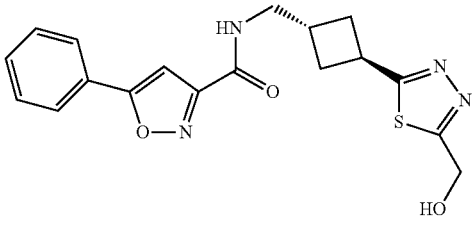 [SMILES: O=C(NC[C@H]1C[C@H](c2nnc(CO)s2)C1)c1cc(-c2ccccc2)on1] | ** | |
| 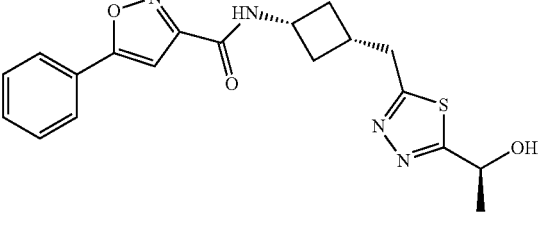 | ** | |
| 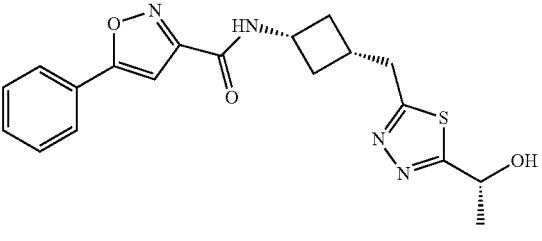 [SMILES: C[C@@H](O)c1nnc(C[C@H]2C[C@@H](NC(=O)c3cc(-c4ccccc4)on3)C2)s1] | ** | |
| 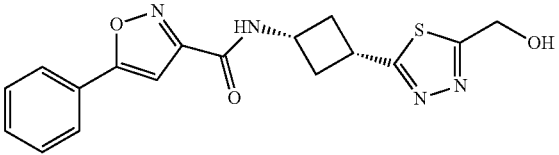 [SMILES: O=C(N[C@H]1C[C@@H](c2nnc(CO)s2)C1)c1cc(-c2ccccc2)on1] | ** | ## |
| 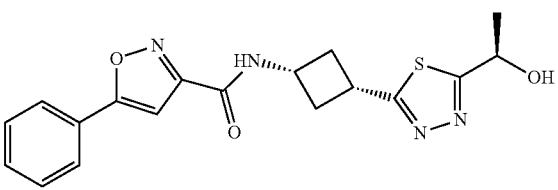 [SMILES: C[C@@H](O)c1nnc([C@H]2C[C@@H](NC(=O)c3cc(-c4ccccc4)on3)C2)o1] | ** | ## |

TABLE A-continued

| Structure | Ieq (% VX-809) | Ussing (% VX-809) |
|---|---|---|
| | ** | ## |
| | ** | ## |
| | ** | ## |
| | ** | ## |
| | | ## |
| | ** | ## |
| | ** | ## |
| | ** | ## |

TABLE A-continued

| Structure | Ieq (% VX-809) | Ussing (% VX-809) |
|---|---|---|
| (structure) | ** | ## |
| (structure) | ** | ## |
| (structure) | ** | |
| (structure) | ** | |
| (structure) | * | |
| (structure) | ** | |
| (structure) | ** | |
| (structure) | ** | |

TABLE A-continued

| Structure | Ieq (% VX-809) | Ussing (% VX-809) |
|---|---|---|
| [phenyl-isoxazole-C(O)NH-cyclobutyl-pyrazole-CH2OH] | ** | |
| [phenyl-isoxazole-C(O)NH-cyclobutyl-pyrazole-CH(CH3)OH] | ** | |
| [phenyl-isoxazole-C(O)NH-cyclobutyl-pyrazole-CH(CH3)OH] | ** | |
| [phenyl-isoxazole-C(O)NH-cyclobutyl-pyrazole-CH2OH] | ** | |
| [phenyl-isoxazole-C(O)NH-cyclobutyl-oxadiazole-CH2OH] | ** | |
| [phenyl-isoxazole-C(O)NH-cyclobutyl-triazole-CH2-O-C(O)-NH-butyl] | ## | |
| [phenyl-isoxazole-C(O)NH-cyclobutyl-triazole-CH2-O-C(O)-NH-butyl] | ## | |
| [phenyl-isoxazole-C(O)NH-cyclobutyl-oxadiazole-CH(CH3)OH] | * | |

TABLE A-continued

| Structure | Ieq (% VX-809) | Ussing (% VX-809) |
|---|---|---|
| | * | |
| | | |
| | ** | ## |
| | ** | |
| | ** | |
| | ** | ## |
| | | |
| | * | |

TABLE A-continued

| Structure | Ieq (% VX-809) | Ussing (% VX-809) |
|---|---|---|
| (phenyl-isoxazole-C(O)NH-cyclobutyl-[1,2,4-oxadiazole]-CH(OH)CH₃) | * | |
| (phenyl-isoxazole-C(O)NH-cyclobutyl-[1,2,4-oxadiazole]-CH₂OH) | ** | ## |
| (phenyl-isoxazole-C(O)NH-cyclobutyl-CH₂CH₂OH) | ** | |
| (phenyl-isoxazole-C(O)NH-cyclobutyl-CH₂CH₂OH) | ** | |
| (phenyl-isoxazole-C(O)NH-cyclobutyl-CH₂-NHS(O)₂CH₃) | * | |
| (phenyl-isoxazole-C(O)NH-cyclobutyl-CH₂-[1,3,4-oxadiazole]-CH(OH)CH₃) | ** | ## |
| (phenyl-isoxazole-C(O)NH-cyclobutyl-CH₂-[1,3,4-oxadiazole]-CH(OH)CH₃) | ** | |

TABLE A-continued

| Structure | Ieq (% VX-809) | Ussing (% VX-809) |
|---|---|---|
| | ** | |
| | * | |
| | ## | |
| | * | |
| | * | |
| | * | |
| | * | ## |
| | * | |
| | * | |

TABLE A-continued

| Structure | Ieq (% VX-809) | Ussing (% VX-809) |
|---|---|---|
| | * | |
| | * | |
| | ** | |
| | * | |
| | * | ## |
| | | ## |
| | ** | |
| | * | |

TABLE A-continued

| Structure | Ieq (% VX-809) | Ussing (% VX-809) |
|---|---|---|
| [structure] | | ## |
| [structure] | | ## |
| [structure] | | |
| [structure] | | |
| [structure] | | |
| [structure] | | ## |
| [structure] | | # |
| [structure] | | ## |
| [structure] | | # |

TABLE A-continued
| Structure | Ieq (% VX-809) | Ussing (% VX-809) |
|---|---|---|
| 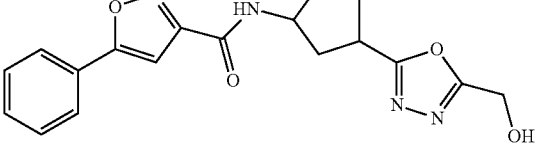 | | # |
| 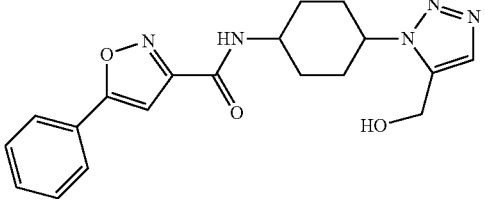 | | # |
| 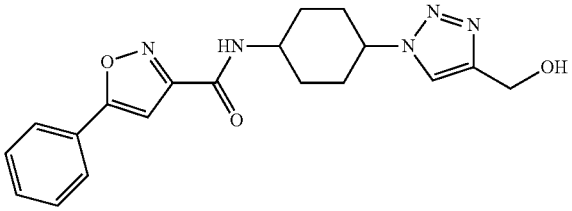 [SMILES: O=C(NC1CCC(n2cc(CO)nn2)CC1)c1cc(-c2ccccc2)on1] | | # |
| 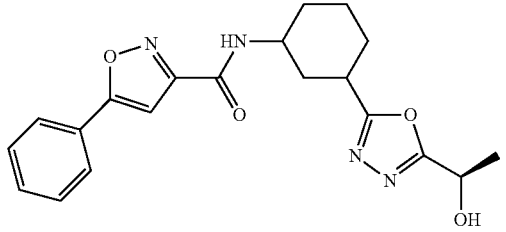 [SMILES: C[C@@H](O)c1nnc(C2CCCC(NC(=O)c3cc(-c4ccccc4)on3)C2)o1] | | * |
| 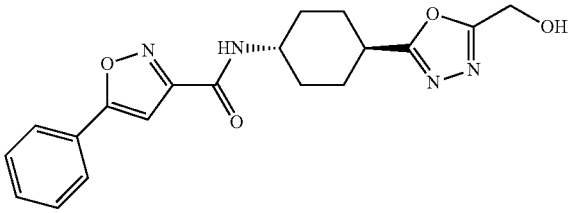 [SMILES: O=C(N[C@H]1CC[C@H](c2nnc(CO)o2)CC1)c1cc(-c2ccccc2)on1] | | |
| 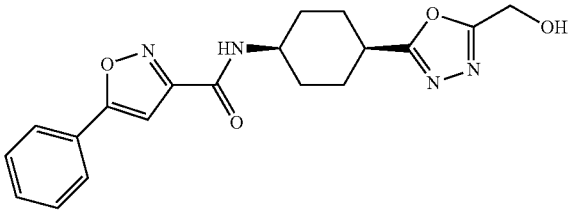 [SMILES: O=C(N[C@H]1CC[C@@H](c2nnc(CO)o2)CC1)c1cc(-c2ccccc2)on1] | | * |
| 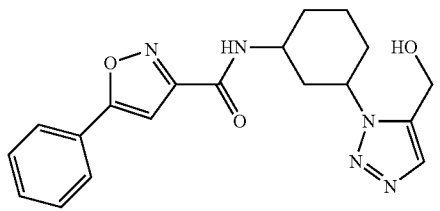 [SMILES: O=C(NC1CCCC(n2nncc2CO)C1)c1cc(-c2ccccc2)on1] | | |

TABLE A-continued

| Structure | Ieq (% VX-809) | Ussing (% VX-809) |
|---|---|---|
| | * | |

Example 72 i. Ussing Measurements

As discussed above, Ussing measurements can be used to measure CFTR activity. In this method, primary lung epithelial cells (hBEs) with a Cystic fibrosis causing class I mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO or aqueous stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data are recorded by pulse readings every 5 seconds. Following baseline current stabilization, the following additions are applied and the changes in current and resistance of the cells are monitored:

1. Benzamil to the apical chamber to inhibit ENaC sodium channel
2. Forskolin to both chambers to activate ΔF508-CFTR by phosphorylation.
3. Ivacaftor or Genistein to the apical chamber to potentiate ΔF508-CFTR channel opening.

4. CFTRinh-172 to the apical chamber to inhibit ΔF508-CFTR Cl-conductance.

The forskolin-sensitive current and inhabitable current (that potentiated current that is blocked by CFTRinh-172) are measured as the specific activity of the ΔF508-CFTR channel, and increase in response to compound in this activity over that observed in vehicle-treated samples are identified as the correction of ΔF508-CFTR function imparted by the compound tested.

Example 73 i. Ussing Measurements

As discussed above, Ussing measurements can be used to measure CFTR activity. In this method, primary lung epithelial cells (hBEs) with a Cystic Fibrosis-causing class III mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data is recorded by pulse readings every 5 seconds. Following baseline current stabilization, the following additions are applied and the changes in current and resistance of the cells is monitored:

1. Benzamil to the apical chamber to inhibit ENaC sodium channel.
2. Forskolin to both chambers to activate ΔF508-CFTR by phosphorylation.
3. VX-770 or Genistein to the apical chamber to potentiate ΔF508-CFTR channel opening.
4. CFTRinh-172 to the apical chamber to inhibit ΔF508-CFTR Cl-conductance.

The forskolin-sensitive current and inhabitable current (that potentiated current that is blocked by CFTRinh-172) are measured as the specific activity of the ΔF508-CFTR channel, and increase in response to compound in this activity over that observed in vehicle-treated samples are identified as the correction of ΔF508-CFTR function imparted by the compound tested.

Example 74 i. Ussing Measurements

As discussed above, Ussing measurements can be used to measure CFTR activity. In this method, primary lung epithelial cells (hBEs) with a Cystic Fibrosis-causing class V mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data is recorded by pulse readings every 5 seconds. Following baseline current stabilization, the following additions are applied and the changes in current and resistance of the cells is monitored:

1. Benzamil to the apical chamber to inhibit ENaC sodium channel
2. Forskolin to both chambers to activate ΔF508-CFTR by phosphorylation.
3. VX-770 or Genistiein to the apical chamber to potentiate ΔF508-CFTR channel opening.
4. CFTRinh-172 to the apical chamber to inhibit ΔF508-CFTR Cl-conductance.

The forskolin-sensitive current and inhabitable current (that potentiated current that is blocked by CFTRinh-172) are measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation are differentiated for a minimum of 4 weeks in an air-liquid interface on Costar 24 well HTS filter plates prior to the equivalent current (Ieq) measurements. Cells are apically mucus-washed for 30 minutes 24 h prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the media is changed to the Ieq experimental solution for 30 minutes before the experiment and plates are maintained in a $CO_2$-free incubator during this period. The plates containing the cells are then placed in pre-warmed heating blocks at 36° C.±0.5 for 15 minutes before measurements are taken. The transepithelial voltage ($V_T$) and conductance ($G_T$) are measured using a custom 24 channel current clamp (TECC-24) with 24 well electrode manifold. The Ieq assay measurements are made following additions with standardized time periods:

1. The baseline $V_T$ and $G_T$ values are measured for approximately 20 minutes.
2. Benzamil is added to block ENaC for 15 minutes.
3. Forskolin plus VX-770 (ivacaftor) are added to maximally activate ΔF508-CFTR for 27 minutes.
4. Bumetanide is added to inhibit the $NaK_2Cl$ cotransporter and shut-off secretion of chloride.

The activity data captured is the area under the curve (AUC) for the traces of the equivalent chloride current. The AUC is collected from the time of the forskolin/VX-770 addition until the inhibition by bumetanide addition. Correction in response to compound treatment is scored as the increase in the AUC for compound-treated samples over that of vehicle-treated samples.

While this invention has been particularly shown and described with references to preferred embodiments thereof, it will be understood by those skilled in the art that various changes in form and details may be made therein without departing from the scope of the invention encompassed by the appended claims.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:
1. A compound represented by:

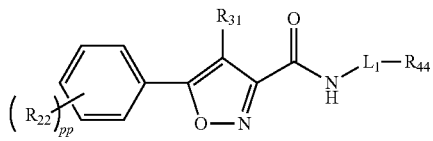

and pharmaceutically acceptable salts and stereoisomers thereof, wherein:
$R_{22}$ is selected independently for each occurrence from the group consisting of H and F;
pp is 0, 1, 2 or 3;
$R_{31}$ is selected from the group consisting of hydrogen, halogen, and $C_{1-4}$alkyl;
$L_1$ is selected from the group consisting of —$C_1$alkylene-$C_4$cycloalkylene, $C_4$cycloalkylene, and $C_4$cycloalkylene-$C_1$alkylene-, wherein $L_1$ may be optionally substituted by one, two or three substituents selected from the group consisting of halogen, hydroxyl, and $C_{1-3}$alkyl (optionally substituted by one, two or three substituents each selected independently from $R_{ff}$);
$R_{44}$ is selected from the group consisting of $C_{1-3}$alkyl, 4 to 6 membered heterocycloalkyl, a 5-6 membered monocyclic heteroaryl, and a 9-10 membered bicyclic heteroaryl, wherein the heteroaryl has one, two or three heteroatoms each selected from O, N, and S; and wherein the heteroaryl or heterocycloalkyl may be optionally substituted by one or two substituents each selected independently from $R_{gg}$;
$R_{ff}$ is selected for each occurrence from group consisting of halogen, hydroxyl, $C_{1-4}$alkyl, $C_{1-4}$alkyoxy, $C_{2-4}$alkenyl, oxo, —NR'R", —NR'—S(O)$_w$—$C_{1-3}$alkyl, S(O)$_w$—NR'R", and —S(O)$_w$—$C_{1-3}$alkyl, where w is 0, 1, or 2, wherein $C_{1-4}$alkyl, $C_{1-4}$alkyoxy, and $C_{2-4}$alkenyl may be optionally substituted by one, two or three substituents each independently selected from the group consisting of halogen, hydroxyl, —NR'R", —NR'—S(O)$_w$—$C_{1-3}$alkyl, S(O)$_w$—NR'R", and —S(O)$_w$—$C_{1-3}$alkyl;

$R_{gg}$ is selected for each occurrence from group consisting of halogen, hydroxyl, $C_{1-6}$alkyl, $C_{1-6}$alkoxy, $C_{2-6}$alkenyl, $C_{3-6}$cycloalkyl, —O—C(O)—$C_{1-6}$alkyl, —C(O)—O—$C_{1-6}$alkyl, —C(O)—O— phenyl, —O—C(O)-phenyl, phenyl, 4 to 6 membered heterocycloalkyl, —NR'R", oxo, —NR'—S(O)$_w$—$C_{1-3}$alkyl, S(O)$_w$—NR'R", and —S(O)$_w$—$C_{1-3}$alkyl, where w is 0, 1, or 2, wherein $C_{1-6}$alkyl, $C_{1-6}$alkyoxy, $C_{2-6}$alkenyl $C_{3-6}$cycloalkyl, phenyl and heterocycloalkyl may each be optionally substituted by one, two or three substituents each independently selected from the group consisting of halogen, $C_{1-6}$alkyl, $C_{1-6}$alkoxy, hydroxyl, C(O)OH, —C(O)OC$_{1-6}$alkyl, —O—C(O)C$_{1-6}$alkyl, O—C(O)-phenyl, —C(O)O—NR'—$C_{1-6}$alkyl, —O—$C_{3-6}$cycloalkyl, —O-heterocycle, phenyl, —O-heteroaryl, —O-phenyl, —NR'R", —NR'—S(O)$_w$—$C_{1-3}$alkyl, S(O)$_w$—NR'R", and —S(O)$_w$—$C_{1-3}$alkyl, where w is 0, 1, or 2; and R' and R" are each independently selected for each occurrence from H and $C_{1-4}$alkyl or taken together with the nitrogen to which they are attached form a heterocyclic ring.

2. The compound of claim 1, wherein $L_1$ is $C_4$cycloalkylene.

3. The compound of claim 1, wherein $L_1$ is substituted by one or two substituents each selected from the group consisting of halogen, hydroxyl, and $C_{1-3}$alkyl.

4. The compound of claim 1, wherein $R_{44}$ is a 5-6 membered monocyclic heteroaryl, optionally substituted by one or two substituents each selected independently from $R_{gg}$.

5. The compound of claim 1, wherein $R_{44}$ is a 9-10 membered bicyclic heteroaryl, optionally substituted by one or two substituents each selected independently from $R_{gg}$.

6. The compound of claim 1, wherein $R_{44}$ is selected from the group consisting of:

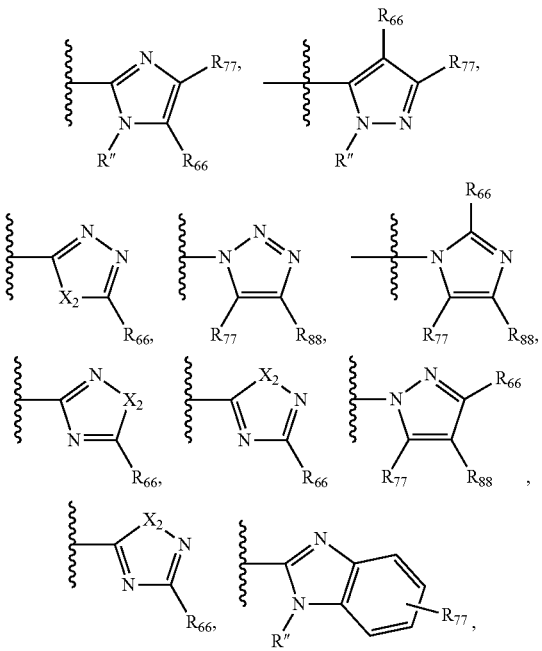

-continued

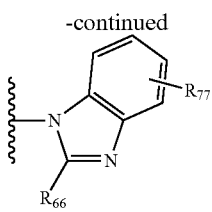

wherein X$_2$ independently for each occurrence is selected from the group consisting of O or S; each R$_{66}$, R$_{77}$ and R$_{88}$ is independently selected for each occurrence from H and R$_{gg}$.

7. The compound of claim 6, wherein R$_{44}$ is represented by:

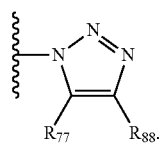

8. The compound of claim 6, wherein R$_{66}$, R$_{77}$ and R$_{88}$ are each independently selected for each occurrence from the group consisting of hydrogen, halogen, hydroxyl, C$_{1-6}$alkyl, C$_{3-6}$cycloalkyl, and heterocycloalkyl, wherein C$_{1-6}$alkyl, C$_{3-6}$cycloalkyl, and heterocycloalkyl are optionally substituted by one, two or three substituents each independently selected from the group consisting of hydroxyl, C$_{1-6}$alkyl, C$_{1-6}$alkoxy, —S(O)$_w$—C$_{1-3}$alkyl (w is 0, 1, or 2) and —NR'S(O)$_2$C$_{1-6}$alkyl; and
R' and R" are each independently selected for each occurrence from H and C$_{1-4}$alkyl.

9. The compound of claim 6, wherein R$_{66}$, R$_{77}$ and R$_{88}$ are each independently selected from the group selected from C$_{1-4}$alkyl, optionally substituted by one or two hydroxyls.

10. The compound of claim 1, wherein R$_{44}$ is heterocycloalkyl.

11. The compound of claim 10, wherein R$_{44}$ is

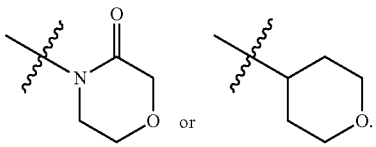 [SMILES: *N1CCOCC1=O ; *C1CCOCC1]

12. The compound of claim 1, where the compound is represented by:

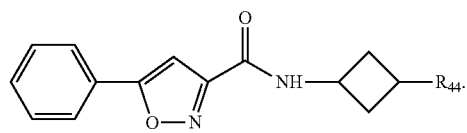

13. The compound of claim 1, wherein R$_{44}$ is a 5-membered heteroaryl having two or three nitrogens.

14. The compound of claim 1, wherein R$_{44}$ is a 5 membered heteroaryl having three nitrogens.

15. The compound of claim 1, wherein R$_{44}$ is a 5 membered heteroaryl having two nitrogens and additional heteroatom selected from O or S.

16. The compound of claim 1, wherein R$_{44}$ is substituted on a free carbon by a substituent selected from the group consisting of: a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy, isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy and isobutyl substituted by one, two or three substituents each selected from halogen, hydroxyl, methoxy and ethoxy.

17. The compound of claim 12, wherein R$_{44}$ is represented by:

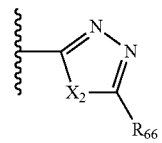

wherein X$_2$ is selected from the group consisting of O or S; and R$_{66}$ is selected from the group consisting of: a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy, isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy, isobutyl substituted by one, two or three substituents each selected from halogen, hydroxyl, methoxy and ethoxy,

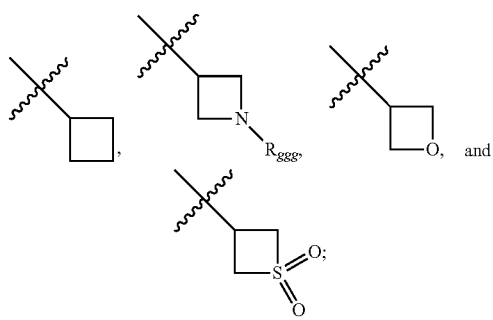

wherein R$_{ggg}$ is selected from the group consisting of H, C$_{1-6}$alkyl, —C(O)OC$_{1-6}$alkyl, and phenyl.

18. The compound of claim 12, wherein $R_{44}$ is represented by:

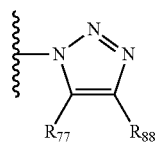

wherein $R_{77}$ and $R_{88}$ are each independently selected from the group consisting of: hydrogen, a methyl substituted by one, two or three substituents each selected from halogen, hydroxyl, methoxy and ethoxy, ethyl substituted by one, two or three substituents each selected from halogen, hydroxyl, methoxy and ethoxy, propyl substituted by one, two or three substituents each selected from halogen, hydroxyl, methoxy and ethoxy, isopropyl substituted by one, two or three substituents each selected from halogen, hydroxyl, methoxy and ethoxy, n-butyl substituted by one, two or three substituents each selected from halogen, hydroxyl, methoxy and ethoxy, t-butyl substituted by one, two or three substituents each selected from halogen, hydroxyl, methoxy and ethoxy, s-butyl substituted by one, two or three substituents each selected from halogen, hydroxyl, methoxy and ethoxy, isobutyl substituted by one, two or three substituents each selected from halogen, hydroxyl, methoxy and ethoxy,

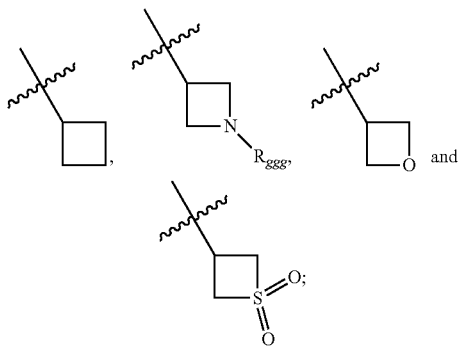

wherein $R_{ggg}$ is selected from the group consisting of H, $C_{1-6}$alkyl, —C(O)OC$_{1-6}$alkyl, and phenyl.

19. A compound having the Formula (IIa) or Formula (IIb):

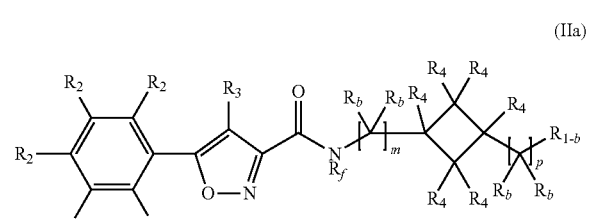

(IIa)

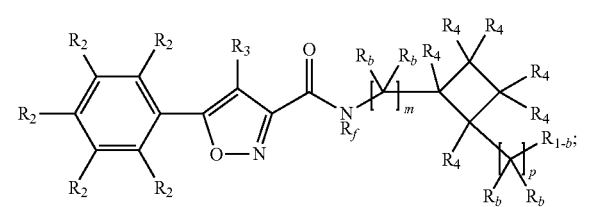

(IIb)

or a pharmaceutically acceptable salt thereof, wherein:

$R_{1-b}$ is selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, phenyl, halo, $OR_e$, $NR_dR_d$, C(O)$OR_c$, $NO_2$, CN, C(O)$R_c$, C(O)C(O)$R_c$, C(O)$NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_nNR_dR_d$, $NR_dS(O)_nR_c$, S(O)$_nR_c$, S(O)$_nNR_dR_d$, OC(O)$OR_c$, (C=NR$_d$)$R_c$, heterocycle and heteroaryl, wherein $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, heterocyclic, phenyl and heteroaryl may each be optionally substituted by one, two or three substituents each independently selected from $R''$;

each $R_2$ is independently selected from the group consisting of hydrogen, halo, CN, and $C_1$-$C_{10}$ alkyl;

$R_3$ is hydrogen or fluoro;

each $R_4$ is independently selected from the group consisting of hydrogen, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, phenyl, halo, $OR_c$, $NR_dR_d$, C(O)$OR_c$, $NO_2$, CN, C(O)$R_c$, C(O)C(O)$R_c$, C(O)$NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_nNR_dR_d$, $NR_dS(O)_nR_c$, S(O)$_nR_c$, S(O)$_nNR_dR_d$, OC(O)$OR_c$, (C=NR$_d$)$R_c$, heterocycle and heteroaryl; alternatively, two geminal $R_4$ groups are taken together with the carbon atom to which they are attached to form a Spiro $C_3$-$C_{12}$ cycloalkyl, a spiro $C_3$-$C_{12}$ cycloalkenyl, a spiro heterocyclic, a spiro aryl or spiro heteroaryl; or yet alternatively, two vicinal $R_4$ groups are taken together with the carbon atoms to which they are attached to form a fused, cyclic group selected from the group consisting of $C_4$-$C_8$ cycloalkyl, $C_4$-$C_8$ cycloalkenyl, 4- to 8-membered heterocyclic, phenyl and heteroaryl, or further alternatively, two $R_4$ groups attached to non-adjacent carbon atoms are taken together with the carbon atoms to which they are attached to form a bridged cyclic group selected from the group consisting of $C_4$-$C_8$ cycloalkyl, $C_4$-$C_8$ cycloalkenyl, and 4- to 8-membered heterocyclic;

each $R_b$ is independently selected from the group consisting of hydrogen, halo, $C_1$-$C_{10}$ alkyl (optionally substituted by one, two, or three substituents selected from halogen and hydroxyl) and $C_3$-$C_6$ cycloalkyl (optionally substituted by one, two, or three substituents selected from halogen and hydroxyl), or two geminal $R_b$ groups are independently taken together with the carbon atom to which they are attached to form a heterocyclic or a heteroaryl;

each $R_c$ is independently selected from the group consisting of hydrogen, $C_1$-$C_{10}$ alkyl(optionally substituted by one, two, or three substituents selected from halogen and hydroxyl), $C_2$-$C_{10}$ alkenyl(optionally substituted by one, two, or three substituents selected from halogen and hydroxyl), $C_2$-$C_{10}$ alkynyl(optionally substituted by one, two, or three substituents selected from halogen and hydroxyl), $C_3$-$C_{12}$ cycloalkyl(optionally substituted by one, two, or three substituents selected from halogen and hydroxyl), $C_3$-$C_{12}$ cycloalkenyl (optionally substituted by one, two, or three substituents selected from halogen and hydroxyl), phenyl(optionally substituted by one, two, or three substituents selected from halogen and hydroxyl) and heteroaryl (optionally substituted by one, two, or three substituents selected from halogen and hydroxyl);

each $R_d$ is independently selected from the group consisting of hydrogen, $C_1$-$C_{10}$ alkyl(optionally substituted by one, two, or three halogens), $C_2$-$C_{10}$ alkenyl, $C_2$-$C_{10}$ alkynyl, $C_1$-$C_{10}$ alkoxy, $C_3$-$C_{12}$ cycloalkyl, $C_3$-$C_{12}$ cycloalkenyl, heterocyclic, phenyl and heteroaryl; or two geminal R$_d$ groups are taken together with the nitrogen atom to which they are attached to form an heterocyclic or an heteroaryl;

R$_e$ is selected from the group consisting of optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{12}$ cycloalkyl, optionally substituted C$_3$-C$_{12}$ cycloalkenyl, optionally substituted heterocyclic, optionally substituted aryl and optionally substituted heteroaryl;

m is 0, 1 or 2;

each n is independently 0, 1 or 2;

p is 0, 1 or 2;

R'' is independently selected for each occurrence from the group consisting of: C$_1$-C$_6$ alkyl (optionally substituted by one, two or three substituents selected from the group consisting of: heterocyclic, —F, —Cl, —Br, —I, —OH, —NO$_2$, —N$_3$, —CN, —NH$_2$, NHR$_d$, —NR$_d$R$_d$, NR$_d$C(O)R$_d$, —NR$_d$SO—R$_d$ and —OR$_c$), —C$_2$-C$_6$ alkenyl (optionally substituted by one, two or three substituents selected from the group consisting of: heterocyclic, —F, —Cl, —Br, —I, —OH, —NO$_2$, —N$_3$, —CN, —NH$_2$, NHR$_d$, —NR$_d$R$_d$, NR$_d$C(O)R$_d$, —NR$_d$SO$_n$R$_d$ and —OR$_c$), —C$_2$-C$_6$ alkynyl (optionally substituted by one, two or three substituents selected from the group consisting of: heterocyclic, —F, —Cl, —Br, —I, —OH, —NO$_2$, —N$_3$, —CN, —NH$_2$, NHR$_d$, —NR$_d$R$_d$, NR$_d$C(O)R$_d$, —NR$_d$SO—R$_d$ and —OR$_c$), —C$_3$-C$_6$ cycloalkyl (optionally substituted by one, two or three substituents selected from the group consisting of: heterocyclic, C$_1$-C$_6$ alkyl, —F, —Cl, —Br, —I, —OH, —NO$_2$, —N$_3$, —CN, —NH$_2$, NHR$_d$, —NR$_d$R$_d$, NR$_d$C(O)R$_d$, —NR$_d$SO—R$_d$ and —OR$_c$), -heterocyclic (optionally substituted by one, two or three substituents selected from the group consisting of: C$_1$-C$_6$ alkyl, heterocyclic, —F, —Cl, —Br, —I, —OH, —NO$_2$, —N$_3$, —CN, —NH$_2$, NHR$_f$, —NR$_f$R$_f$, NR$_f$C(O)R$_f$, —NR$_f$SO—R$_f$ and —OR$_c$), —F, —Cl, —Br, —I, —OH, —NO$_2$, —N$_3$, —CN, —NH$_2$, oxo, thioxo, —NHR$_d$, —NR$_d$R$_d$, —OR$_e$, —C(O)R$_c$, —C(O)C(O)R$_c$, —OCO$_2$R$_c$, —OC(O)R$_c$, OC(O)C(O)R$_c$, —NHC(O)R$_c$, —NHCO$_2$R$_c$, —NHC(O)C(O)R$_c$, NHC(S)NH$_2$, —NHC(S)NHR$_d$, —NHC(NH)NH$_2$, —NHC(NH)NHR$_c$, —NHC(NH)R$_c$, —C(NH)NHR$_c$, (C=NR$_c$)R$_c$; —NR$_c$C(O)R$_c$, —NR$_c$C(S)NH$_2$, —NR$_c$C(S)NHR$_c$, —NHSO$_2$R$_c$, —CH$_2$NH$_2$, —CH$_2$SO$_2$CH$_3$, -phenyl, and heteroaryl; and R$_f$ is selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_1$-C$_{10}$ alkoxy, optionally substituted C$_3$-C$_{12}$ cycloalkyl, optionally substituted C$_3$-C$_{12}$ cycloalkenyl, optionally substituted heterocyclic, optionally substituted aryl and optionally substituted heteroaryl.

20. The compound of claim 19, wherein the compound has the Formula (IIc):

(IIc)

21. The compound of claim 19, wherein the compound has the Formula (IId):

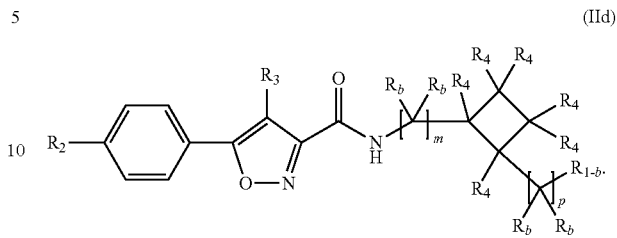

(IId)

22. The compound of claim 19, wherein R$_{1-b}$ is heteroaryl.

23. A compound selected from the group consisting of: N-trans-3-(5-(hydroxymethyl)-1H-1,2,3-triazol-1-yl)cyclobutyl)-5-phenylisoxazole-3-carboxamide; N-trans-3-(4-(hydroxymethyl)-1H-1,2,3-triazol-1-yl)cyclobutyl)-5-phenylisoxazole-3-carboxamide; N-cis-3-(5-(hydroxymethyl)-1H-1,2,3-triazol-1-yl) cyclobutyl)-5-phenylisoxazole-3-carboxamide; N-cis-3-(4-(hydroxymethyl)-1H-1,2,3-triazol-1-yl) cyclobutyl)-5-phenylisoxazole-3-carboxamide; N-cis-3-(4-((S)-1-hydroxyethyl)-1H-1,2,3-triazol-1-yl)cyclobutyl)-5-phenylisoxazole-3-carboxamide; N-cis-3-(5-((S)-1-hydroxyethyl)-1H-1,2,3-triazol-1-yl)cyclobutyl)-5-phenylisoxazole-3-carboxamide; N-((trans-3-(5-(hydroxymethyl)-1,3,4-thiadiazol-2-yl)cyclobutyl)methyl)-5-phenylisoxazole-3-carboxamide; N-((cis-3-(5-(hydroxymethyl)-1,3,4-thiadiazol-2-yl)cyclobutyl)methyl)-5-phenylisoxazole-3-carboxamide; N-((trans-3-((5-(hydroxymethyl)-1,3,4-thiadiazol-2-yl)methyl)cyclobutyl)-5-phenylisoxazole-3-carboxamide; N-((cis-3-((5-(hydroxymethyl)-1,3,4-thiadiazol-2-yl)methyl)cyclobutyl)-5-phenylisoxazole-3-carboxamide; N-(trans-3-(5-((S)-1-hydroxyethyl)-1H-1,2,3-triazol-1-yl)cyclobutyl)-5-phenylisoxazole-3-carboxamide; N-(trans-3-(4-((S)-1-hydroxyethyl)-1H-1,2,3-triazol-1-yl)cyclobutyl)-5-phenylisoxazole-3-carboxamide; N-(trans-3-(5-((R)-1-hydroxyethyl)-1H-1,2,3-triazol-1-yl)cyclobutyl)-5-phenylisoxazole-3-carboxamide; N-(trans-3-(4-((R)-1-hydroxyethyl)-1H-1,2,3-triazol-1-yl)cyclobutyl)-5-phenylisoxazole-3-carboxamide; N-(cis-3-(5-((R)-1-hydroxyethyl)-1H-1,2,3-triazol-1-yl)cyclobutyl)-5-phenylisoxazole-3-carboxamide; N-(cis-3-(4-((R)-1-hydroxyethyl)-1H-1,2,3-triazol-1-yl)cyclobutyl)-5-phenylisoxazole-3-carboxamide; N-(trans-3-(5-((R)-1-hydroxyethyl)-1,3,4-oxadiazol-2-yl)cyclobutyl)-5-phenylisoxazole-3-carboxamide; N-(trans-3-(5-((S)-1-hydroxyethyl)-1,3,4-oxadiazol-2-yl)cyclobutyl)-5-phenylisoxazole-3-carboxamide; N-(trans-3-(5-(hydroxymethyl)-1,3,4-oxadiazol-2-yl)cyclobutyl)-5-phenylisoxazole-3-carboxamide; N-trans-3-(5-((R)-1-hydroxyethyl)-1,3,4-thiadiazol-2-yl)cyclobutyl)-5-phenylisoxazole-3-carboxamide; N-trans-3-(5-((S)-1-hydroxyethyl)-1,3,4-thiadiazol-2-yl)cyclobutyl)-5-phenylisoxazole-3-carboxamide; N-trans-3-(5-(hydroxymethyl)-1,3,4-thiadiazol-2-yl)cyclobutyl)-5-phenylisoxazole-3-carboxamide; N-cis-3-(5-(hydroxymethyl)-1,3,4-thiadiazol-2-yl)cyclobutyl)-5-phenylisoxazole-3-carboxamide; N-cis-3-(5-((S)-1-hydroxyethyl)-1,3,4-thiadiazol-2-yl)cyclobutyl)-5-phenylisoxazole-3-carboxamide; N-cis-3-(5-((R)-1-hydroxyethyl)-1,3,4-thiadiazol-2-yl)cyclobutyl)-5-phenylisoxazole-3-carboxamide; N-cis-3-(5-(hydroxymethyl)-1,3,4-oxadiazol-2-yl)cyclobutyl)-5- phenylioxazole-3-carboxamide; N-cis-3-(5-((R)-1-hydroxyethyl)-1,3,4-oxadiazol-2-yl)cyclobutyl)-5-phenylisoxazole-3-carboxamide; N-cis-3-(5-((S)-1-hydroxyethyl)-1,3,4-oxadiazol-2-yl)cyclobutyl)-5-phenylisoxazole-3-carboxamide; N-cis-3-(5-((R)-1,2-dihydroxyethyl)-1,3,4-thiadiazol-2-yl)cyclobutyl)-5-phenylisoxazole-3-carboxamide; (1-cis-3-(5-phenylisoxazole-3-carboxamido)cyclobutyl)-1H-1,2,3-triazol-4-yl)methyl butylcarbamate; N-trans-3-(4-(R)-1-hydroxyethyl)-1H-pyrazol-1-yl)cyclobutyl)-5-phenylisoxazole-3-carboxamide; N-trans-3-(4-(S)-1-hydroxyethyl)-1H-pyrazol-1-yl)cyclobutyl)-5-phenylisoxazole-3-carboxamide; N-trans-3-(5-((R)-1-hydroxyethyl)-1H-pyrazol-1-yl)cyclobutyl)-5-phenylisoxazole-3-carboxamide; N-trans-3-(5-((S)-1-hydroxyethyl)-1H-pyrazol-1-yl)cyclobutyl)-5-phenylisoxazole-3-carboxamide; N-(cis-3-(4-(hydroxymethyl)-1H-pyrazol-1-yl)cyclobutyl)-5-phenylisoxazole-3-carboxamide; N-(trans-3-(4-(hydroxymethyl)-1H-pyrazol-1-yl)cyclobutyl)-5-phenylisoxazole-3-carboxamide; N-cis-3-(3-(hydroxymethyl)-1H-pyrazol-1-yl)cyclobutyl)-5-phenylisoxazole-3-carboxamide; N-trans-3-(3-(hydroxymethyl)-1H-pyrazol-1-yl)cyclobutyl)-5-phenylisoxazole-3-carboxamide; N-trans-3-(3-(hydroxymethyl)-1,2,4-oxadiazol-5-yl)cyclobutyl)-5-phenylisoxazole-3-carboxamide; N-cis-3-(3-(hydroxymethyl)-1,2,4-oxadiazol-5-yl)cyclobutyl)-5-phenylisoxazole-3-carboxamide; N-(cis-3-(5-(hydroxymethyl)-1,2,4-oxadiazol-3-yl)cyclobutyl)-5-phenylisoxazole-3-carboxamide; N-(trans-3-(5-(hydroxymethyl)-1,2,4-oxadiazol-3-yl)cyclobutyl)-5-phenylisoxazole-3-carboxamide; N-(trans-3-((5-((S)-1-hydroxyethyl)-1,3,4-thiadiazol-2-yl)methyl)cyclobutyl)-5-phenylisoxazole-3-carboxamide; N-(cis-3-((5-((S)-1-hydroxyethyl)-1,3,4-thiadiazol-2-yl)methyl)cyclobutyl)-5-phenylisoxazole-3-carboxamide; 5-phenyl-N-[(trans-3-([5-[(1R)-1-hydroxyethyl]-1,3,4-thiadiazol-2-yl]methyl)cyclobutyl]isoxazole-3-carboxamide; 5-phenyl-N-[(cis-3-([5-[(1R)-1-hydroxyethyl]-1,3,4-thiadiazol-2-yl]methyl)cyclobutyl]isoxazole-3-carboxamide; N-trans-3-(2-hydroxyethyl)cyclobutyl)-5-phenylisoxazole-3-carboxamide; N-cis-3-(2-hydroxyethyl)cyclobutyl)-5-phenylisoxazole-3-carboxamide; N-(cis-3-(methylsulfonamidomethyl)cyclobutyl)-5-phenylisoxazole-3-carboxamide; N-(trans-3-(3-((S)-1-hydroxyethyl)-1,2,4-oxadiazol-5-yl)cyclobutyl)-5-phenylisoxazole-3-carboxamide; N-(trans-3-(3-((R)-1-hydroxyethyl)-1,2,4-oxadiazol-5-yl)cyclobutyl)-5-phenylisoxazole-3-carboxamide; N-(cis-3-((5-((R)-1-hydroxyethyl)-1,3,4-oxadiazol-2-yl)methyl)cyclobutyl)-5-phenylisoxazole-3-carboxamide; N-(trans-3-((5-((R)-1-hydroxyethyl)-1,3,4-oxadiazol-2-yl)methyl)cyclobutyl)-5-phenylisoxazole-3-carboxamide; N-((trans-3-((5-((S)-1-hydroxyethyl)-1,3,4-oxadiazol-2-yl)methyl)cyclobutyl)-5-phenylisoxazole-3-carboxamide; N-((cis-3-((5-((S)-1-hydroxyethyl)-1,3,4-oxadiazol-2-yl)methyl)cyclobutyl)-5-phenylisoxazole-3-carboxamide; N-(trans-3-(5-((R)-1-hydroxyethyl)-1,2,4-oxadiazol-3-yl)cyclobutyl)-5-phenylisoxazole-3-carboxamide; N-(trans-3-(5-((S)-1-hydroxyethyl)-1,2,4-oxadiazol-3-yl)cyclobutyl)-5-phenylisoxazole-3-carboxamide; 5-phenyl-N-[trans-3-[5-(1-methylazetidin-3-yl)-1,3,4-oxadiazol-2-yl]cyclobutyl]isoxazole-3-carboxamide; 5-(4-fluorophenyl)-N-[trans-3-[5-[(1R)-1-hydroxyethyl]-1,3,4-oxadiazol-2-yl]cyclobutyl]isoxazole-3-carboxamide; 5-phenyl-N-[trans-3-[5-[(1R)-1-methoxyethyl]-1,3,4-oxadiazol-2-yl]cyclobutyl]isoxazole-3-carboxamide; (1R)-1-[5-[trans-3-(5-phenylisoxazole-3-amido)cyclobutyl]-1,3,4-oxadiazol-2-yl]ethyl acetate; (R)-1-(5-(trans-3-(5-phenylisoxazole-3-carboxamido)cyclobutyl)-1,3,4-oxadiazol-2-yl)ethyl benzoate; N-(trans-3-(5-((R)-1-isopropoxyethyl)-1,3,4-oxadiazol-2-yl)cyclobutyl)-5-phenylisoxazole-3-carboxamide; N-(trans-3-(5-((R)-1-isobutoxyethyl)-1,3,4-oxadiazol-2-yl)cyclobutyl)-5-phenylisoxazole-3-carboxamide; tert-butyl 3-(5-(trans-3-(5-phenylisoxazole-3-carboxamido)cyclobutyl)-1,3,4-oxadiazol-2-yl)azetidine-1-carboxylate; 5-phenyl-N-[trans-3-[5-(azetidin-3-yl)-1,3,4-oxadiazol-2-yl]cyclobutyl]isoxazole-3-carboxamide; N-(trans-3-(5-(oxetan-3-yl)-1,3,4-oxadiazol-2-yl)cyclobutyl)-5-phenylisoxazole-3-carboxamide; N-(trans-3-(1-methyl-1H-benzo[d]imidazol-2-yl)cyclobutyl)-5-phenylisoxazole-3-carboxamide; 5-(2,4-difluorophenyl)-N-(trans-3-(5-((R)-1-hydroxyethyl)-1,3,4-oxadiazol-2-yl)cyclobutyl)isoxazole-3-carboxamide; 5-(3-fluorophenyl)-N-(trans-3-(5-((R)-1-hydroxyethyl)-1,3,4-oxadiazol-2-yl)cyclobutyl)isoxazole-3-carboxamide; 5-(2-fluorophenyl)-N-(trans-3-(5-((R)-1-hydroxyethyl)-1,3,4-oxadiazol-2-yl)cyclobutyl)isoxazole-3-carboxamide; 5-(4-hydroxyphenyl)-N-(trans-3-(5-((R)-1-hydroxyethyl)-1,3,4-oxadiazol-2-yl)cyclobutyl)isoxazole-3-carboxamide; 5-(3-hydroxyphenyl)-N-(trans-3-(5-((R)-1-hydroxyethyl)-1,3,4-oxadiazol-2-yl)cyclobutyl)isoxazole-3-carboxamide; 5-(3,4-difluorophenyl)-N-(trans-3-(5-((R)-1-hydroxyethyl)-1,3,4-oxadiazol-2-yl)cyclobutyl)isoxazole-3-carboxamide; N-(trans-3-(5-((R)-1-(methylsulfonyl)ethyl)-1,3,4-oxadiazol-2-yl)cyclobutyl)-5-phenylisoxazole-3-carboxamide; N-(trans-3-(5-cyclobutyl-1,3,4-oxadiazol-2-yl)cyclobutyl)-5-phenylisoxazole-3-carboxamide; N-(trans-3-(1H-imidazol-1-yl)cyclobutyl)-5-phenylisoxazole-3-carboxamide; N-(3-(5-((R)-1-hydroxyethyl)-1,3,4-oxadiazol-2-yl)cyclohexyl)-5-phenylisoxazole-3-carboxamide; N-(3-(4-(hydroxymethyl)-1H-1,2,3-triazol-1-yl)cyclohexyl)-5-phenylisoxazole-3-carboxamide; N-(3-(5-(hydroxymethyl)-1H-1,2,3-triazol-1-yl)cyclohexyl)-5-phenylisoxazole-3-carboxamide; N-[3-[5-(hydroxymethyl)-1,3,4-oxadiazol-2-yl]cyclopentyl]-5-phenylisoxazole-3-carboxamide; N-(cis/trans-4-(5-(hydroxymethyl)-1,3,4-oxadiazol-2-yl)cyclohexyl)-5-phenylisoxazole-3-carboxamide; 5-(3,4-dihydroxyphenyl)-N-(trans-3-(5-((R)-1-hydroxyethyl)-1,3,4-oxadiazol-2-yl)cyclobutyl)isoxazole-3-carboxamide; N-(trans-3-(1H-benzo[d]imidazol-1-yl)cyclobutyl)-5-phenylisoxazole-3-carboxamide; N-(trans-3-(5-(1,1-dioxidothietan-3-yl)-1,3,4-oxadiazol-2-yl)cyclobutyl)-5-phenylisoxazole-3-carboxamide; N-(3-(4-(hydroxymethyl)-1H-1,2,3-triazol-1-yl)cyclopentyl)-5-phenylisoxazole-3-carboxamide; and N-(3-(5-(hydroxymethyl)-1H-1,2,3-triazol-1-yl)cyclopentyl)-5-phenylisoxazole-3-carboxamide, and pharmaceutically acceptable salts thereof.

24. A pharmaceutical composition comprising a compound of claim 1 and a pharmaceutically acceptable carrier or excipient.

25. The pharmaceutical composition of claim 24, wherein the composition further comprises at least one CFTR modulator.

* * * * *